(12) United States Patent
Green et al.

(10) Patent No.: US 7,514,448 B2
(45) Date of Patent: Apr. 7, 2009

(54) AZAINDOLES USEFUL AS INHIBITORS OF ROCK AND OTHER PROTEIN KINASES

(75) Inventors: Jeremy Green, Burlington, MA (US); Andrew Miller, Abingdon (GB); Juan-Miguel Jimenez, Abingdon (GB); Craig Marhefka, Frederick, MD (US); Jingrong Cao, Newton, MA (US); John Court, Littleton, MA (US); Upul Bandarage, Lexington, MA (US); Huai Gao, Lincoln, MA (US); Suganthini Nanthakumar, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 519 days.

(21) Appl. No.: 11/098,751

(22) Filed: Apr. 4, 2005

(65) Prior Publication Data

US 2006/0003968 A1 Jan. 5, 2006

Related U.S. Application Data

(60) Provisional application No. 60/559,041, filed on Apr. 2, 2004.

(51) Int. Cl.
| | |
|---|---|
| A01N 43/42 | (2006.01) |
| A61K 31/44 | (2006.01) |
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |

(52) U.S. Cl. ...................... 514/300; 546/113
(58) Field of Classification Search .......... 546/113; 514/300
See application file for complete search history.

(56) References Cited

U.S. PATENT DOCUMENTS

2006/0122213 A1   6/2006   Pierard et al.

FOREIGN PATENT DOCUMENTS

| WO | WO 99/65897 A1 | 12/1999 |
|---|---|---|
| WO | 00/43393 | 7/2000 |
| WO | 01/64674 | * 7/2001 |
| WO | WO 03/028724 A1 | 4/2003 |
| WO | WO 03/082869 A1 | 10/2003 |
| WO | 2004/016609 A1 | 2/2004 |
| WO | WO 2004/016610 A1 | 2/2004 |
| WO | WO 2004/078756 A2 | 9/2004 |
| WO | 2005/028475 A2 | 3/2005 |

OTHER PUBLICATIONS

Tu et al., Journal of Chromatography B, vol. 789, 2003, pp. 323-335.*
Rao et al., Biodrugs, 2007, 21(3), pp. 167-177.*
Yoshitaka Hirooka and Hiroaki Shimokawa, "Therapeutic Potential of Rho-Kinase Inhibitors in Cardiovascular Diseases" Am J Cardiovasc Drugs 2005; 5(1) p. 31-39.
P. Vasantha Rao, Pei-Feng Deng, et al., "Modulation of Aqueous Humor Outflow Facility by the Rho Kinase-Specific Inhibitor Y-27632" Investigative Ophthalmology & Visual Science, Apr. 2001, vol. 42, No. 5 p. 1029-1037.

* cited by examiner

*Primary Examiner*—D. Margaret Seaman
*Assistant Examiner*—Niloofar Rahmani
(74) *Attorney, Agent, or Firm*—Daniel A. Pearson

(57) ABSTRACT

The present invention relates to compounds useful as inhibitors of protein kinases. The invention also provides pharmaceutically acceptable compositions comprising said compounds and methods of using the compositions in the treatment of various disease, conditions, or disorders.

17 Claims, No Drawings

AZAINDOLES USEFUL AS INHIBITORS OF ROCK AND OTHER PROTEIN KINASES

CROSS-REFERENCE TO RELATED APPLICATIONS

This application claims the benefit of U.S. Provisional Application No. 60/559,041, filed Apr. 2, 2004, which is herein incorporated by reference.

TECHNICAL FIELD OF INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

One kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885-1893) and ROKα/Rho-kinase/ROCK-II (Leung et al., *J. Biol. Chem.* 1995, 270, 29051-29054; Matsui et al., *EMBO J.* 1996, 15, 2208-2216; Nakagawa et al., *FEBS Lett.* 1996, 392, 189-193), protein kinase PKN (Amano et al., *Science* 1996, 271, 648-650; Watanabe et al., *Science* 1996, 271, 645-648), and citron and citron kinase (Madaule et al. *Nature,* 1998, 394, 491-494; Madaule et al., *FEBS Lett.* 1995, 377, 243-248). The ROCK family of kinases have been shown to be involved in a variety of functions including Rho-induced formation of actin stress fibers and focal adhesions (Leung et al., *Mol. Cell Biol.* 1996, 16, 5313-5327; Amano et al., *Science,* 1997, 275, 1308-1311; Ishizaki et al., *FEBS Lett.* 1997, 404, 118-124) and in down-regulation of myosin phosphatase (Kimura et al., *Science,* 1996, 273, 245-248), platelet activation (Klages et al., *J. Cell. Biol.,* 1999, 144, 745-754), aortic smooth muscle contraction by various stimuli (Fu et al., *FEBS Lett.,* 1998, 440, 183-187), thrombin-induced responses of aortic smooth muscle cells (Seasholtz et al., *Cir. Res.,* 1999, 84, 1186-1193), hypertrophy of cardiomyocytes (Kuwahara et al., *FEBS Lett.,* 1999, 452, 314-318), bronchial smooth muscle contraction (Yoshii et al., *Am. J. Respir. Cell Mol. Biol.,* 1999, 20, 1190-1200), smooth muscle contraction and cytoskeletal reorganization of non-muscle cells (Fukata et al., *Trends in Pharm. Sci* 2001, 22, 32-39), activation of volume-regulated anion channels (Nilius et al., *J. Physiol.,* 1999, 516, 67-74), neurite retraction (Rirose et al., *J. Cell. Biol.,* 1998, 141, 1625-1636), neutrophil chemotaxis (Niggli, *FEBS Lett.,* 1999, 445, 69-72), wound healing (Nobes and Hall, *J. Cell. Biol.,* 1999, 144, 1235-1244), tumor invasion (Itoh et al., *Nat. Med.,* 1999, 5, 221-225) and cell transformation (Sahai et al., *Curr. Biol.,* 1999, 9, 136-145). More specifically, ROCK has been implicated in various diseases and disorders including hypertension (Satoh et al., *J. Clin. Invest.* 1994, 94, 1397-1403; Mukai et al., *FASEB J.* 2001, 15, 1062-1064; Uehata et al., *Nature* 1997, 389, 990-994; Masumoto et al., *Hypertension,* 2001, 38, 1307-1310), cerebral vasospasm (Sato et al., *Circ. Res.* 2000, 87, 195-200; Miyagi et al., *J. Neurosurg.* 2000, 93, 471-476; Tachibana et al., *Acta Neurochir* (Wien) 1999, 141, 13-19), coronary vasospasm (Shimokawa et al., *Jpn. Cir. J.* 2000, 64, 1-12; Kandabashi et al., *Circulation* 2000, 101, 1319-1323; Katsumata et al., *Circulation* 1997, 96, 4357-4363; Shimokawa et al., *Cardiovasc. Res.* 2001, 51, 169-177; Utsunomiya et al., *J. Pharmacol.* 2001, 134, 1724-1730; Masumoto et al., *Circulation* 2002, 105, 1545-1547), bronchial asthma (Chiba et al., *Comp. Biochem. Physiol. C Pharmacol. Toxicol. Endocrinol.* 1995, 11, 351-357; Chiba et al., *Br. J. Pharmacol.* 1999, 127, 597-600; Chiba et al., *Br. J. Pharmacol.* 2001, 133, 886-890; lizuka et al., *Eur. J. Pharmacol.* 2000, 406, 273-279), preterm labor (Niro et al., *Biochem. Biophys. Res. Commun.* 1997, 230, 356-359; Tahara et al., *Endocrinology* 2002, 143, 920-929; Kupittayanant et al., *Pflugers Arch.* 2001, 443, 112-114), erectile dysfunction (Chitaley et al., *Nat. Med.* 2001, 7, 119-122; Mills et al., *J. Appl. Physiol.* 2001, 91, 1269-1273), glaucoma (Honjo et al., *Arch. Ophthalmol.* 2001, 1171-1178; Rao et al., *Invest. Ophthalmol. Vis. Sci.* 2001, 42, 1029-1037), vascular smooth muscle cell proliferation (Shimokawa et al., *Cardiovasc. Res.* 2001, 51, 169-177; Morishige et al., *Arterioscler. Thromb. Vasc. Biol.* 2001, 21, 548-554; Eto et al., *Am. J. Physiol. Heart Circ. Physiol.* 2000, 278, H1744-H1750; Sawada et al., *Circulation* 2000, 101, 2030-2023; Shibata et al., *Circulation* 2001, 103, 284-289), myocardial hypertrophy (Hoshijima et al., *J. Biol. Chem.* 1998, 273, 7725-77230; Sah et al., *J. Biol. Chem.* 1996, 271, 31185-31190; Kuwahara et al., *FEBS Lett.* 1999, 452, 314-318; Yanazume et al., *J. Biol. Chem.* 2002, 277, 8618-8625), malignoma (Itoh et al., *Nat. Med.* 1999, 5, 221-225; Genda et al., *Hepatology* 1999, 30, 1027-1036; Somlyo et al., *Biochem. Biophys. Res. Commun.* 2000, 269, 652-659), ischemia/reperfusion-induced injury (Ikeda et al., *J. of Surgical Res.* 2003, 109, 155-160; Miznuma et al. *Transplantation* 2003, 75, 579-586), endothelial dysfunction (Hernandez-Perera et al., *Circ. Res.* 2000, 87, 616-622; Laufs et al., *J. Biol. Chem.* 1998, 273, 24266-24271; Eto et al., *Circ. Res.* 2001, 89, 583-590), Crohn's Disease and colitis (Segain et al. *Gastroenterology* 2003, 124(5), 1180-1187), neurite outgrowth (Fournier et al. *J. Neurosci.* 2003, 23, 1416-1423), Raynaud's Disease (Shimokawa et al. *J. Cardiovasc. Pharmacol.* 2002, 39, 319-327), angina (Utsunomiya et al. *Br. J.*

Pharmacol. 2001, 134, 1724-1730; Masumoto et al, *Circulation* 2002, 105, 1545-1547; Shimokawa et al, *J. Cardiovasc. Pharmacol.*, 2002, 40, 751-761; Satoh et al., *Jpn. J. Pharmacol.*, 2001, 87, 34-40), Alzheimer's disease (Zhou et al., *Science* 2003, 302, 1215-1218), benign prostatic hyperplasia (Rees et al., *J. Urology,* 2003, 170, 2517-2522) and atherosclerosis (Retzer et al. *FEBS Lett.* 2000, 466, 70-74; Ishibashi et al. *Biochim. Biophys. Acta* 2002, 1590, 123-130). Accordingly, the development of inhibitors of ROCK kinase would be useful as therapeutic agents for the treatment of disorders implicated in the ROCK kinase pathway.

ERK2 (extracellular signal regulated kinase) is a member of the mammalian mitogen-activated protein (MAP)1 kinase family. (MAP)1 kinases are serine/threonine kinases that mediate intracellular signal transduction pathways (Cobb and Goldsmith, *J. Biol. Chem.*, 1995, 270, 14843; Davis, *Mol. Reprod. Dev.* 1995, 42, 459) and are activated by mitogens and growth factors (Bokemeyer et al. *Kidney Int.* 1996, 49, 1187). Members of the MAP kinase family share sequence similarity and conserved structural domains, and, in addition to ERK2, include the JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., *Cell* 1994, 76, 1025; Han et al., *Science* 1994, 265, 808; Raingeaud et al., *J. Biol. Chem.* 1995, 270, 7420; Shapiro and Dinarello, *Proc. Natl. Acad. Sci. USA* 1995, 92, 12230). In contrast, ERKs are activated by mitogens and growth factors (Bokemeyer et al., *Kidney Int.* 1996, 49, 1187).

ERK2 is a widely distributed protein kinase that achieves maximum activity when both Thr183 and Tyr185 are phosphorylated by the upstream MAP kinase kinase, MEK1 (Anderson et al., *Nature* 1990, 343, 651; Crews et al., *Science* 1992, 258, 478). Upon activation, ERK2 phosphorylates many regulatory proteins, including the protein kinases Rsk90 (Bjorbaek et al., *J. Biol. Chem.* 1995, 270, 18848) and MAPKAP2 (Rouse et al., *Cell* 1994, 78, 1027), and transcription factors such as ATF2 (Raingeaud et al., *Mol. Cell Biol.* 1996, 16, 1247), Elk-1 (Raingeaud et al., *Mol. Cell Biol.* 1996, 16, 1247), c-Fos (Chen et al., *Proc. Natl. Acad. Sci. USA* 1993, 90, 10952), and c-Myc (Oliver et al., *Proc. Soc. Exp. Biol. Med.* 1995, 210, 162). ERK2 is also a downstream target of the Ras/Raf dependent pathways (Moodie et al., *Science* 1993, 260, 1658) and may help relay the signals from these potentially oncogenic proteins. ERK2 has been shown to play a role in the negative growth control of breast cancer cells (Frey and Mulder, *Cancer Res.* 1993, 57, 628) and hyperexpression of ERK2 in human breast cancer has been reported (Sivaraman et al., *J. Clin. Invest.* 1997, 99, 1478). Activated ERK2 has also been implicated in the proliferation of endothelin-stimulated airway smooth muscle cells, suggesting a role for this kinase in asthma (Whelchel et al., *Am. J. Respir. Cell Mol. Biol.* 1997, 16, 589).

Glycogen synthase kinase-3 (GSK-3) is a serine/threonine protein kinase comprised of α and β forms that are each encoded by distinct genes [Coghlan et al., *Chemistry & Biology* 2000, 7, 793-803; and Kim and Kimmel, *Curr. Opinion Genetics Dev.*, 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., *J. Cell Biol.* 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., *PNAS* 1996, 93, 8455-8459; Cross et al., *Biochem. J.* 1994, 303, 21-26); Cohen, *Biochem. Soc. Trans.* 1993, 21, 555-567; and Massillon et al. *Biochem J.* 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is also associated with Alzheimer's disease. This disease is characterized by the well-known β-amyloid peptide and the formation of intracellular neurofibrillary tangles. Aβ peptides are derived from the amyloid precursor protein (APP) by sequential proteolysis, catalysed by the aspartyl protease BACE2, followed by presenilin-dependent γ-secretase cleavage. It has been demonstrated that antibodies against β-amyloid plaques can slow cognitive decline in patients with Alzheimer's disease (Hock et al., *Neuron,* 2003, 38, 547-554), and thus other β-amyloid-lowering strategies (e.g., the development of agents capable of inhibiting β-amyloid peptide) would be useful in the treatment of Alzherimer's disease and other psychotic and neurodegenerative disorders. Additionally, the neurofibrillary tangles contain hyperphosphorylated Tau protein, in which Tau is phosphorylated on abnormal sites, and thus agents capable of inhibiting the hyperphosphorylation of Tau protein would be useful in the treatment of Alzherimer's disease and other psychotic and neurodegenerative disorders.

GSK-3 is known to phosphorylate these abnormal sites in cell and animal models. Furthermore, inhibition of GSK-3 has been shown to prevent hyperphosphorylation of Tau in cells [Lovestone et al., *Current Biology* 1994, 4, 1077-86; and Brownlees et al., *Neuroreport* 1997, 8, 3251-55]. Therefore, GSK-3 activity promotes generation of the neurofibrillary tangles and the progression of Alzheimer's disease. It has also been shown that GSK-3 facilitates APP processing and that a GSK-3 inhibitor (lithium) inhibits of the generation of Aβ peptides through the inhibition of GSK-3 (Phiel et al. *Nature* 2003, 423, 435-439). Thus, the development of inhibitors of GSK-3 would be useful for the reduction of the formation of amyloid plaques and neurofibrillry tangles, the pathological hallmarks of Alzheimer's Disease, and would also be useful for the treatment of other psychotic and neurodegenerative disorders.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698-702; Takashima et al., *PNAS* 1993, 90, 7789-93; and Pei et al., *J. Neuropathol. Exp* 1997, 56, 70-78].

GSK-3 activity is also associated with stroke [Wang et al., *Brain Res* 2000, 859, 381-5; Sasaki et al., *Neurol Res* 2001, 23, 588-92; Hashimoto et al., *J. Biol. Chem* 2002, 277, 32985-32991].

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., *Curr. Biol.* 1999, 9, R521). This sub-family includes PKA, PKB (c-Akt), PKC, PRK1, PRK2, p70$^{S6K}$, and PDK.

AKT (also known as PKB or Rac-PK beta), a serine/threonine protein kinase, has been shown to be overexpressed in several types of cancer and is a mediator of normal cell functions [(Khwaja, A., *Nature* 1999, 401, 33-34); (Yuan, Z. Q., et al., *Oncogene* 2000, 19, 2324-2330); (Namikawa, K., et al., *J. Neurosci.* 2000, 20, 2875-2886)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., *Proc. Natl. Acad. Sci. USA* 1992, 89, 9267-9271); (Brodbeck, D. et al., *J. Biol. Chem.* 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., *Mol. Cell. Biol.*, 1997, 17, 1595-1606); (Hemmings, B. A., *Science*, 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.* 1998, 273, 7201-7204) induction of differentiation and/or proliferation, protein synthesis and stress responses (Alessi, D. R. et al., *Curr. Opin. Genet. Dev.* 1998, 8, 55-62).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., *Proc. Natl. Acad. Sci. U.S.A.* 1992, 89, 9267-9271). It has also been found to be overexpressed in 12% of pancreatic cancers (Cheng, J. Q. et al., *Proc. Natl. Acad. Sci. U.S.A.* 1996, 93, 3636-3641). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., *Int. J. Cancer* 1995, 64, 280-285).

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., *Semin. Cancer Biol.* 1994, 5, 285-294). PKA is a tetrameric holoenzyme, which contains two catalytic subunits bound to a homo-dimeric regulatory subunit (which acts to inhibit the catalytic subunits). On binding of cAMP (enzyme activation), the catalytic subunits dissociate from the regulatory subunits to yield the active serine/threonine kinase (McKnight, G. S. et al., *Recent Prog. Horm. Res.* 1988, 44, pp. 307). Three isoforms of the catalytic subunit (C-α, C-β and C-γ) have been reported to date (Beebe, S. J. et al., *J. Biol. Chem.* 1992, 267, 25505-25512) with the C-α subunit being the most extensively studied, primarily because of its elevated expression in primary and metastatic melanomas (Becker, D. et al., *Oncogene* 1990, 5, 1133). To date, strategies to modulate the activity of the C-α subunit involve the use of antibodies, molecules that block PKA activity by targeting regulatory dimers and antisense oligonucleotides expression.

The ribosomal protein kinases p70$^{S6K}$-1 and -2 are also members of the AGC sub-family of protein kinases and catalyze the phosphorylation and subsequent activation of the ribosomal protein S6, which has been implicated in the translational up-regulation of mRNAs coding for the components of the protein synthetic apparatus. These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101-186). p70$^{S6K}$ dependent S6 phosphorylation is stimulated in response to a variety of hormones and growth factors primarily via the PI3K pathway (Coffer, P. J. et al., *Biochem. Biophys. Res. Commun,* 1994 198, 780-786), which may be under the regulation of mTOR, since rapamycin acts to inhibit p70$^{S6K}$ activity and blocks protein synthesis, specifically as a result of a down-regulation of translation of these mRNA's encoding ribosomal proteins (Kuo, C. J. et al., *Nature* 1992, 358, 70-73).

In vitro PDK1 catalyses the phosphorylation of Thr252 in the activation loop of the p70 catalytic domain, which is indispensable for p70 activity (Alessi, D. R., *Curr. Biol.,* 1998, 8, 69-81). The use of rapamycin and gene deletion studies of dp70S6K from Drosophila and p70$^{S6K}$, from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frödin, M. et al., *EMBO J.* 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.* 2001, 114, 2903-2910), (Lawlor, M. A. et al., *EMBO J.* 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, R93-R96). Many human cancers including prostate and NSCL have elevated PDK1 signaling pathway function resulting from a number of distinct genetic events such as PTEN mutations or over-expression of certain key regulatory proteins [(Graff, J. R., *Expert*

Opin. Ther. Targets 2002, 6, 103-113), (Brognard, J., et al., Cancer Res. 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., Curr. Biol. 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., Cell 2000, 100, 57-70). PDK1 is a critical mediator of the PI3K signaling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Specifically, increased levels of PI3K pathway activity has been directly associated with the development of a number of human cancers, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as PKB, examples include: brain (gliomas), breast, colon, head and neck, kidney, lung, liver, melanoma, ovarian, pancreatic, prostate, sarcoma, thyroid [(Teng, D. H. et al., Cancer Res., 1997 57, 5221-5225), (Brognard, J. et al., Cancer Res., 2001, 61, 3986-3997), (Cheng, J. Q. et al., Proc. Natl. Acad. Sci. 1996, 93, 3636-3641), (Int. J. Cancer 1995, 64, 280), (Graff, J. R., Expert Opin. Ther. Targets 2002, 6, 103-113), (Am. J. Pathol. 2001, 159, 431)]. Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., Proc. Natl. Acad. Sci. 1996, 93, 3636-3641), (Neoplasia 2001, 3, 278)], lung [(Brognard, J. et al., Cancer Res. 2001, 61, 3986-3997), (Neoplasia 2001, 3, 278)], ovarian [(Hayakawa, J. et al., Cancer Res. 2000, 60, 5988-5994), (Neoplasia 2001, 3, 278)], breast (Mol. Cancer Ther. 2002, 1, 707), colon [(Neoplasia 2001, 3, 278), (Arico, S. et al., J. Biol. Chem. 2002, 277, 27613-27621)], cervical (Neoplasia 2001, 3, 278), prostate [(Endocrinology 2001, 142, 4795), (Thakkar, H. et al. J. Biol. Chem. 2001, 276, 38361-38369), (Chen, X. et al., Oncogene 2001, 20, 6073-6083)] and brain (glioblastomas) [(Flynn, P. et al., Curr. Biol. 2000, 10, 1439-1442)].

The Tec family of non-receptor tyrosine kinases plays a central role in signaling through antigen-receptors such as the TCR, BCR and Fcγ receptors (reviewed in Miller A, et al. Current Opinion in Immunology 14; 331-340 (2002). Tec family kinases are essential for T cell activation. Three members of the Tec family, Itk, Rlk and Tec, are activated downstream of antigen receptor engagement in T cells and transmit signals to downstream effectors, including PLC-γ. Deletion of Itk in mice results in reduced T cell receptor (TCR)-induced proliferation and secretion of the cytokines IL-2, IL-4, IL-5, IL-10 and IFN-γ (Schaeffer et al, Science 284; 638-641 (1999)), Fowell et al, Immunity 11; 399-409 (1999), Schaeffer et al Nature Immunology 2, 12; 1183-1188 (2001))). The immunological symptoms of allergic asthma are attenuated in Itk−/− mice. Lung inflammation, eosinophil infiltration and mucous production are drastically reduced in Itk−/− mice in response to challenge with the allergen OVA (Mueller et al, Journal of Immunology 170: 5056-5063 (2003)). Itk has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International archives of Allergy and Immunology 129; 327-340 (2002)).

Splenocytes from Rlk−/− mice secrete half the IL-2 produced by wild type animals in response to TCR engagement (Schaeffer et al, Science 284; 638-641 (1999)), while combined deletion of Itk and Rlk in mice leads to a profound inhibition of TCR-induced responses including proliferation and production of the cytokines IL-2, IL-4, IL-5 and IFN-γ (Schaeffer et al Nature Immunology 2, 12; 1183-1188 (2001)), Schaeffer et al, Science 284; 638-641 (1999)). Intracellular signaling following TCR engagement is effected in Itk/Rlk deficient T cells; inositol triphosphate production, calcium mobilization, MAP kinase activation, and activation of the transcription factors NFAT and AP-1 are all reduced (Schaeffer et al, Science 284; 638-641 (1999), Schaeffer et al Nature Immunology 2, 12; 1183-1188 (2001)).

Tec family kinases are also essential for B cell development and activation. Patients with mutations in Btk have a profound block in B cell development, resulting in the almost complete absence of B lymphocytes and plasma cells, severely reduced Ig levels and a profound inhibition of humoral response to recall antigens (reviewed in Vihinen et al Frontiers in Bioscience 5:d917-928). Mice deficient in Btk also have a reduced number of peripheral B cells and greatly decreased levels of IgM and IgG3. Btk deletion in mice has a profound effect on B cell proliferation induced by anti-IgM, and inhibits immune responses to thymus-independent type II antigens (Ellmeier et al, J Exp Med 192:1611-1623 (2000)).

Tec kinases also play a role in mast cell activation through the high-affinity IgE receptor (FcεRI). Itk and Btk are expressed in mast cells and are activated by FcεRI cross-linking (Kawakami et al, Journal of Immunology; 3556-3562 (1995)). Btk deficient murine mast cells have reduced degranulation and decreased production of proinflammatory cytokines following FcεRI cross-linking (Kawakami et al. Journal of leukocyte biology 65:286-290). Btk deficiency also results in a decrease of macrophage effector functions (Mukhopadhyay et al, Journal of Immunology; 168, 2914-2921 (2002)).

Accordingly, there is a great need to develop inhibitors of ROCK, ERK, GSK, and members of the AGC sub-family of protein kinases (e.g., PKA, PDK, $p70^{S6K}$-1 and -2, and PKB) that would be useful in treating various diseases or conditions associated with ROCK, ERK or GSK activation, or activation of the AGC sub-family of protein kinases (e.g., PKA, PDK, $p70^{S6K}$-1 and -2, and PKB), particularly given the inadequate treatments currently available for the majority of these disorders. It would also be desirable to develop compounds that are useful as inhibitors of Tec family (e.g., Tec, Btk, Itk/Emt/Tsk, Bmx, Txk/Rlk) protein kinases, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of ROCK, ERK, GSK, and members of the AGC sub-family of protein kinases (e.g., PKA, PDK, $p70^{S6K}$-1 and -2, and PKB). These compounds have the general formula I:

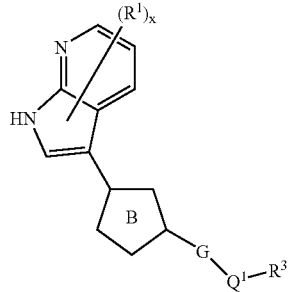

or a pharmaceutically acceptable derivative thereof, wherein ring B, $R^1$, $R^2$, $R^3$, x, G, and $Q^1$ are as defined below.

These compounds, and pharmaceutically acceptable compositions thereof, are useful for treating or lessening the severity of a variety of disorders, including allergic disorders such as asthma and atopic dermatitis, autoimmune diseases such as SLE lupus and psoriasis, conditions associated with organ transplantation, proliferative disorders such as cancer, inflammatory diseases, destructive bone disorders, hypertension, angina pectoris, cerebrovascular contraction, asthma, peripheral circulation disorder, premature birth, arteriosclerosis, spasm, retinopathy, erectile dysfunction (ED), Alzheimer's Disease, reperfusion/ischemia induced injury (e.g., stroke), and AIDS, to name a few.

The compounds provided by this invention are also useful for the study of kinases in biological and pathological phenomena; the study of intracellular signal transduction pathways mediated by such kinases, and the comparative evaluation of new kinase inhibitors.

DETAILED DESCRIPTION OF THE INVENTION

I. General Description of Compounds of the Invention:
The present invention relates to a compound of formula I:

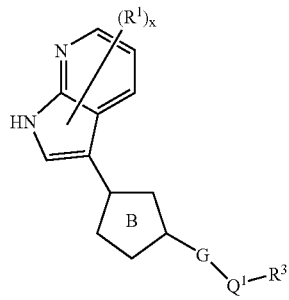

or a pharmaceutically acceptable salt thereof, wherein:

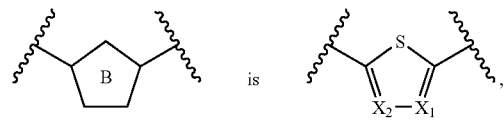

-continued

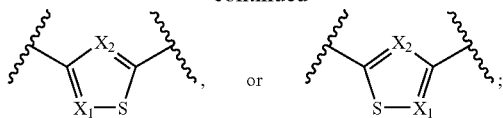

wherein
x is 0, 1, 2, or 3;
$R^1$ is halogen, —CN, —$NO_2$, or —$V_mR'$;
G is —$NR^2$ or C=O;
$R^2$ is —$U_nR'$;
$X^1$ and $X^2$ are each independently $CR^4$ or N;
each occurrence of $R^4$ is independently halogen, —CN, —$NO_2$, or —$V_mR$;
each occurrence of U or V is independently an optionally substituted $C_{1-6}$ alkylidene chain, wherein up to two methylene units of the chain are optionally and independently replaced by —NR—, —S—, —O—, —CS—, —$CO_2$—, —OCO—, —CO—, —COCO—, —CONR—, —NRCO—, —$NRCO_2$—, —$SO_2NR$—, —$NRSO_2$—, —CONRNR—, —NRCONR—, —OCONR—, —NRNR—, —$NRSO_2NR$—, —SO—, —$SO_2$—, —PO—, —$PO_2$—, or —POR—;
m and n are each independently 0 or 1;
each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;
$Q^1$ is —CO—, —$SO_2$—, —$NR^2$—, —$NR^2CO$—, —$CONR^2$—, —$SO_2NR^2$—, or is a bond;
$R^3$ is $Q^2$-$Ar^1$, or when G is —$NR^2$, $R^2$ and $Q^1$-$R^3$, taken together with the nitrogen atom, form the cyclic group:

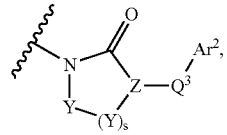

where s is 1 or 2, Z is CH or N; each occurrence of Y is independently, as valency and stability permit, —CO—, —CS—, —$SO_2$—, —O—, —S—, —$NR^5$—, or —$C(R^5)_2$—, and $R^5$ is $U_nR'$;
$Q^2$ and $Q^3$ are each independently a bond or a $C_{1-6}$ alkylidene chain, wherein up to two methylene units of the chain are each optionally and independently replaced by —NR'—, —S—, —O—, —CS—, —$CO_2$—, —OCO—, —CO—, —COCO—, —CONR'—, —NR'CO—, —$NR'CO_2$—, —$SO_2NR'$—, —$NR'SO_2$—, —CONR'NR'—, —NR'CONR'—, —OCONR'—, —NR'NR'—, —$NR'SO_2NR'$—, —SO—, —$SO_2$—, —PO—, —$PO_2$—, or —POR'—; and wherein any carbon atom in the one or more methylene units is optionally substituted with one two occurrences of $R^6$, wherein each occurrence of $R^6$ is independently halogen, —CN, —NO$_2$, or -U$_n$R', or two occurrences of $R^6$, or R' and $R^6$, taken together with the atoms to which they are bound, form an optionally substituted 3-6-membered cycloalkyl, heterocyclyl, aryl or heteroaryl ring; and $Ar^1$ and $Ar^2$ are each independently a $C_{1-6}$ aliphatic, a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ and $Ar^2$ are each optionally substituted with 0-5 independent occurrences of $TR^7$; wherein T is a bond or is a $C_1$-$C_6$ alkylidene chain wherein up to two methylene units of T are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of $R^7$ is independently —R', halogen, —NO$_2$, —CN or =O.

In other embodiments, the compound is as described above, wherein $Q^1$ is —CO—, —SO$_2$—, —NR$^2$, —NR$^2$CO—, —CONR$^2$—, —SO$_2$NR$^2$—; and $Ar^1$ and $Ar^2$ are each independently a 5-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ and $Ar^2$ are each optionally substituted with 0-5 independent occurrences of $TR^7$; wherein T is a bond or is a $C_1$-$C_6$ alkylidene chain wherein up to two methylene units of T are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NR-CONR—, —OCONR—, —NRNR—, —NRSO$_2$NR—, —SO—, —SO$_2$—, —PO—, —PO$_2$—, or —POR—; and each occurrence of $R^7$ is independently —R', halogen, —NO$_2$ or —CN.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxyii, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R$^o$; —OR$^o$; —SR$^o$; phenyl (Ph) optionally substituted with R$^o$; —O(Ph) optionally substituted with R$^o$; —(CH$_2$)$_{1-2}$(Ph), optionally substituted with R$^o$; —CH═CH(Ph), optionally substituted with R$^o$; —NO$_2$; —CN; —N(R$^o$)$_2$; —NR$^o$C(O)R$^o$; —NR$^o$C(S)R$^o$; —NR$^o$C(O)N(R$^o$)$_2$; —NR$^o$C(S)N(R$^o$)$_2$; —NR$^o$CO$_2$R$^o$; —NR$^o$NR$^o$C(O)R$^o$; —NR$^o$NR$^o$C(O)N(R$^o$)$_2$; —NR$^o$NR$^o$CO$_2$R$^o$; —C(O)C(O)R$^o$; —C(O)CH$_2$C(O)R$^o$; —CO$_2$R$^o$; —C(O)R$^o$; —C(S)R$^o$; —C(O)N(R$^o$)$_2$; —C(S)N(R$^o$)$_2$; —OC(O)N(R$^o$)$_2$; —OC(O)R$^o$; —C(O)N(OR$^o$) R$^o$; —C(NOR$^o$) R$^o$; —S(O)$_2$R$^o$; —S(O)$_3$R$^o$; —SO$_2$N(R$^o$)$_2$; —S(O)R$^o$; —NR$^o$SO$_2$N(R$^o$)$_2$; —NR$^o$SO$_2$R$^o$; —N(OR$^o$)R$^o$; —C(═NH)—N(R$^o$)$_2$; —P(O)$_2$R$^o$; —PO(R$^o$)$_2$; —OPO(R$^o$)$_2$; —(CH$_2$)$_{0-2}$NHC(O)R$^o$; phenyl (Ph) optionally substituted with R$^o$; —O(Ph) optionally substituted with R$^o$; —(CH$_2$)$_{1-2}$(Ph), optionally substituted with R$^o$; or —CH═CH(Ph), optionally substituted with R$^o$; wherein each independent occurrence of R$^o$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R$^o$, on the same substituent or different substituents, taken together with the atom(s) to which each R$^o$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R$^o$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or halo C$_{1-4}$aliphatic, wherein each of the foregoing C$_{1-4}$aliphatic groups of R$^o$ is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHCO$_2$(alkyl), ═NNHSO$_2$(alkyl), or ═NR*, where each R* is independently selected from hydrogen or an optionally substituted C$_{1-6}$ aliphatic group.

Unless otherwise defined above and herein, optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(═S)N(R$^{+1}$)$_2$, —C(═NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH═CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R$^+$ are selected from —NH$^2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R$^o$ (or R$^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R$^o$ (or R$^+$, R, R' or any other variable similarly defined herein), are taken together with the atom(s) to which each variable is bound include, but are not limited to the following: a) two independent occurrences of R$^o$ (or R$^+$, R, R' or any other variable similarly defined herein) that are bound to the same atom and are taken together with that atom to form a ring, for example, N(R$^o$)$_2$, where both occurrences of R$^o$ are taken together with the nitrogen atom to form a piperidin-1-yl, piperazin-1-yl, or morpholin-4-yl group; and b) two independent occurrences of R$^o$ (or R$^+$, R, R' or any other variable similarly defined herein) that are bound to different atoms and are taken together with both of those atoms to form a ring, for example where a phenyl group is substituted with two occurrences of OR°

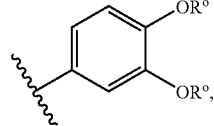

these two occurrences of R° are taken together with the oxygen atoms to which they are bound to form a fused 6-membered oxygen containing ring:

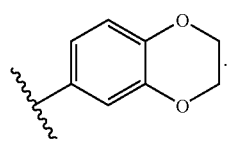

It will be appreciated that a variety of other rings can be formed when two independent occurrences of R° (or R+, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

3. Description of Exemplary Compounds:

As described generally above for compounds of formula I,

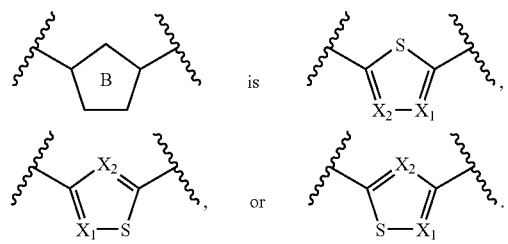

Thus, in certain embodiments, compounds of formulae I-A, I-B, or I-C are provided:

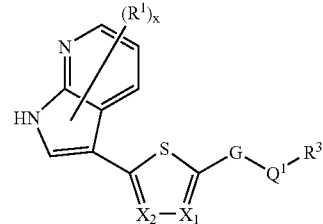

I-A

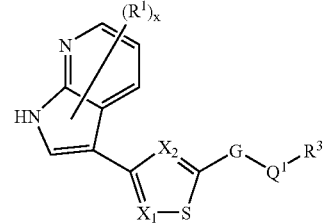

I-B

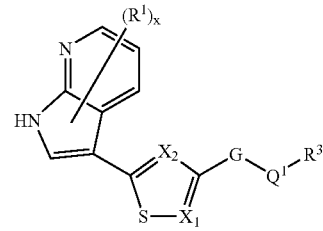

I-C

As also described generally above for compounds of formula I, $R^3$ is $Q^2$-$Ar^1$, or $R^2$ and $Q^1$—$R^3$, taken together with the nitrogen atom, form the cyclic group:

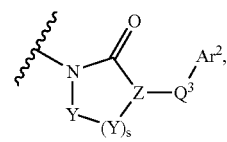

where s is 1 or 2, Z is CH or N, each occurrence of Y is independently, as valency and stability permit, —CO—, —CS—, —SO$_2$—, —O—, —S—, —NR$^5$—, or —C(R$^5$)$_2$—, and R$^5$ is U$_n$R'.

In some embodiments, wherein the compound has the formula I-B, G is —NR$^2$ and Q$^1$ is —CO— or G is C=O and Q$^1$ is —NR$^2$. In further embodiments, G is —NR$^2$ and Q$^1$ is —CO—. In yet further embodiments, X$_1$ is CR$^4$ and X$_2$ is CR$^4$ or N.

Accordingly, in one embodiment, R$^3$ is Q$^2$-Ar$^1$ and compounds of formulae I-A-i, I-B-i, and I-C-i are provided.

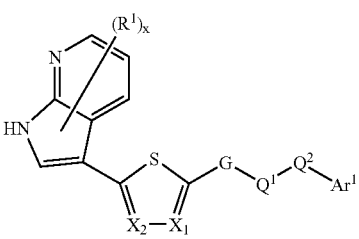

I-A-i

-continued

I-B-i

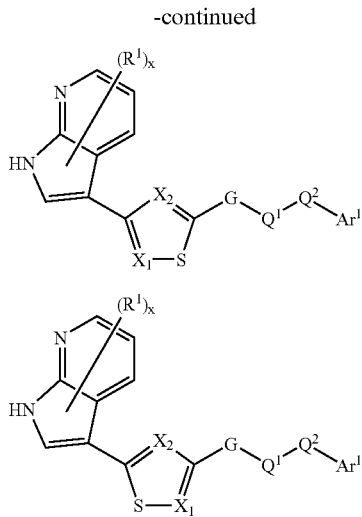

I-C-i

I-B-i-b

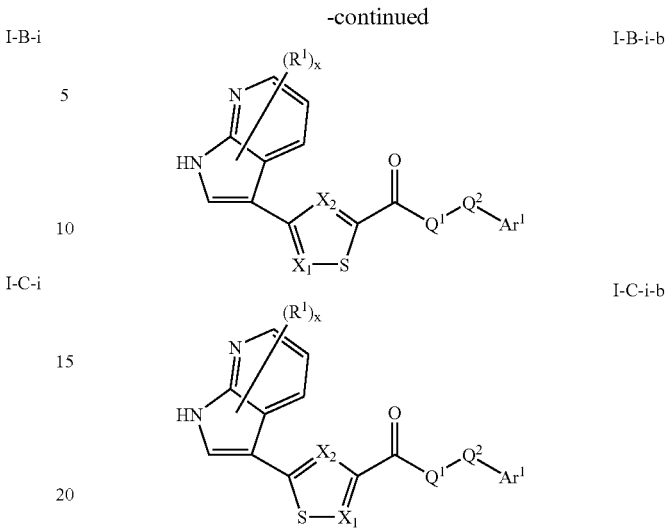

I-C-i-b

In some embodiments, G is $NR^2$, $R^3$ is $Q^2$-$Ar^1$, and compounds of formulae I-A-i-a, I-B-i-a, and I-C-i-a are provided:

I-A-i-a

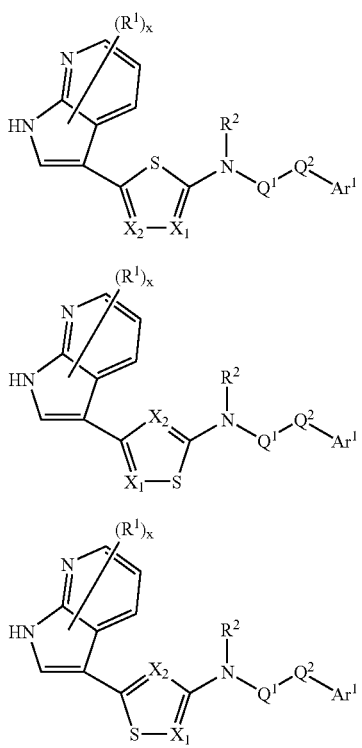

I-B-i-a

I-C-i-a

In other embodiments, G is C=O, $R^3$ is $Q^2$-$Ar^1$, and compounds of formulae I-A-i-b, I-B-i-b, and I-C-i-b are provided:

I-A-i-b

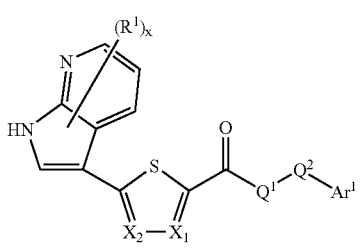

In general, for compounds of formula I, and subsets thereof, $R^2$ is $U_nR'$. In certain embodiments, $R^2$ is hydrogen, or is $U_nR'$, where n is 1, and U is a $C_{1-6}$ alkylidene chain wherein one or two methylene units are optionally and independently replaced by —O—, —NR—, —S—, or —CO—. In other embodiments, U is —CH$_2$—, —CH$_2$CH$_2$—, —CH$_2$CH$_2$CH$_2$—, —CH$_2$CH$_2$CH$_2$CH$_2$—, —CH$_2$O—, —CH$_2$S—, —CH$_2$NR—, —CH$_2$CH$_2$O—, —CH$_2$CH$_2$S—, —CH$_2$CH$_2$NR—, —CH$_2$CH$_2$CH$_2$O—, —CH$_2$CH$_2$CH$_2$S—, —CH$_2$CH$_2$CH$_2$NR—, —CH$_2$CH$_2$CH$_2$CH$_2$O—, —CH$_2$CH$_2$CH$_2$CH$_2$S—, —CH$_2$CH$_2$CH$_2$CH$_2$NR—, —CH$_2$CH$_2$OCH$_2$CH$_2$—, —(CH$_2$)$_4$NHCH$_2$—, —(CH$_2$)$_3$NHCH$_2$CH$_2$—, or —CH$_2$CH$_2$NHCH$_2$CH$_2$—, and exemplary R' groups are hydrogen, $C_1$-$C_4$alkyl, an optionally substituted group selected from tetrahydropyranyl, pyrrolidinyl, piperidinyl, piperazinyl, morpholinyl, thiomorpholinyl, pyridinyl, imidazolyl, phenyl, or cyclohexyl, or R and R', taken together with the nitrogen atom to which they are bound, form an optionally substituted 5- or 6-membered saturated, partially unsaturated, or unsaturated heterocyclyl ring.

As described generally above, for compounds of formula I, and subsets thereof, $Q^1$ is —CO—, —SO$_2$—, —NR$^2$—, —NR$^2$CO—, —CONR$^2$—, or —SO$_2$NR$^2$—. In some embodiments, $Q^1$ is —CO—, —CONR$^2$—, —NR$^2$—, —SO$_2$—, or —SO$_2$NR$^2$—. In other embodiments, $Q^1$ is —CO—, —NR$^2$—, or —CONR$^2$—.

For compounds of general formula I, and subsets thereof, $Q^2$ is a bond or a $C_{1-6}$ alkylidene chain, wherein up to two methylene units of the chain are each optionally and independently replaced by —NR'—, —S—, —O—, —CS—, —CO$_2$—, —OCO—, —CO—, —COCO—, —CONR'—, —NR'CO—, —NR'CO$_2$—, —SO$_2$NR'—, —NR'SO$_2$—, —CONR'NR'—, —NR'CONR'—, —OCONR'—, —NR'NR'—, —NR'SO$_2$NR'—, —SO—, —SO$_2$—, —PO—, —PO$_2$—, or —POR'—; and wherein any carbon atom in the one or more methylene units is optionally substituted with one or two occurrences of $R^6$, wherein each occurrence of $R^6$ is independently halogen, CN, NO$_2$, or $U_nR'$, or two occurrences of $R^6$, or R' and $R^6$, taken together with the atoms to which they are bound, form an optionally substituted 3-6-membered cycloalkyl, heterocyclyl, aryl or heteroaryl ring. In some embodiments, $Q^2$ is a direct bond, or is —(CHR$^6$)$_q$—, —(CHR$^6$)$_q$O—, —(CHR$^6$)$_q$S—, —(CHR$^6$)$_q$S(O)$_2$—, —(CHR$^6$)$_q$S(O)—, —(CHR$^6$)$_q$NR—, or —(CH $R^6{}_qC(O)$—, wherein q is 0, 1, 2, or 3. In certain other embodiments, $R^6$ is R', —N(R)(R'), —(CH$_2$)$_{1-4}$N(R)(R'), —(CH$_2$)$_{1-4}$C(CH$_3$)$_2$N(R)(R'), —OR', —(CH$_2$)$_{1-4}$OR', —NR(CH$_2$)$_{1-4}$N(R)(R'), —NR(CH$_2$)$_{1-4}$SO$_2$R', —NR(CH$_2$)$_{1-4}$COOR', or —NR(CH$_2$)$_{1-4}$COR', or two occurrences of $R^6$, taken together with the atoms to which they are bound, form an optionally substituted 3-6-membered saturated, partially unsaturated, or fully unsaturated ring. Examples of such $R^6$ groups include, but are not limited to —CH$_2$OH, —CH$_2$CH$_2$OH, —OH, —OMe, —OEt, —NH$_2$, —NH(Me), —NH(Et), —N(Me)(Me), —CH$_2$NH$_2$, —CH$_2$CH$_2$NH$_2$, —NHCO$_2$t-butyl, phenyl, cyclopentyl, methyl, ethyl, isopropyl, cyclopropyl, —NH(CH$_2$)$_3$NH$_2$, —NH(CH$_2$)$_2$NH$_2$, —NH(CH$_2$)$_2$NHEt, —NHCH$_2$pyridyl, —NHSO$_2$phenyl, —NHCOCH$_2$C(O)Ot-butyl, —NHCOCH$_2$NH$_3$, —CH$_2$C(CH$_3$)$_2$NH$_2$, —NHCH$_2$-imidazol-4-yl.

In certain exemplary embodiments, $Ar^1$ groups are:

-continued
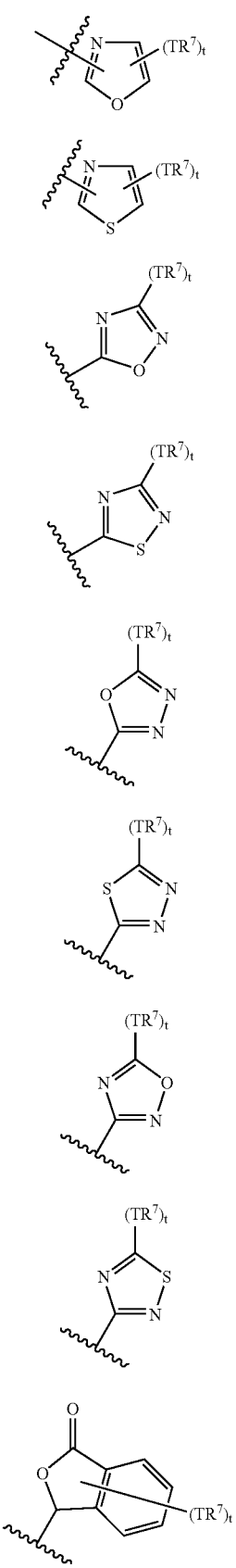
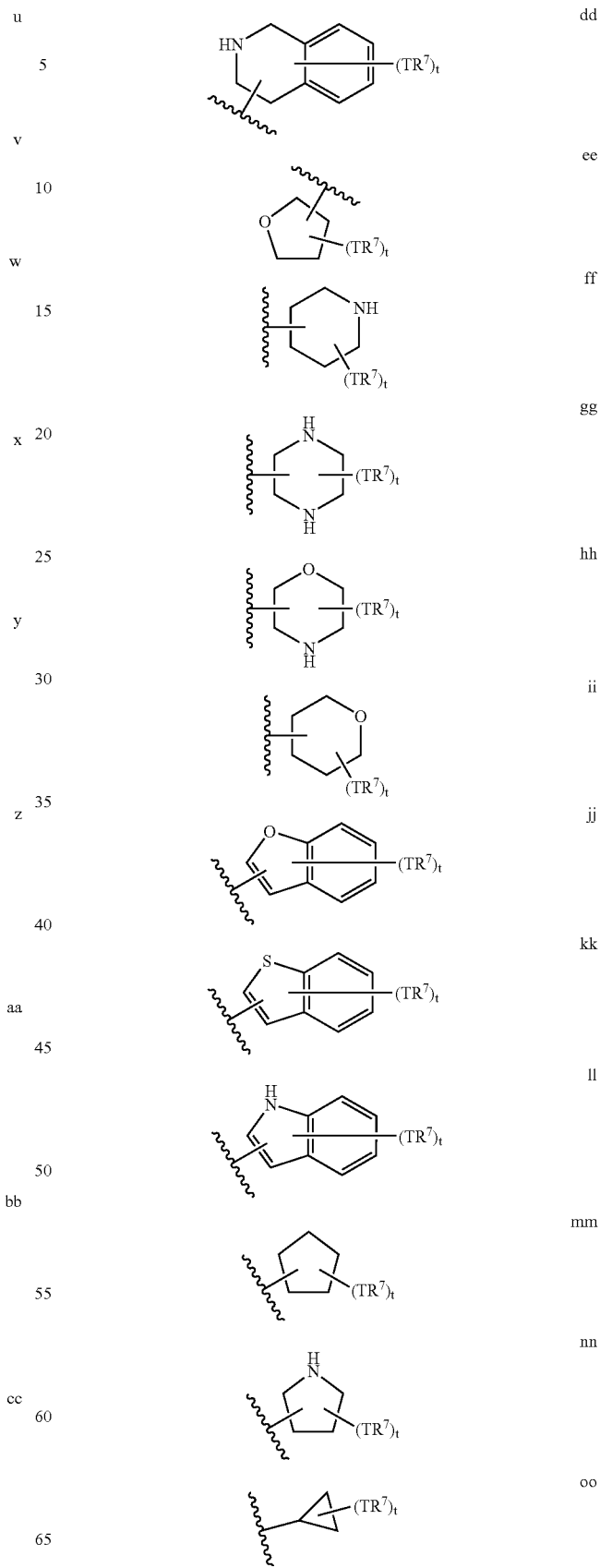

-continued

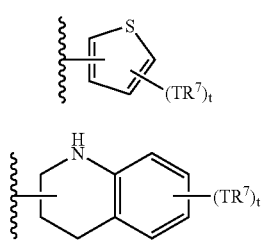

pp qq wherein t is 0, 1, 2, 3, 4, or 5, and wherein any $Ar^1$ is bonded to $Q^2$ through any substitutable nitrogen or carbon atom, and wherein one or more hydrogen atoms on any substitutable nitrogen or carbon atom is substituted with one or more independent occurrences of $TR^7$, wherein $TR^7$ is defined generally above.

In other embodiments, $Ar^1$ is a, b, e, f, g, h, i, j, k, r, cc, dd, ff, jj, ll, or pp. As described generally above, $Ar^1$ is optionally substituted with 0-5 independent occurrences of $TR^7$; wherein T is a bond or is a $C_1$-$C_6$ alkylidene chain wherein up to two methylene units of T are optionally replaced by —NR—, —S—, —O—, —CS—, —$CO_2$—, —OCO—, —CO—, —COCO—, —CONR—, —NRCO—, —$NRCO_2$—, —$SO_2NR$—, —$NRSO_2$—, —CONRNR—, —NRCONR—, —OCONR—, —NRNR—, —$NRSO_2NR$—, —SO—, —$SO_2$—, —PO—, —$PO_2$—, or —POR—; and each occurrence of $R^7$ is independently R', halogen, $NO_2$, or CN. In certain embodiments, T is a bond or is an optionally substituted $C_{1-6}$ alkylidene chain wherein one or two methylene units are optionally and independently replaced by —O—, —NR—, —S—, —SO—, —$SO_2$—, —COO—, —CO—, —$OSO_2$—, —$NRSO_2$, —CONR—, or —$SO_2NR$—, and $R^7$ is R' or halogen. In other embodiments, each occurrence of $TR^7$ is independently —$C_{1-3}$alkyl, —OR', —SR', —$CF_3$, —$OCF_3$, —$SCF_3$, —F, —Cl, I, —Br, —COOR', —COR', —$O(CH_2)_4N(R)(R')$, —$O(CH_2)_3N(R)(R')$, —$O(CH_2)_2N(R)(R')$, —$O(CH_2)N(R)(R')$, —$O(CH_2)_4CON(R)(R')$, —$O(CH_2)_3CON(R)(R')$, —$O(CH_2)_2CON(R)(R')$, —$O(CH_2)CON(R)(R')$, —$CON(R)(R')$, —$(CH_2)_4OR'$, —$(CH_2)_3OR'$, —$(CH_2)_2OR'$, —$CH_2OR'$, optionally substituted phenyl or benzyl, —$N(R)(R')$, —$(CH_2)_4N(R)(R')$, —$(CH_2)_3N(R)(R')$, —$(CH_2)_2N(R)(R')$, —$(CH_2)N(R)(R')$, —$SO_2N(R)(R')$, —$NRSO_2R'$, —$CON(R)(R')$, —$NRSO_2(CH_2)_{1-4}N(R)(R')$, —$CONR(CH_2)_{1-4}N(R)(R')$, —$COO(CH_2)_{1-4}N(R)(R')$, or —$OSO_2R'$, where, as defined generally above, each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In another embodiment, $R^3$ is $Q^2$-$Ar^1$, or $R^2$ and $Q^1$-$R^3$, taken together with the nitrogen atom, form the cyclic group:

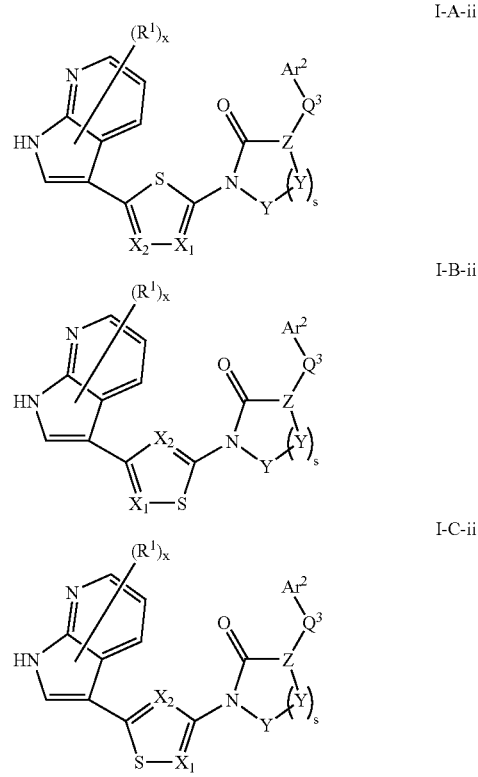

where Z is CH or N, s is 1 or 2, each occurrence of Y is independently, as valency and stability permit, —CO—, —CS—, —$SO_2$—, —O—, —S—, —$NR^5$—, or —$C(R^5)_2$—, and $R^5$ is $U_nR'$, and compounds of formulae I-A-ii, I-B-ii, and I-C-ii are provided:

I-A-ii

I-B-ii

I-C-ii

For compounds of formula I-A-ii, I-B-ii, and I-C-ii, $Q^3$ is a bond or a $C_{1-6}$ alkylidene chain, wherein up to two methylene units of the chain are each optionally and independently replaced by —NR'—, —S—, —O—, —CS—, —$CO_2$—, —OCO—, —CO—, —COCO—, —CONR'—, —NR'CO—, —$NR'CO_2$—, —$SO_2NR'$—, —$NR'SO_2$—, —CONR'NR'—, —NR'CONR'—, —OCONR'—, —NR'NR'—, —$NR'SO_2NR'$—, —SO—, —$SO_2$—, —PO—, —$PO_2$—, or —POR'—; and wherein any carbon atom in the one or more methylene units is optionally substituted with one or two occurrences of $R^6$, wherein each occurrence of $R^6$ is independently halogen, CN, $NO_2$, or $U_nR'$, or two occurrences of $R^6$, or R' and $R^6$, taken together with the atoms to which they are bound, form an optionally substituted 3-6-membered cycloalkyl, heterocyclyl, aryl or heteroaryl ring. In some embodiments, $Q^2$ is a direct bond, or is —$(CHR^6)_q$—, —$(CHR^6)_qO$—, —$(CHR^6)_qS$—, —$(CHR^6)_qS(O)_2$—, —$(CHR^6)_qS(O)$—, —$(CHR^6)_qNR$—, or —$(CHR^6)_qC(O)$—, wherein q is 0, 1, 2, or 3. In certain other embodiments, $R^6$ is R', —$N(R)(R')$, —$(CH_2)_{1-4}N(R)(R')$, —(CH$_2$)$_{1-4}$C(CH$_3$)$_2$N(R)(R'), —(CH$_2$)$_{1-4}$CH(CH$_3$)N(R)(R'), —OR', —(CH$_2$)$_{1-4}$OR', —NR(CH$_2$)$_{1-4}$N(R)(R'), —NR(CH$_2$)$_{1-4}$SO$_2$R', —NR(CH$_2$)$_{1-4}$COOR', or —NR(CH$_2$)$_{1-4}$COR', or two occurrences of R$^6$, taken together with the atoms to which they are bound, form an optionally substituted 3-6-membered saturated, partially unsaturated, or fully unsaturated ring. Examples of such R$^6$ groups include, but are not limited to —CH$_2$OH, —CH$_2$CH$_2$OH, —OH, —OMe, —OEt, —NH$_2$, —NH(Me), —NH(Et), —N(Me)(Me), —CH$_2$NH$_2$, —CH$_2$CH$_2$NH$_2$, —NHCO$_2$t-butyl, phenyl, cyclopentyl, methyl, ethyl, isopropyl, cyclopropyl, —NH(CH$_2$)$_3$NH$_2$, —NH(CH$_2$)$_2$NH$_2$, —NH(CH$_2$)$_2$NHEt, —NHCH$_2$pyridyl, —NHSO$_2$phenyl, —NHCOCH$_2$C(O)Ot-butyl, —NHCOCH$_2$NH$_3$, —CH$_2$C(CH$_3$)$_2$NH$_2$, —NHCH$_2$-imidazol-4-yl.

For compounds of general formula I-A-ii, I-B-ii, and I-C-ii, exemplary Ar$^2$ groups are the same as those described for Ar$^1$ (a-qq) groups in [0066].

In more preferred embodiments, Ar$^2$ is a, b, e, f, g, h, i, j, k, n, r, cc, dd, ff, jj, ll, or pp.

As described generally above, Ar$^1$ is optionally substituted with 0-5 independent occurrences of -TR$^7$; wherein T is a bond or is a C$_1$-C$_6$ alkylidene chain wherein up to two methylene units of T are optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of R$^7$ is independently R', halogen, —NO$_2$, or —CN. In certain embodiments, T is a bond or is an optionally substituted C$_{1-6}$ alkylidene chain wherein one or two methylene units are optionally and independently replaced by —O—, —NR—, —S—, —SO—, —SO$_2$—, —COO—, —CO—, —OSO$_2$—, —NRSO$_2$, —CONR—, or —SO$_2$NR—, and R$^7$ is R' or halogen. In other embodiments, each occurrence of TR$^7$ is independently —C$_{1-3}$alkyl, —OR', —SR', —CF$_3$, —OCF$_3$, —SCF$_3$, —F, —Cl, —I, —Br, —COOR', —COR', —O(CH$_2$)$_4$N(R)(R'), —O(CH$_2$)$_3$N(R)(R'), —O(CH$_2$)$_2$N(R)(R'), —O(CH$_2$)N(R)(R'), —O(CH$_2$)$_4$CON(R)(R'), —O(CH$_2$)$_3$CON(R)(R'), —O(CH$_2$)$_2$CON(R)(R'), —O(CH$_2$)CON(R)(R'), —C(O)N(R)(R'), —(CH$_2$)$_4$OR', —(CH$_2$)$_3$OR', —(CH$_2$)$_2$OR', —CH$_2$OR', optionally substituted phenyl or benzyl, —N(R)(R'), —(CH$_2$)$_4$N(R)(R'), —(CH$_2$)$_3$N(R)(R'), —(CH$_2$)$_2$N(R)(R'), —(CH$_2$)N(R)(R'), —SO$_2$N(R)(R'), —NRSO$_2$R', —CON(R)(R'), —NRSO$_2$(CH$_2$)$_{1-4}$N(R)(R'), —CONR(CH$_2$)$_{1-4}$N(R)(R'), —COO(CH$_2$)$_{1-4}$N(R)(R'), or —OSO$_2$R', where, as defined generally above, each occurrence of R is independently hydrogen or an optionally substituted C$_{1-6}$ aliphatic group; and each occurrence of R' is independently hydrogen or an optionally substituted C$_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain embodiments, for compounds of formula I-b, R$^5$ is hydrogen, —(CH$_2$)$_3$OR', —(CH$_2$)$_2$OR', —(CH$_2$)OR', —(CH$_2$)$_3$N(R')$_2$, —(CH$_2$)$_2$N(R')$_2$, —(CH$_2$)N(R')$_2$, or —C$_{1-4}$aliphatic.

As described generally above, for compounds of formula I, I-A-i, I-B-i, I-C-i, I-A-i-a, I-B-i-a, I-C-i-a, I-A-i-b, I-B-i-b, and I-B-i-c, X$^1$ and X$^2$ are each independently CR$^4$ or N, and thus compounds of formulae II-A, II-B, III-A, III-B, IV-A, IV-B, V-A, V-B, VI-A, VI-B, VII-A, VII-B, VIII-A, VIII-B, IX-A, IX-B, X-A, X-B, XI-A, XI-B, XII-A, XII-B, XIII-A, and XIII-B are provided:

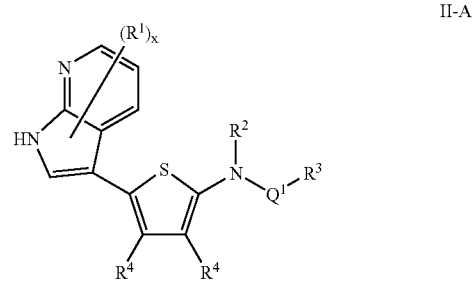

II-A

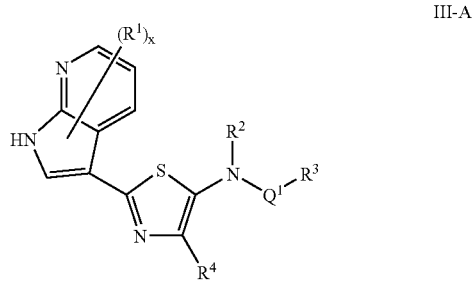

III-A

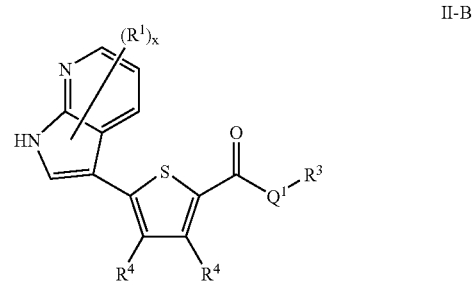

II-B

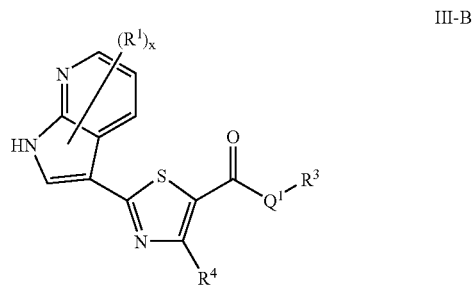

III-B

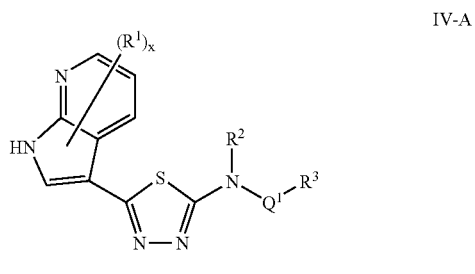

IV-A

-continued
V-A
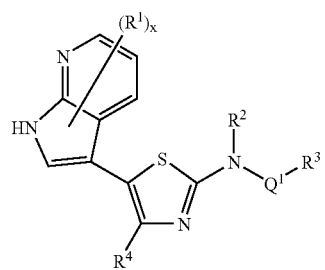
IV-B
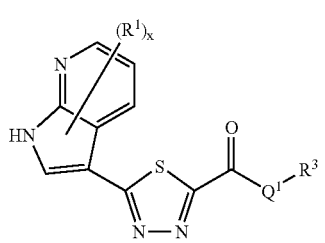
V-B
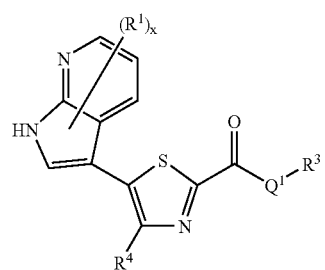
VI-A
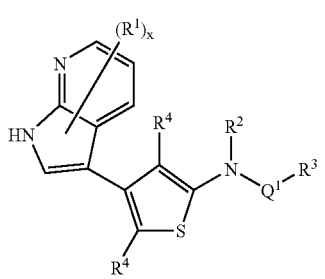
VII-A
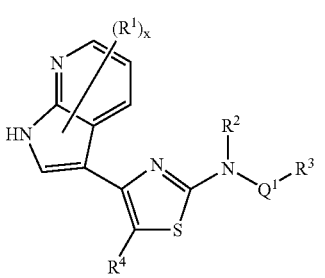
VI-B
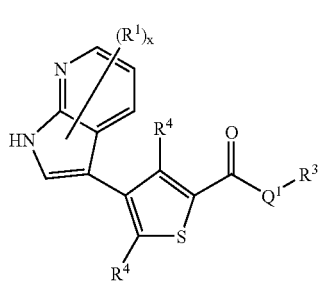
-continued
VII-B
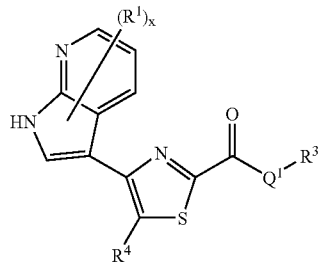
VIII-A
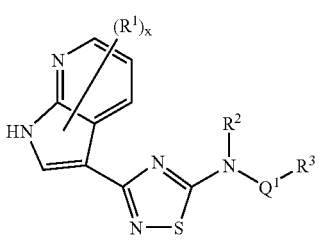
IX-A
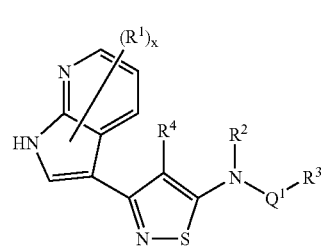
VIII-B
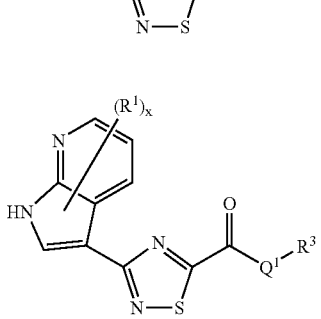
IX-B
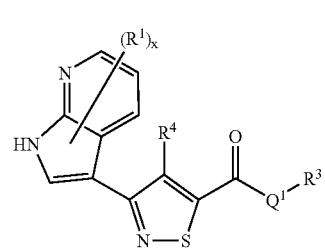
X-A
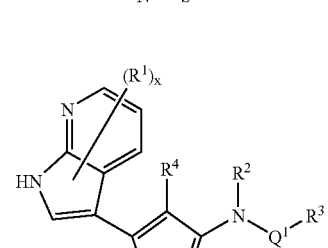
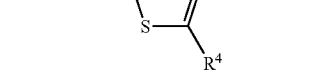

-continued

XI-A
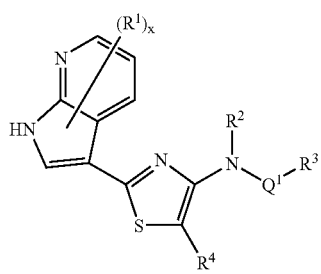

X-B
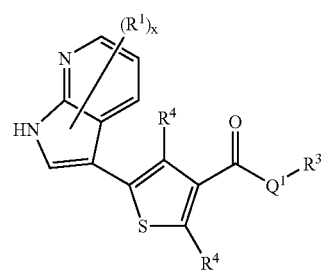

XI-B
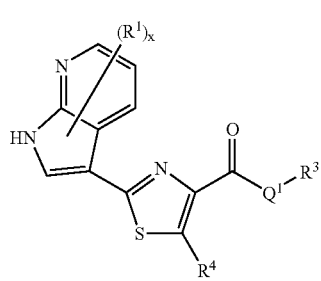

XII-A
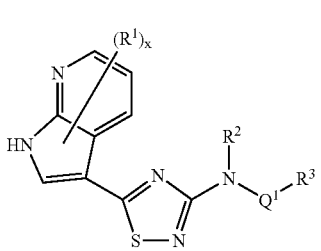

XIII-A
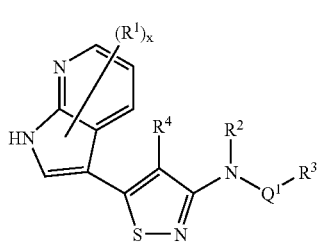

XII-B
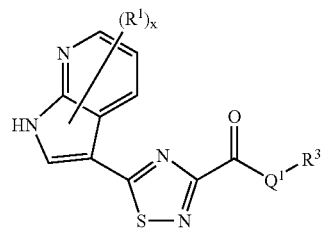

-continued

XIII-B
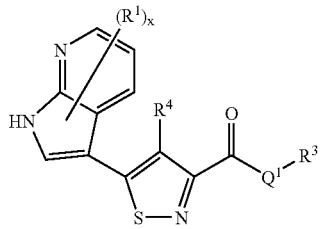

In general, for compounds of formula I, and subsets thereof, x is 0, 1, 2, or 3, and each occurrence of $R^1$ is independently halogen, —CN, —NO$_2$, or -V$_m$R'. In certain embodiments, x is 0, 1, or 2, and $R^1$ groups, when present, are each independently hydrogen, halogen, optionally substituted C$_1$-C$_4$aliphatic, —OH, —OR', —SR', or —N(R')$_2$. In other embodiments, $R^1$ groups are each independently hydrogen, halogen, —CH$_3$, —CH$_2$CH$_3$, —OH, —OCH$_3$, —SCH$_3$, —NH$_2$, —N(CH$_3$)$_2$, —N(CH$_2$CH$_3$)$_2$, —NH(CH$_2$)$_2$NHCH$_3$, —NH(cyclopropyl), —NH(CH$_2$)cyclopropyl, or —NH(CH$_2$)$_2$N(CH$_3$)$_2$. In other embodiments, $R^1$ groups are not an optionally substituted phenyl. In other embodiments, $R^1$ groups are not heterocyclic, heteroaryl, cycloaliphatic or aryl.

As described generally above, the thiadiazole, thiazole, thiophene, and isothiazole rings are each optionally substituted with zero, one or two occurrences of $R^4$, as valency permits, wherein each occurrence of $R^4$ is independently halogen, —CN, —NO$_2$, or —V$_m$R. In some embodiments, $R^4$ groups are each independently hydrogen, C$_{1-6}$aliphatic, —CN, —COR, —COOR, CON(R)$_2$, or halogen. In other embodiments, $R^4$ groups are each hydrogen.

It will also be appreciated that for compounds of formulae II-A, II-B, III-A, III-B, IV-A, IV-B, V-A, V-B, VI-A, VI-B, VII-A, VII-B, VIII-A, VIII-B, IX-A, IX-B, X-A, X-B, XI-A, XI-B, XII-A, XII-B, XIII-A, and XIII-B, in some embodiments $R^3$ is Q$^2$-Ar$^1$, wherein Q$^2$ and Ar$^1$ are described generally and in subsets above and herein. In other exemplary embodiments, for each of the above-described classes and subclasses of compounds, $R^2$ and Q$^1$-R$^3$, taken together with the nitrogen atom, form the cyclic group:

$$\begin{array}{c}\text{(structure)}\end{array}$$

where Z is CH or N, s is 1 or 2, each occurrence of Y is independently, as valency and stability permit, —CO—, —CS—, —SO$_2$—, —O—, —S—, —NR$^5$—, or —C(R$^5$)$_2$—, and $R^5$ is -U$_n$R', wherein Q$^3$, Ar$^2$, and $R^5$ are described generally above and in classes and subclasses above and herein.

For compounds of formula VII-B, in some embodiments, Q$^1$ is —CO—. In further embodiments, $R^2$ is H, —C$_{1-4}$ aliphatic, -cyclopropyl or $$(H_2C)_{2-4}-N\overset{\frown}{\underset{\smile}{\phantom{x}}}N-CH_3.$$

In further embodiments, $R^2$ is H. In other embodiments for compounds of formula VII-B, $R^4$ is H or —$C_{1-4}$ aliphatic. In further embodiments, $R^4$ is H.

In further embodiments, x is 1 and said compound has a formula selected from formulae VII-B-i or VII-B-ii:

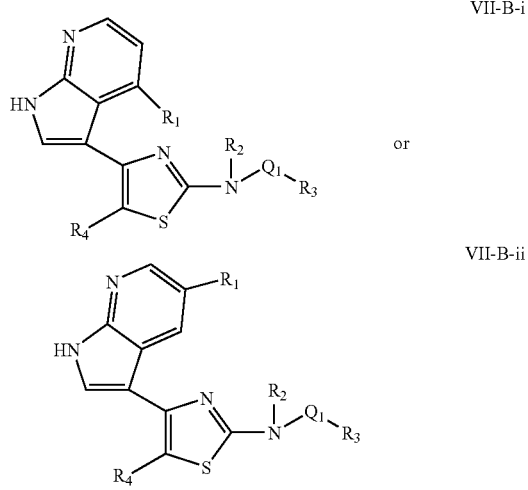

VII-B-i or

VII-B-ii

In certain embodiments of VII-B-i or V-B-ii, $R^1$ is H, halogen, OH or $CH_3$. In some embodiments of VII-B-i, $R^1$ is H or F. In some embodiments of VII-B-ii, $R^1$ is Br. In some embodiments of VII-B-i or V-B-ii, $Q^1$ is —CO—, $R^1$ is H, halogen, OH or $CH_3$, $R^2$ is H, —$C_{1-4}$ aliphatic, -cyclopropyl or

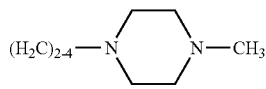

and $R^4$ is H or —$C_{1-4}$ aliphatic. $R^1$ is H or F, $R^2$ is H and $R^4$ is H or —$C_{1-4}$ aliphatic.

In further embodiments, $R^1$ is H or F, $R^2$ is H and $R^4$ is H, and the compound has a structure of formula V-B-iii:

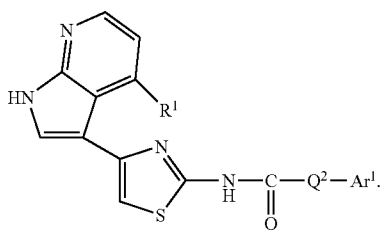

VII-B-iii

In further embodiments, for compounds having a structure of formula V-B-iii, $Q^2$ is —$(CHR^6)_q$—, —$(CHR^6)_qO$—, —$(CHR^6)_qS$—, —$(CHR^6)_qS(O)_2$—, —$(CHR^6)_qS(O)$—, —$(CHR^6)_qNR$—, or —$(CHR^6)_qC(O)$—, wherein q is 0, 1, 2, or 3, and each $R^6$ is R', —N(R)(R'), —$(CH_2)_{1-4}N(R)(R')$, —$(CH_2)_{1-4}C(CH_3)_2N(R)(R')$, —$(CH_2)_{1-4}CH(CH_3)N(R)(R')$, —OR', —$(CH_2)_{1-4}OR'$, —$NR(CH_2)_{1-4}N(R)(R')$, —$NR(CH_2)_{1-4}SO_2R'$, —$NR(CH_2)_{1-4}COOR'$, or —$NR(CH_2)_{1-4}COR'$, or two occurrences of $R^6$, taken together with the atoms to which they are bound, form an optionally substituted 3-6-membered saturated, partially unsaturated, or fully unsaturated ring. In further embodiments, $Q^2$ is —$(CHR^6)_q$—, q is 1 or 2, and $R^6$ is R', —N(R)(R'), —$(CH_2)_{1-4}N(R)(R')$, —OR', —$(CH_2)_{1-4}OR'$ or —$NR(CH_2)_{1-4}SO_2R'$. In yet further embodiments, $Q^2$ is —$(CHR^6)_q$—, q is 1 or 2, and each $R^6$ is H. In still further embodiments, $Q^2$ is —$(CHR^6)_q$—, q is 1, and $R^6$ is H. In other embodiments of V-B-iii, $Ar^1$ is selected from rings a-qq as described in paragraph [0067] above, wherein t is 0, 1, 2, 3, 4, or 5, and wherein any $Ar^1$ is bonded to $Q^2$ through any substitutable nitrogen or carbon atom, and wherein one or more hydrogen atoms on any substitutable nitrogen or carbon atom is substituted with one or more independent occurrences of $TR^7$. In further embodiments, $Ar^1$ is

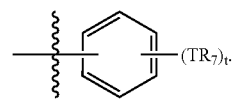

In still further embodiments, t is 0, 1 or 2, and each $TR^7$ is independently selected from halogen, —CN, —R', —$O(CH_2)_{0-5}R'$, —NRR', —$OSO_2(CH_2)_{0-4}R'$, —$NRSO_2(CH_2)_{0-5}R'$, —$NRSO_2NR(CH_2)_{0-5}R'$, —$SO_2NR(CH_2)_{0-5}R'$, —CONRR', —COR', —COOR', —NRCOR' or —$SO_2(CH_2)_{0-5}R'$. In yet further embodiments, $TR^7$ is selected from —F, —Cl, —CN, —$NH_2$, —$CH_3$, —$CH_2CH_3$, —$CH(CH_3)_2$, —OH, —$OCH_3$, —NR"$SO_2$R", —NR"$SO_2$N(R")$_2$, —$COOC(CH_3)_3$, —$OSO_2CH_3$, —OH, —$SO_2N(R")_2$, —$SO_2NHR'$, —$SO_2R"$, —pyrollidinone, tetrahydrofuran or -D-$(CH_2)_p$-Z, wherein R" is a H or a $C_{1-4}$ alkyl, D is —$SO_2$—, —$SO_2NH$—, —$NHSO_2$— or —O—, p is 0-3, and Z is selected from:

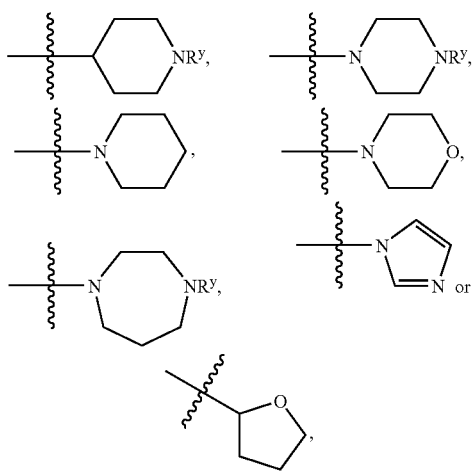

wherein $R^y$ is H or $C_{1-3}$ alkyl, and wherein one or more carbon atoms of Z is optionally substituted with =O. In further embodiments, t is 1 or 2, one $TR^7$ is -D-$(CH_2)_p$-Z, D is —O—, p is 2 or 3, Z is

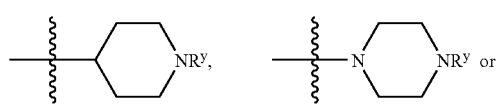

-continued

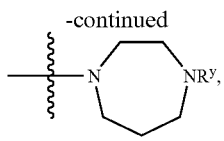

and $R^y$ is H or $CH_3$, and wherein one or more carbon atoms of Z is optionally substituted with =O. In yet further embodiments, t is 1 or 2, and one $TR^7$ is —NR"$SO_2$R", NHSO$_2$R", OR", F or Cl.

In another embodiment of $Ar^1$, $Ar^1$ is

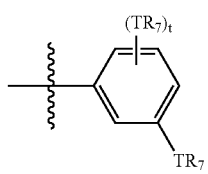

and t is 0 or 1.

It will be appreciated that for compounds as described above, certain additional compounds are of special interest. For example, in certain exemplary embodiments, thiophene compounds are provided where G is $NR^2$, $Q^1$ is —CO—, $Q^2$ is $CHR^6$, q is 1 2, or 3, and compounds have one of formulae XIV-A, XV-A, or XVI-A:

XIV-A
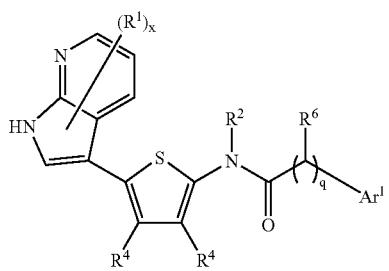

XV-A
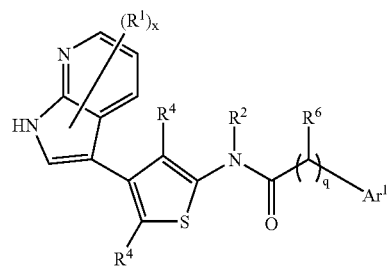

XVI-A
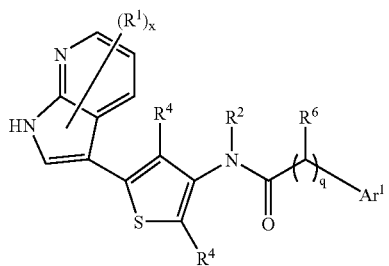

In other embodiments, thiophene compounds are provided where G is $NR^2$, $Q^1$ is —CONR$^2$—, $Q^2$ is $CHR^6$, q is 1 2, or 3, and compounds have one of formulae XIV-B, XV-B, or XVI-B:

XIV-B
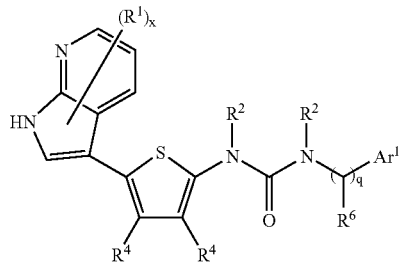

XV-B
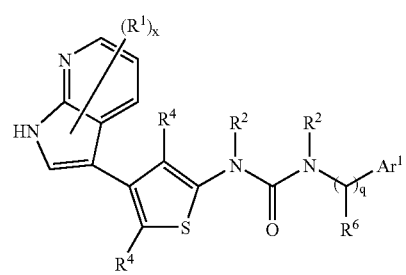

XVI-B
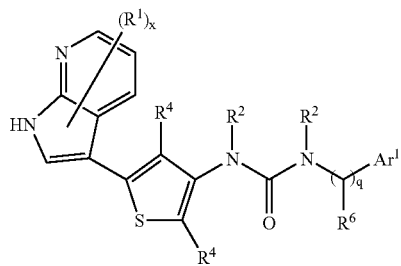

In other embodiments, thiazole compounds are provided where G is $NR^2$, $Q^1$ is —CO—, $Q^2$ is $CHR^6$, q is 1, 2 or 3, and compounds have one of formulae XVII-A, XVIII-A, or XIX-A:

XVII-A
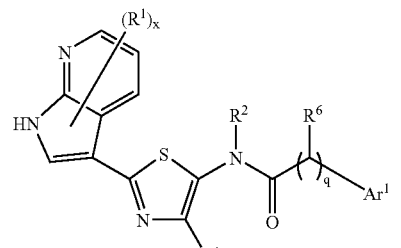

XVIII-A
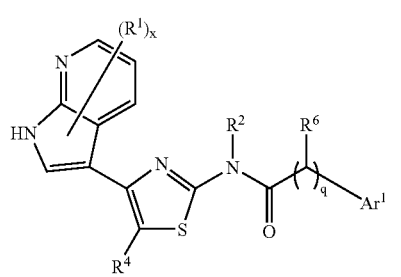

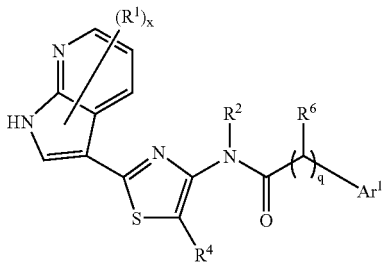

XIX-A

In other embodiments, thiazole compounds are provided where G is $NR^2$, $Q^1$ is —$CONR^2$—, $Q^2$ is $CHR^6$, q is 1, 2 or 3, and compounds have one of formulae XVII-B, XVIII-B, or XIX-B:

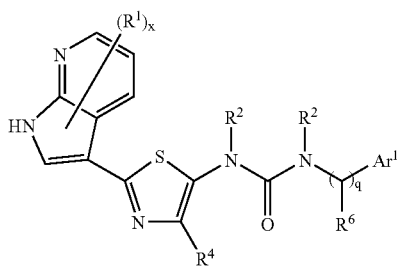

XVII-B

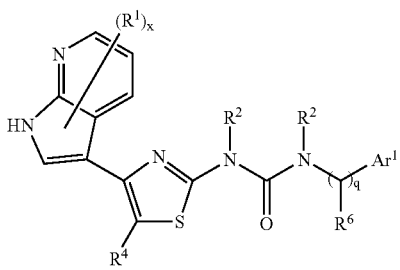

XVIII-B

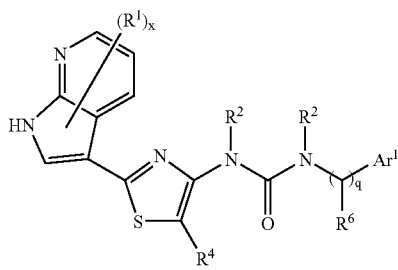

XIX-B

In certain embodiments, for compounds of formulae XIV-A, XIV-B, XV-A, XV-B, XVI-A, XVI-B, XVII-A, XVII-B, XVIII-A, XVIII-B, XIX-A or XIX-A, compound variables are selected from one of more of the following groups:

a) each occurrence of $R^1$ is independently hydrogen, halogen, optionally substituted $C_1$-$C_4$aliphatic, —OR', —SR', or —N(R')$_2$;

b) each occurrence of $R^1$ is independently hydrogen, halogen, —$CH_3$, —$CH_2CH_3$, —OH, —$OCH_3$, —$SCH_3$, —$NH_2$, —N($CH_3$)$_2$, —N($CH_2CH_3$)$_2$, —NH($CH_2$)$_2$NH$CH_3$, —NH(cyclopropyl), —NH($CH_2$)cyclopropyl, or —NH($CH_2$)$_2$N($CH_3$)$_2$;

c) $R^2$ is hydrogen, or is $U_nR'$, where n is 1, and U is —$CH_2$—, —$CH_2CH_2$—, —$CH_2CH_2CH_2$—, —$CH_2CH_2CH_2CH_2$—, —$CH_2O$—, —$CH_2S$—, —$CH_2NR$—, —$CH_2CH_2O$—, —$CH_2CH_2S$—, —$CH_2CH_2NR$—, —$CH_2CH_2CH_2O$—, —$CH_2CH_2CH_2S$—, —$CH_2CH_2CH_2NR$—, —$CH_2CH_2CH_2CH_2O$—, —$CH_2CH_2CH_2CH_2S$—, —$CH_2CH_2CH_2CH_2NR$—, —$CH_2CH_2OCH_2CH_2$—, —($CH_2$)$_4$NH$CH_2$—, —($CH_2$)$_3$NH$CH_2CH_2$—, or —$CH_2CH_2$NH$CH_2CH_2$—, wherein R' groups are hydrogen, $C_1$-$C_4$alkyl, an optionally substituted group selected from tetrahydropyranyl, pyrrolidinyl, piperidinyl, piperazinyl, morpholinyl, thiomorpholinyl, pyridinyl, imidazolyl, phenyl, or cyclohexyl, or R and R', taken together with the nitrogen atom to which they are bound, form an optionally substituted 5- or 6-membered saturated, partially unsaturated, or unsaturated heterocyclyl ring;

d) each occurrence of $R^4$ is independently hydrogen, $C_{1-6}$aliphatic, CN, COR, COOR, CON(R)$_2$, or halogen;

e) q is 1, 2, or 3;

f) $R^6$ is R', —N(R)(R'), —($CH_2$)$_{1-4}$N(R)(R'), —($CH_2$)$_{1-4}$C($CH_3$)$_2$N(R)(R'), —($CH_2$)$_{1-4}$CH($CH_3$)N(R)(R')—OR', —($CH_2$)$_{1-4}$OR', —NR($CH_2$)$_{1-4}$N(R)(R'), —NR($CH_2$)$_{1-4}$SO$_2$R', —NR($CH_2$)$_{1-4}$COOR', or —NR($CH_2$)$_{1-4}$COR', or two occurrences of $R^6$, taken together with the atoms to which they are bound, form an optionally substituted 3-6-membered saturated, partially unsaturated, or fully unsaturated ring;

g) $R^6$ is —$CH_2OH$, —$CH_2CH_2OH$, —OH, —OMe, —OEt, —$NH_2$, —NH(Me), —NH(Et), —N(Me)(Me), —$CH_2NH_2$, —$CH_2CH_2NH_2$, —$NHCO_2$t-butyl, phenyl, cyclopentyl, methyl, ethyl, isopropyl, cyclopropyl, —NH($CH_2$)$_3$NH$_2$, —NH($CH_2$)$_2$NH$_2$, —NH($CH_2$)$_2$NHEt, —NH$CH_2$pyridyl, —NHSO$_2$phenyl, —NHCO$CH_2$COOt-butyl, —NHCO$CH_2$NH$_3$, —$CH_2$C($CH_3$)$_2$NH$_2$, —NH$CH_2$-imidazol-4-yl;

h) $Ar^1$ is ring a, b, e, f, g, h, i, j, k, r, cc, dd, ff, jj, ll, or pp, wherein t is 0, 1, 2, or 3, and T is a bond or is an optionally substituted $C_{1-6}$ alkylidene chain wherein one or two methylene units are optionally and independently replaced by —O—, —NR—, —S—, —SO—, —SO$_2$—, —COO—, —CO—, —OSO$_2$—, —NRSO$_2$, —CONR—, or —SO$_2$NR—, and $R^7$ is R' or halogen; or i) $Ar^1$ is ring a, b, e, f, g, h, i, j, k, r, cc, dd, ff, jj, ll, or pp, wherein t is 0, 1, 2, or 3, and each occurrence of $TR^7$ is independently —$C_{1-3}$alkyl, —OR', —SR', —CF$_3$, —OCF$_3$, —SCF$_3$, —F, —Cl, I, —Br, —COOR', —COR', —O($CH_2$)$_4$N(R)(R'), —O($CH_2$)$_3$N(R)(R'), —O($CH_2$)$_2$N(R)(R'), —O($CH_2$)N(R)(R'), —O($CH_2$)$_4$CON(R)(R'), —O($CH_2$)$_3$CON(R)(R'), —O($CH_2$)$_2$CON(R)(R'), —O($CH_2$)CON(R)(R'), —CON(R)(R'), —($CH_2$)$_4$OR', —($CH_2$)$_3$OR', —($CH_2$)$_2$OR', —$CH_2$OR', optionally substituted phenyl or benzyl, —N(R)(R'), —($CH_2$)$_4$N(R)(R'), —($CH_2$)$_3$N(R)(R'), —($CH_2$)$_2$N(R)(R'), —($CH_2$)N(R)(R'), —SO$_2$N(R)(R'), —NRSO$_2$R', —CON(R)(R'), —NRSO$_2$($CH_2$)$_{1-4}$N(R)(R'), —CONR($CH_2$)$_{1-4}$N(R)(R'), —COO($CH_2$)$_{1-4}$N(R)(R'), or —OSO$_2$R'.

In other embodiments, for certain of the thiophene and thiazole compounds of formulae XIV-A through XIX-A, q is 1, and $Ar^1$ is optionally substituted phenyl and compounds of formulae XIV-C through XIX-C are provided:

XIV-C

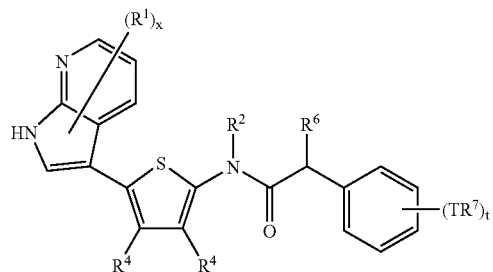

XV-C

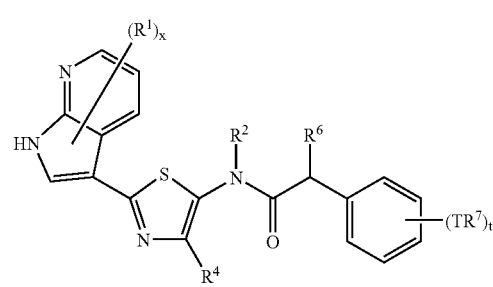

XVI-C

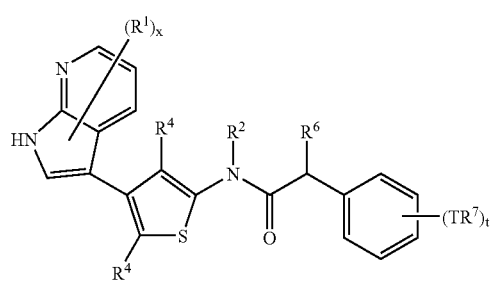

XVII-C

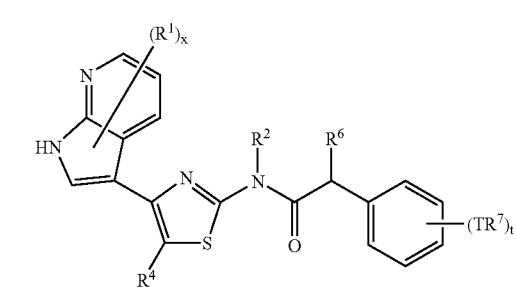

XVIII-C

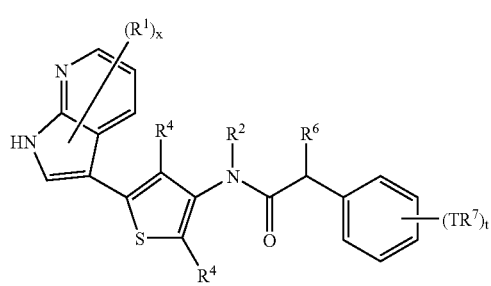

-continued

XIX-C

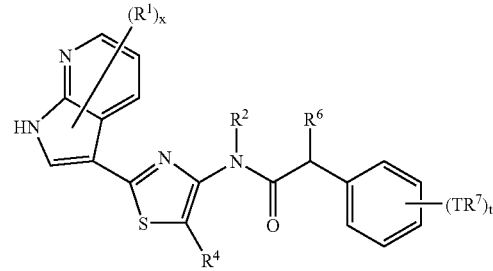

wherein $R^1$, $R^z$, $R^2$, $R^4$, $R^6$, T, $R^7$ and t are as defined generally and in classes and subclasses above and herein.

In preferred embodiments, for compounds of formulae XIV-C through XIX-C:

each occurrence of $R^1$ is hydrogen;

$R^2$ is hydrogen, or is $U_nR'$, where n is 1, and U is —CH$_2$—, —CH$_2$CH$_2$—, —CH$_2$CH$_2$CH$_2$—, —CH$_2$CH$_2$CH$_2$CH$_2$—, —CH$_2$O—, —CH$_2$S—, —CH$_2$NR—, —CH$_2$CH$_2$O—, —CH$_2$CH$_2$S—, —CH$_2$CH$_2$NR—, —CH$_2$CH$_2$CH$_2$O—, —CH$_2$CH$_2$CH$_2$S—, —CH$_2$CH$_2$CH$_2$NR—, —CH$_2$CH$_2$CH$_2$CH$_2$O—, —CH$_2$CH$_2$CH$_2$CH$_2$S—, —CH$_2$CH$_2$CH$_2$CH$_2$NR—, —CH$_2$CH$_2$OCH$_2$CH$_2$—, —(CH$_2$)$_4$NHCH$_2$—, —(CH$_2$)$_3$NHCH$_2$CH$_2$—, or —CH$_2$CH$_2$NHCH$_2$CH$_2$—, wherein R' groups are hydrogen, $C_1$-$C_4$alkyl, an optionally substituted group selected from tetrahydropyranyl, pyrrolidinyl, piperidinyl, piperazinyl, morpholinyl, thiomorpholinyl, pyridinyl, imidazolyl, phenyl, or cyclohexyl, or R and R', taken together with the nitrogen atom to which they are bound, form an optionally substituted 5- or 6-membered saturated, partially unsaturated, or unsaturated heterocyclyl ring;

each occurrence of $R^4$ is independently hydrogen, $C_{1-6}$aliphatic, CN, COR, COOR, CON(R)$_2$, or halogen;

$R^6$ is —R', —N(R)(R'), —(CH$_2$)$_{1-4}$N(R)(R'), —(CH$_2$)$_{1-4}$C(CH$_3$)$_2$N(R)(R'), —(CH$_2$)$_{1-4}$CH(CH$_3$)N(R)(R'), —OR', —(CH$_2$)$_{1-4}$OR', —NR(CH$_2$)$_{1-4}$N(R)(R'), —NR(CH$_2$)$_{1-4}$SO$_2$R', —NR(CH$_2$)$_{1-4}$COOR', or —NR(CH$_2$)$_{1-4}$COR'; and t is 0, 1, 2, or 3, and each occurrence of $TR^7$ is independently —$C_{1-3}$alkyl, —OR', —SR', —CF$_3$, —OCF$_3$, —SCF$_3$, —F, —Cl, —I, —Br, —COOR', —COR', —O(CH$_2$)$_4$N(R)(R'), —O(CH$_2$)$_3$N(R)(R'), —O(CH$_2$)$_2$N(R)(R'), —O(CH$_2$)N(R)(R'), —O(CH$_2$)$_4$CON(R)(R'), —O(CH$_2$)$_3$CON(R)(R'), —O(CH$_2$)$_2$CON(R)(R'), —O(CH$_2$)CON(R)(R'), —CON(R)(R'), —(CH$_2$)$_4$OR', —(CH$_2$)$_3$OR', —(CH$_2$)$_2$OR', —CH$_2$OR', optionally substituted phenyl or benzyl, —N(R)(R'), —(CH$_2$)$_4$N(R)(R'), —(CH$_2$)$_3$N(R)(R'), —(CH$_2$)$_2$N(R)(R'), —(CH$_2$)N(R)(R'), —SO$_2$N(R)(R'), —NRSO$_2$R', —CON(R)(R'), —NRSO$_2$(CH$_2$)$_{1-4}$N(R)(R'), —CONR(CH$_2$)$_{1-4}$N(R)(R'), —COO(CH$_2$)$_{1-4}$N(R)(R'), or —OSO$_2$R'.

Other subsets include those compounds where G is $NR^2$, and $R^2$ and $Q^1$-$R^3$, taken together with the atoms to which they are bound form a 5-membered cyclic group, and compounds have one of formulae XX through XXVIII:

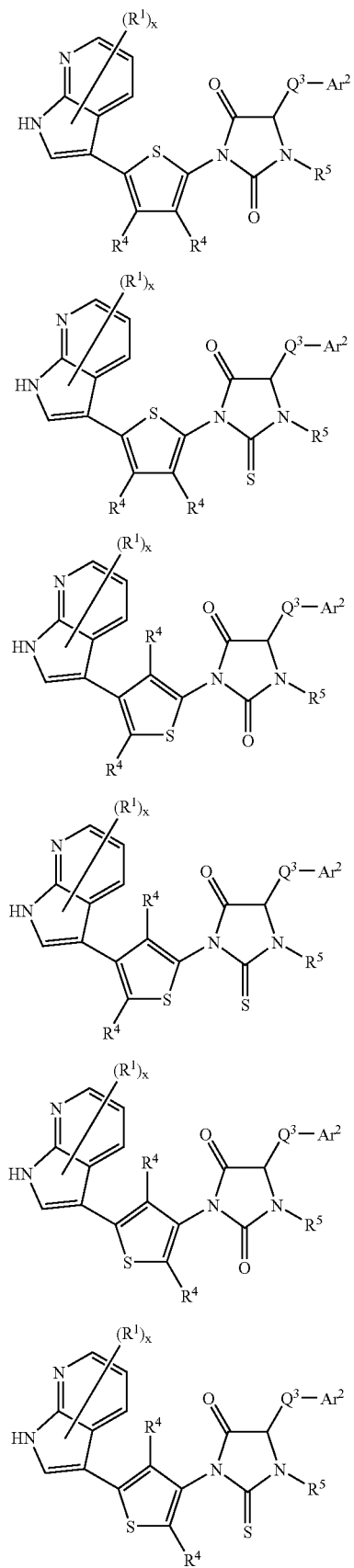
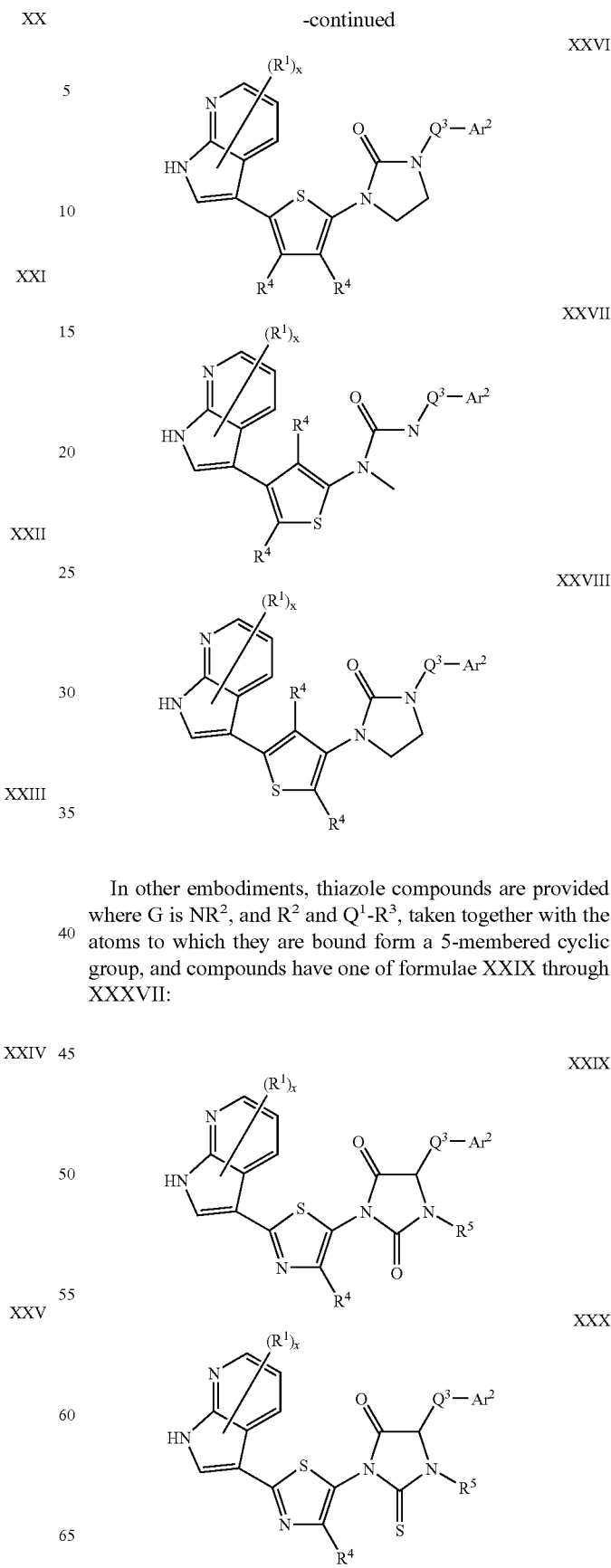
In other embodiments, thiazole compounds are provided where G is NR², and R² and Q¹-R³, taken together with the atoms to which they are bound form a 5-membered cyclic group, and compounds have one of formulae XXIX through XXXVII:

-continued
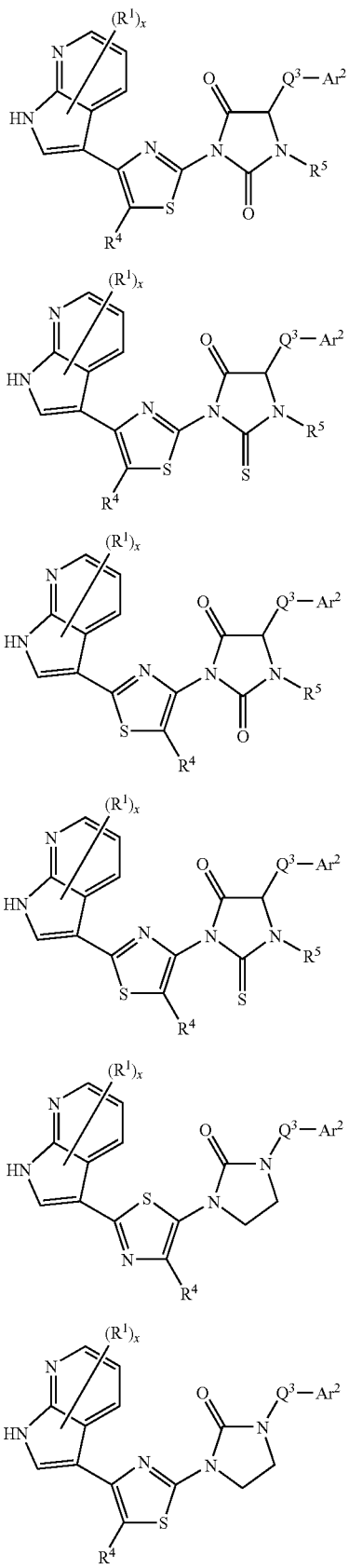
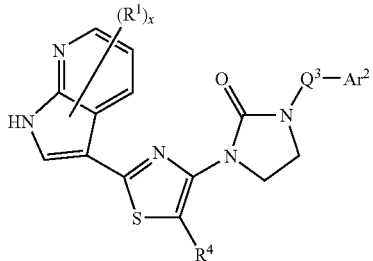
In still other embodiments, thiophene and thiazole compounds are provided where G is $NR^2$, and $R^2$ and $Q^1$-$R^3$, taken together with the atoms to which they are bound form a 6-membered cyclic group, and compounds have one of formulae XXXVIII through XLIII:
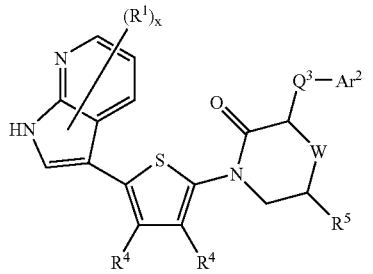
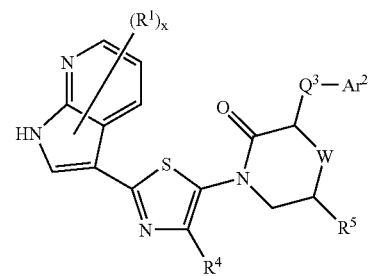
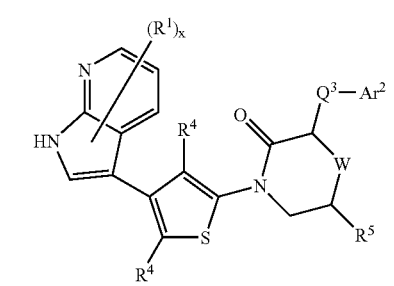
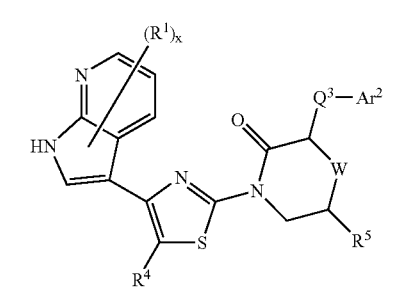

-continued

XLII, XLIII wherein W is O, NR⁵, or CHR⁵.

In yet other embodiments, thiophene and thiazole compounds are provided where G is NR², and R² and Q¹-R³, taken together with the atoms to which they are bound form a 5- or 6-membered cyclic group, and compounds have one of formulae XLIV through LXI:

XLIV, XLV, XLVI, XLVII, XLVIII, XLIX, L, LI, LII

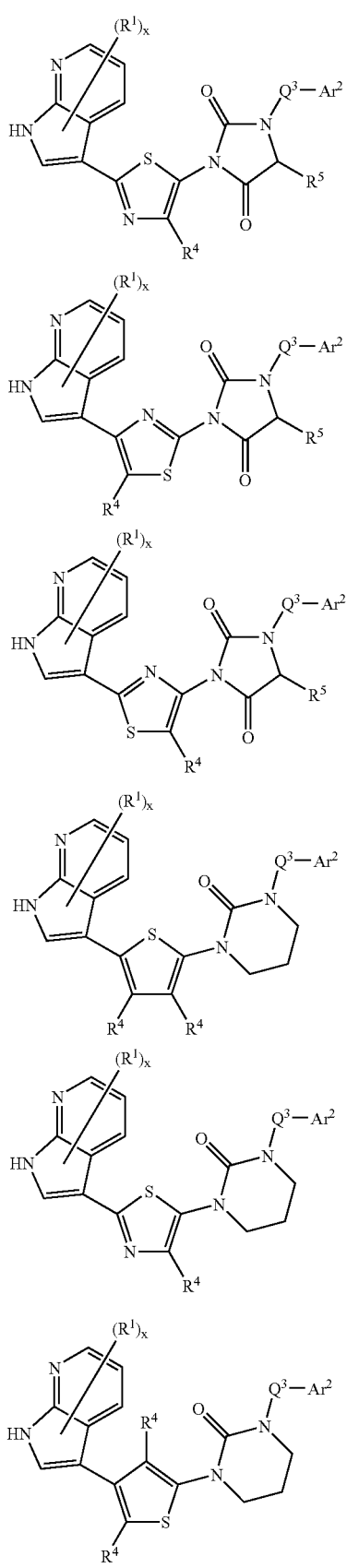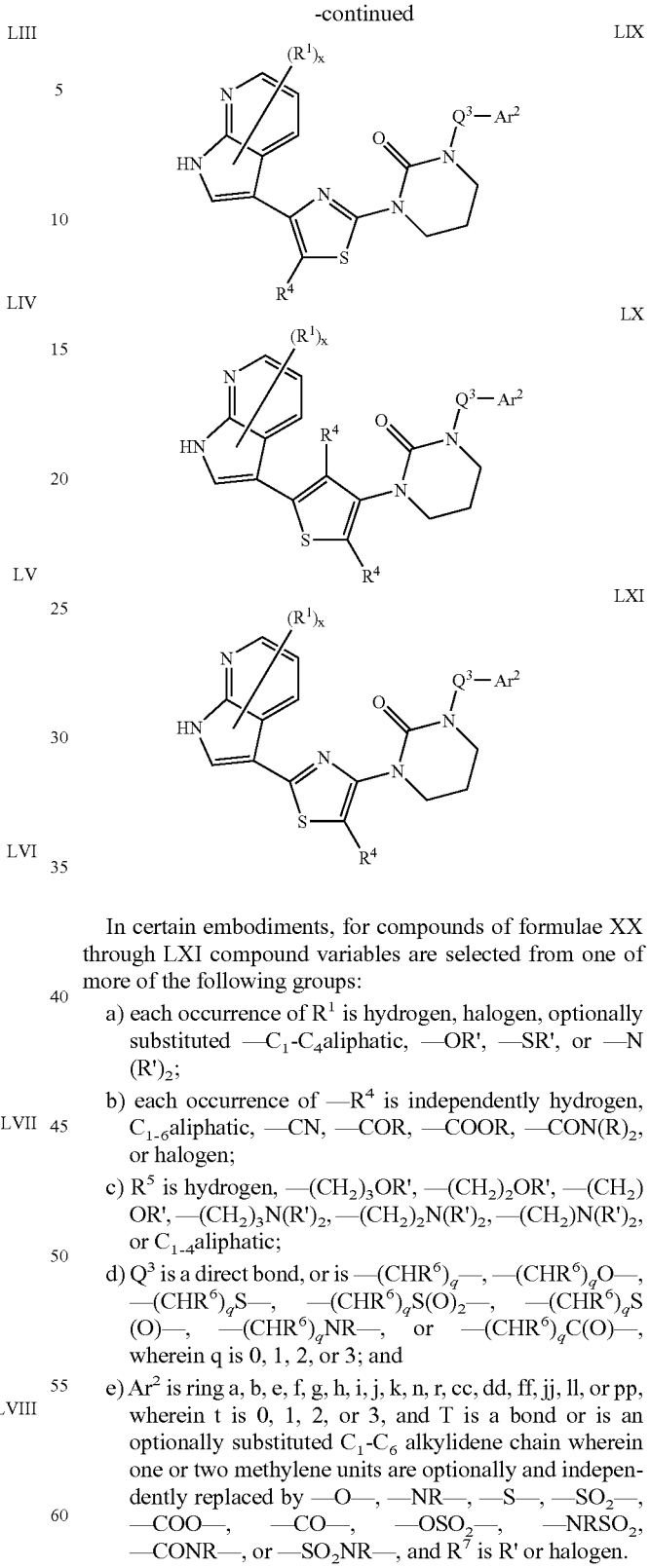

In certain embodiments, for compounds of formulae XX through LXI compound variables are selected from one of more of the following groups:

a) each occurrence of $R^1$ is hydrogen, halogen, optionally substituted —$C_1$-$C_4$aliphatic, —OR', —SR', or —N(R')$_2$;

b) each occurrence of —$R^4$ is independently hydrogen, $C_{1-6}$aliphatic, —CN, —COR, —COOR, —CON(R)$_2$, or halogen;

c) $R^5$ is hydrogen, —(CH$_2$)$_3$OR', —(CH$_2$)$_2$OR', —(CH$_2$)OR', —(CH$_2$)$_3$N(R')$_2$, —(CH$_2$)$_2$N(R')$_2$, —(CH$_2$)N(R')$_2$, or $C_{1-4}$aliphatic;

d) $Q^3$ is a direct bond, or is —(CHR$^6$)$_q$—, —(CHR$^6$)$_q$O—, —(CHR$^6$)$_q$S—, —(CHR$^6$)$_q$S(O)$_2$—, —(CHR$^6$)$_q$S(O)—, —(CHR$^6$)$_q$NR—, or —(CHR$^6$)$_q$C(O)—, wherein q is 0, 1, 2, or 3; and e) $Ar^2$ is ring a, b, e, f, g, h, i, j, k, n, r, cc, dd, ff, jj, ll, or pp, wherein t is 0, 1, 2, or 3, and T is a bond or is an optionally substituted $C_1$-$C_6$ alkylidene chain wherein one or two methylene units are optionally and independently replaced by —O—, —NR—, —S—, —SO$_2$—, —COO—, —CO—, —OSO$_2$—, —NRSO$_2$, —CONR—, or —SO$_2$NR—, and $R^7$ is R' or halogen.

In certain other embodiments, for compounds of formulae XX through LXI compound variables are selected from one of more of the following groups:

a) each occurrence of $R^1$ is independently hydrogen, halogen, —CH$_3$, —CH$_2$CH$_3$, —OH, —OCH$_3$, —SCH$_3$, —NH₂, —N(CH₃)₂, —N(CH₂CH₃)₂, NH(CH₂)₂ NHCH₃, NH(cyclopropyl), NH(CH₂)cyclopropyl, or NH(CH₂)₂N(CH₃)₂;

b) each occurrence of $R^4$ is independently hydrogen, $C_{1-6}$aliphatic, —CN, —COR, —COOR, —CON(R)₂, or halogen;

c) $R^5$ is hydrogen, —(CH₂)₃OR', —(CH₂)₂OR', —(CH₂)OR', —(CH₂)₃N(R')₂, —(CH₂)₂N(R')₂, —(CH₂)N(R')₂, or $C_{1-4}$aliphatic;

d) $Q^3$ is a direct bond, or is —(CHR⁶)$_q$—, —(CHR⁶)$_q$O—, —(CHR⁶)$_q$S—, —(CHR⁶)$_q$S(O)₂—, —(CHR⁶)$_q$S(O)—, —(CHR⁶)$_q$NR—, or —(CHR⁶)$_q$C(O)—, wherein q is 0, 1, 2, or 3; and e) $Ar^2$ is ring a, b, e, f, g, h, i, j, k, n, r, cc, dd, ff, jj, ll, or pp, wherein t is 0, 1, 2, or 3, and each occurrence of -TR⁷ is independently —$C_{1-3}$alkyl, —OR', —SR', —CF₃, —OCF₃, —SCF₃, —F, —Cl, —I, —Br, —COOR', —COR', —O(CH₂)₄N(R)(R'), —O(CH₂)₃N(R)(R'), —O(CH₂)₂N(R)(R'), —O(CH₂)N(R)(R'), —O(CH₂)₄CON(R)(R'), —O(CH₂)₃CON(R)(R'), —O(CH₂)₂CON(R)(R'), —O(CH₂)CON(R)(R'), —CON(R)(R'), —(CH₂)₄OR', —(CH₂)₃OR', —(CH₂)₂OR', —CH₂OR', optionally substituted phenyl or benzyl, —N(R)(R'), —(CH₂)₄N(R)(R'), —(CH₂)₃N(R)(R'), —(CH₂)₂N(R)(R'), —(CH₂)N(R)(R'), —SO₂N(R)(R'), —NRSO₂R', —CON(R)(R'), —NRSO₂(CH₂)₁₋₄N(R)(R'), —CONR(CH₂)₁₋₄N(R)(R'), —COO(CH₂)₁₋₄N(R)(R'), or —OSO₂R'.

In other embodiments, for the thiophene and thiazole compounds of formulae XX-LIX as described above, $Ar^2$ is optionally substituted phenyl.

In still other embodiments, for the thiophene and thiazole compounds of formulae XX-LIX:

$Ar^2$ is optionally substituted phenyl;

each occurrence of $R^1$ is hydrogen;

each occurrence of $R^4$ is independently hydrogen, $C_{1-6}$aliphatic, —CN, —COR, —COOR, —CON(R)₂, or halogen.

In another embodiment of the invention, $Ar^1$ is a $C_{1-6}$ optionally substituted aliphatic. In further embodiments, $Ar^1$ is a $C_{1-3}$ optionally substituted alkyl and $Q^2$ is —(CHR⁶)$_q$—, —(CHR⁶)$_q$O—, —(CHR⁶)$_q$S—, —(CHR⁶)$_q$S(O)₂—, —(CHR⁶)$_q$S(O)—, —(CHR⁶)$_q$NR—, or —(CHR⁶)$_q$C(O)—, wherein q is 0, 1, 2, or 3, and each $R^6$ is R', —N(R)(R'), —(CH₂)₁₋₄N(R)(R'), —(CH₂)₁₋₄C(CH₃)₂N(R)(R'), —(CH₂)₁₋₄CH(CH₃)N(R)(R'), —OR', —(CH₂)₁₋₄OR', —NR(CH₂)₁₋₄N(R)(R'), —NR(CH₂)₁₋₄SO₂R', —NR(CH₂)₁₋₄COOR', or —NR(CH₂)₁₋₄COR'. In further embodiments, $Q^2$-$Ar^1$ is —CH₂CN.

In still other embodiments, $X_1$ is $CR^4$, $X_2$ is $CR^4$ or N, G is —NR² or —CO— and $Q^1$ is a bond for compounds of formula I-B. In further embodiments, $Q^2$ is a bond.

Representative examples of compounds of formula I are set forth below in Tables 1 and 2 below.

TABLE 1

Examples of Compounds of Formula I:

| Compound | Cmpd # |
|---|---|
| | I-1 |
| | I-2 |

TABLE 1-continued
Examples of Compounds of Formula I:
| Compound | Cmpd # |
|---|---|
| 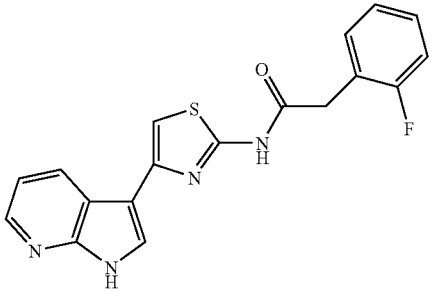 | I-3 |
| 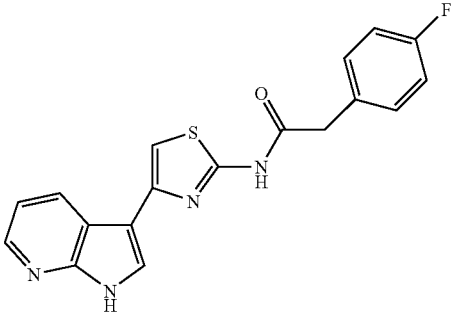 | I-4 |
| 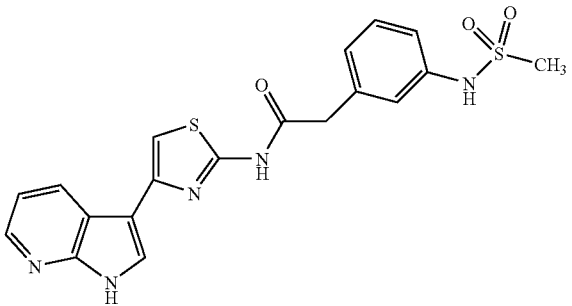 | I-5 |
| 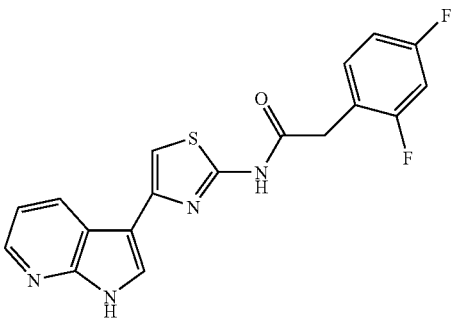 | I-6 |
| 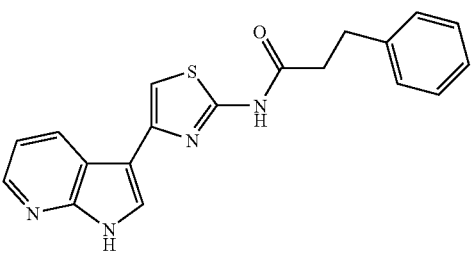 | I-7 |

TABLE 1-continued
Examples of Compounds of Formula I:
| Compound | Cmpd # |
|---|---|
| 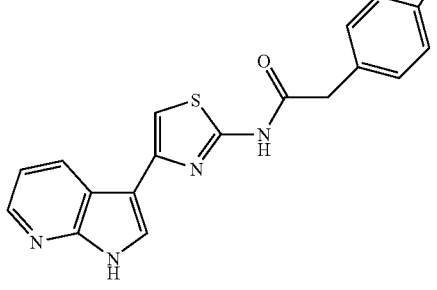 | I-8 |
| 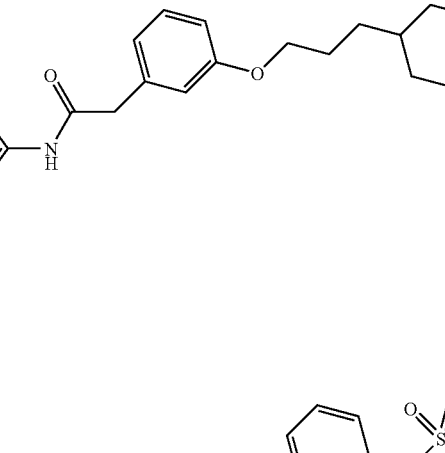 | I-9 |
| 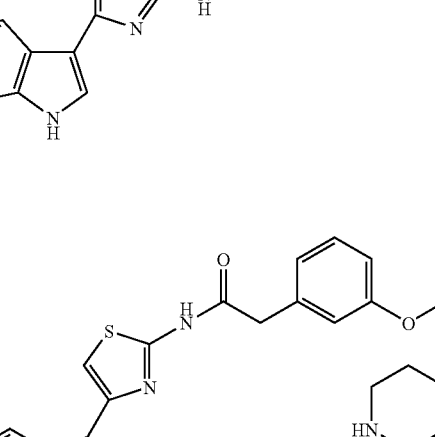 | I-10 |
|  | I-11 |

TABLE 1-continued

Examples of Compounds of Formula I:

| Compound | Cmpd # |
|---|---|
| | I-12 |
| | I-13 |
| | I-14 |
| | I-15 |
| | I-16 |

TABLE 1-continued

Examples of Compounds of Formula I:

| Compound | Cmpd # |
|---|---|
| (structure) | I-17 |
| (structure) | I-18 |
| (structure) | I-19 |
| (structure) | I-20 |
| (structure) | I-21 |
| (structure) | I-22 |

TABLE 1-continued
Examples of Compounds of Formula I:
| Compound | Cmpd # |
|---|---|
| 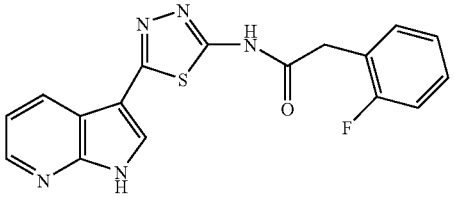 | I-23 |
TABLE 2
Examples of Compounds of Formula I:
| Compound | Cmpd # |
|---|---|
| 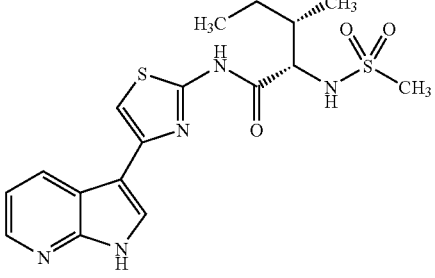 | II-1 |
| 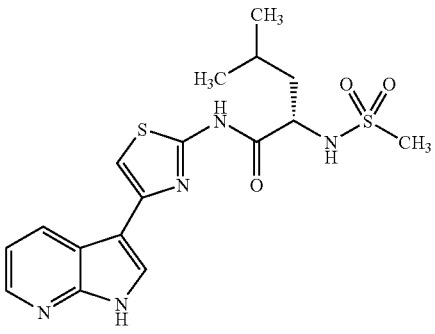 | II-2 |
| 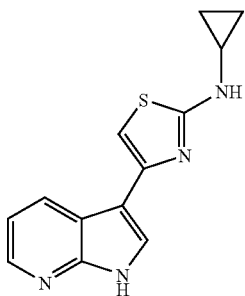 | II-3 |

-continued
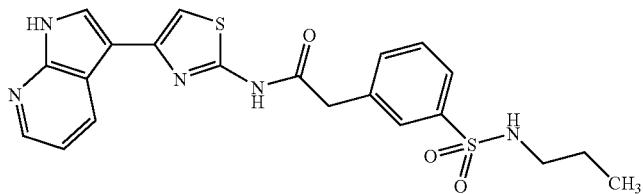
II-4
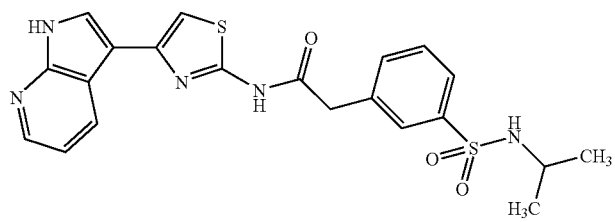
II-5
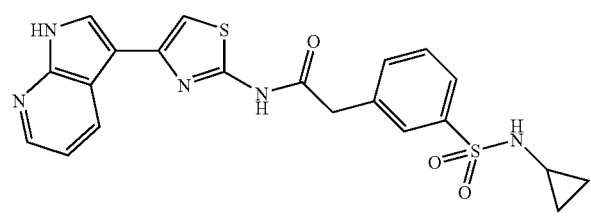
II-6
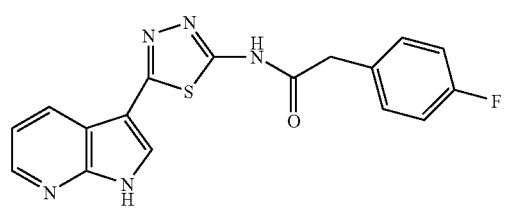
II-7
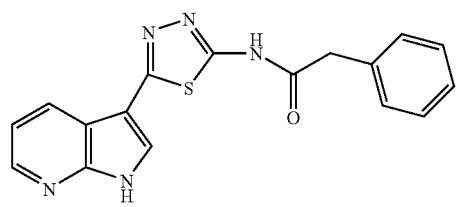
II-8
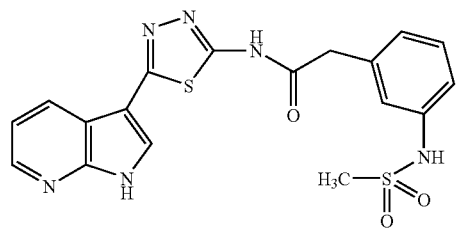
II-9
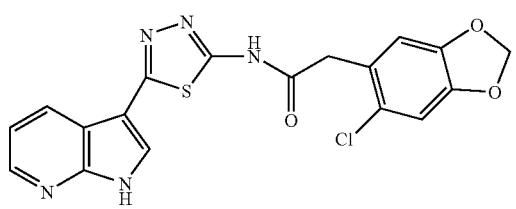
II-10

-continued
| | |
|---|---|
| 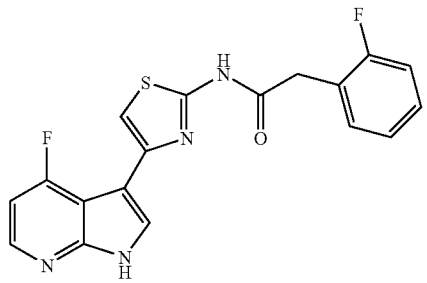 | II-11 |
| 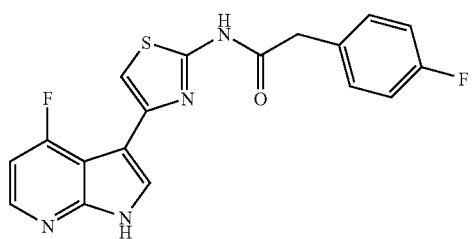 | II-12 |
| 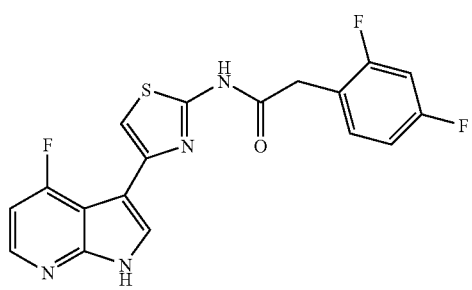 | II-13 |
| 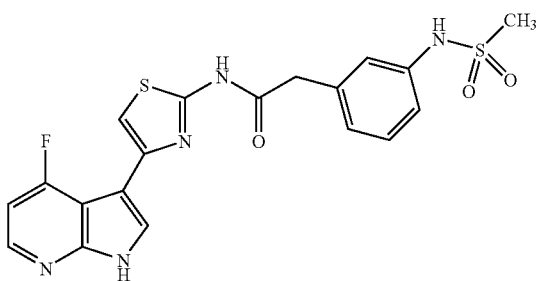 | II-14 |
| 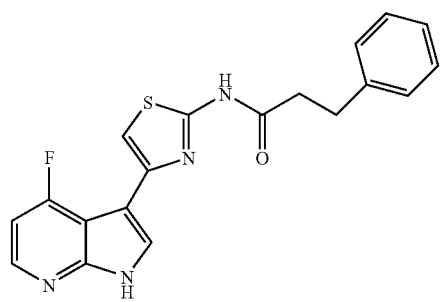 | II-15 |

-continued
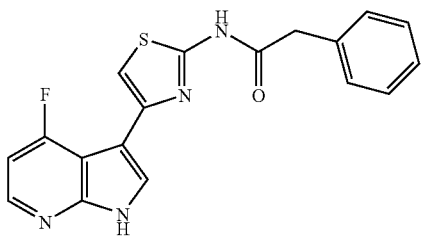
II-16
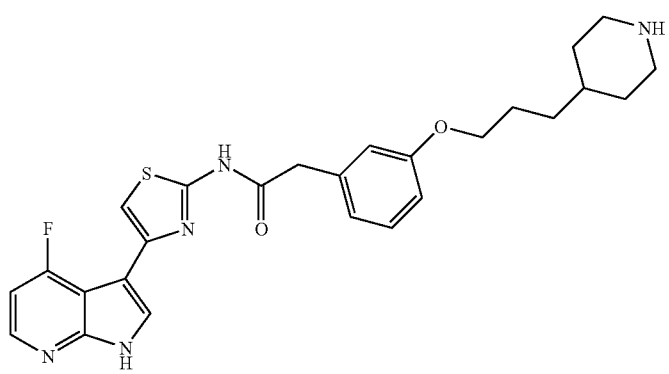
II-17
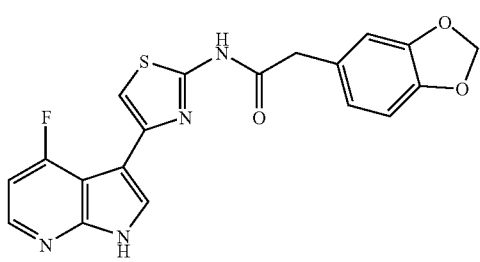
II-18
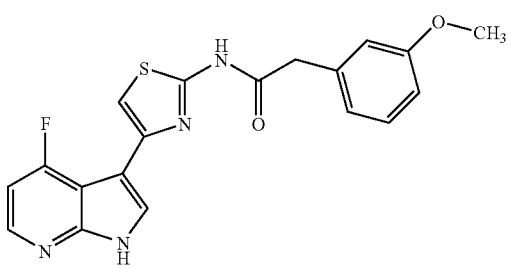
II-19
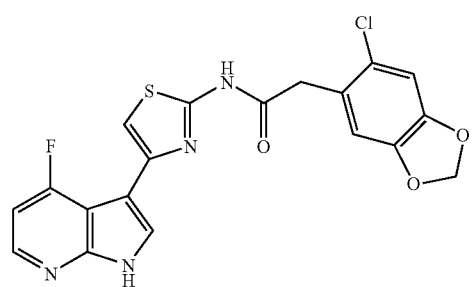
II-20

-continued
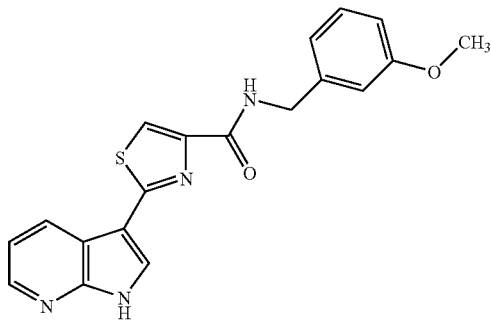
II-21
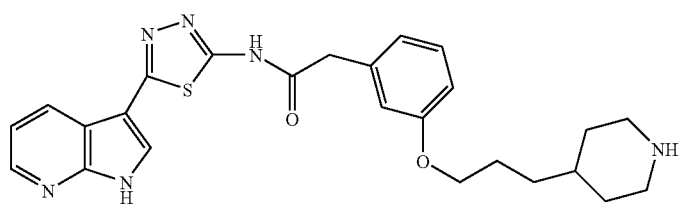
II-22
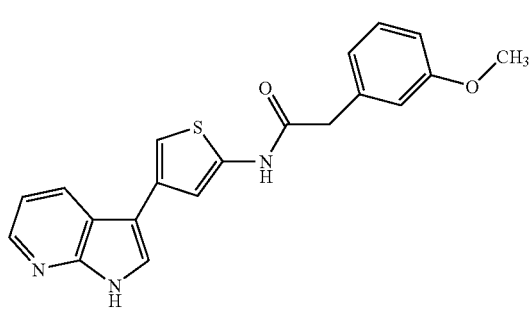
II-23
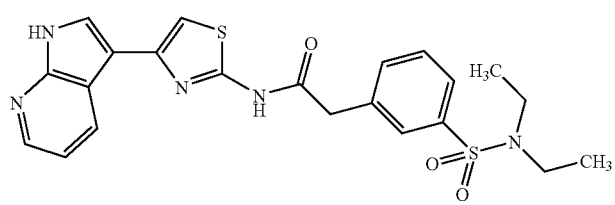
II-24
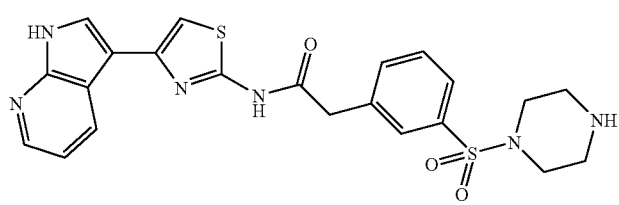
II-25
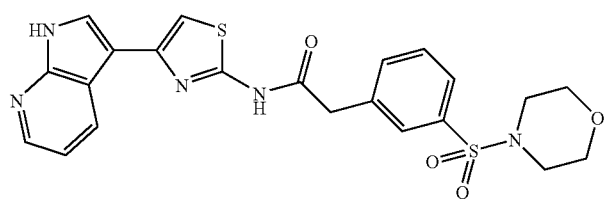
II-26

-continued
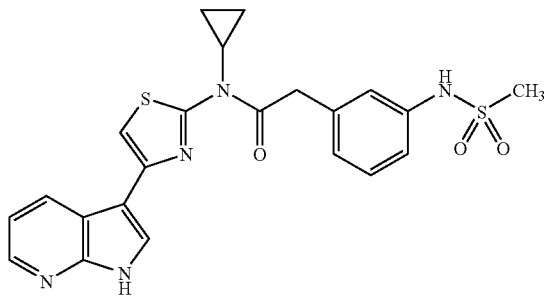
II-27
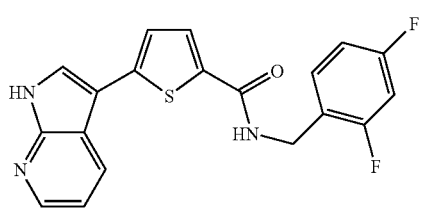
II-28
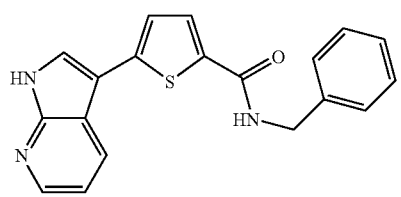
II-29
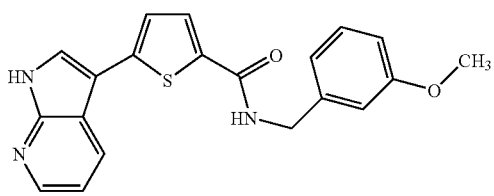
II-30
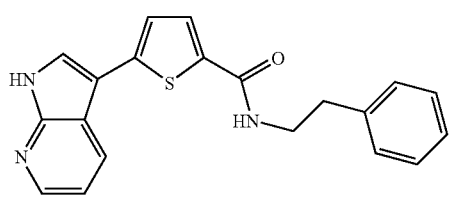
II-31
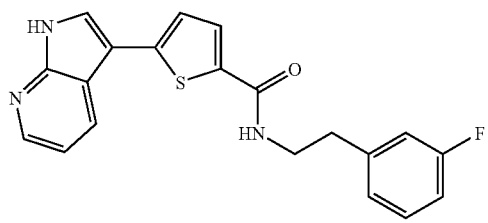
II-32

-continued
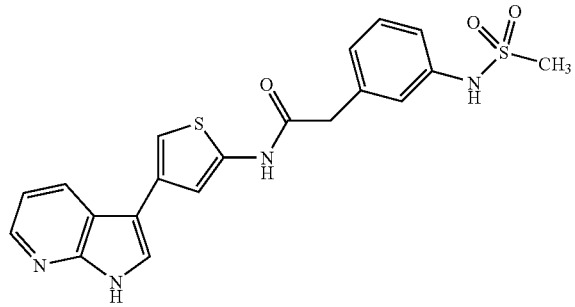
II-33
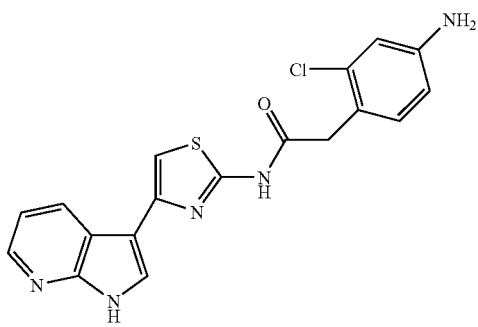
II-34
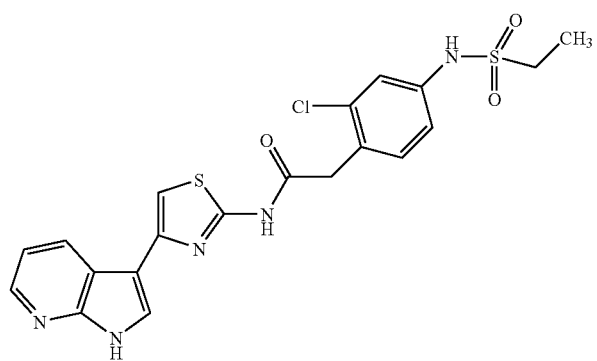
II-35
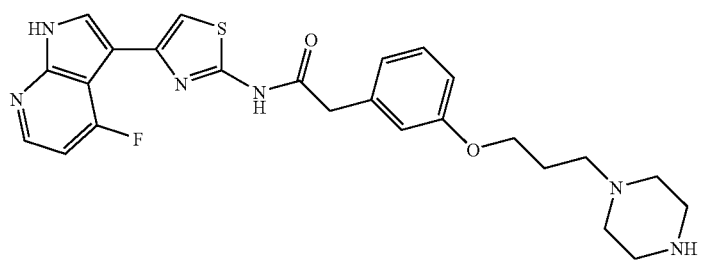
II-36
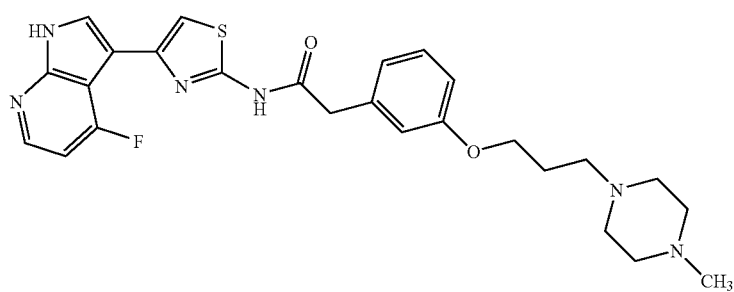
II-37

-continued
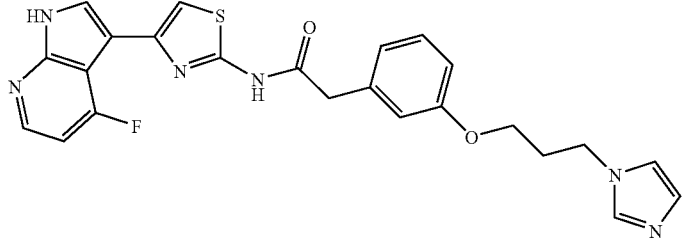
II-38
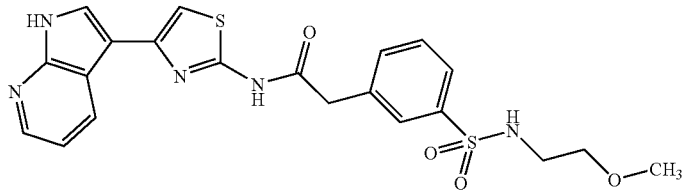
II-39
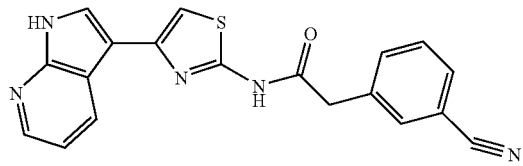
II-40
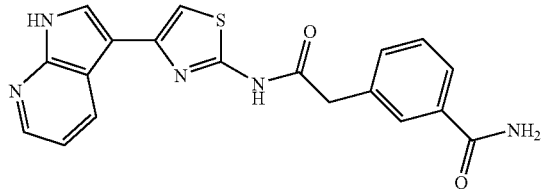
II-41
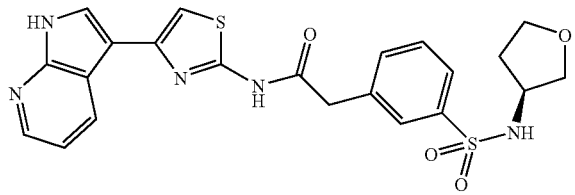
II-42
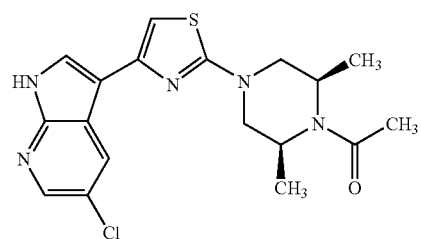
II-43
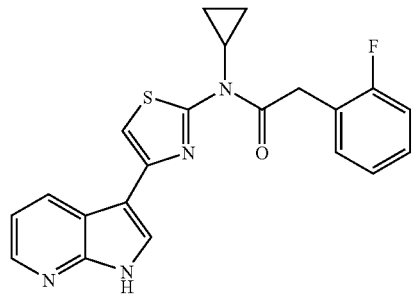
II-44

-continued
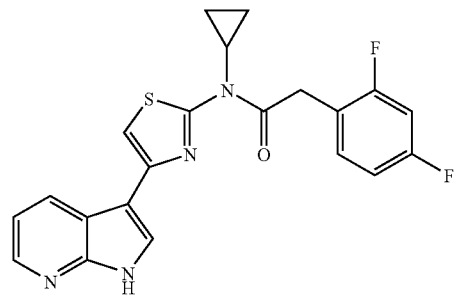
II-45
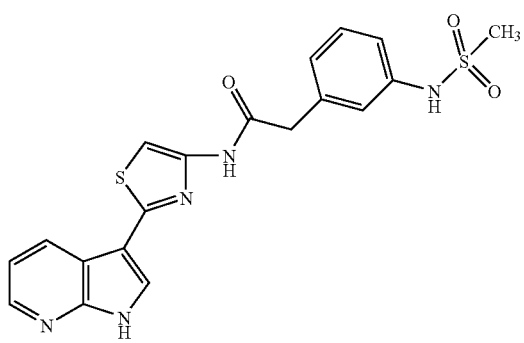
II-46
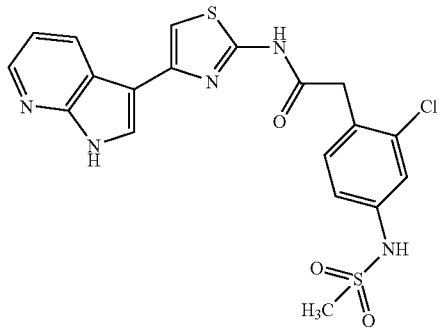
II-47
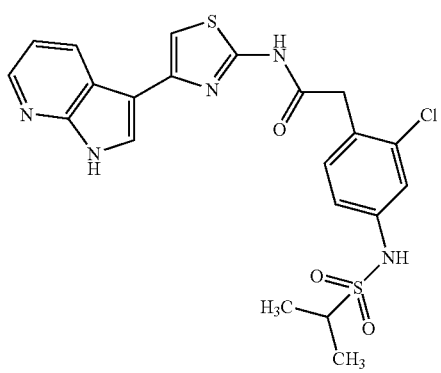
II-48
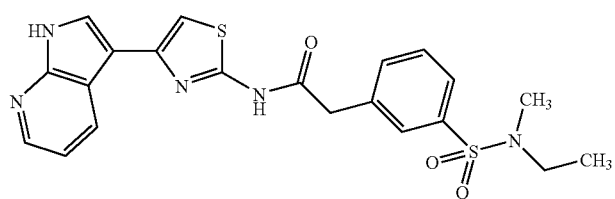
II-49

-continued
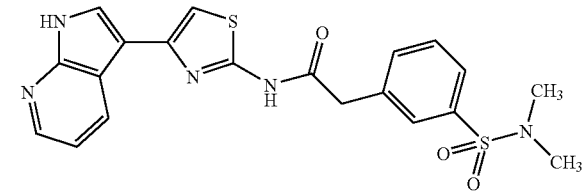 II-50
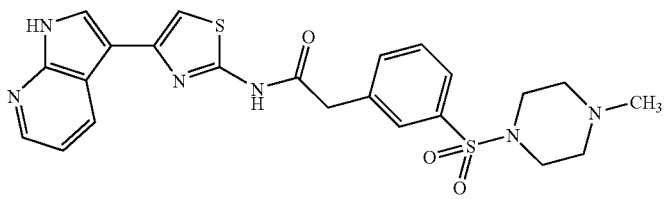 II-51
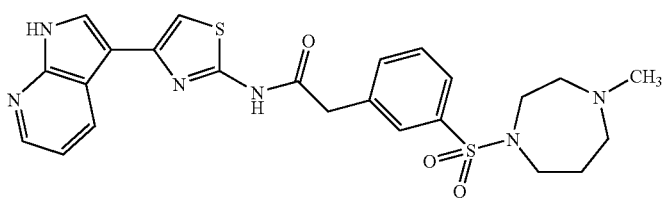 II-52
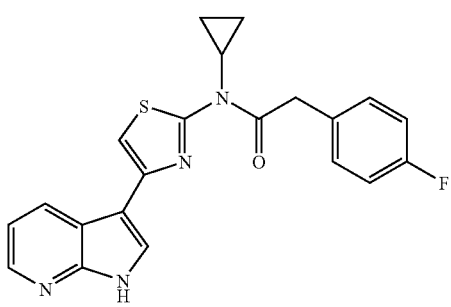 II-53
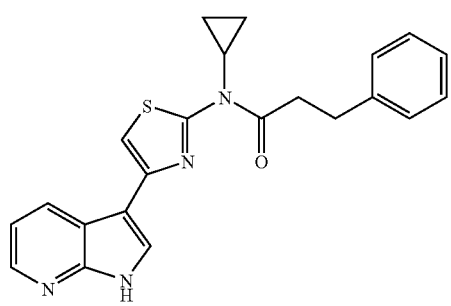 II-54
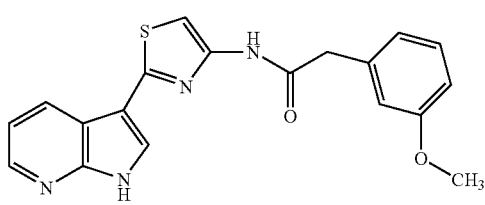 II-55
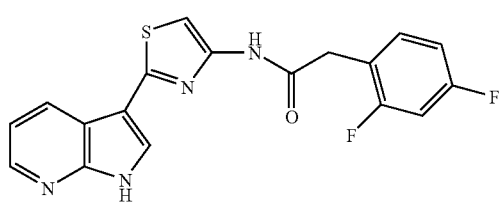 II-56

-continued
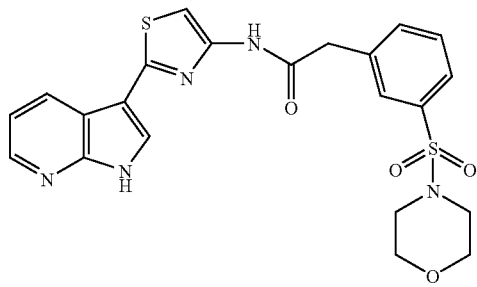
II-57
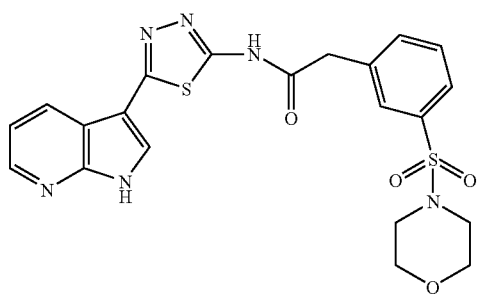
II-58
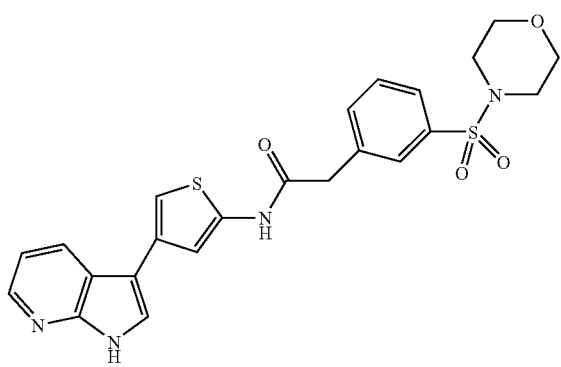
II-59
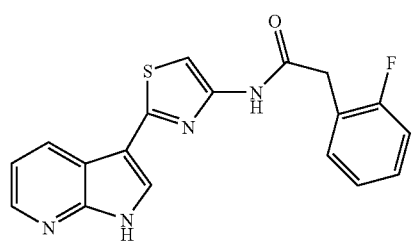
II-60
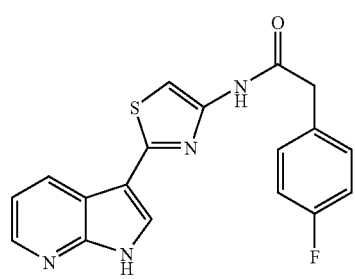
II-61

-continued
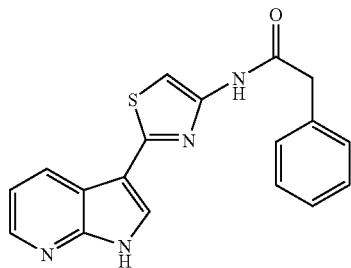
II-62
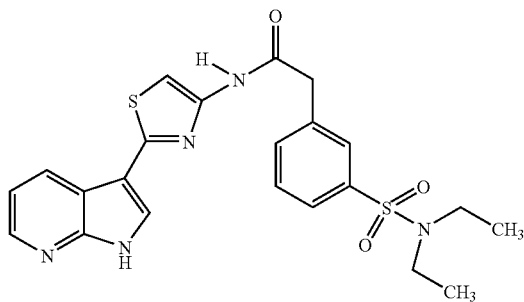
II-63
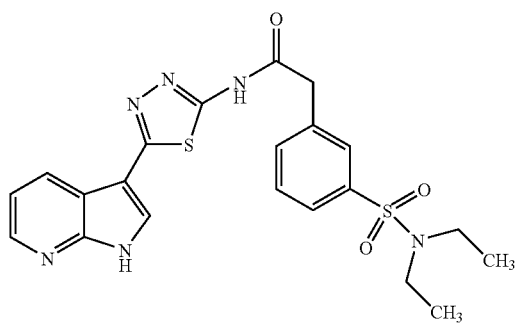
II-64
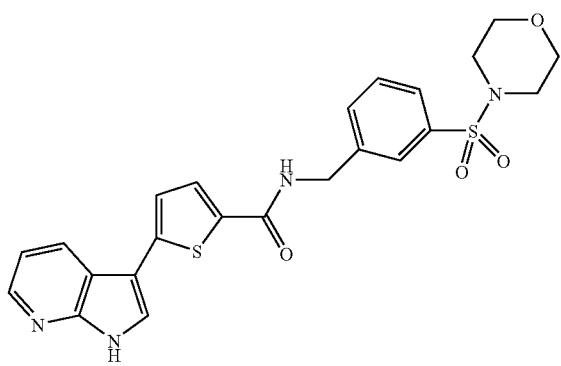
II-65
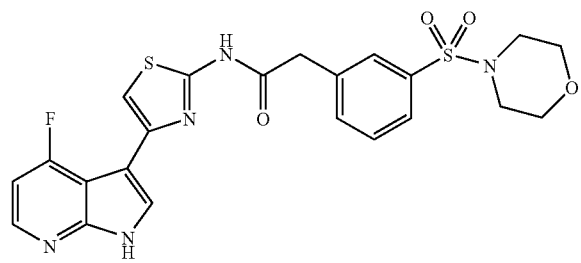
II-66

-continued
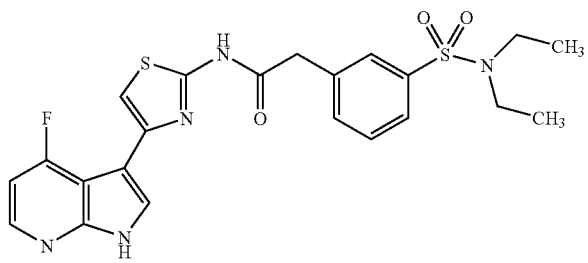
II-67
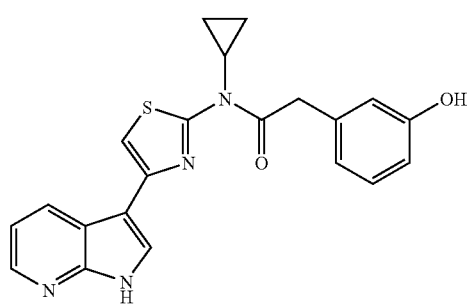
II-68
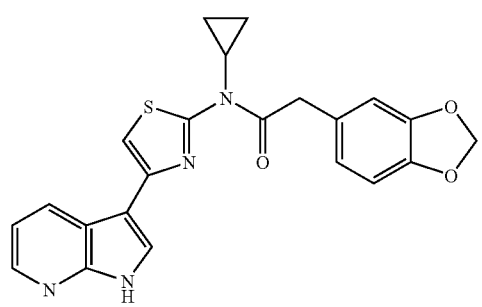
II-69
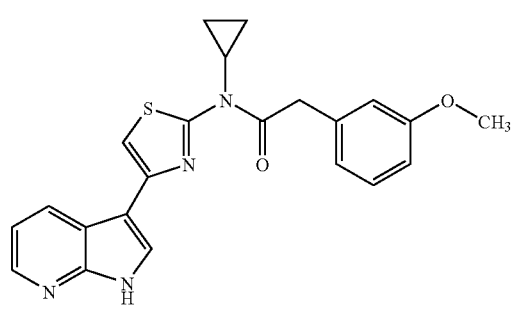
II-70
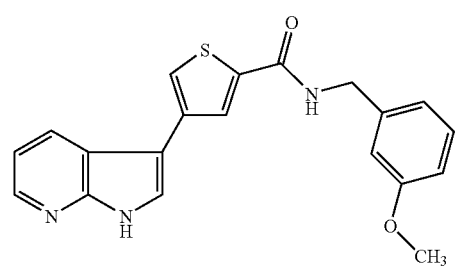
II-71

-continued
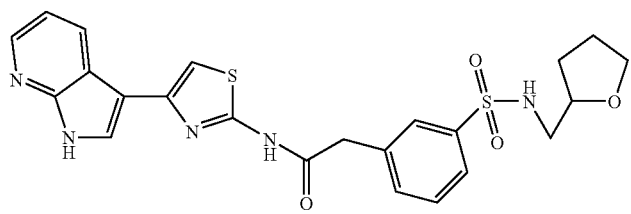
II-72
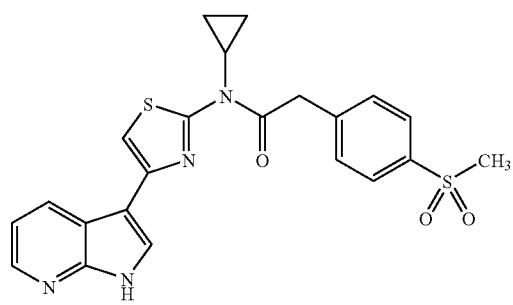
II-73
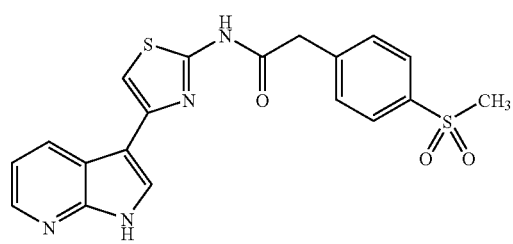
II-74
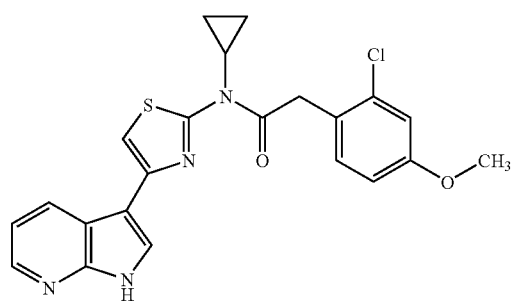
II-75
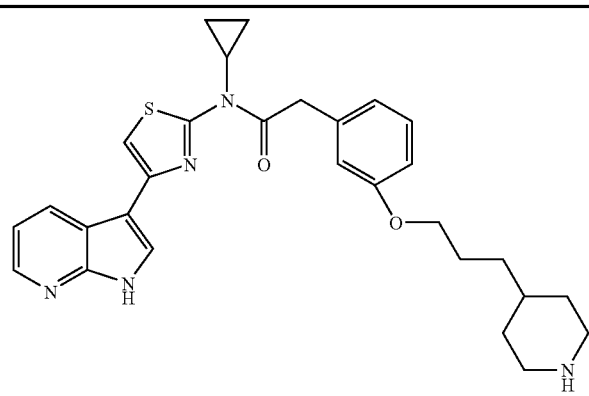
II-76

-continued
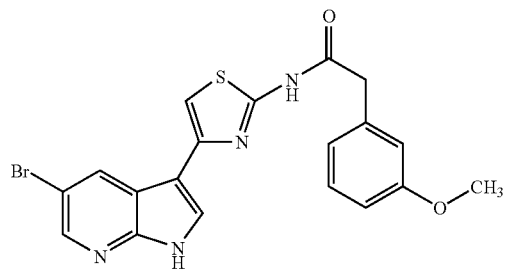
II-77
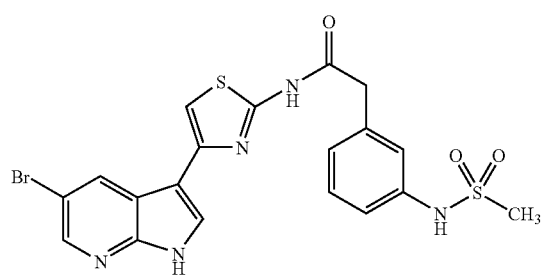
II-78
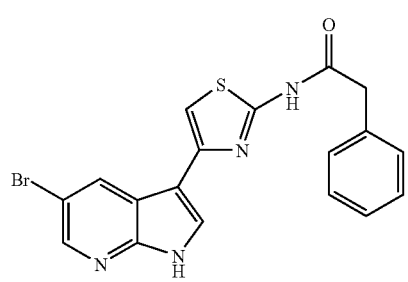
II-79
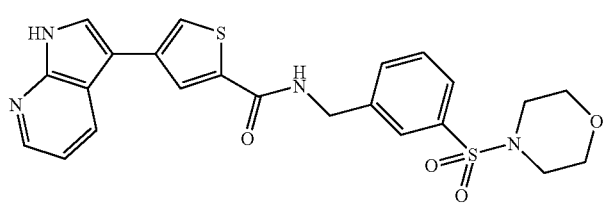
II-80
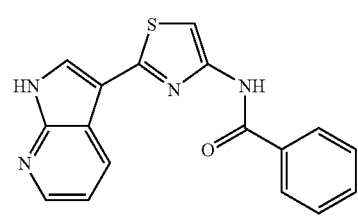
II-81
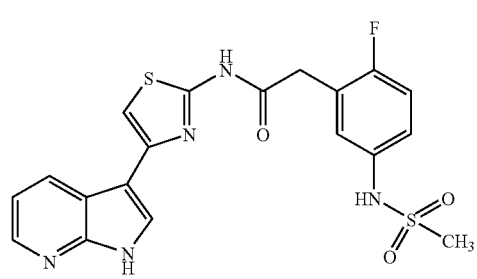
II-82

-continued
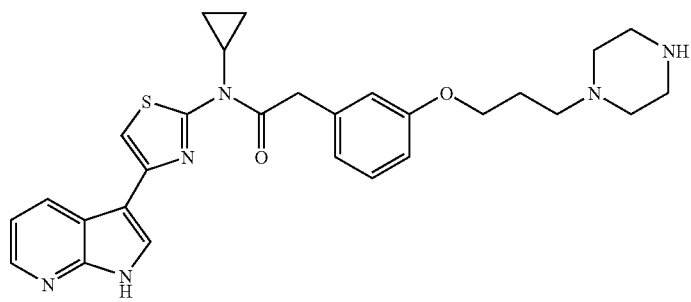
II-83
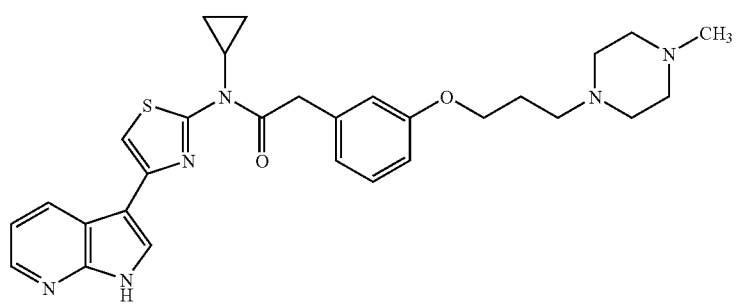
II-84
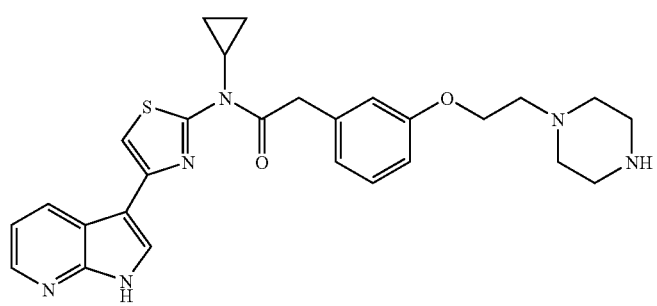
II-85
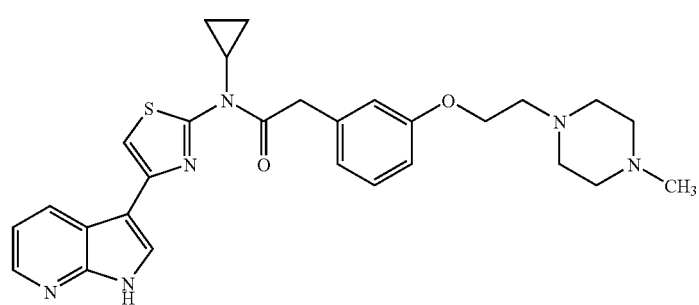
II-86
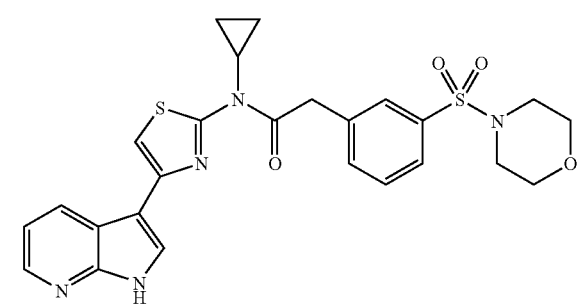
II-87

-continued
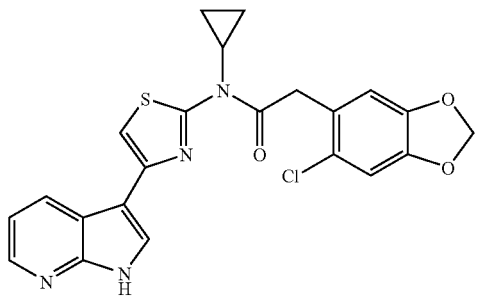
II-88
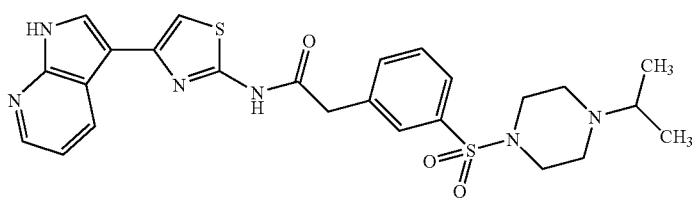
II-89
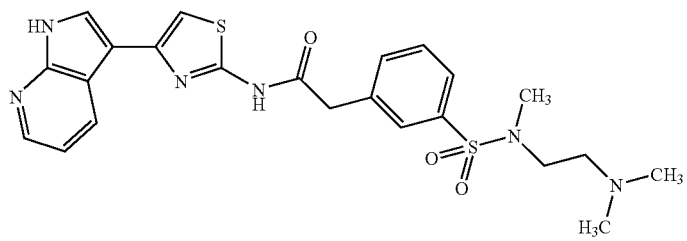
II-90
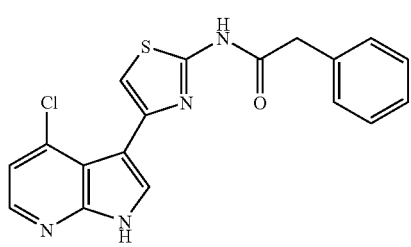
II-91
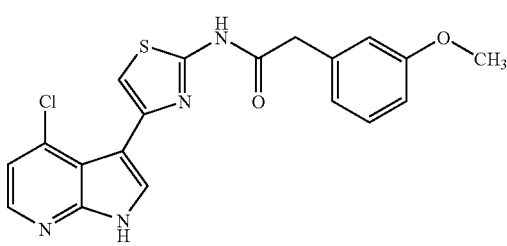
II-92
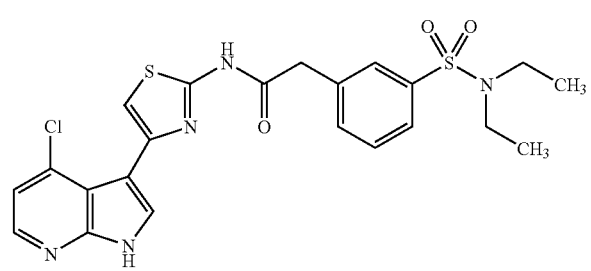
II-93

-continued
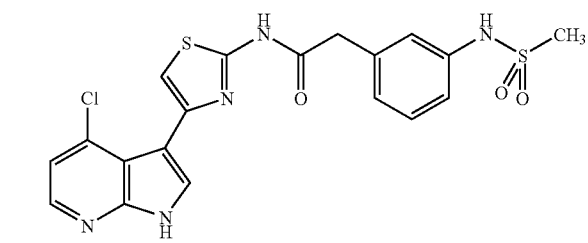
II-94
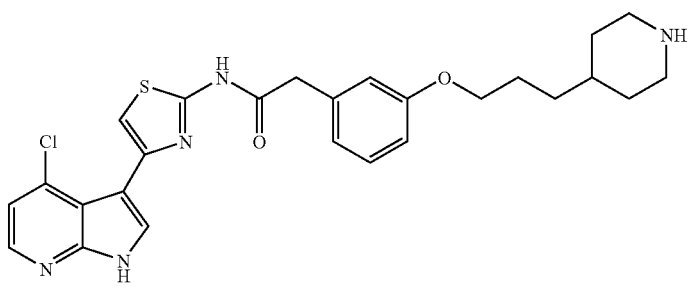
II-95
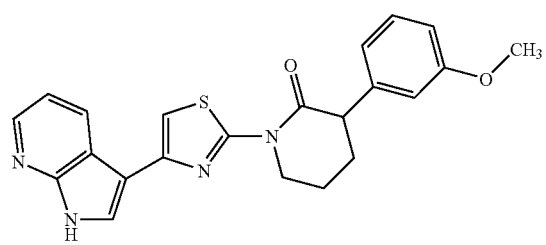
II-96
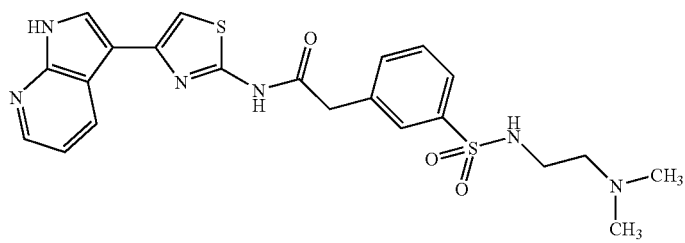
II-97
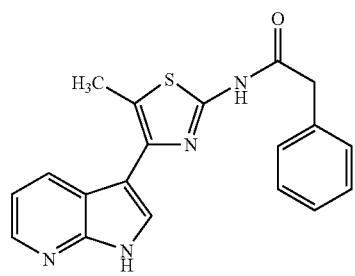
II-98
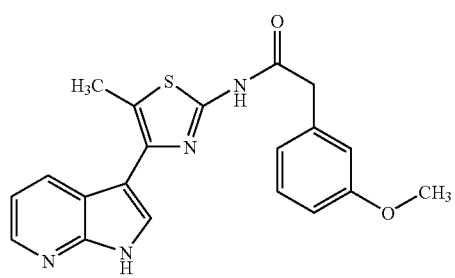
II-99

-continued
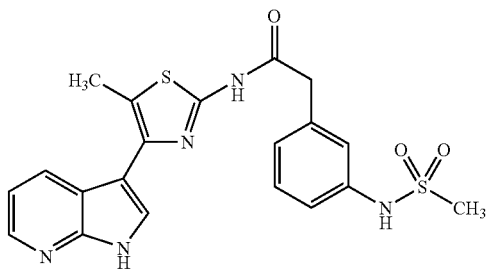
II-100
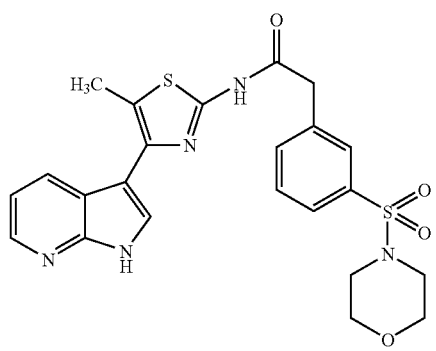
II-101
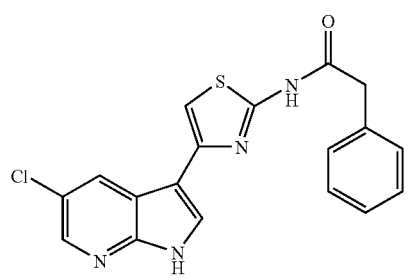
II-102
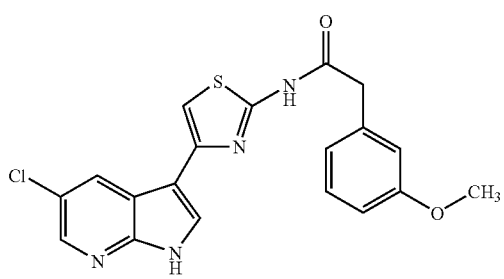
II-103
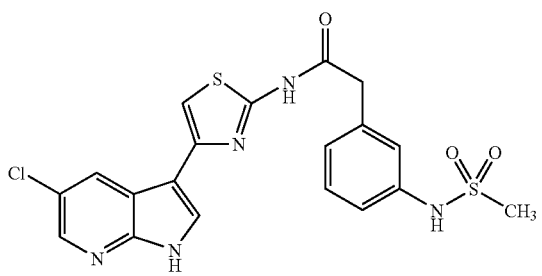
II-104

-continued
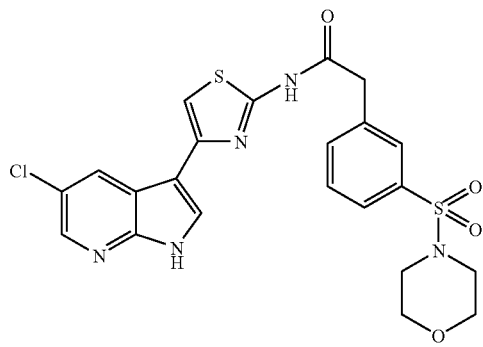
II-105
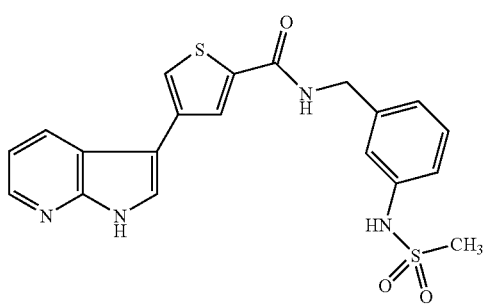
II-106
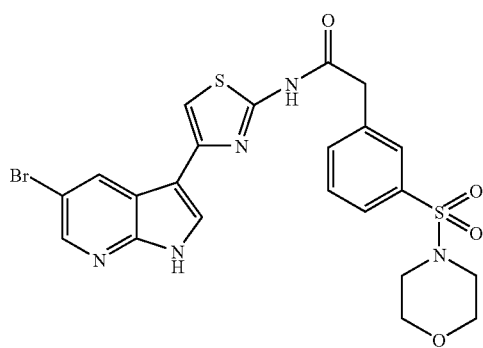
II-107
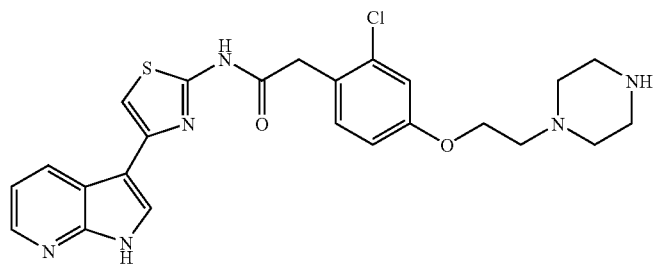
II-108
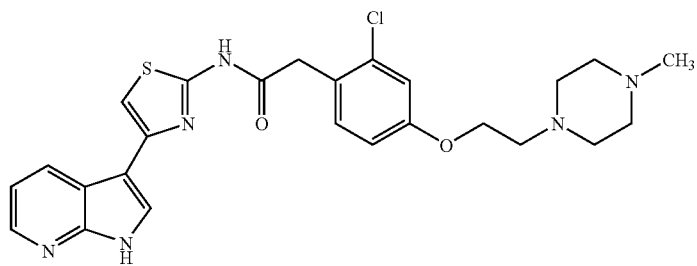
II-109

-continued
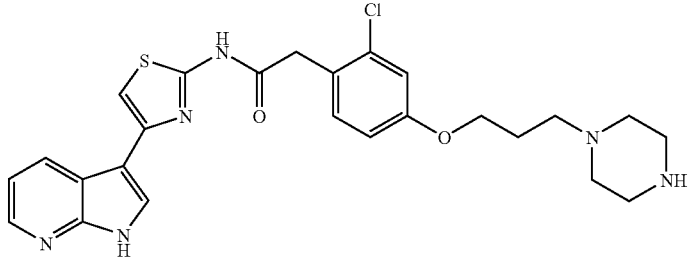
II-110
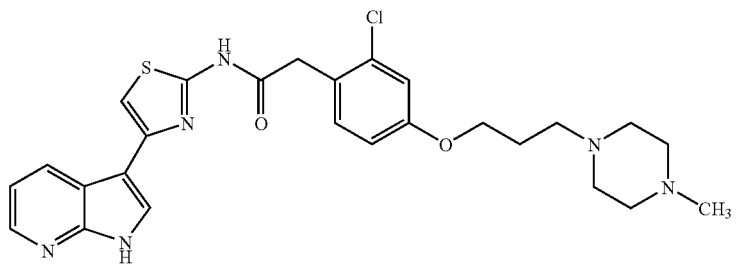
II-111
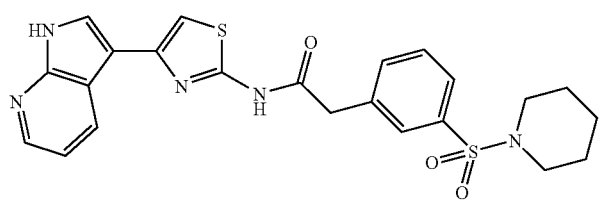
II-112
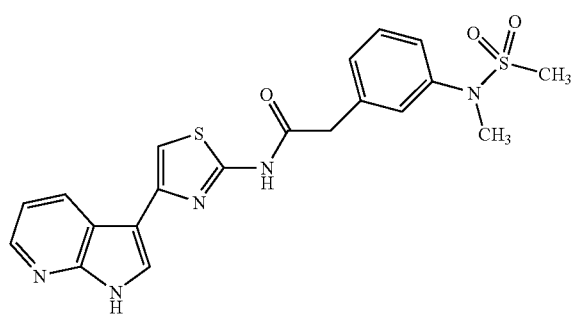
II-113
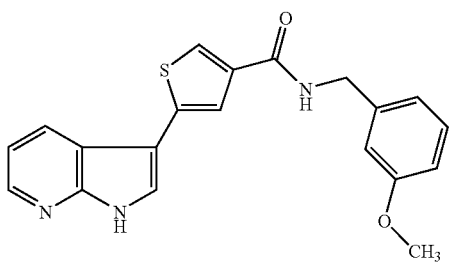
II-114
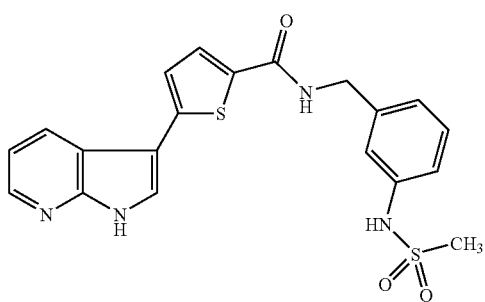
II-115

-continued
II-116
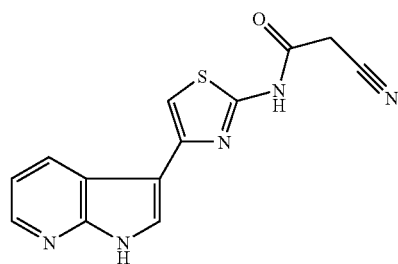
II-117
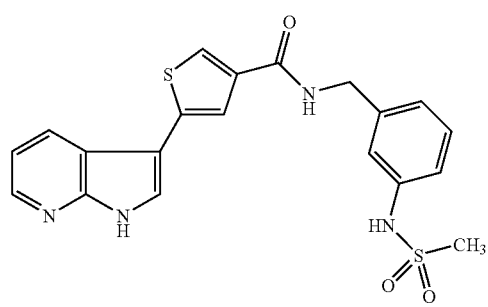
II-118
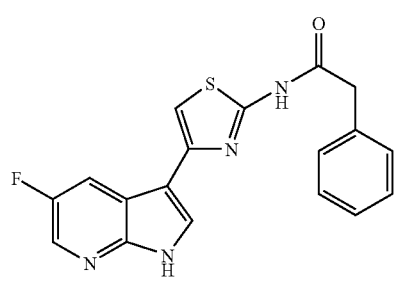
II-119
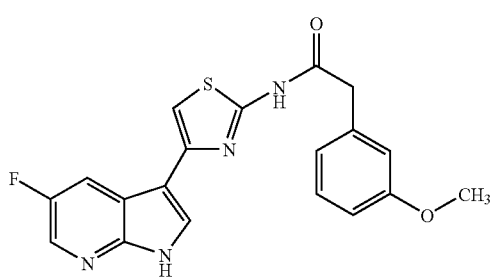
II-120
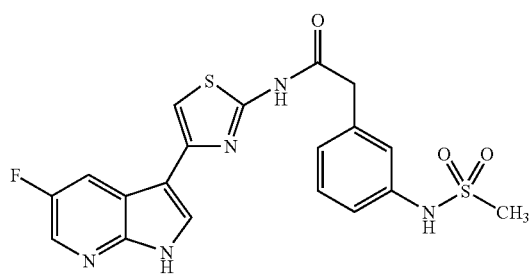

-continued
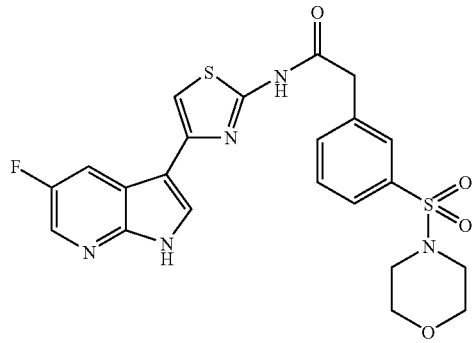
II-121
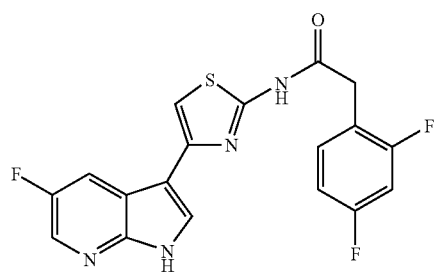
II-122
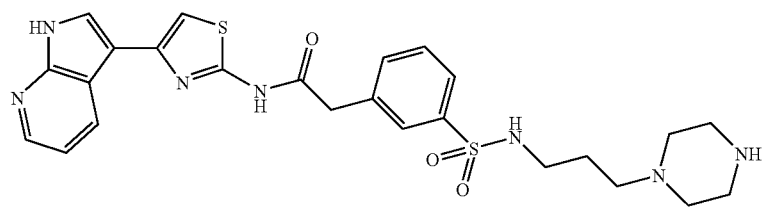
II-123
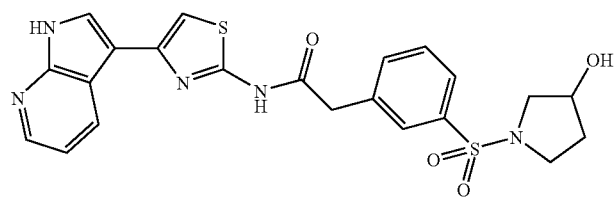
II-124
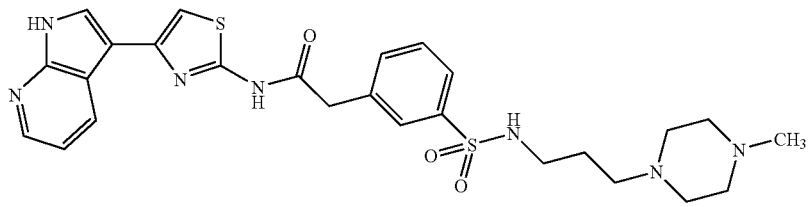
II-125
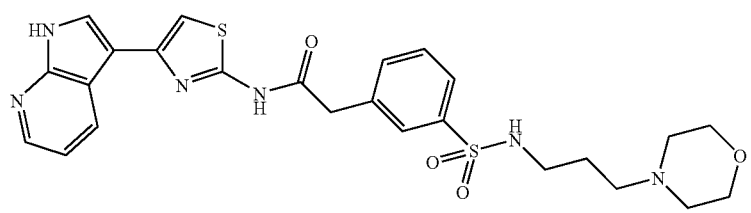
II-126

-continued
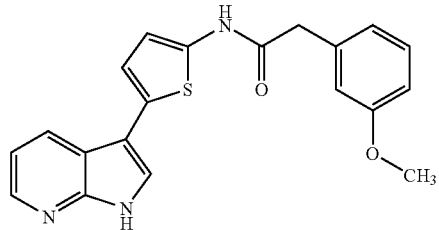 II-127
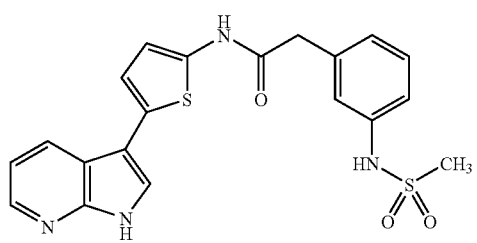 II-128
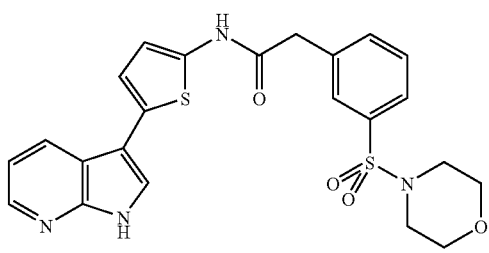 II-129
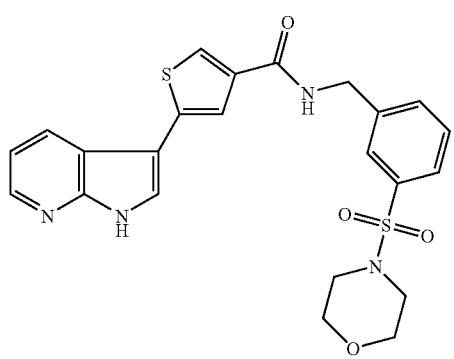 II-130
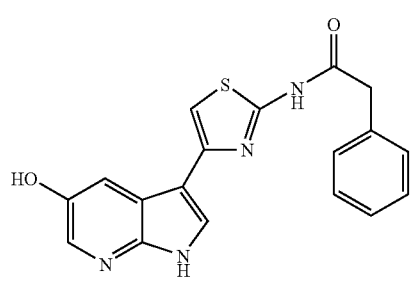 II-131

-continued
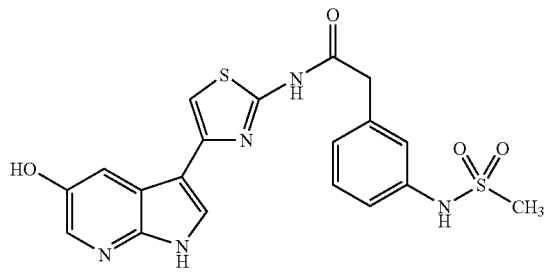
II-132
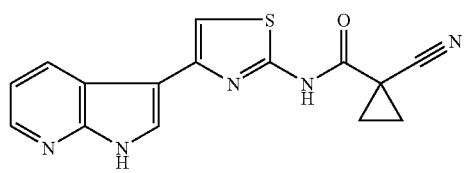
II-133
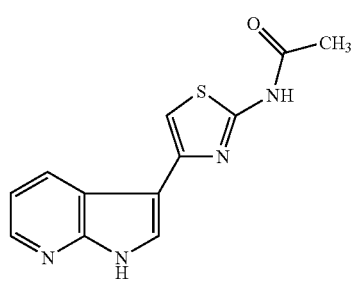
II-134
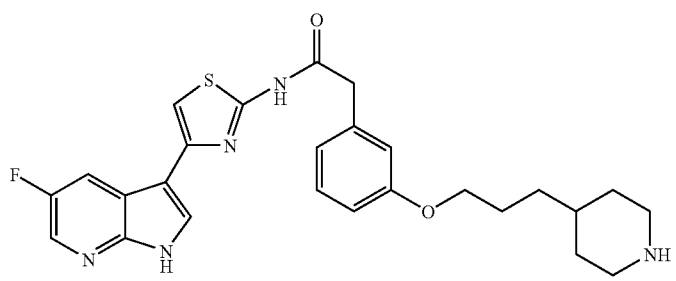
II-135
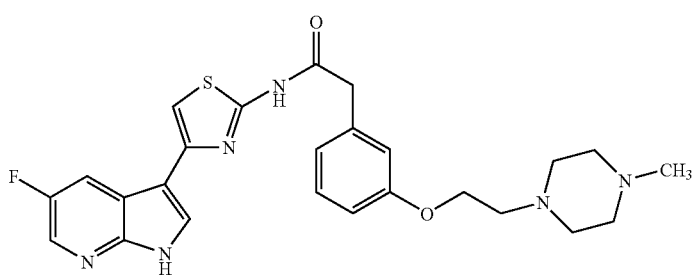
II-136
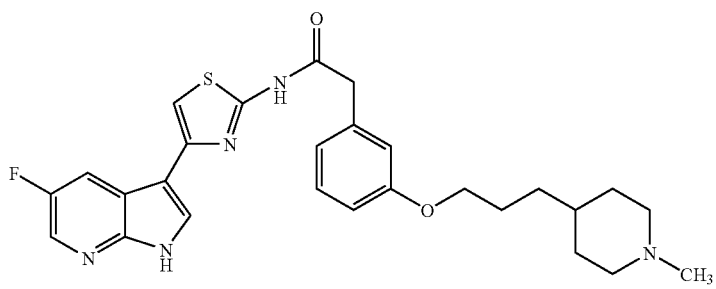
II-137

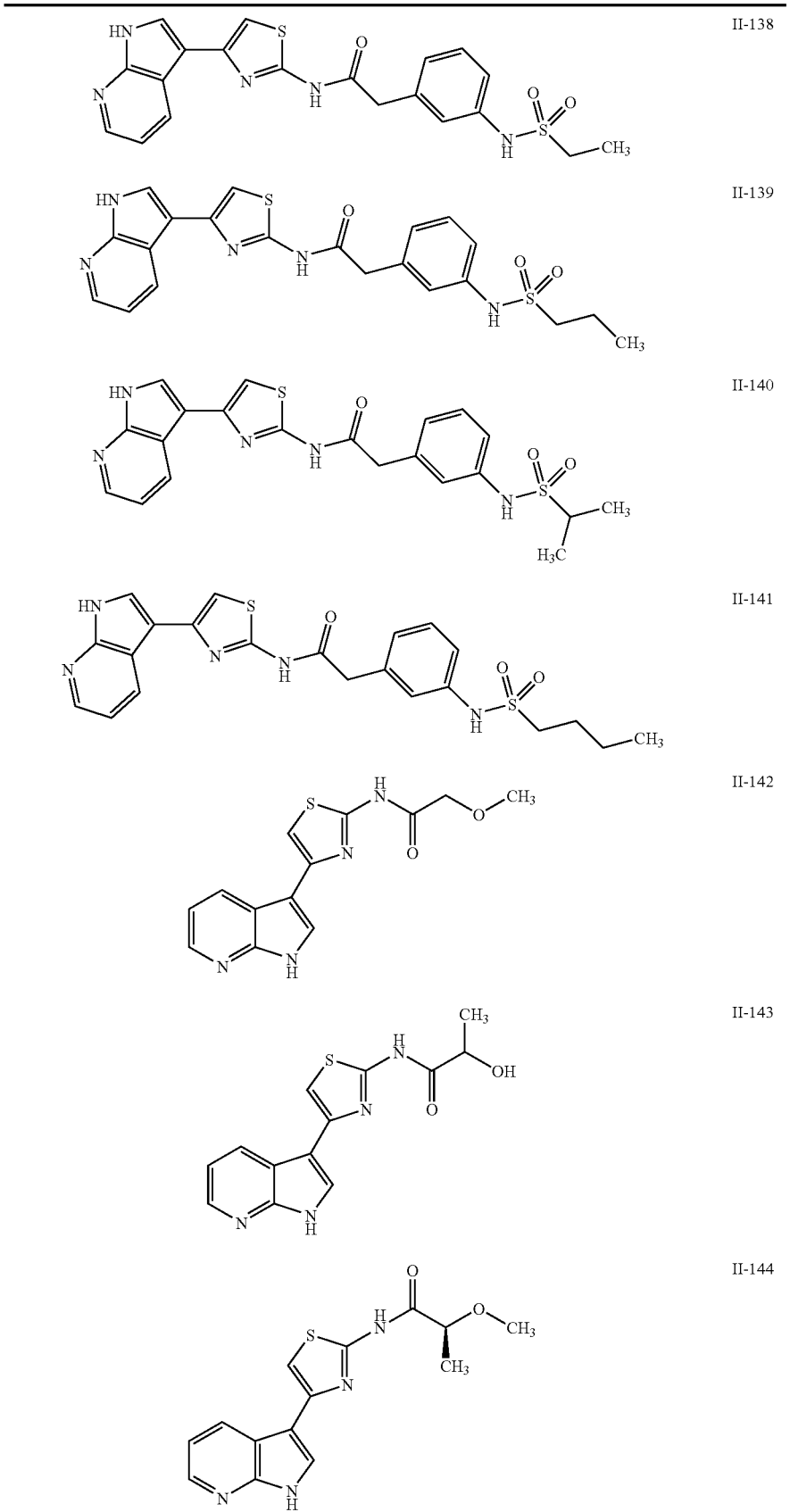

-continued
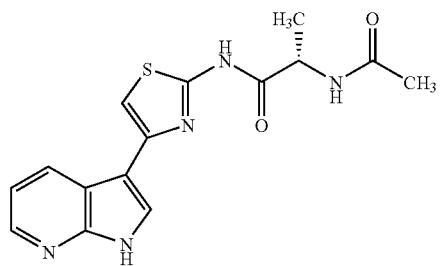
II-145
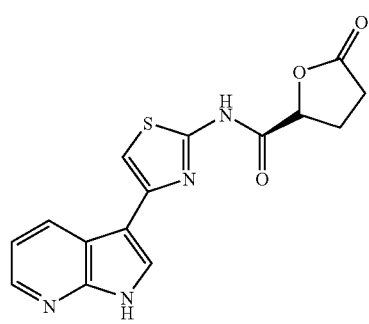
II-146
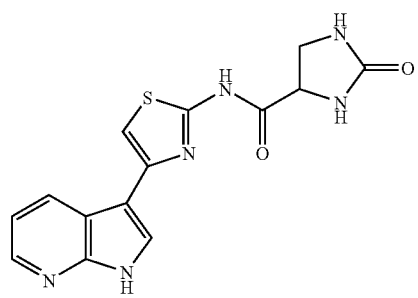
II-147
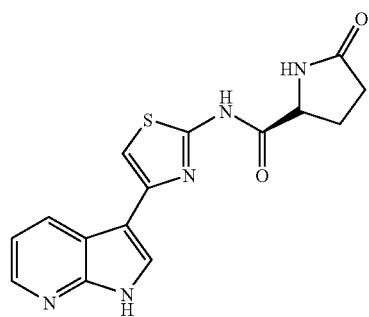
II-148
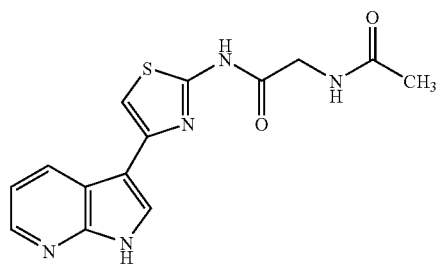
II-149

-continued
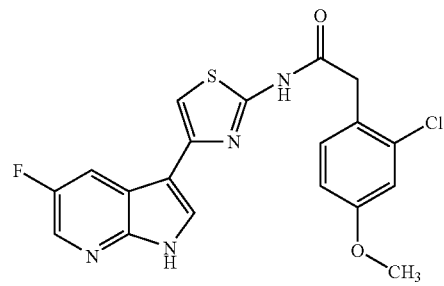
II-150
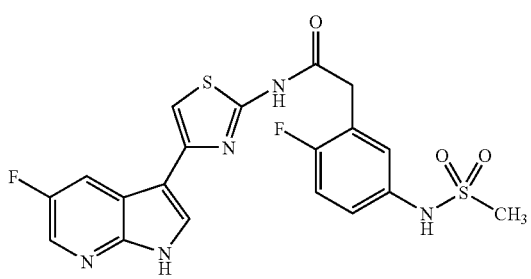
II-151
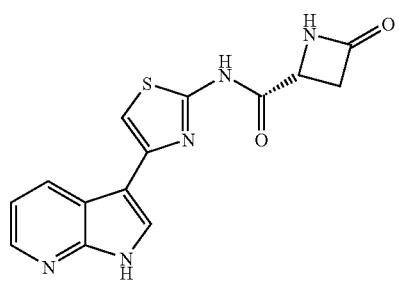
II-152
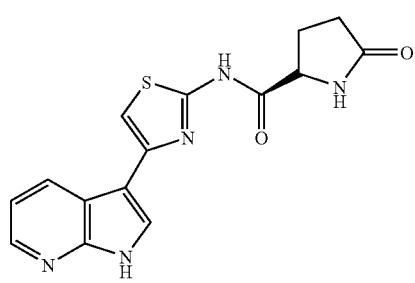
II-153
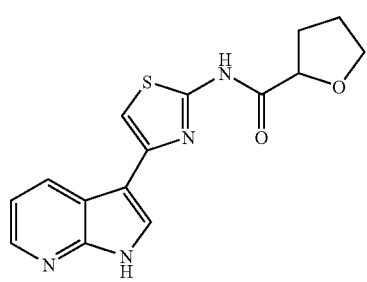
II-154

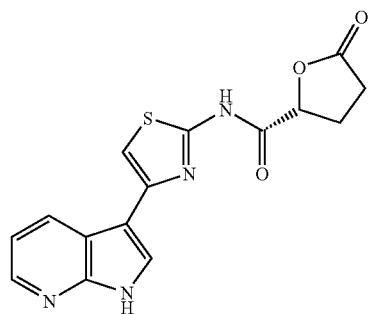
II-155
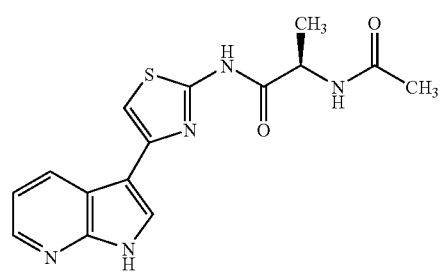
II-156
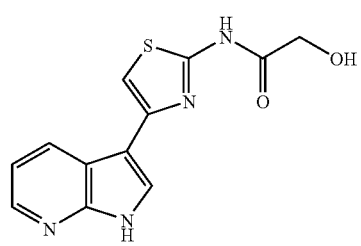
II-157
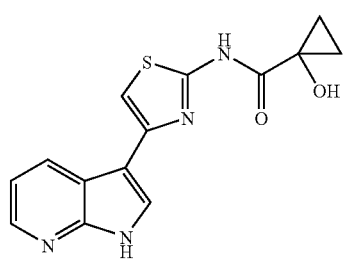
II-158
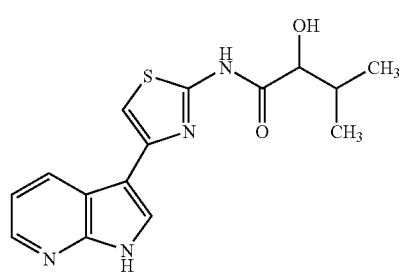
II-159

-continued
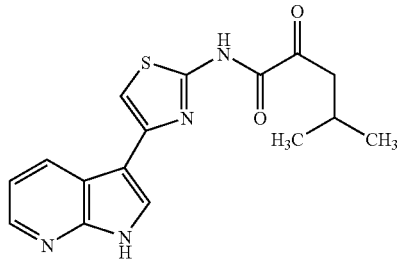 II-160
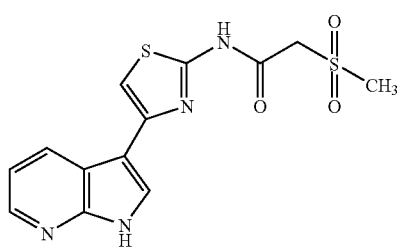 II-161
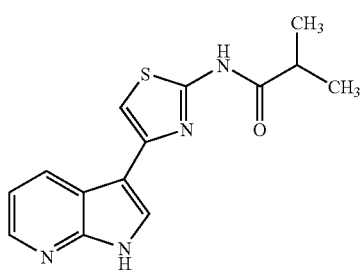 II-162
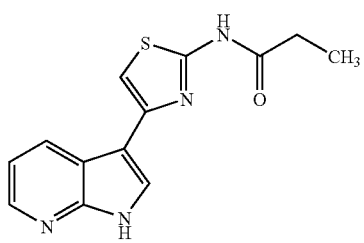 II-163
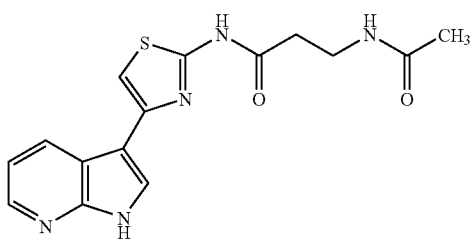 II-164
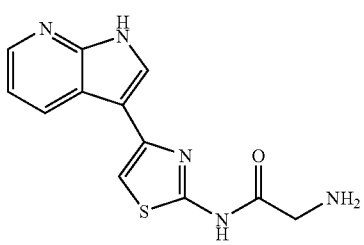 II-165

-continued
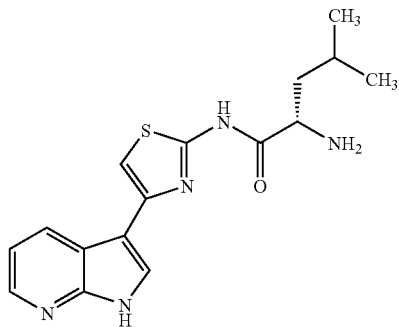
II-166
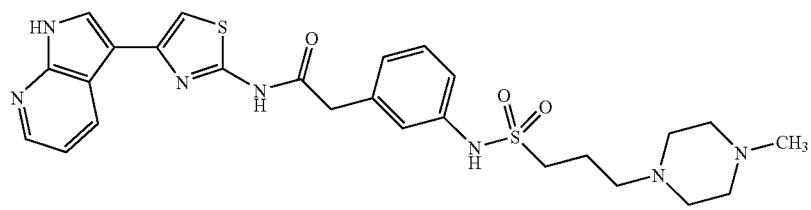
II-167
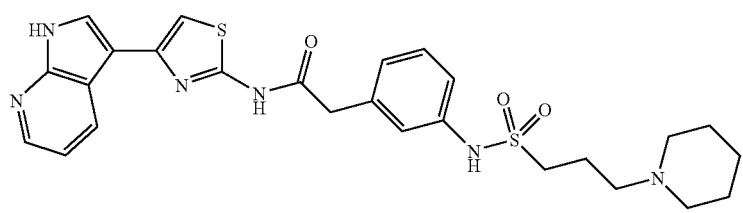
II-168
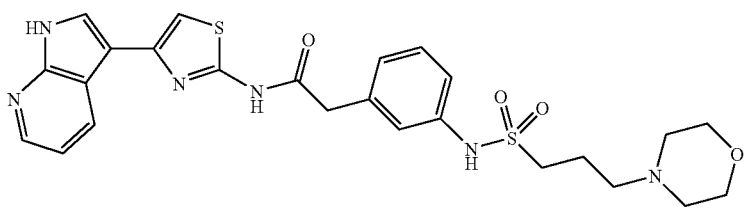
II-169
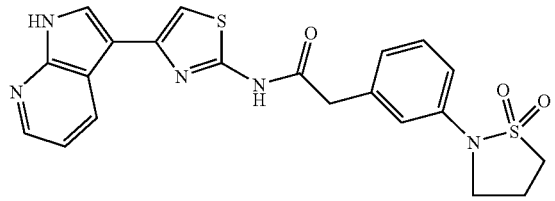
II-170
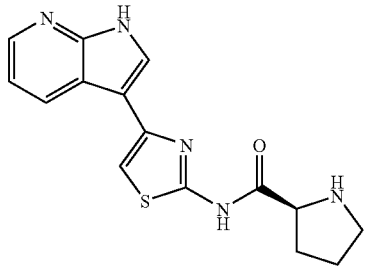
II-171

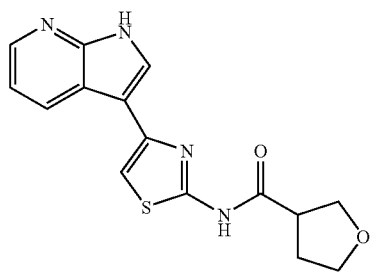
II-172
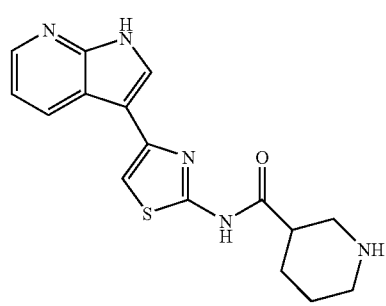
II-173
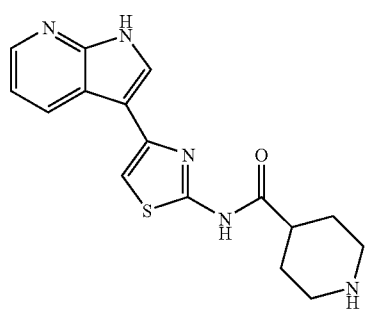
II-174
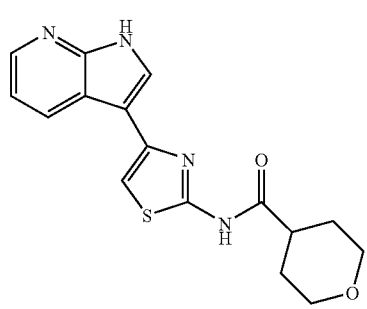
II-175
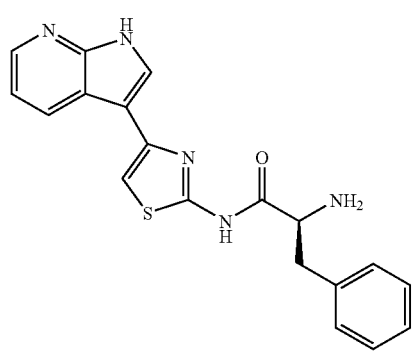
II-176

-continued
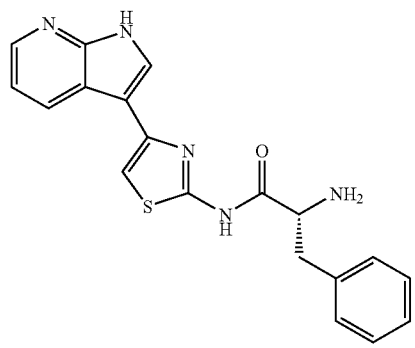
II-177
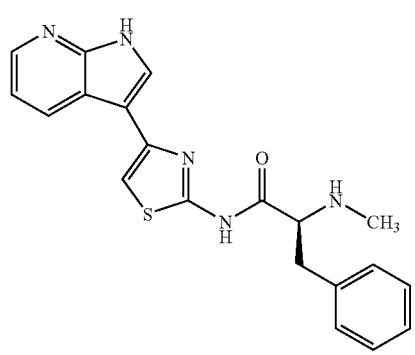
II-178
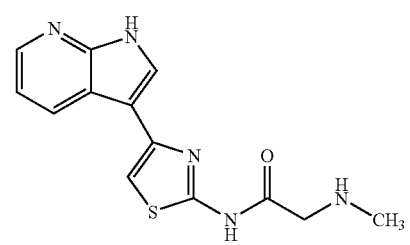
II-179
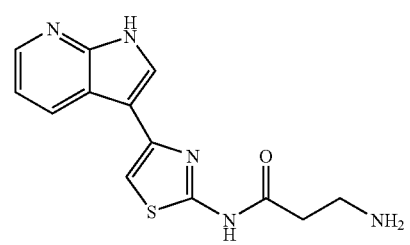
II-180
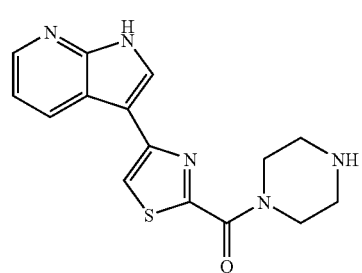
II-181

-continued
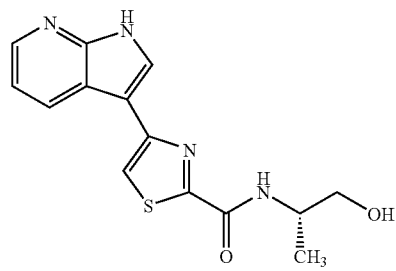
II-182
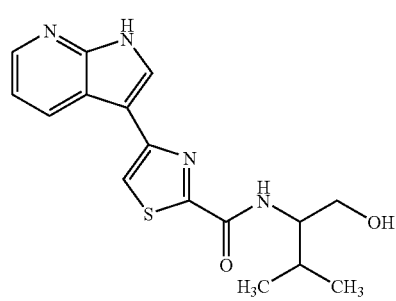
II-183
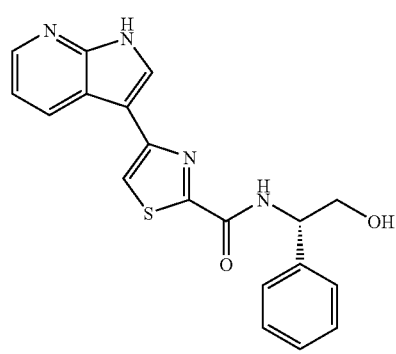
II-184
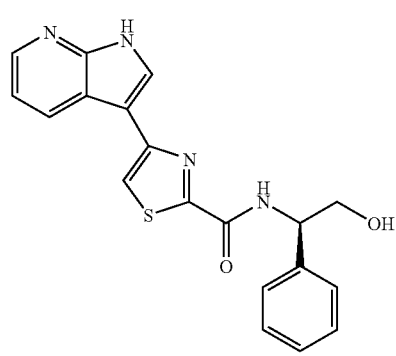
II-185

-continued
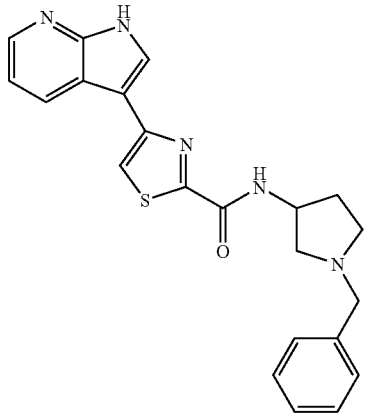
II-186
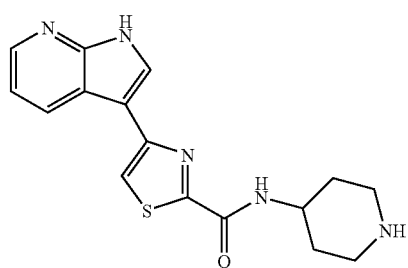
II-187
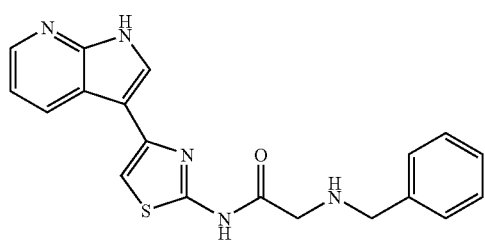
II-188
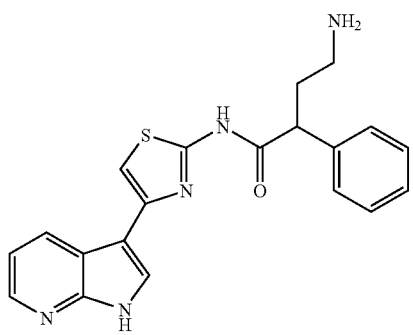
II-189
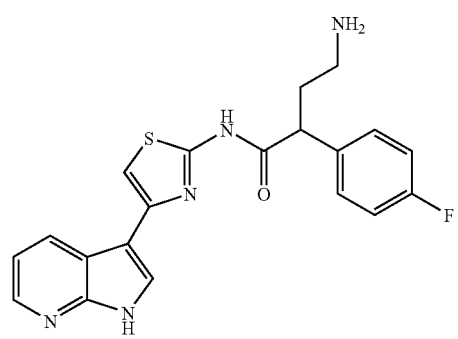
II-190

-continued
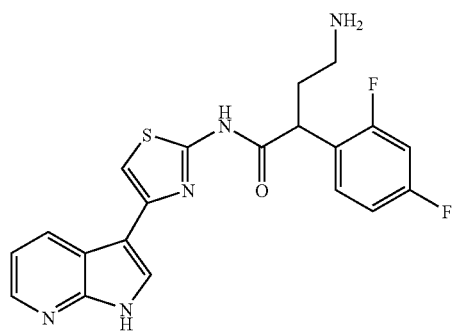
II-191
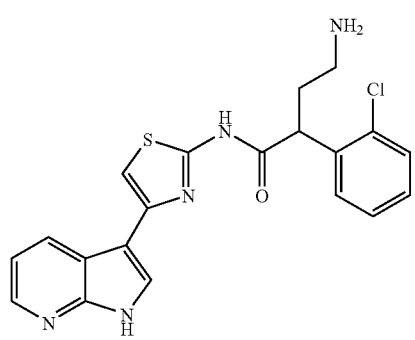
II-192
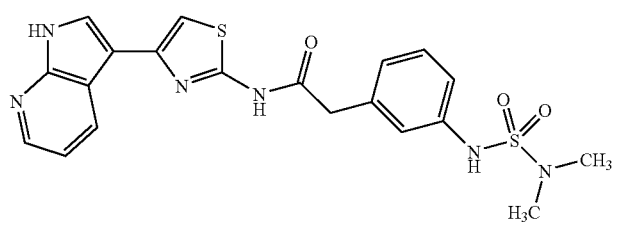
II-193
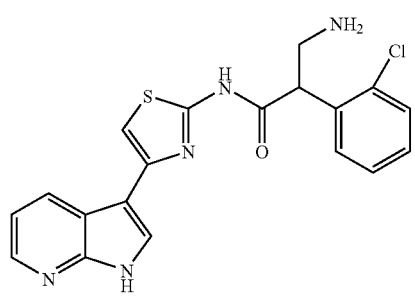
II-194
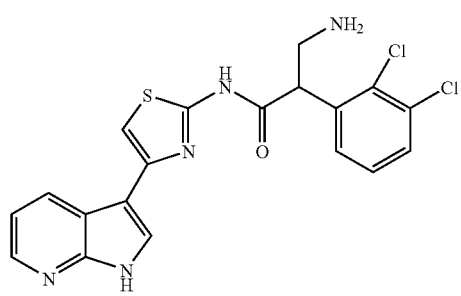
II-195

-continued
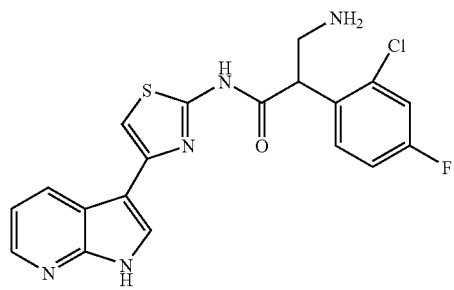
II-196
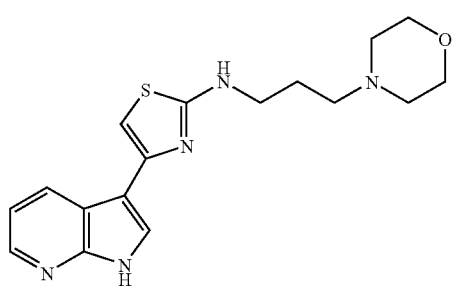
II-197
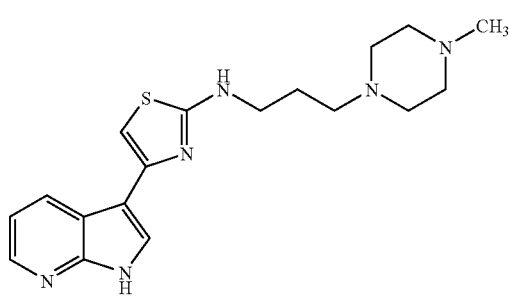
II-198
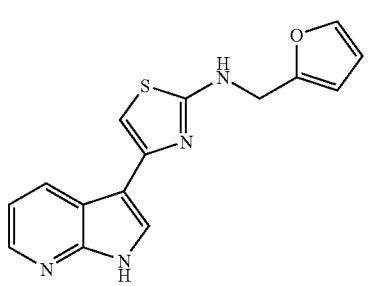
II-199
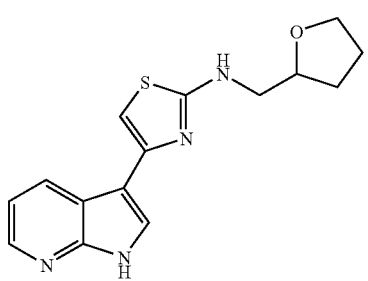
II-200

-continued
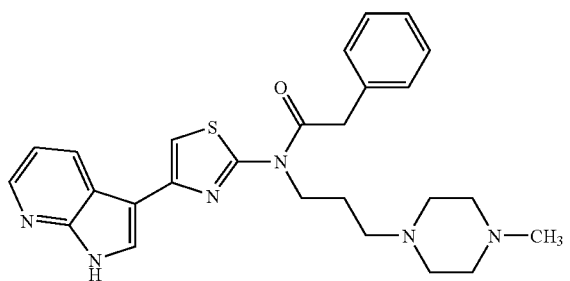
II-201
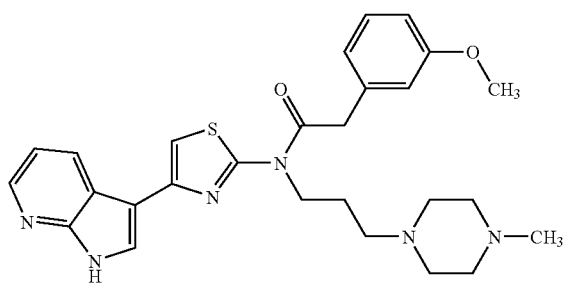
II-202
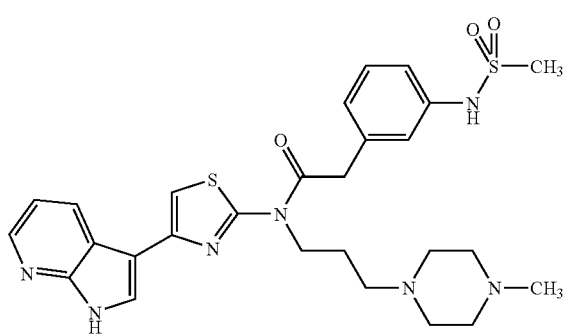
II-203
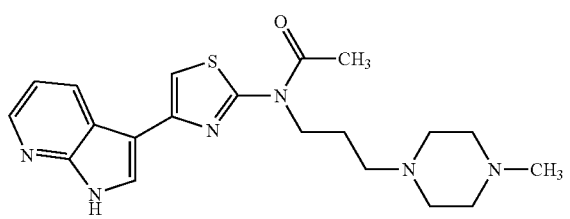
II-204
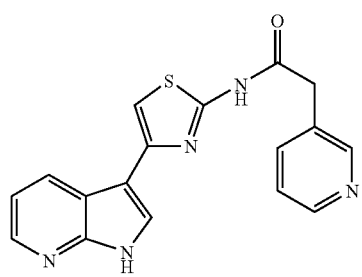
II-205

-continued
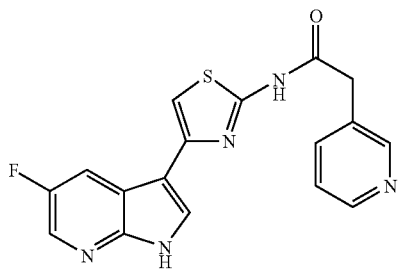
II-206
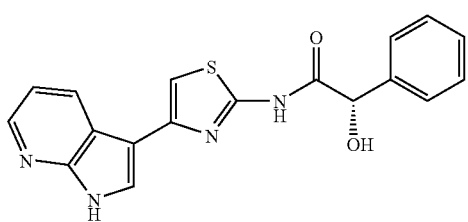
II-207
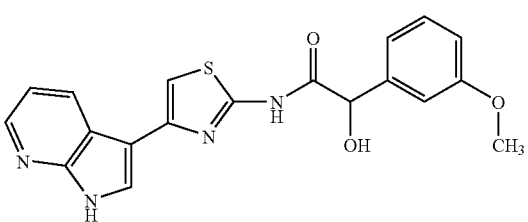
II-208
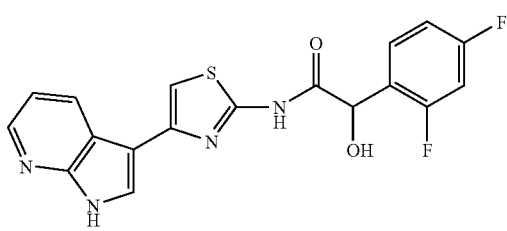
II-209
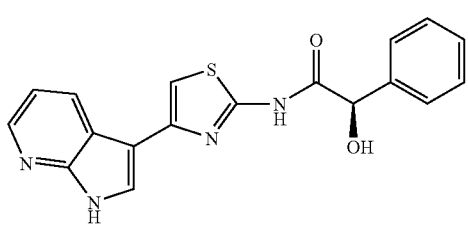
II-210
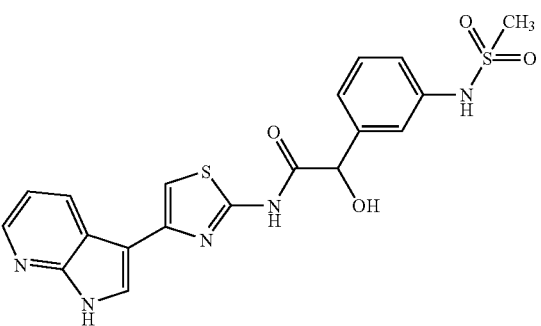
II-211

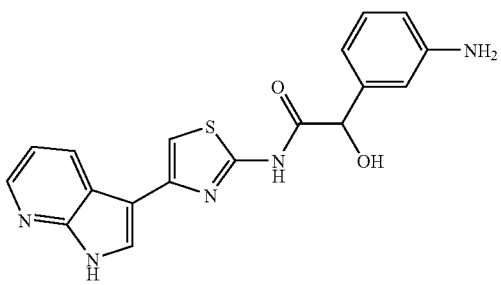
II-212
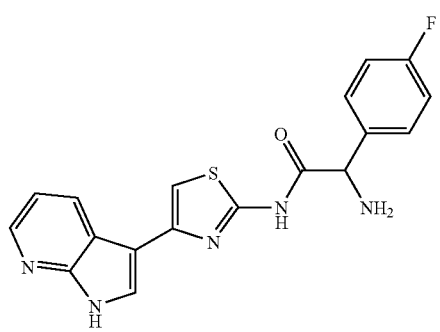
II-213
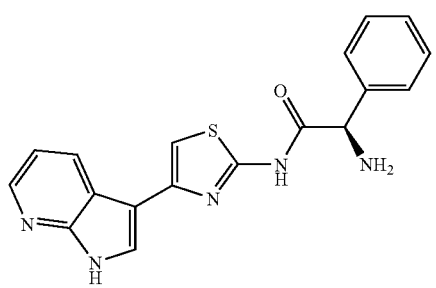
II-214
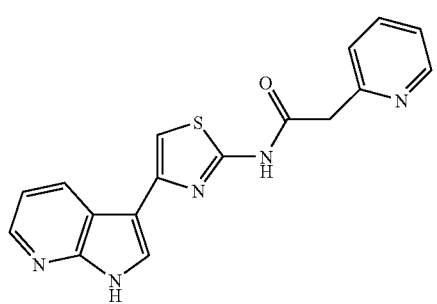
II-215
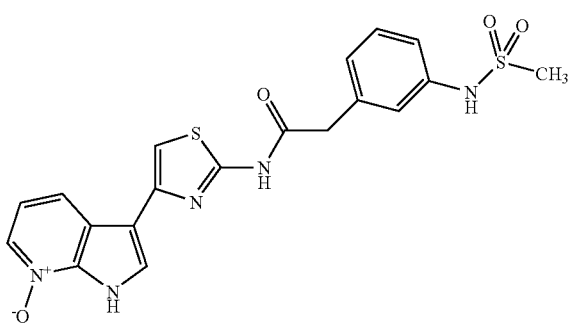
II-216

-continued
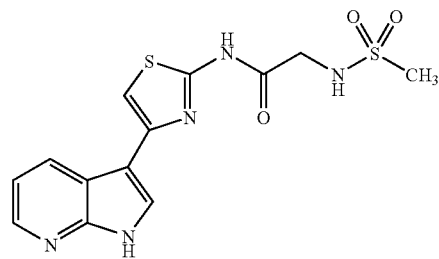
II-217
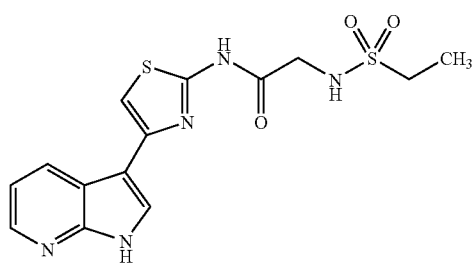
II-218
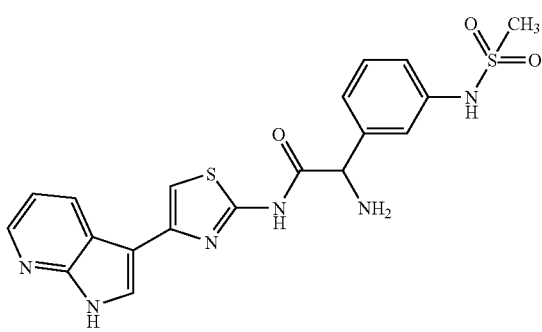
II-219
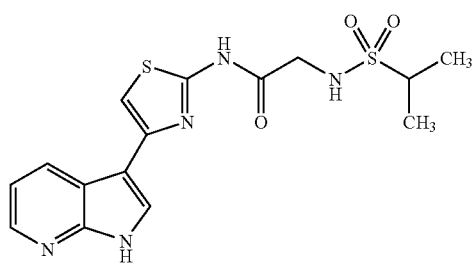
II-220
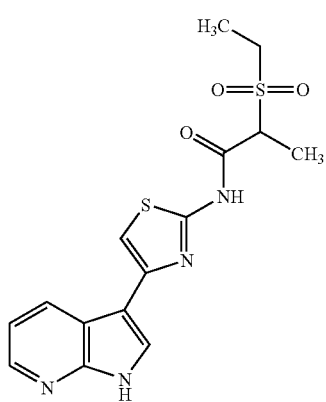
II-221

-continued
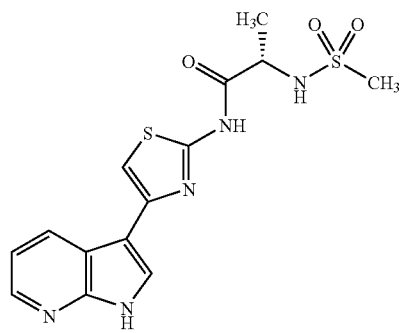
II-222
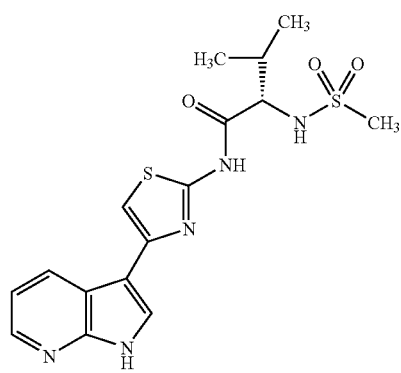
II-223
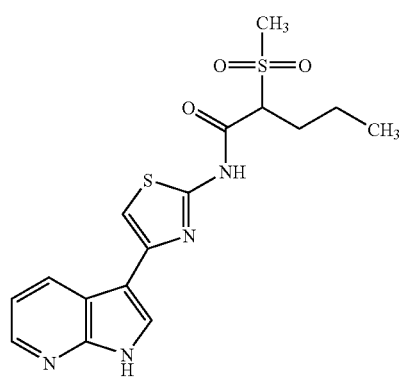
II-224
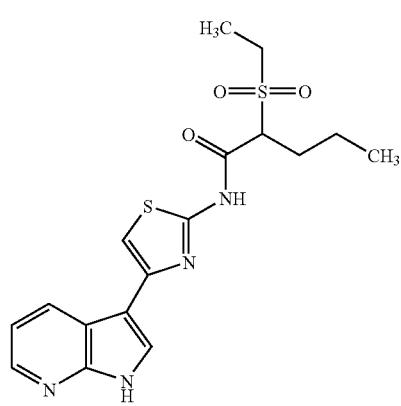
II-225

-continued
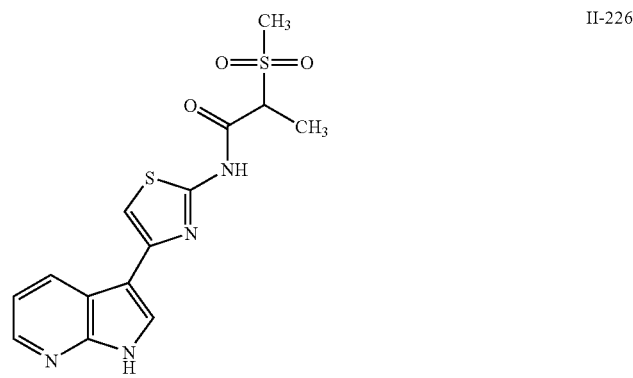
II-226
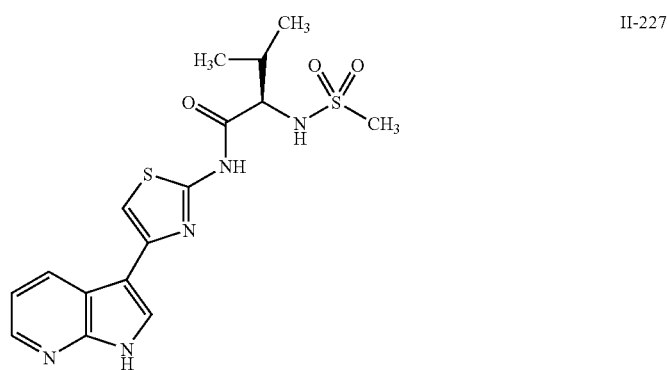
II-227
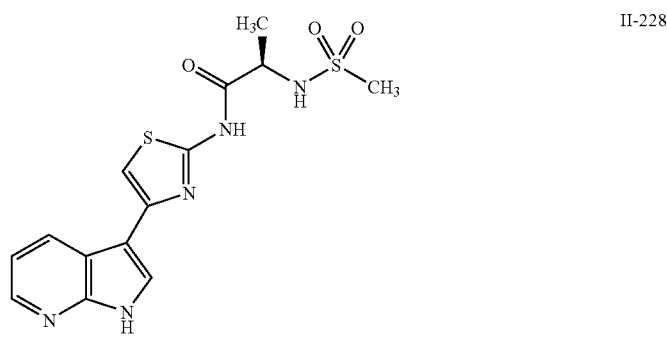
II-228
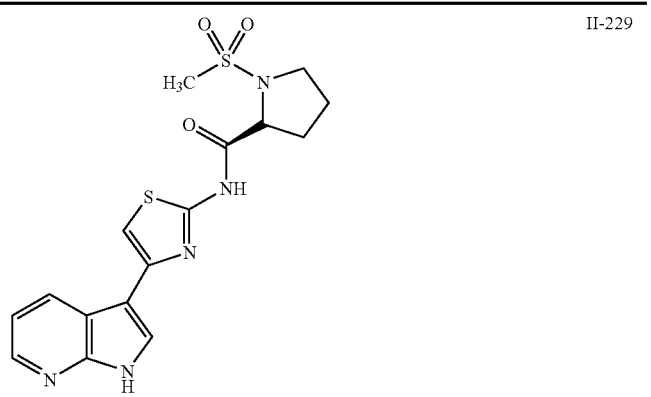
II-229

-continued
| | |
|---|---|
| 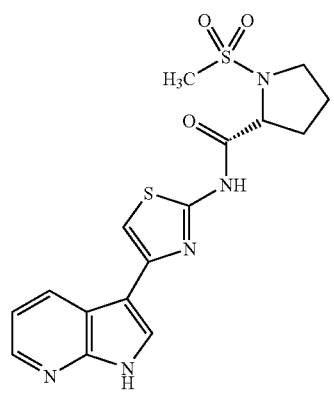 | II-230 |
| 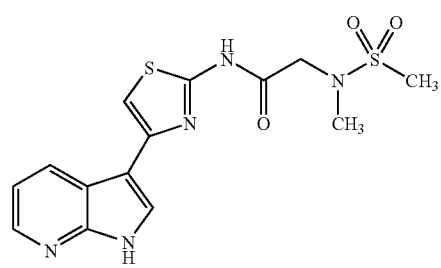 | II-231 |
| 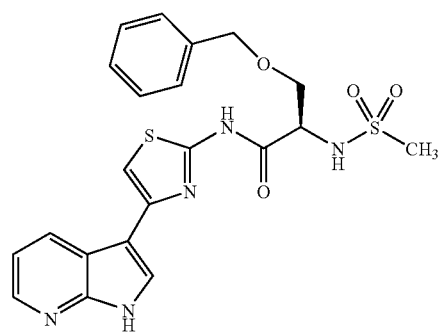 | II-232 |
| 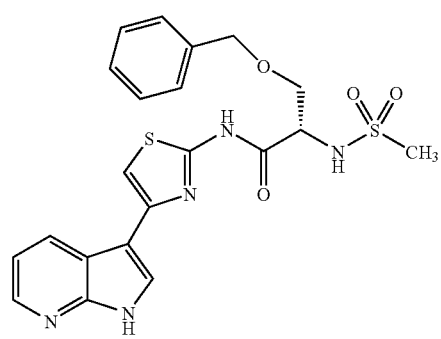 | II-233 |
| 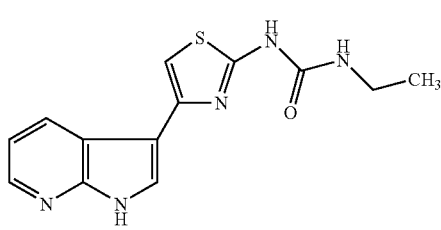 | II-234 |

-continued
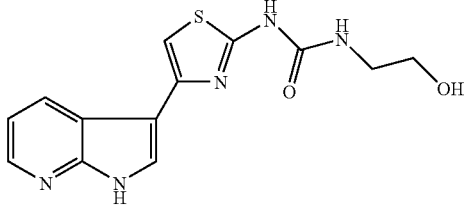
II-235
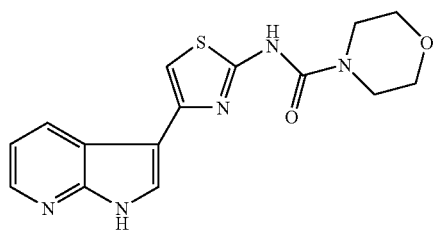
II-236
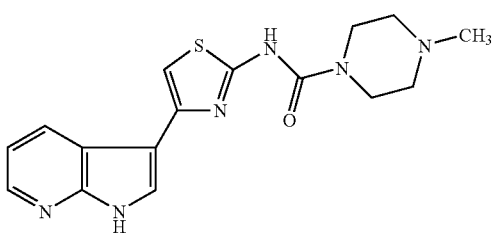
II-237
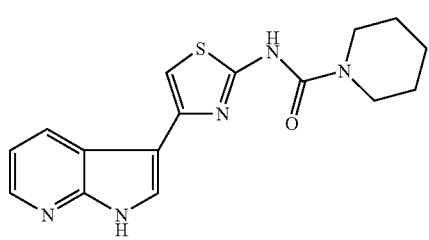
II-238
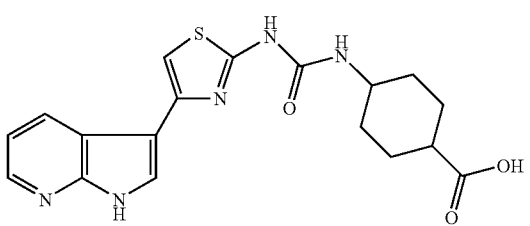
II-239
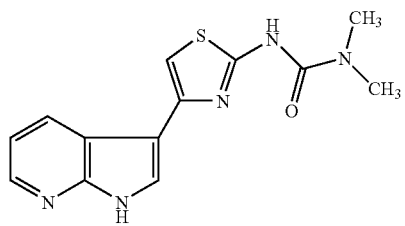
II-240
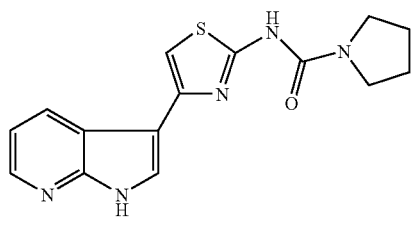
II-241

-continued
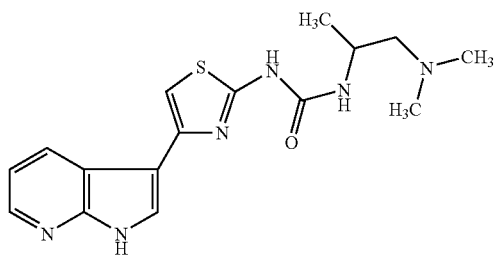
II-242
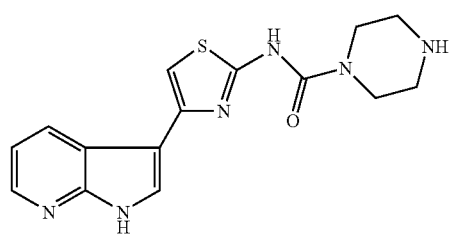
II-243
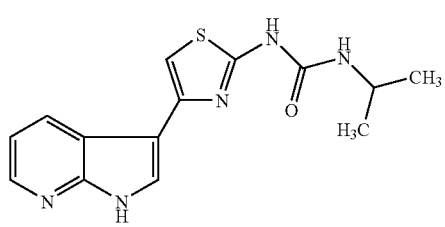
II-244
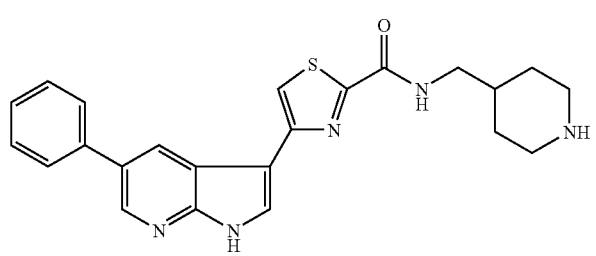
II-245
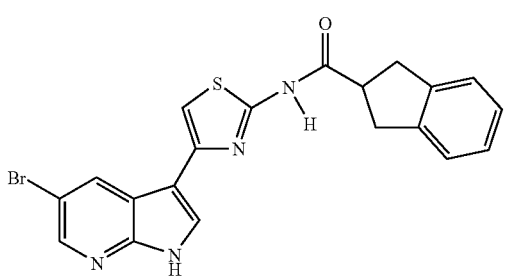
II-246
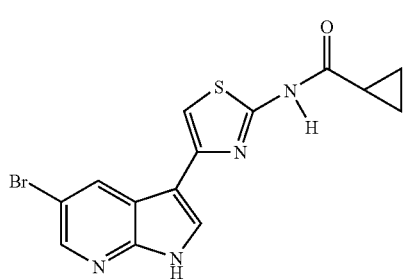
II-247

-continued
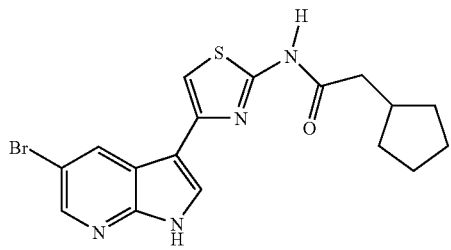
II-248
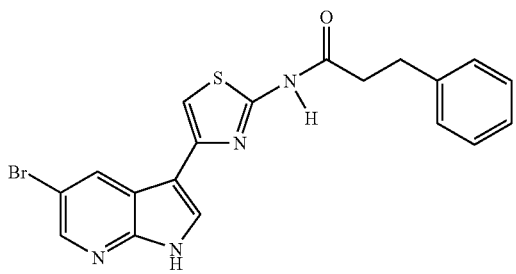
II-249
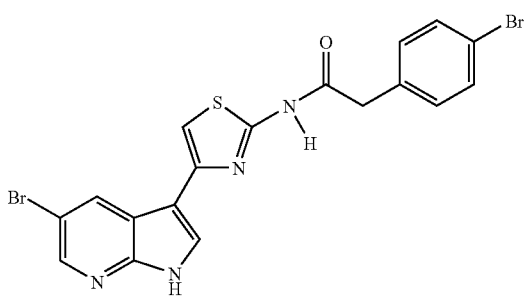
II-250
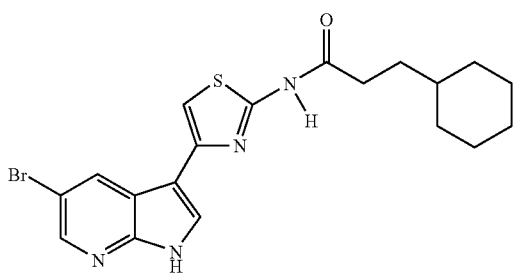
II-251
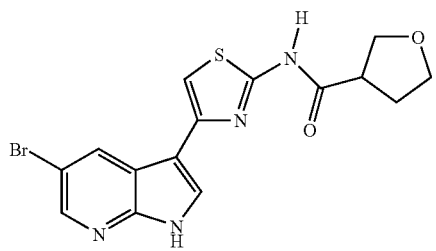
II-252
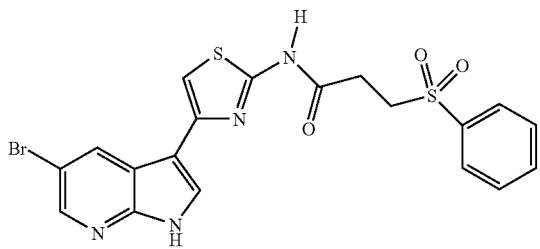
II-253

-continued

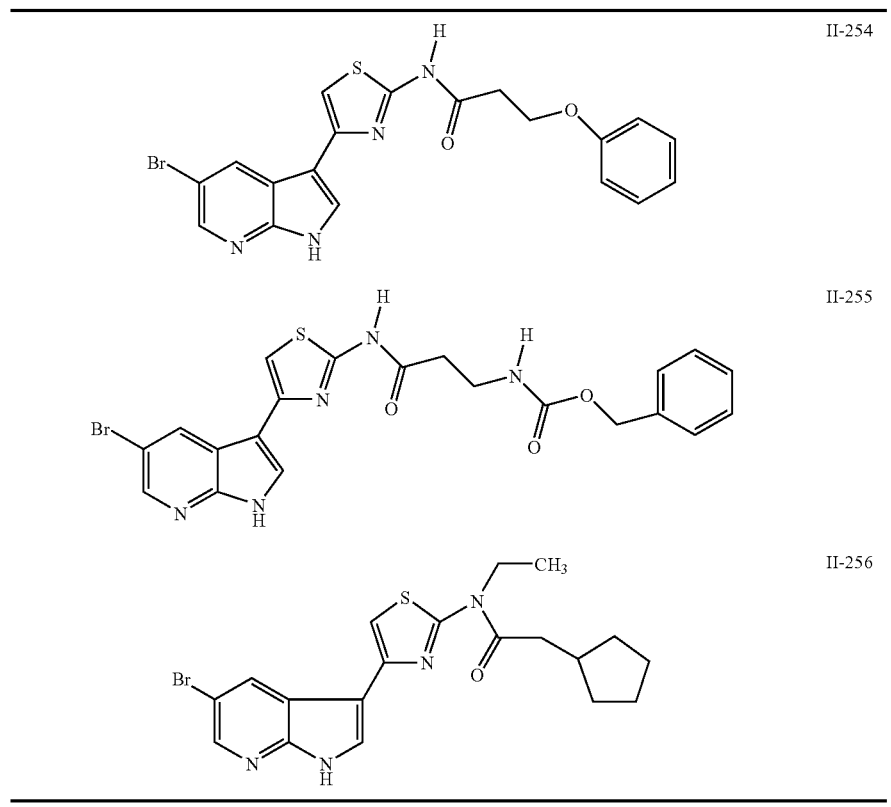

II-254

II-255

II-256

4. General Synthetic Methodology:

The compounds of this invention may be prepared in general by methods known to those skilled in the art for analogous compounds, as illustrated by the general schemes below, and the preparative examples that follow.

Scheme 1 below shows a general method for preparing compounds of formula I-A.

Scheme 1

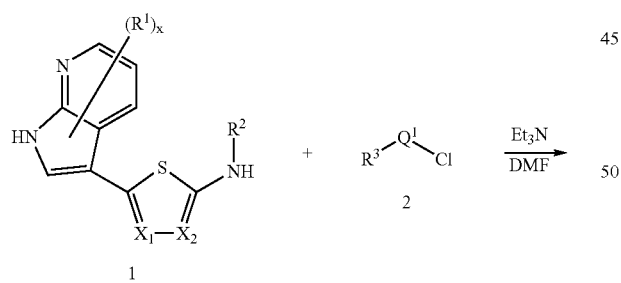

Specifically, as shown in Scheme 1, the intermediate amine 1 is reacted with a desired acid chloride 2 in the presence of dimethylformamide (DMF) and triethylamine ($Et_3N$) to yield desired compounds of formula I-A as described generally and in classes, subclasses and species herein.

In certain embodiments, for compounds of formula I-A, $Q^1$ is CO, and $R^3$ is $Q^2$-$Ar^1$, wherein $Q^2$ is $(CHR^6)_q$, wherein $R^6$ and q are defined generally and in classes, subclasses and species herein. Scheme 2 below depicts a general procedure for the preparation of compounds of formula I'-A, where $Q^1$ is CO, and $R^3$ is $Q^2$-$Ar^1$, wherein $Q^2$ is $(CHR^6)_q$:

Scheme 2

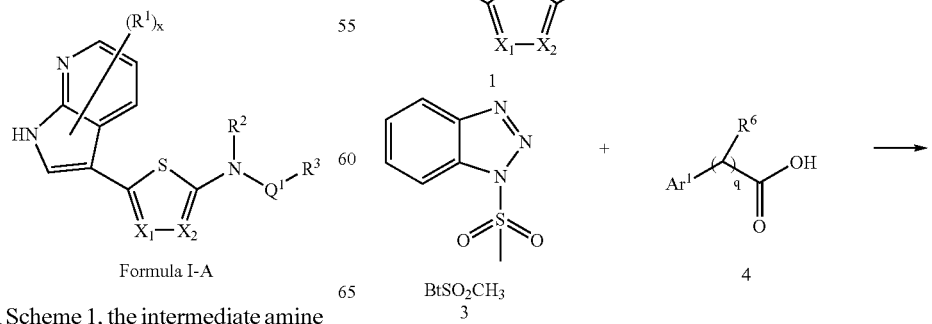

-continued

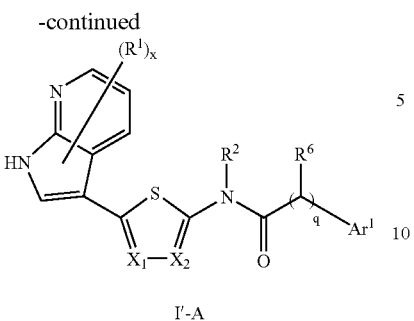

I'-A

Specifically, as shown in Scheme 2, the intermediate amine 1 is reacted with BtSO$_2$CH$_3$ 3 and a desired acid 4 in the presence of the presence of triethylamine (Et$_3$N) to yield desired compounds of formula I'-A as described generally and in classes, subclasses and species herein.

Scheme 3 below shows a general method for preparing intermediate compounds of formula 1-a.

Scheme 3

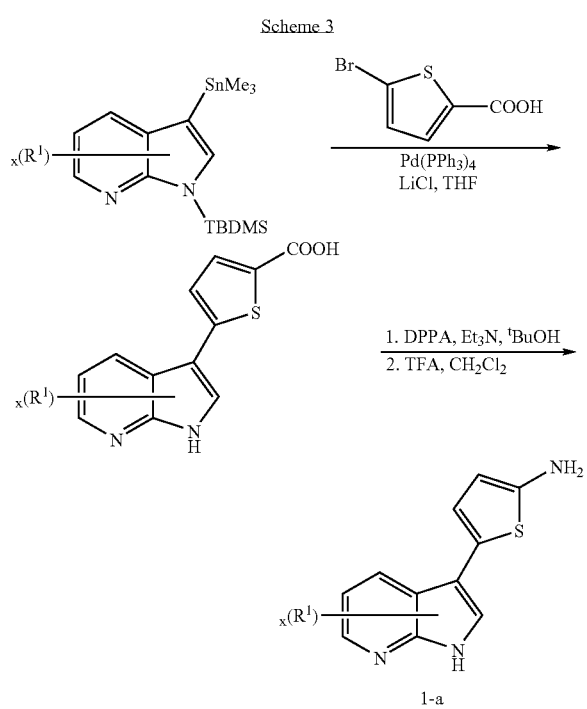

1-a

M. Alvarez, D. Fernandez, J. A. Joule, Synthesis, 1999, 615-620

Scheme 4 below shows a general method for preparing intermediate compounds of formula 1-b.

Scheme 4

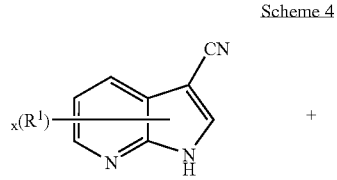

+

-continued

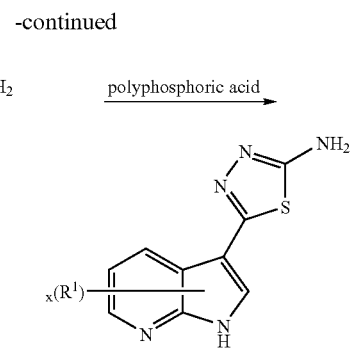

1-b

M. Allegreti et al., Org. Proc. Res. Dev., 2003, 7, 209-213

Scheme 5 below shows a general method for preparing intermediate compounds of formula 1-c.

Scheme 5

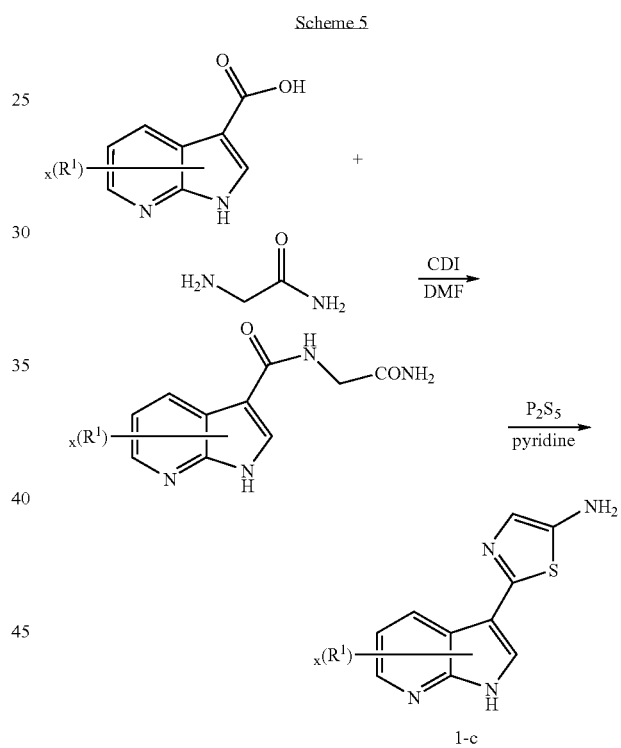

1-c

M. Allegreti et al., Org. Proc. Res. Dev., 2003, 7, 209-213

Scheme 6 below shows a general method for preparing compounds of formula I-B.

Scheme 6

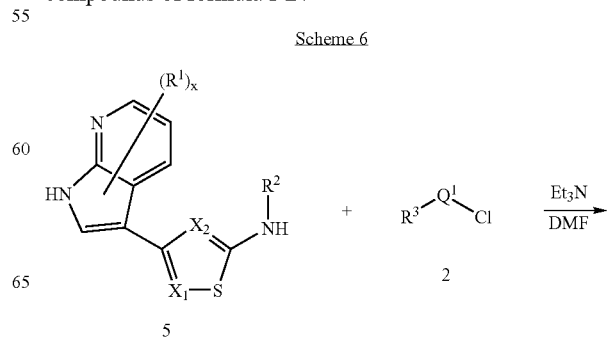

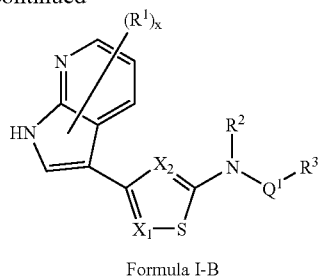

Formula I-B

Specifically, as shown in Scheme 6, the intermediate amine 5 is reacted with a desired acid chloride 2 in the presence of dimethylformamide (DMF) and triethylamine (Et₃N) to yield desired compounds of formula I-B as described generally and in classes, subclasses and species herein.

In certain embodiments, for compounds of formula I-B, $Q^1$ is CO, and $R^3$ is $Q^2$-$Ar^1$, wherein $Q^2$ is $(CHR^6)_q$, wherein $R^6$ and q are defined generally and in classes, subclasses and species herein. Scheme 4 below depicts a general procedure for the preparation of compounds where $Q^1$ is CO, and $R^3$ is $Q^2$-$Ar^1$, wherein $Q^2$ is $(CHR^6)_q$:

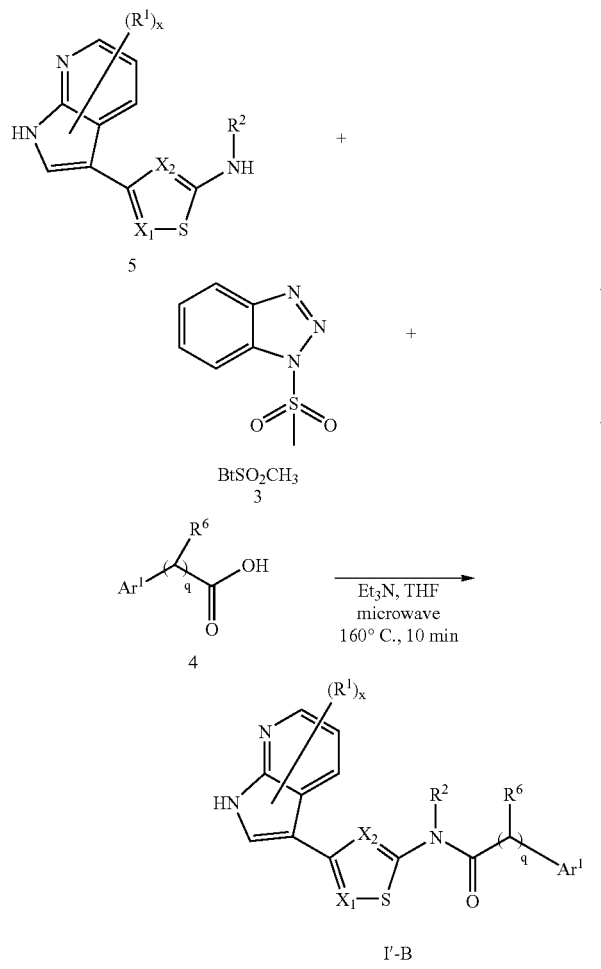

Specifically, as shown in Scheme 7, the intermediate amine 5 is reacted with BtSO₂CH₃ 3 and a desired acid 4 in the presence of the presence of triethylamine (Et₃N) to yield desired compounds of formula I'-B as described generally and in classes, subclasses and species herein.

Scheme 8 below shows a general method for preparing intermediate compounds of formula 5-a.

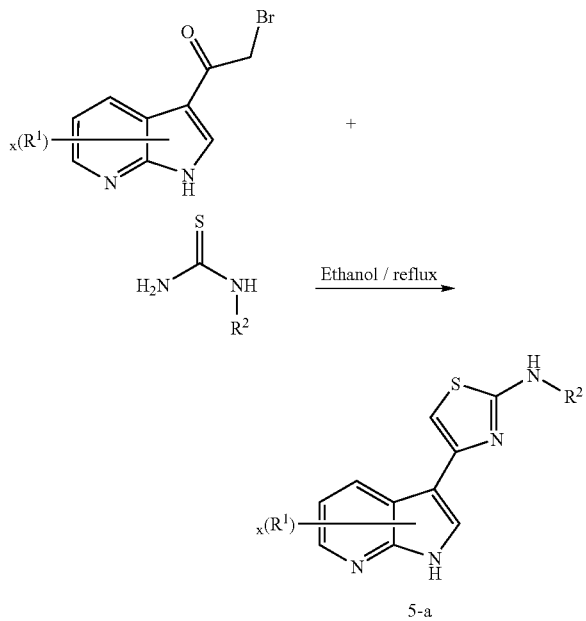

Scheme 9 below shows a general method for preparing intermediate compounds of formula 5-b.

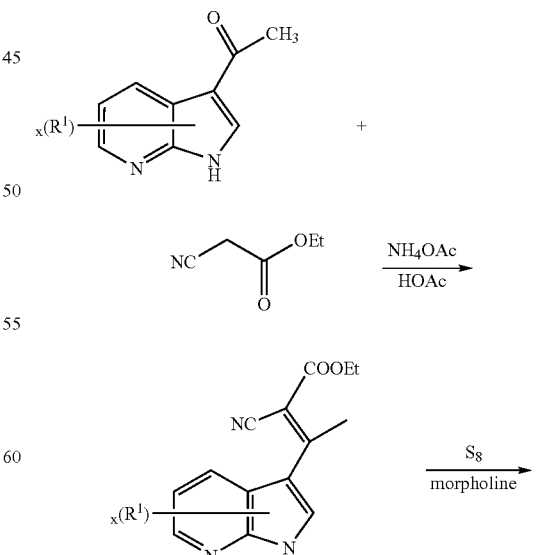

-continued

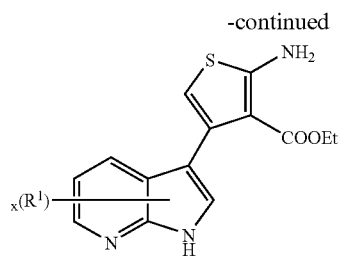

K-S. Yeung et al.,
Tetrahedron Lett., 2002, 43, 5793-5795

Scheme 10 below shows a general method for preparing compounds of formula I-C.

Scheme 10

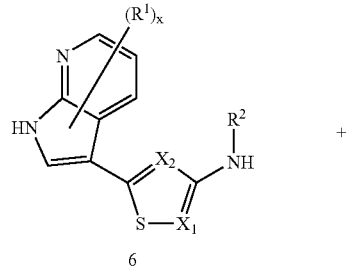

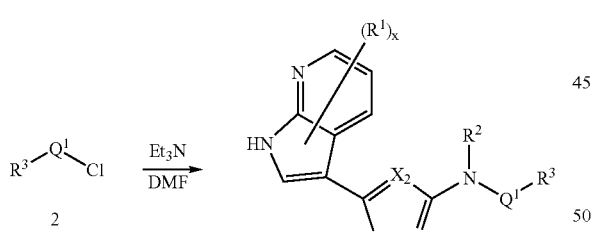

Formula I-C

Specifically, as shown in Scheme 10, the intermediate amine 6 is reacted with a desired acid chloride 2 in the presence of dimethylformamide (DMF) and triethylamine (Et₃N) to yield desired compounds of formula I-C as described generally and in classes, subclasses and species herein.

In certain embodiments, for compounds of formula I-C, $Q^1$ is CO, and $R^3$ is $Q^2$-$Ar^1$, wherein $Q^2$ is $(CHR^6)_q$, wherein $R^6$ and q are defined generally and in classes, subclasses and species herein. Scheme 6 below depicts a general procedure for the preparation of compounds where $Q^1$ is CO, and $R^3$ is $Q^2$-$Ar^1$, wherein $Q^2$ is $(CHR^6)_q$:

Scheme 11

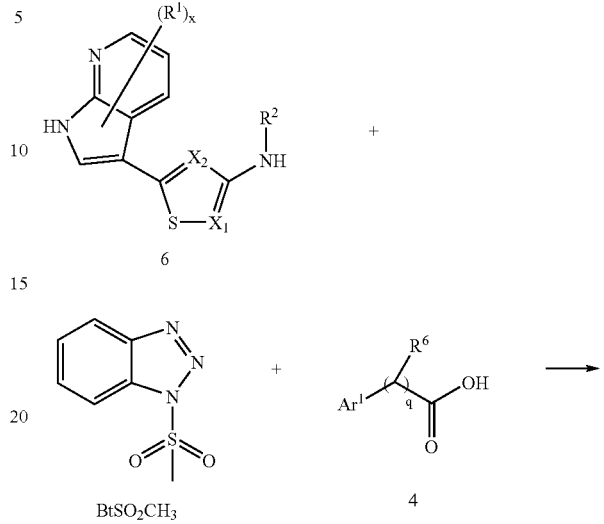

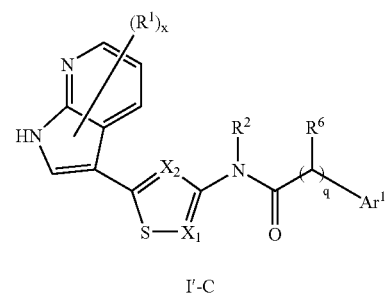

Specifically, as shown in Scheme 11, the intermediate amine 6 is reacted with BtSO₂CH₃ 3 and a desired acid 4 in the presence of the presence of triethylamine (Et₃N) to yield desired compounds of formula I'-C as described generally and in classes, subclasses and species herein.

Scheme 12 below shows a general method for preparing intermediate compounds of formula 6-a.

Scheme 12

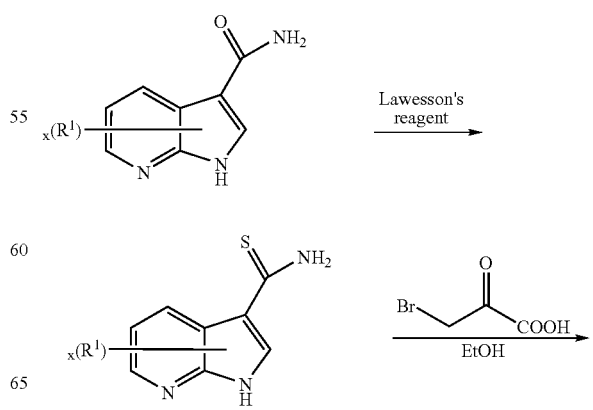

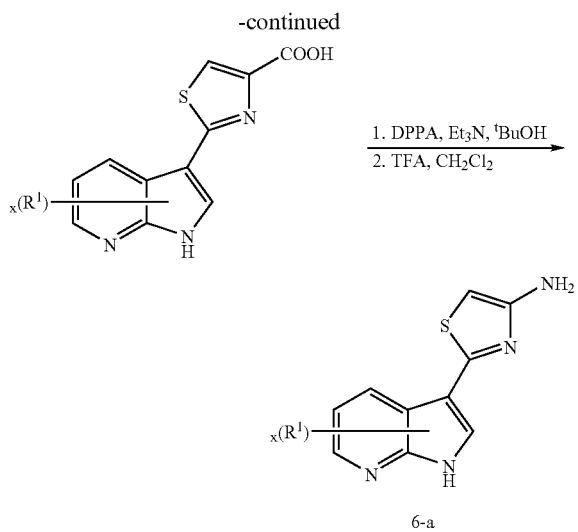

S. W. Schneller and J-K. Luo, J. Org. Chem., 1980, 45, 4045-4048

Scheme 13 below shows a general method for preparing intermediate compounds of formula 6-b.

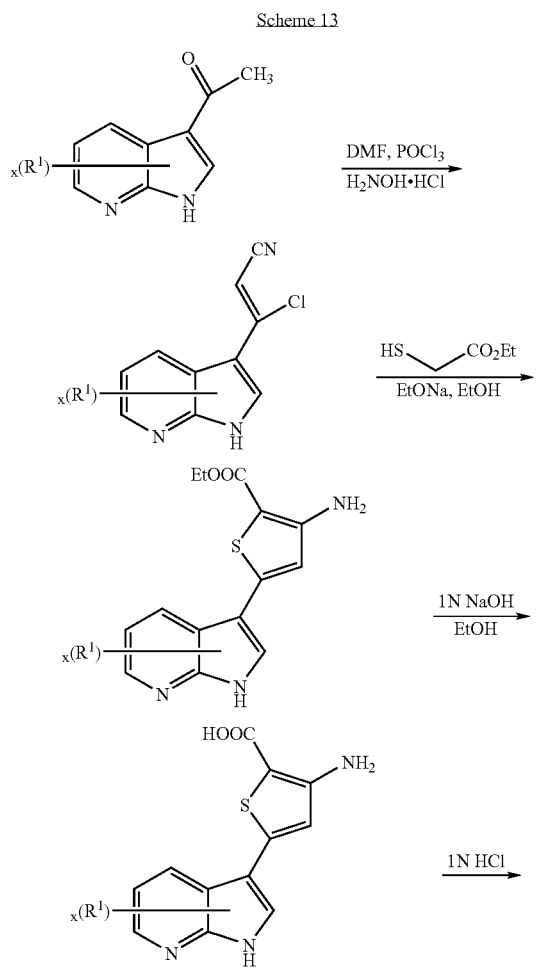

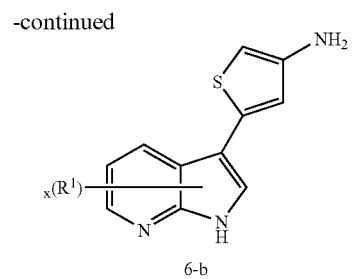

K-S. Yeung et al., Tetrahedron Lett., 2002, 43, 5793-5795

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimrnune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In other embodiments, the compounds are useful for the treatment of hypertension, cerebral vasospasm, coronary vasospasm, bronchial asthma, preterm labor, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, benign prostatic hyperplasia, or atherosclerosis.

In still other embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a ROCK, ERK, or GSK kinase, or members of the AGC sub-family of protein kinases (e.g., PKA, PDK, $p70^{S6K}$-1 and -2, and PKB).

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of ROCK, ERK, or GSK kinase, or members of the AGC sub-family of protein kinases (e.g., PKA, PDK, $p70^{S6K}$-1 and -2, and PKB), and thus, without wishing to be bound by any particular theory, the compounds and compositions are particularly useful for treating or lessening the severity of a disease, condition, or disorder where activation of one or more of ROCK, ERK, or GSK kinase, or members of the AGC sub-family of protein kinases (e.g., PKA, PDK, $p70^{S6K}$-1 and -2, and PKB) is implicated in the disease, condition, or disorder. When activation of ROCK, ERK, or GSK kinase, or members of the AGC sub-family of protein kinases (e.g., PKA, PDK, $p70^{S6K}$-1 and -2, and PKB) is implicated in a particular disease, condition, or disorder, the disease, condition, or disorder may also be referred to as "ROCK, ERK, GSK, AGC (e.g., PKA, PDK, $p70^{S6K}$-1 and -2, and PKB)-mediated disease" or disease symptom. Accordingly, in another aspect, the present invention provides a method for treating or lessening the severity of a disease, condition, or disorder where activation or one or more of ROCK, ERK, or GSK kinase, or members of the AGC sub-family of protein kinases (e.g., PKA, PDK, $p70^{S6K}$-1 and -2, and PKB) is implicated in the disease state.

The activity of a compound utilized in this invention as an inhibitor of ROCK, ERK, or GSK kinase, or members of the AGC sub-family of protein kinases (e.g., PKA, PDK, $p70^{S6K}$-1 and -2, and PKB), may be assayed in vitro, in vivo or in a cell line. In vitro assays include assays that determine inhibition of either the phosphorylation activity or ATPase activity of activated ROCK, ERK, or GSK kinase, or members of the AGC sub-family of protein kinases (e.g., PKA, PDK, $p70^{S6K}$-1 and -2, and PKB). Alternate in vitro assays quantitate the ability of the inhibitor to bind to ROCK, ERK, or GSK kinase, or members of the AGC sub-family of protein kinases (e.g., PKA, PDK, $p70^{S6K}$-1 and -2, and PKB). Inhibitor binding may be measured by radiolabelling the inhibitor prior to binding, isolating the inhibitor/ROCK, inhibitor/ERK, inhibitor/GSK kinase, or inhibitor/AGC (e.g., PKA, PDK, $p70^{S6K}$-1 and -2, and PKB) complex and determining the amount of radiolabel bound. Alternatively, inhibitor binding may be determined by running a competition experiment where new inhibitors are incubated with ROCK, ERK, or GSK kinase, or members of the AGC sub-family of protein kinases (e.g., PKA, PDK, $p70^{S6K}$-1 and -2, and PKB) bound to known radioligands.

The term "measurably inhibit", as used herein means a measurable change in ROCK, ERK, or GSK kinase, or members of the AGC sub-family of protein kinases (e.g., PKA, PDK, $p70^{S6K}$-1 and -2, and PKB) activity between a sample comprising said composition and a ROCK, ERK, or GSK kinase, or members of the AGC sub-family of protein kinases (e.g., PKA, PDK, $p70^{S6K}$-1 and -2, and PKB) kinase and an equivalent sample comprising ROCK, ERK, or GSK kinase, or members of the AGC sub-family of protein kinases (e.g., PKA, PDK, $p70^{S6K}$-1 and -2, and PKB) kinase in the absence of said composition.

The terms "AKT-mediated disease" or "AKT-mediated condition", as used herein, mean any disease or other deleterious condition in which AKT is known to play a role. The terms "AKT-mediated disease" or "AKT-mediated condition" also mean those diseases or conditions that are alleviated by treatment with a AKT inhibitor. AKT-mediated diseases or conditions include, but are not limited to, proliferative disorders, cancer, and neurodegenerative disorders. The association of AKT, also known as protein kinase B, with various diseases has been described [Khwaja, A. *Nature* 1999, 401, 33-34; Yuan, Z. Q. et al., *Oncogene* 2000, 19, 2324-2330; Namikawa, K. et al., *The Journal of Neuroscience* 2000, 20, 2875-2886].

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from pancreatic, prostate, or ovarian cancer.

The term "PKA-mediated condition" or "disease", as used herein, means any disease or other deleterious condition in which PKA is known to play a role. The term "PKA-mediated condition" or "disease" also means those diseases or conditions that are alleviated by treatment with a PKA inhibitor. PKA-mediated diseases or conditions include, but are not limited to, proliferative disorders and cancer.

The term "$p70^{S6K}$-mediated condition" or "disease", as used herein, means any disease or other deleterious condition in which $p70^{S6K}$ is known to play a role. The term "$p70^{S6K}$-mediated condition" or "disease" also means those diseases or conditions that are alleviated by treatment with a $p70^{S6K}$ inhibitor. $p70^{S6K}$-mediated diseases or conditions include, but are not limited to, proliferative disorders, such as cancer and tuberous sclerosis.

The terms "ERK-mediated disease" or "ERK-mediated condition", as used herein mean any disease or other deleterious condition in which ERK is known to play a role. The terms "ERK-2-mediated disease" or "ERK-2-mediated condition" also mean those diseases or conditions that are alleviated by treatment with an ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders, and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. ERK-2 protein kinase and its implication in various diseases has been described [Bokemeyer et al., *Kidney Int.* 1996, 49, 1187; Anderson et al., *Nature* 1990, 343, 651; Crews et al., *Science* 1992, 258, 478; Bjorbaek et al., *J. Biol. Chem.* 1995, 270, 18848; Rouse et al., *Cell* 1994, 78, 1027; Raingeaud et al., *Mol. Cell Biol.* 1996, 16, 1247; Chen et al., *Proc. Natl. Acad. Sci. USA* 1993, 90, 10952; Oliver et al., *Proc. Soc. Exp. Biol. Med.* 1995, 210, 162; Moodie et al., *Science* 1993, 260, 1658; Frey and Mulder, *Cancer Res.* 1997, 57, 628; Sivaraman et al., *J. Clin. Invest.* 1997, 99, 1478; Whelchel et al., *Am. J. Respir. Cell Mol. Biol.* 1997, 16, 589].

The term "GSK-3-mediated disease" as used herein, means any disease or other deleterious condition or disease in which GSK-3 is known to play a role. Such diseases or conditions include, without limitation, autoimmune diseases, inflammatory diseases, metabolic, neurological and neurodegenerative diseases (e.g., Alzheimer's disease, Huntington's disease, Parkinson's disease and basal ganglia movement disorders, chorea, dystonia, Wilson Disease, Pick Disease, frontal lobe degeneration, progressive supranuclear palsy (PSP), Creutzfeldt-Jakob Disease, taupathology and corticobasal degeneration (CBD)), psychotic disorders (e.g., schizophrenia, AIDS-associated dementia, depression, bipolar disorder, and anxiety disorders), cardiovascular diseases, allergy, asthma, diabetes, amyotrophic lateral sclerosis (AML, Lou Gehrig's disease), multiple sclerosis (MS), cardiomyocyte hypertrophy, reperfusion/ischemia, stroke, and baldness.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, endothelial dysfunction, Alzheimer's disease, or benign prostatic hyperplasia. In other embodiments, such conditions in which ROCK is known to play a role include, without limitation, hypertension, cerebral vasospasm, coronary vasospasm, bronchial asthma, preterm labor, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, benign prostatic hyperplasia, or atherosclerosis.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

The term "Tec family tyrosine kinases-mediated condition", as used herein means any disease or other deleterious condition in which Tec family kinases are known to play a role. Such conditions include, without limitation, autoimmune, inflammatory, proliferative, and hyperproliferative diseases and immunologically-mediated diseases including rejection of transplanted organs or tissues and Acquired Immunodeficiency Syndrome (AIDS).

For example, Tec family tyrosine kinases-mediated conditions include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additionally, Tec family tyrosine kinases diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Tec family tyrosine kinases-mediated conditions also include diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Tec family kinases-mediated conditions also include diseases and disorders of the skin, including, without limitation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, greata and vernal conjunctivitis.

Tec family tyrosine kinases-mediated conditions also include diseases and disorders of the gastrointestinal tract, including, without limitation, Coeliac disease, proctitis, eosinophilic gastro-enteritis, mastocytosis, pancreatitis, Crohn's disease, ulcerative colitis, food-related allergies which have effects remote from the gut, e.g. migraine, rhinitis and eczema.

Tec family tyrosine kinases-mediated conditions also include those diseases and disorders of other tissues and systemic disease, including, without limitation, multiple sclerosis, atherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

Tec family tyrosine kinases-mediated conditions also include allograft rejection including, without limitation, acute and chronic allograft rejection following for example transplantation of kidney, heart, liver, lung, bone marrow, skin and cornea; and chronic graft versus host disease.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting ROCK, ERK, GSK, or AGC (e.g., PKA, PDK, p70$^{S6K}$-1 and -2, and PKB) activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ROCK, ERK, GSK, or AGC (e.g., PKA, PDK, p70$^{S6K}$-1 and -2, and PKB) kinase activity in a biological sample is useful for a variety of purposes that are known to one of skill in the art. Examples of such purposes include, but are not limited to, blood transfusion, organ-transplantation, biological specimen storage, and biological assays.

EXAMPLES

General Experimental Procedures:

As depicted in Schemes 14, 15, 16, 17, and 18 below, in certain exemplary embodiments, compounds are prepared according to the following general procedures. It will be appreciated that although the general methods depict the synthesis of compounds of general formula VII, the following general methods can be applied to all compounds and subclasses and species of each of these compounds, as described herein.

General Method A: Acylation of Amines

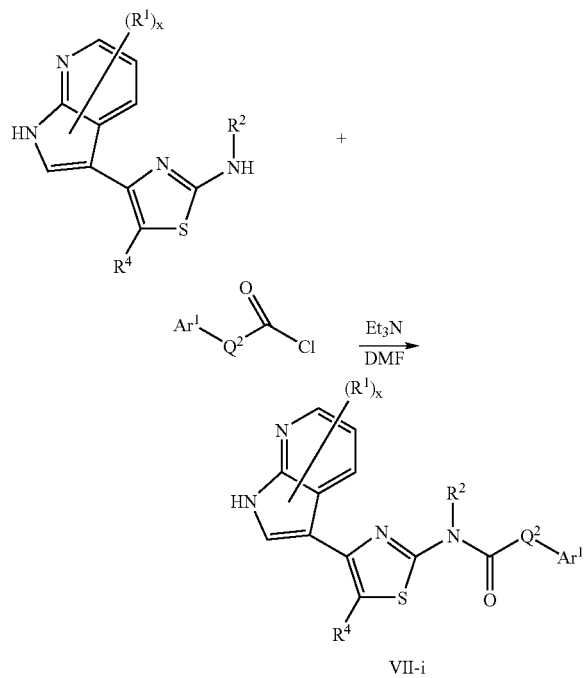

0.25 mmol of amine, and 0.5 mmol of acid chloride were dissolved in 2 mL of anhydrous DMF. 0.75 mmol of Et₃N was then added to the reaction mixture, and the mixture was stirred at RT for overnight. After completion of the reaction, EtOAc was added, the organic layer was washed with H₂O and brine, and was then dried over Na₂SO₄. Removal of the solvent gave a solid, VII-i, which was further purified by preparative HPLC.

General Method B: Acylation of Amines

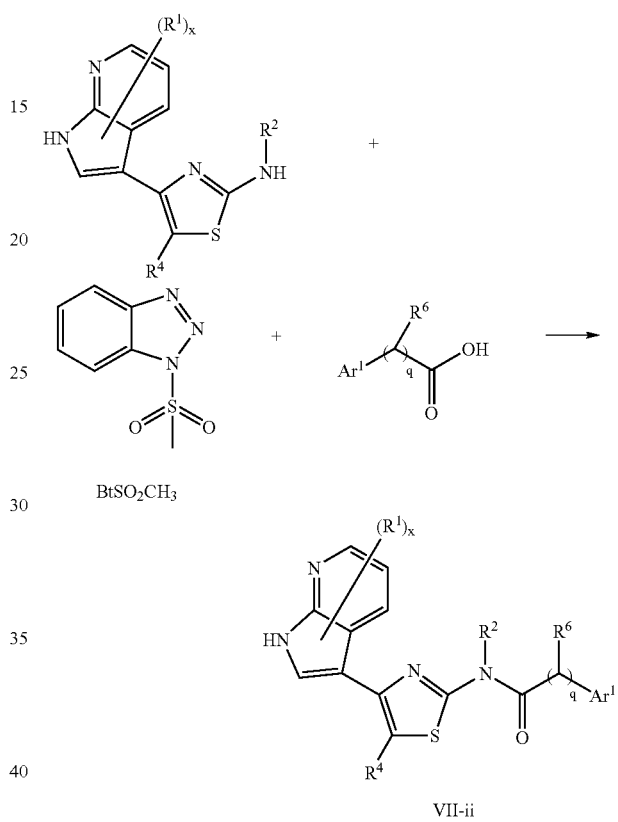

A mixture of BtSO₂CH₃ (preparation described below) (0.25 mmol), acid (0.25 mmol), and Et₃N (0.35 mmol) was refluxed in dry THF for about 20 min. Amine (0.25 mmol) was then added to the reaction mixture, and the mixture was refluxed for 18 h. After the mixture was concentrated, EtOAc (5 mL) was added, and the organic phase was washed with 2 M NaOH and dried over anhydrous MgSO₄. Removal of the solvent gave a solid, VII-ii, which was purified by preparative HPLC.

General Method C: Acylation of Amines

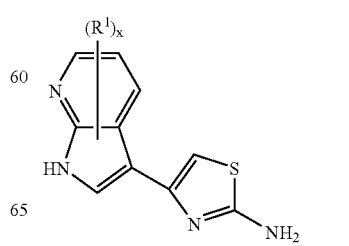

-continued

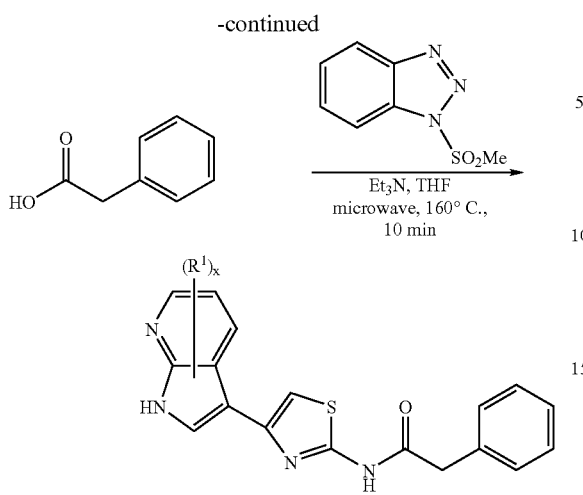

Amine (1 mmol), carboxylic acid (1.2 mmol) and Bt-SO₂Me (1.2 mmol) are combined in a microwave reaction vessel. Anhydrous THF (2 mL) is added followed by triethylamine (2 mmol) and the mixture heated by microwave irradiation at 160° C. for 10 minutes. Product is isolated by precipitation following addition of acetonitrile, or by preparative HPLC.

Standard Protection and Deprotection of Amino and Hydroxyl Functionalities:

General Method D: Protection of Amino Groups

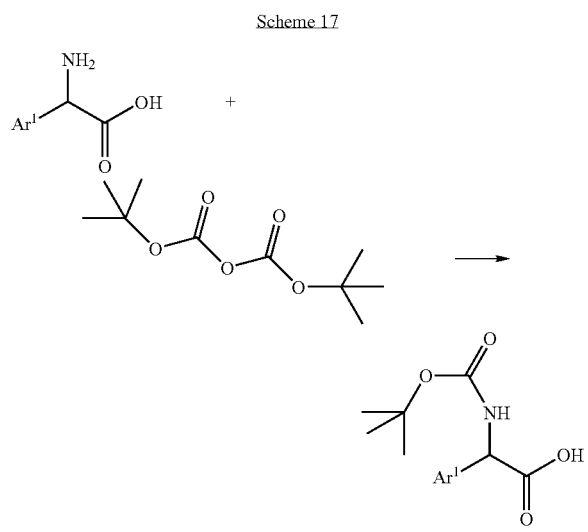

0.25 mmol of amine, 0.25 mmol of Boc anhydride were mixed in 2 mL of anhydrous CH₂Cl₂. To the reaction mixture, 0.75 mmol of Et₃N was added and the mixture was stirred at RT for overnight. The solvent was evaporated to give the Boc protected amine.

General Method E: Deprotection of Boc-Protected Amines

To the Boc protected amine (0.25 mmol) in a vial, 2 mL 4N HCl in dioxane was added and the reaction mixture was stirred at RT for 30 min. The solvent was evaporated to give the free amine product.

General Method F: Protection of Phenols and Alcohols

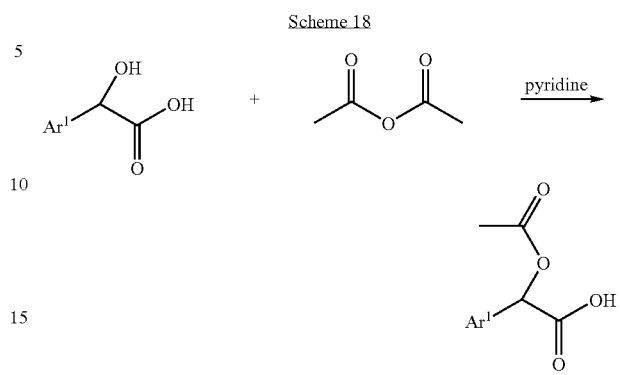

Hydroxy acid (2.5 mol) was stirred with acetic anhydride (0.57 mL, 6 mol) in pyridine (5 mL) overnight and then evaporated in vacuo. The resulting oil was partitioned between EtOAc and 1N HCl and the resulting organic layer washed successively with 1 N HCl, water and brine, dried over MgSO₄, and evaporated to dryness.

General Method G: Deprotection of Acetylated Phenols and Alcohols

The acetyl-protected alcohol or phenol (0.25 mmol) was dissolved in EtOH, 0.5 mL 2N NaOH was added and the mixture was stirred at RT for 1 h. The solvent was evaporated and redissolved in DMF/CH₃CN/H₂O, and subjected to preparative HPLC for purification.

General Method H: Preparation of Phenylacetic Acids

Substituted benzaldehyde (5 mmol) and zinc iodide (10 mg) were dissolved or suspended in anhydrous acetonitrile (5-10 mL). Trimethylsilyl cyanide (12 mmol) was added dropwise and the mixture stirred at room temperature overnight. The mixture was rotary evaporated and the residue dissolved in glacial acetic acid (2 mL) and concentrated hydrochloric acid (3 mL). Tin (II) chloride dihydrate (12 mmol) was added and the mixture heated to reflux for 1-2 hours. To the cooled mixture was added water (20 mL) and the mixture was extracted with methylene chloride (3×15 mL). The extracts were washed with water (×2) and brine and dried over MgSO₄. The solution is concentrated and the product precipitated by addition of hexane.

General Method I: Preparation of α-Hydroxyphenylacetic Acids

Substituted benzaldehyde (5 mmol) and zinc iodide (10 mg) were dissolved or suspended in anhydrous acetonitrile (5-10 mL). Trimethylsilyl cyanide (12 mmol) was added dropwise and the mixture stirred at room temperature overnight. The mixture was rotary evaporated and the residue dissolved in glacial acetic acid (2 mL) and concentrated hydrochloric acid (3 mL) and the mixture heated to reflux for 1-2 hours. To the cooled mixture was added water (20 mL) and the mixture was extracted with methylene chloride (3×15 mL). The extracts were washed with water (×2) and brine and dried over MgSO₄. The solution is concentrated and the product precipitated by addition of hexane.

Although the preparation of certain amines are described below, it will be appreciated that a variety of alternate amines can be prepared as described generally below and can be utilized in the preparation of compounds of the invention.

Experimental Procedures

Preparation of N-(1-Methanesulfonyl)benzotriazole (BtSO$_2$CH$_3$)

To an ice-cold solution of benzotriazole (11.9 g, 0.10 mol) and pyridine (12.0 g, 0.16 mol) in dry toluene (120 mL) was added methylsulfonyl chloride (9.3 mL, 0.12 mol) in toluene (30 mL) dropwise. The mixture was then stirred overnight at room temperature. EtOAc (150 mL) and H$_2$O (100 mL) were added, the organic layer was separated, successively washed with water and brine, and dried over anhydrous MgSO$_4$. Removal of solvents in vacuo gave BtSO$_2$CH$_3$ as a white solid.

The synthesis of certain exemplary acids is described below. It will be appreciated that a variety of acids can be prepared according to the general methods described below.

Preparation of 3-(3-(N-Boc-piperidin-4-yl)-propoxy)-phenylacetic acid

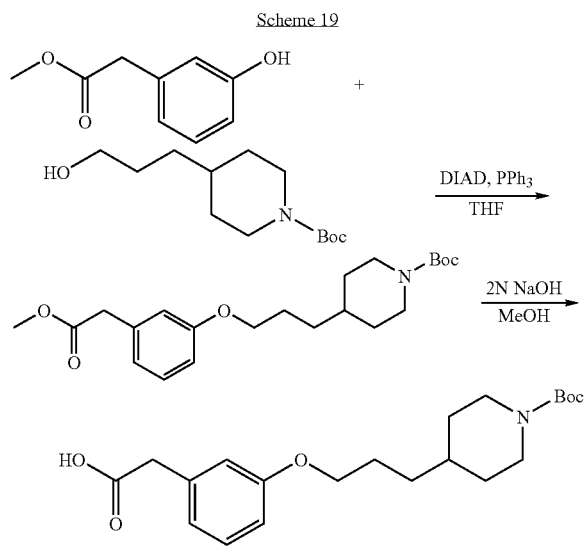

Methyl 3-hydroxyphenylacetate: 3-Hydroxyphenylacetic acid (75.3 g, 0.5 mol) was dissolved in methanol (900 mL). Concentrated sulfuric acid (2 mL) was added and the mixture refluxed for 5 hours. The solvent was evaporated and the residue dissolved in ethyl acetate (1000 mL) and washed with water (2×600 mL) and brine, and dried (MgSO4). Solvent was evaporated to afford methyl 3-hydroxyphenylacetate as an oil (82 g, quantitative yield). $^1$H NMR (500 MHz, CDCl$_3$) δ 7.2 (1H, t), 6.9-6.75 (3H, m), 5.5 (1H, br), 3.75 (3H, s), 3.63 (2H, s).

Methyl 3-(3-(N-Boc-piperidin-4-yl)-propoxy)-phenylacetate: To THF solution of 0.409 g (2.4 mmol) methyl 3-hydroxyphenylacetate, 0.50 g (20.5 mmol) N-Boc-piperidin-4-yl-propanol and 0.645 g (24.6 mmol) triphenylphosphine was added diisopropyl azodicarboxylate at 0° C. slowly, then the ice bath was removed and the reaction mixture was stirred at room temperature overnight. The solvent was removed by rotary evaporation, the residue was dissolved in 2 mL methylene chloride and was loaded on a silica gel column and, the product eluted with 80% hexane and 20% ethyl acetate. Methyl 3-(3-(N-Boc-piperidin-4-yl)-propoxy)-phenylacetate (0.5 g, 62%) was obtained. $^1$H NMR (500 MHz, CDCl$_3$) δ 1.1 (m, 2H), 1.4 (m, 2H), 1.46 (s, 9H), 1.66 (d, 2H), 1.78(m, 2H), 2.67 (t, 2H), 3.58 (s, 2H), 3.68 (s, 3H), 4.05 (m, 2H), 6.75 (m, 3H), 7.18 (dd, 1H).

3-(3-(N-Boc-piperidin-4-yl)-propoxy)-phenylacetic acid: Methyl 3-(3-(N-Boc-piperidin-4-yl)-propoxy)-phenylacetate (0.5 g, 1.3 mmol) was dissolved in methanol, and 2N NaoH (3 mL) added. The reaction was stirred at 60° C. for 2 h, then the solution was adjusted to pH 6.5, the product was extracted into ethyl acetate and the organic phase was dried by MgSO$_4$. Removal of solvent revealed 3-(3-(N-Boc-piperidin-4-yl)-propoxy)-phenylacetic acid (0.30 g). $^1$H NMR (500 MHz, CDCl$_3$) δ 1.02 (m, 2H), 1.25 (m, 2H), 1.55 (m, 2H), 1.65 (m, 2H), 2.57 (m, 2H), 3.33 (m, 1H), 3.75 (s, 2H), 3.95 (m, 2H), 6.63 (m, 3H), 6.98 (m, 1H).

Preparation of 3-(3-chloro-propoxy)-phenylacetic acid

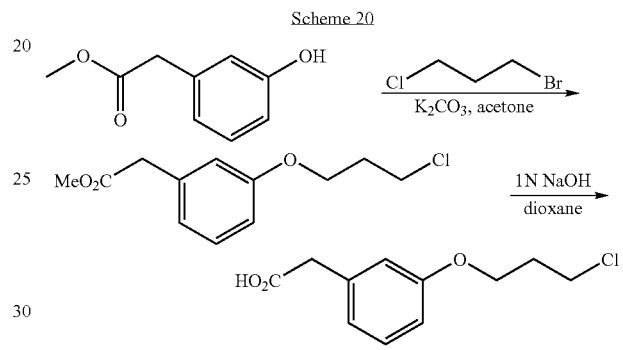

Methyl 3-(3-chloro-propoxy)-phenylacetate: Methyl 3-hydroxyphenylacetate (87 g, 0.52 mol) was dissolved in acetone (500 mL). 1-Bromo-3-chloropropane (55 mL, 0.56 mol) was added, followed by potassium carbonate (73 g, 0.53 mol) and acetone (100 mL). The reaction was heated to reflux. After 24 hours, more 1-bromo-3-chloropropane (5 mL, 50 mmol) was added and the reaction refluxed for a further 24 hours. The mixture was cooled, filtered and rotary evaporated. The product was purified by passage over a short column of silica gel (650 g: 135 mm diameter column) eluted with hexane, and 30% ethyl acetate in hexane, to afford methyl 3-(3-chloro-propoxy)-phenylacetate (120 g, 95%) as an oil. $^1$H NMR (500 MHz, CDCl$_3$) δ 7.25 (1H, dd), 6.93-6.85 (3H, m), 4.16 (2H, t), 3.79 (2H, t), 3.73 (3H, s), 3.62 (2H, s), 2.28 (2H, m).

3-(3-Chloro-propoxy)-phenylacetic acid: Methyl 3-(3-chloro-propoxy)-phenylacetate (12.7 g, 52.3 mmol) was dissolved in dioxane (25 mL) and 1N NaOH (53 mL) was added. The mixture was stirred at room temperature for 45 minutes then acidified by addition of 1N hydrochloric acid (60 mL). A white precipitate formed which was filtered, washed with 1N HCl, water and dried. 3-(3-Chloro-propoxy)-phenylacetic acid (11.7 g, 98%). $^1$H NMR (500 MHz, CDCl$_3$) δ 7.25 (1H, dd), 6.93-6.85 (3H, m), 4.11 (2H, t), 3.79 (2H, t), 3.70 (2H, s), 2.25 (2H, m).

Preparation of 3-(2-chloro-ethoxy)-phenylacetic acid

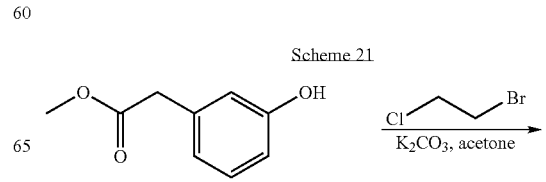

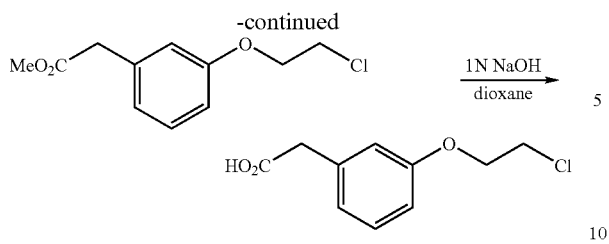

Methyl 3-(2-chloroethoxy)-phenylacetate: Methyl 3-hydroxyphenylacetate (10.8 g, 65 mmol) was dissolved in acetone (120 mL). 1-Bromo-2-chloroethane (5.5 mL, 66 mmol) was added, followed by potassium carbonate (10.1 g, 73.6 mmol). The reaction was heated to reflux. After 24 hours, more 1-bromo-2-chloroethane (11 mL, 132 mmol) was added and the reaction refluxed for a further 24 hours. The mixture was cooled, filtered and rotary evaporated. The product was purified by passage over a short column of silica gel eluted with hexane, and 30% ethyl acetate in hexane, to afford methyl 3-(3-chloroethoxy)-phenylacetate as an oil.

3-(2-Chloroethoxy)-phenylacetic acid: Methyl 3-(2-chloro-ethoxy)-phenylacetate (7.0 g, 32.9 mmol) was dissolved in methanol (40 mL) and 6N NaOH (5.5 mL) was added. The mixture was stirred at room temperature overnight then acidified by addition of 6N hydrochloric acid (5.5 mL). A white precipitate formed which was filtered, washed with 1N HCl, water and dried. 3-(3-Chloroethoxy)-phenylacetic acid (6.5 g, 99%). $^1$H NMR (500 MHz, CDCl$_3$) δ3.55 (s, 2H), 3.75 (t, 2H), 4.15 (t, 2H), 6.78 (dd, 1H), 6.80 (d, 1H), 6.84 (dd, 1H), 7.16 (dd, 1H).

Preparation of 3-Ethoxyphenylacetic acid

Methyl 3-ethoxyphenylacetate: Methyl 3-hydroxyphenylacetate (6.4 g, 38.5 mmol) was dissolved in acetone (50 mL). Ethyl bromide (3.5 mL, 46.9 mmol) was added, followed by potassium carbonate (6.37 g, 46 mmol). The reaction was heated to reflux. After 24 hours, more ethyl bromide (3.55 mL, 46.9 mmol) was added and the reaction refluxed for a further 24 hours. The mixture was cooled, filtered and rotary evaporated. The product was dissolved in ethyl acetate and the solution washed with saturated sodium bicarbonate (2×50 mL) and brine, and dried (MgSO4). Removal of solvent revealed methyl 3-ethoxyphenylacetate as an oil that crystallized upon standing. $^1$H NMR (500 MHz, CDCl$_3$) δ 7.25 (1H, dd), 6.87 (3H, m), 4.08 (2H, q), 3.73 (3H, s), 3.65 (2H, s), 1.45 (3H, t).

3-Ethoxyphenylacetic acid: Methyl 3-ethoxyphenylacetate (7.5 g, 38.6 mmol) was dissolved in ethanol (15 mL) and 1N NaOH (40 mL) was added. The mixture was stirred at room temperature for 30 minutes then acidified by addition of 1N hydrochloric acid (45 mL). A white precipitate formed which was filtered, washed with 1N HCl, water and dried. 3-Ethoxyphenylacetic acid (6.4 g, 92%). $^1$H NMR (500 MHz, CDCl$_3$) δ 7.20 (1H, dd), 6.8 (3H, m), 4.0 (2H, q), 3.6 (2H, s), 1.4 (3H, t).

Scheme 22

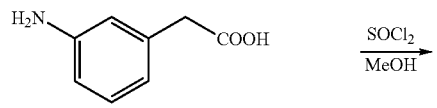

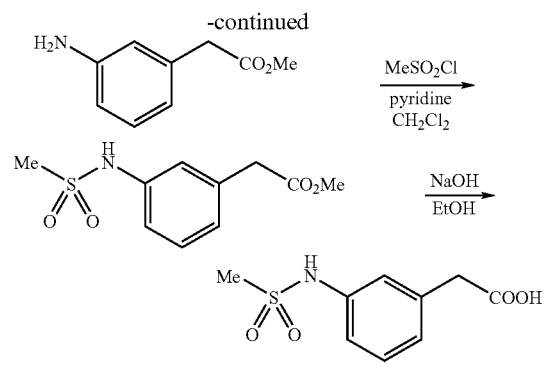

Preparation of 3-(Methanesulfonylamino)-phenylacetic acid

Methyl 3-aminophenylacetate: 3-Aminophenylacetic acid (15.5 g, 0.10 mol) was suspended in methanol (150 mL) and cooled to 0° C. Thionyl chloride (11.2 mL, 0.15 mol) was added dropwise under stirring. A clear orange solution was obtained, which was stirred for 4 hours, then evaporated. The solid residue was partitioned between ethyl acetate (150 mL) and saturated sodium bicarbonate (150 mL) and the organic phase washed with saturated sodium bicarbonate (100 mL), and brine and dried (Na$_2$SO$_4$). Methyl 3-aminophenylacetate was isolated as a brown oil. (14.1 g, 83%). $^1$H NMR (500 MHz, CDCl$_3$) δ 7.12 (1H, dd), 6.7-6.6 (3H, m), 3.71 (3H, s), 3.55 (2H, s).

Methyl (3-Methanesulfonylamino-phenyl)-acetate: Methyl 3-aminophenylacetate (2.26 g, 13.7 mmol) was dissolved in dry methylene chloride (20 mL) and cooled to 0° C. Pyridine (2.2 mL, 27.2 mmol) was added followed by dropwise addition of methanesulfonyl chloride (1.3 mL, 16.8 mmol). The mixture was stirred at 0° C. for 1 hour and at room temperature for 3 hours, then poured into 100 mL of saturated sodium bicarbonate solution. The organic layer was washed with saturated sodium bicarbonate (100 mL), 1N HCl (2×100 mL) and brine. Dried over MgSO$_4$. Solvent was evaporated to reveal methyl 3-(methanesulfonyl)phenylacetate. (3.36 g, 100%). $^1$H NMR (500 MHz, CDCl$_3$) δ 7.32 (1H, dd), 7.2-7.1 (3H, m), 6.57 (1H, s), 3.72 (3H, s), 3.64 (2H, s), 3.02 (3H, s).

3-(Methanesulfonylamino)-phenylacetic acid: Methyl 3-(methanesulfonylamino)-phenylacetate (3.36 g, 13.8 mmol) was dissolved in ethanol (16 mL) and 1N NaOH (30 mL) added. The reaction was stirred for 1 hour, then 1N HCl (50 mL) and water (50 mL) were added. The product was extracted into ethyl acetate (3×50 mL) and the combined extracts were washed with water and brine and dried (MgSO$_4$). Removal of solvent afforded 3-(methanesulfonyl)phenylacetic acid (2.90 g, 92%). $^1$H NMR (500 MHz, DMSO-d6) □ 12.32 (1H, br), 9.69 (1H, br), 7.26 (1H, dd), 7.10 (2H, m), 7.00 (1H, d), 6.57 (1H, s), 3.54 (2H, s), 2.97 (3H, s).

Scheme XX

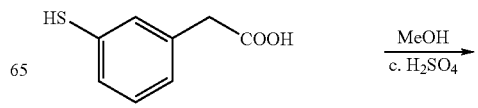

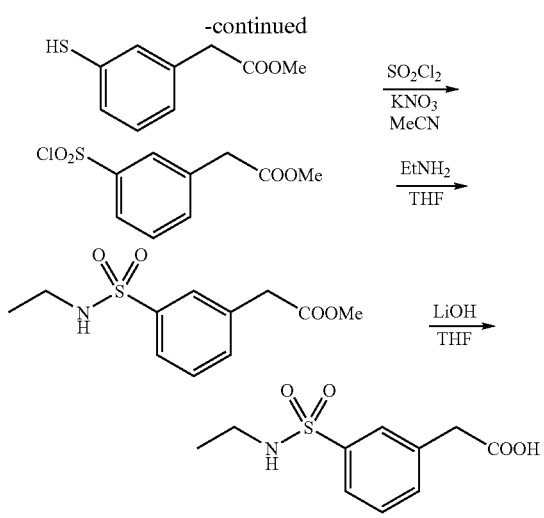

Preparation of 2-(3-ethylsulfonamidophenyl)-N-(4-(pyridin-4-yl)thiazol-2-yl) acetamide Methyl 2-(3-mercaptophenyl)acetate: 2-(3-mercaptophenyl)acetic acid (1.0 g, 6.0 mmol) was dissolved in dry methanol (40 mL). To this solution 10 drops concentrated sulfuric acid was added and the reaction mixture was heated to reflux for 36 hours. The reaction mixture was then concentrated to about half the volume, diluted with ethyl acetate, and the organic layer washed with saturated sodium bicarbonate solution, then dried over sodium sulfate and concentrated to an oil, 0.55 g, 3.0 mmol, 50% yield. 1H NMR 500 MHz (CDCl3) 7.05 ppm, 3H, m; 6.88 ppm, 1H, m; 3.53 ppm, 3H, s; 3.38 ppm, 2H, s.

Methyl 2-(3-chlorosulfonylphenyl)acetate: Methyl 2-(3-mercaptophenyl)acetate (0.55 g, 3.0 mmol) was dissolved in 10 mL acetonitrile and potassium nitrate (0.76 g, 7.5 mmol) was added and the reaction mixture cooled to 0° C. To this suspension sulfuryl chloride was added (0.6 mL, 7.5 mmol) at 0° C. and the reaction mixture was let warm to room temperature and stirred overnight. A solution of saturated sodium bicarbonate was added followed by ethyl acetate (100 mL each). The organic layer was washed with brine, dried over sodium sulfate and concentrated to an oil 0.59 g, 2.4 mmol, 79% yield. $^1$H NMR 500 MHz (CDCl$_3$) 7.91 ppm, 2H, m; 7.60 ppm, 1H, d; 7.53 ppm, 1H, t; 3.73 ppm, 2H, s; 3.72 ppm, 3H, s.

(3-Ethylsulfamoyl-phenyl)-acetic acid methyl ester: Methyl 2-(3-chlorosulfonyl-phenyl)acetate (0.29 g, 1.17 mmol) was dissolved in THF (10 mL) and to this solution 1 mL (2 mmol) of 2M ethylamine in THF was added. Let stir at room temperature 30 minutes, diluted with ethyl acetate and the organic layer was washed with 10% citric acid, brine, dried over sodium sulfate and concentrated to an oil. 0.28 g, 1.09 mmol, 93% yield. $^1$H NMR 500 MHz (CDCl$_3$) 7.72 ppm, 2H, m; 7.41 ppm, 2H, m; 4.32 ppm, 1H, t; 3.68 ppm, 3H, s; 3.67 ppm, 2H, s; 2.98 ppm, 2H, m; 1.07 ppm, 3H, t.

(3-Ethylsulfamoyl-phenyl)-acetic acid: (3-Ethylsulfamoyl-phenyl)-acetic acid methyl ester (0.28 g, 1.1 mmol) was dissolved in THF and LiOH hydrate (63 mg, 1.5 mmol) in water was added. The reaction mixture was stirred at room temperature for 4 hours and then diluted with ethyl acetate and 10% citric acid. The organic layer was washed with brine, dried over sodium sulfate, and concentrated to a solid. 0.25 g, 1.1 mmol 99% yield. $^1$H NMR 500 MHz (DMSO) 7.71 ppm, 1H, s; 7.70 ppm, 1H, m; 7.50 ppm, 3H, m; 4.11 ppm, 1H, br s; 3.70 ppm, 2H, s; 2.81 ppm, 2H, m; 0.99 ppm, 3H, t.

Preparation of 3-(3-(N-Boc-piperidin-4-yl)-propoxy)-phenylacetic acid

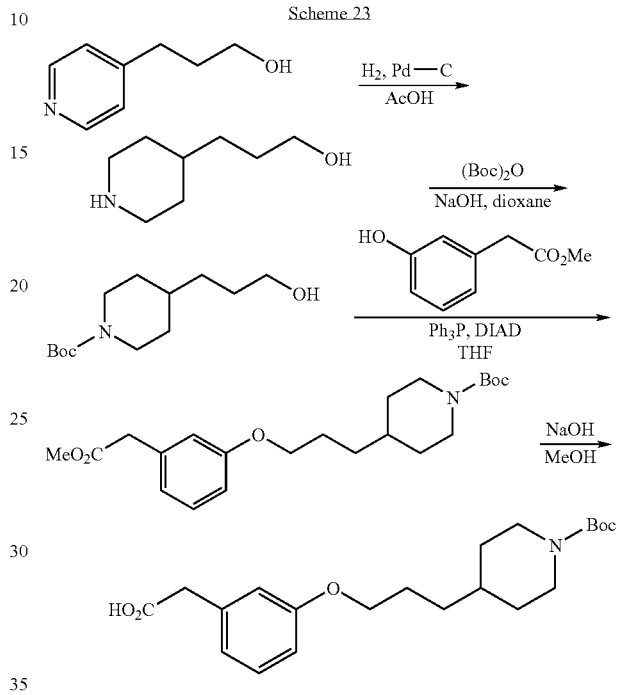

3-Piperidin-4-yl-propan-1-ol: 4-Pyridinepropanol (10.0 g, 73 mmol) was dissolved in glacial acetic acid (50 mL). 10% Palladium on carbon (1.1 g) was added and the mixture hydrogenated under 50 psi hydrogen gas for 6 days. The mixture was filtered through Celite and the solvent removed by rotary evaporation. The crude product 3-piperidin-4-yl-propan-1-ol (acetic acid salt) was used as obtained. $^1$H NMR (500 MHz, CDCl$_3$) ☐ 6.3 (br), 3.65 (2H, t), 3.36 (2H, m), 2.79 (2H, dt), 2.01 (3H, s), 1.85 (2H, m), 1.7-1.3 (7H, m).

3-(N-Boc-Piperidin-4-yl)-propan-1-ol: The crude 3-piperidin-4-yl-propan-1-ol (73 mmol) was dissolved in dioxane (100 mL) and 3N NaOH (25 mL) was added to give a pH9 solution. Di-tert-butyl dicarbonate (16.0 g, 73 mmol) in dioxane (35 mL) was added dropwise, with simultaneous addition of 3N NaOH to maintain the solution at approximately pH9. After 2 hours no residual amine was visible by TLC (ninhydrin stain) and the reaction was diluted with water (200 mL) and extracted with ethyl acetate (3×100 mL). The combined extracts were washed with water and brine and dried (MgSO$_4$). Removal of solvent afforded 20 g crude product which was purified by silica gel chromatography (200 g silica) in a sintered glass funnel (L. M. Harwood, Aldrichimica Acta, 1985, 18, 25) eluted with 500 mL each of hexane, 20%, 40%, 60% and 80% ethyl acetate in hexane. 3-(N-Boc-Piperidin-4-yl)-propan-1-ol was isolated as a clear, colorless oil (14.5 g, 82%). $^1$H NMR (500 MHz, CDCl$_3$) ☐ 4.09 (2H, m), 3.66 (2H, t), 2.69 (2H, dt), 1.7-1.5 (4H, m), 1.47 (9H, s), 1.4-1.3 (5H, m), 1.12 (2H, m).

Methyl 3-(3-(N-Boc-piperidin-4-yl)-propoxy)-phenylacetate: To a solution of methyl 3-hydroxyphenylacetate (0.409 g, 2.4 mmol), 3-(N-Boc-piperidin-4-yl)-propan-1-ol (0.50 g, 20.5 mmol) and triphenylphosphine (0.645, 24.6 mmol) in THF, was added diisopropyl azodicarboxylate at 0° C. slowly, then the ice bath was removed and the reaction mixture was stirred at room temperature overnight. The solvent was removed and the residue was dissolved in methylene chloride (2 mL) and loaded on a silica gel column. The product was eluted with 20% ethyl acetate in hexane, to afford methyl 3-(3-(N-Boc-piperidin-4-yl)-propoxy)-phenylacetate (0.5 g, 62%). $^1$H NMR (500 MHz, CDCl$_3$) ☐1.1 (m, 2H), 1.4 (m, 2H), 1.46 (s, 9H), 1.66 (d, 2H), 1.78 (m, 2H), 2.67 (t, 2H), 3.58 (s, 2H), 3.68 (s, 3H), 4.05 (m, 2H), 6.75 (m, 3H), 7.18 (dd, 1H).

3-(3-(N-Boc-piperidin-4-yl)-propoxy)-phenylacetic acid: Methyl 3-(3-(N-Boc-piperidin-4-yl)-propoxy)-phenylacetate (0.5 g, 1.3 mmol) was dissolved in methanol and 2N NaOH (3 mL) added. The reaction was stirred at 60° C. for 2 hours then the solution was adjusted to pH 6.5. The product was extracted into ethyl acetate, and the organic phase was dried by MgSO$_4$. The solvent was evaporated to afford 3-(3-(N-Boc-piperidin-4-yl)-propoxy)-phenylacetic acid (0.30 g). $^1$H NMR (500 MHz, CDCl$_3$) ☐1.02 (m, 2H), 1.25 (m, 2H), 1.55 (m, 2H), 1.65 (m, 2H), 2.57 (m, 2H), 3.33 (m, 1H), 3.75 (s, 2H), 3.95 (m, 2H), 6.63 (m, 3H), 6.98 (m, 1H).

The synthesis of certain exemplary amines (described generally above in Schemes 1-13) are described more specifically below. It will be appreciated that a variety of alternate amines can be prepared according to methods known in the art and can be utilized in the preparation of compounds of the invention. Additionally, although certain exemplary acids are described in more detail below and in Schemes 14-23, it will be appreciated that a variety of alternate acids can be prepared according to methods known in the art and can be utilized in the preparation of compounds of the invention.

4-(1H-Pyrrolo[2,3-b]pyridin-3-yl)-thiazol-2-ylamine; hydrobromide (A)

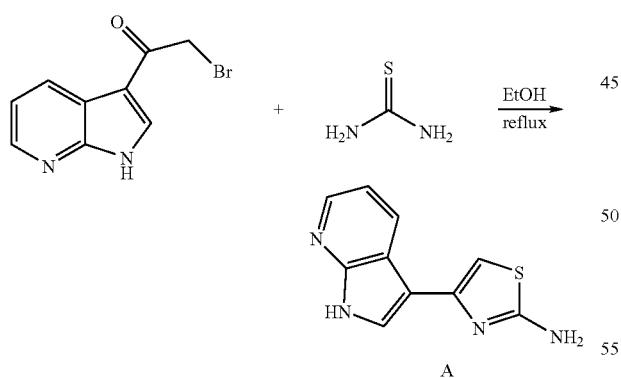

A mixture of 2-Bromo-1-(1H-pyrrolo[2,3-b]pyridin-3-yl)-ethanone (prepared according to Galvez C. et al, *J. Het. Chem.* 21, 1984, p421-423) (2.2 g, 10.5 mmol) and thiourea (0.8 g, 10.5 mmol) was heated in ethanol (60 mL), at reflux for 4 hours. The reaction mixture was cooled to 0° C. with and ice-water bath, then the solids were filtered and dried to give 5-pyridin-4-yl-[1,3,4]thiadiazol-2-ylamine as a tan solid. (2.5 g, 83%). $^1$H NMR DMSO: 12.234 (s,1H), 8.92 (bs,2H), 8.34 (m,2H), 8.10 (s,1H), 7.26 (m, 1H), 7.08 (s,1H).

Scheme 24

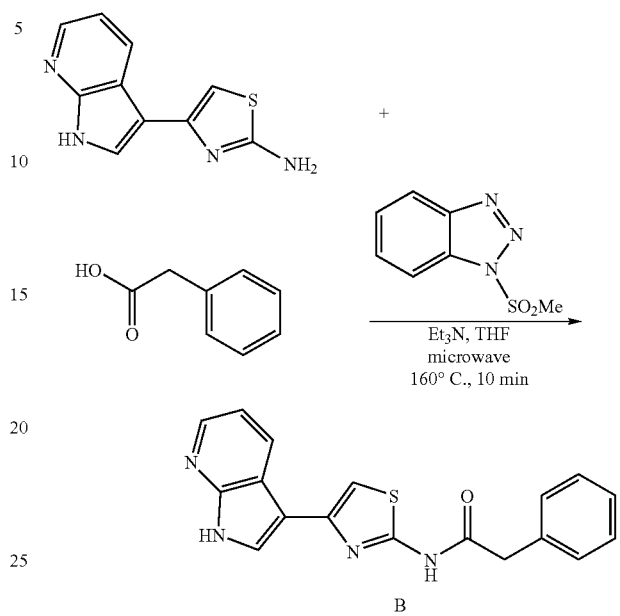

2-Phenyl-N-[4-(1H-pyrrolo[2,3-b]pyridin-3-yl)-thiazol-2-yl]-acetamide (B): 4-(1H-Pyrrolo[2,3-b]pyridin-3-yl)-thiazol-2-ylamine (216 mg, 1.0 mmol), phenylacetic acid (150 mg, 1.10 mmol) and N-(1-methanesulfonyl)benzotriazole (220 mg, 1.10 mmol) were placed in a microwave reaction vessel (Personal Chemistry, Uppsala, Sweden). THF (2 mL) was added followed by triethylamine (0.5 mL, 3.59 mmol) and the mixture heated in the sealed tube at 160° C. for 10 minutes. Upon cooling to room temperature the reaction was concentrated to 1 mL, and then acetonitrile was added (4 mL) and the product 2-Phenyl-N-[4-(1H-pyrrolo[2,3-b]pyridin-3-yl)-thiazol-2-yl]-acetamide precipitated, was filtered, washed with acetonitrile and dried. (150 mg, 45%). $^1$H NMR (500 MHz, DMSO-d6) ☐12.39 (1H, s), 11.83 (s,1H), 8.50 (1H, d, J=7.91 Hz), 8.27 (m,1H), 7.84 (1H, d, J=2.48 Hz), 7.36-7.15 (7H, m), 3.81 (2H, s). LC-MS Rt=2.8 min, [M+H]$^+$ =335.0, [M−H]$^-$=333.1.

Cyclopropyl-[4-(1H-pyrrolo[2,3-b]pyridin-3-yl)-thiazol-2-yl]-amine

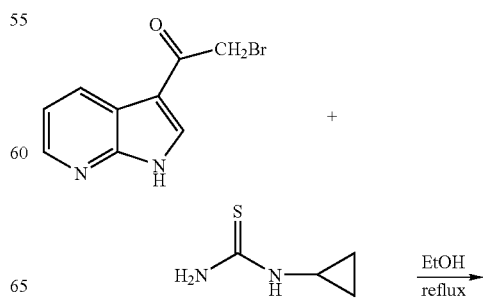

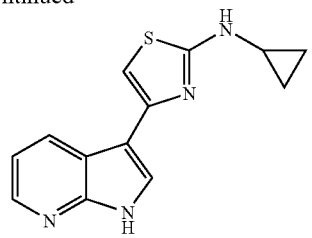

A mixture of 2-Bromo-1-(1H-pyrrolo[2,3-b]pyridin-3-yl)-ethanone (prepared according to Galvez C. et al, J. Het. Chem. 21, 1984, p421-423) (0.90 g, 3.76 mmol) and cyclopropyl-thiourea (prepared according to Marletta, M. et al, J. Med. Chem. 35, 1992, p1137-1144) (0.46 g, 3.96 mmol) was heated in ethanol (20 mL), at reflux for 4 hours. The reaction mixture was cooled to 0° C. with and ice-water bath, then the solids were filtered and dried to give cyclopropyl-[4-(1H-pyrrolo[2,3-b]pyridin-3-yl)-thiazol-2-yl]-amine as a tan solid (1.2 g, 92%). LC/MS MH+ =257.02, LC/MS RT: 1.62 min. $^1$H NMR (500 MHz, DMSO-d6, ppm) 12.22 (s,1H), 9.20 (bs,1H), 8.42 (d,1H, J=7.82 Hz), 8.36 (dd,1H, J=4.81, 1.22 Hz), 8.00 (s,1H), 7.25 (m,1H), 6.12 (s,1H), 2.77 (t, 1H,J=4.75), 0.86 (m,2H), 0.71 (m,2H).

N-Cyclopropyl-2-phenyl-N-[4-(1H-pyrrolo[2,3-b]pyridin-3-yl)-thiazol-2-yl]-acetamide

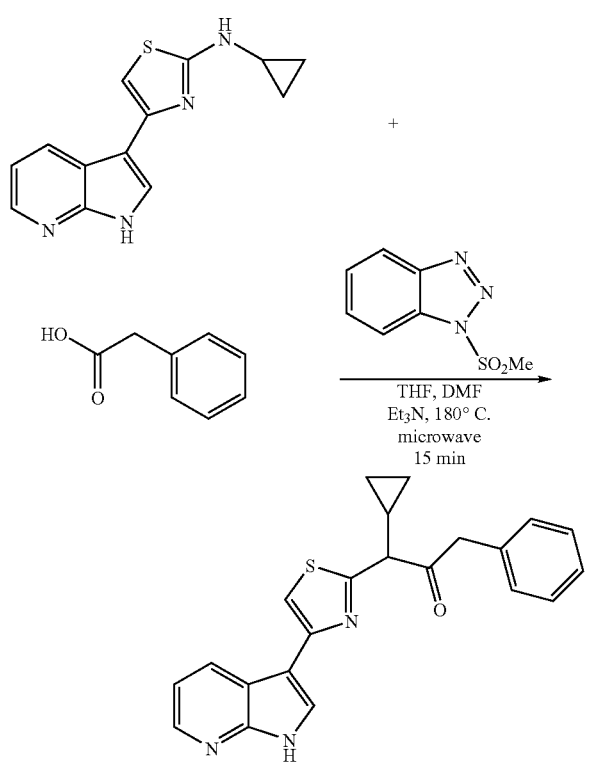

Cyclopropyl-[4-(1H-pyrrolo[2,3-b]pyridin-3-yl)-thiazol-2-yl]-amine (50 mg, 0.39 mmol), phenylacetic acid (63 mg, 0.47 mmol) and N-(1-methanesulfonyl)benzotriazole (93 mg, 0.47 mmol) were placed in a microwave reaction vessel (Personal Chemistry, Uppsala, Sweden). 5% DMF-THF (4 mL) was added followed by triethylamine (0.163 mL, 1.17 mmol) and the mixture heated in the sealed tube at 180° C. for 15 minutes. Upon cooling to room temperature the reaction was concentrated and then purified by prepartative TLC (thin layer chromatography) and eluted with ethylacetate and hexane (3:1). Extraction of the silica gel with 5% MeOH-EtOAc was carried out to give product (15 mg, 10%). Alternatively, Cyclopropyl-[4-(1H-pyrrolo[2,3-b]pyridin-3-yl)-thiazol-2-yl]-amine (50 mg, 0.39 mmol), phenylacetic acid (63 mg, 0.47 mmol) and fluoro-N,N',N',N'-tetramethylformamidiniun hexafluorophosphate (148 mg, 0.59 mmol) were placed in a microwave reaction vessel (Personal Chemistry, Uppsala, Sweden). 5% DMF-THF (4 mL) was added followed by triethylamine (0.163 mL, 1.17 mmol) and the mixture heated in the sealed tube at 180° C. for 15 minutes. Upon cooling to room temperature the reaction was concentrated and then purified by prepartative TLC (thin layer chromatography) and eluted with ethylacetate and hexane (3:1). Extraction of the silica gel with 5% MeOH-EtOAc was carried out to give product (18 mg, 12%). The material was isolated as an HCl salt. LC/MS MH+ =375.2, LC/MS RT: 3.39 min. $^1$H NMR (500 MHz, DMSO-d6, ppm) 11.92 (s,1H), 8.63 (d,1H, J=7.88 Hz), 8.29 (dd,1H, J=4.71, 1.49 Hz), 8.96 (d,J=2.58, 1H), 7.44 (s,1H), 7.36-7.19 (m,6H), 4.27 (s,2H), 3.29 (t, 1H,J=3.78), 1.33 (m,2H), 1.06 (m,2H).

5-(1H-pyrrolo[2,3-b]pyridin-3-yl)-1,3,4-thiadiazol-2-amine

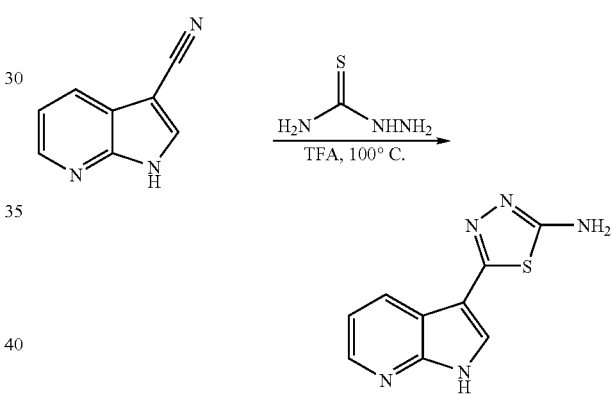

A mixture of 3-cyano-7-azaindole (prepared as described in Org. Proc. Res. Dev. 2003, 7, 209) (1.0 g, 7 mmol) and thiosemicarbazide (2.34 g, 21 mmol) in trifluoroacetic acid (25 mL) was heated in a sealed tube at 100° C. for 2 hr. The brown solution was cooled to room temperature and poured into ice. The mixture was then basified with c.NH$_4$OH and the pale brown precipitate formed was filtered on a sintered glass filter. The solid was washed thoroughly with water (3×50 mL) and ethyl acetate (3×50 mL) and dried under vacuum to afford 5-(1H-pyrrolo[2,3-b]pyridin-3-yl)-1,3,4-thiadiazol-2-amine (1.3 g, 85%) as a gray solid; Mass Spec FIA MS 218 (M+1). $^1$H NMR (DMSO-d6, 500 MHz) δ 12.11 (s, 1H), 8.43 (dd, 1H), 8.31 (dd, 1H), 7.96 (d,1H), 7.19 (m, 1H), 7.14 (br s, 2H).

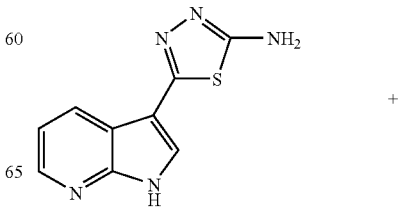

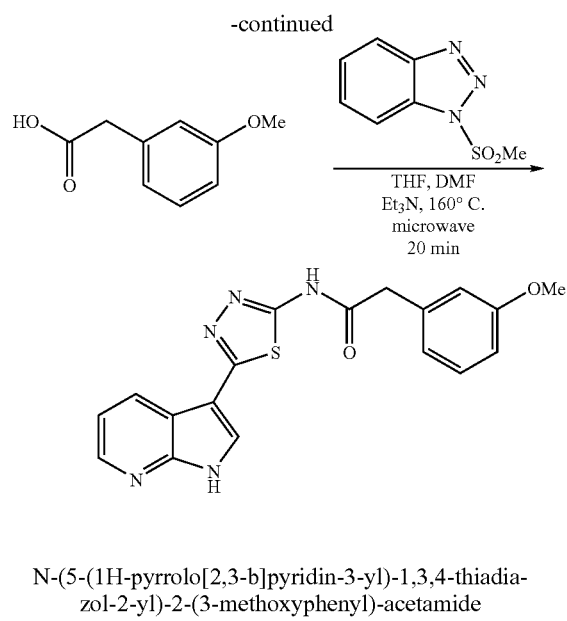

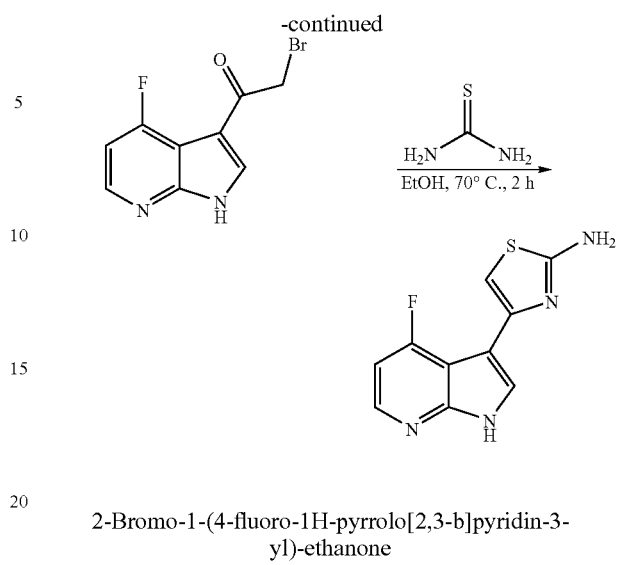

N-(5-(1H-pyrrolo[2,3-b]pyridin-3-yl)-1,3,4-thiadiazol-2-yl)-2-(3-methoxyphenyl)-acetamide A suspension of 5-(1H-pyrrolo[2,3-b]pyridin-3-yl)-1,3,4-thiadiazol-2-amine (0.050 g, 0.23 mmol), 3-methoxyphenylacetic acid (0.038 g, 0.23 mml), triethylamine (0.1 mL) and BtSO$_2$CH$_3$ (0.055 g, 0.28 mml) in THF (3 mL) and DMF (0.3 mL) was heated in a microwave oven for 20 min. The brown solution was added to water (50 mL) and ethyl acetate (50 mL). Brine (10 ml) was added to separate the layers. The organic phase was separated and washed with water (2×50 mL). The organic layer was concentrated to give a solid which was placed in a small Buchner funnel and washed with methanol (2×5 mL) and ethyl acetate (2×5 mL). The brown solid collected was dried under vacuum to afford the desired product (0.018 g, 21%).

4-(4-Fluoro-1H-pyrrolo[2,3-b]pyridin-3-yl)-thiazol-2-ylamine

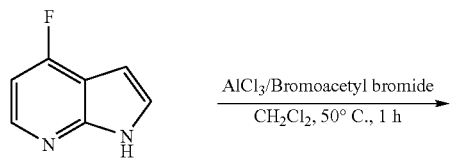

2-Bromo-1-(4-fluoro-1H-pyrrolo[2,3-b]pyridin-3-yl)-ethanone

To a solution of 4-fluoro-1H-pyrrolo[2,3-b]pyridine (2.00 g, 0.0147 mol) (*Org. Lett.*, 2003, 5, 5023-5025) in dichloromethane was added aluminum chloride (3.92 g, 0.0294 mol) in portions, the mixture was stirred at RT for 30 min, then bromoacetyl bromide (4.45 g, 0.022 mol) was added dropwise. The reaction mixture was stirred at 50° C. for 1 h, when TLC indicated no starting material. To the reaction mixture was added 150 mL water, and the resulting suspension was heated at 100° C. for 1 h, then filtered to afford the desired product, 90% pure. H NMR, DMSO-d6: 4.72(s, 2H), 7.12(m, 1H), 8.36(m, 1H), 8.67(s, 1H).

4-(4-Fluoro-1H-pyrrolo[2,3-b]pyridin-3-yl)-thiazol-2-ylamine

To an ethanol suspension of 2-bromo-1-(4-fluoro-1H-pyrrolo[2,3-b]pyridin-3-yl)-ethanone (3.00 g 0.0117 mol) was added thiourea (1.18 g, 0.0234 mol), the reaction mixture was heated at 70° C. for 1 h. The suspension was filtered while still warm and to the filtration cake was added sat. sodium carbonate solution until the aqueous phase pH was around 7.5. The suspension was filtered to afford 1.8 g free base (75%). H NMR, DMSO-d6: 6.78 (s, 1H), 6.9 (s, br, 2H), 6.98 (m, 1H), 7.71 (s, 1H), 8.25 (m, 1H).

Preparation of 4-(5-Fluoro-1H-pyrrolo[2,3-b]pyridin-3-yl)-thiazol-2-ylamine

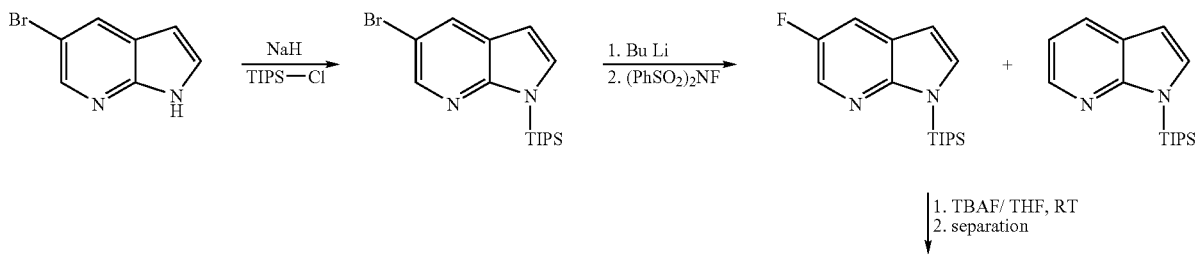

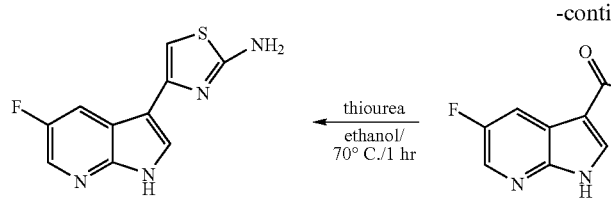 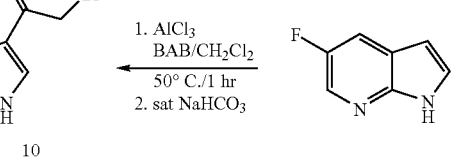

5-Bromo-1-(triisopropylsilyl)-1H-pyrrolo[2,3-b]pyridine

Sodium hydride (0.63 g, 25.15 mol) was added in small portion to a stirred solution of 5-bromo-7-azaindole (3.3 g, 16.75 mmol) in THF (50 mL) at room temperature and the resulting suspension was stirred at room temperature for 15 min. Triisopropylsilyl chloride (5.3 mL, 25.15 mmol) was added and the mixture was heated at 80° C. for 3 h. The solvent was evaporated and the residue was dissolved in water (50 mL). The aqueous layer was extracted with EtOAc (3×50 mL), dried ($Na_2SO_4$) and concentrated under reduced pressure. The crude product was purified by Biotage HPFC system (10% EtOAc/Hexane) to afford the desired 5-bromo-1-(triisopropylsilyl)-1H-pyrrolo[2,3-b]pyridine as a white solid (5.2 g, 88%); Mass Spec 355 (M+1).

5-Fluoro-1-(triisopropylsilyl)-1H-pyrrolo[2,3-b]pyridine 2.5M Butyl lithium (4.4 mL, 10.8 mmol) was added dropwise to a stirred solution of 5-bromo-1-(triisopropylsilyl)-1H-pyrrolo[2,3-b]pyridine (2.55 g, 7.23 mmol) in THF (65 mL) over 10 min at −78° C. under nitrogen in three necked flask. The resulting solution was stirred at −78° C. for 1 h and solid N-fluorobenzenesulfonimide (2.84 g, 9.03 mmol) was added in one portion and stirred at −78° C. for 2 h. The solvent was evaporated and the crude material was dissolved in water (50 mL) and extracted with EtOAc (3×25 mL). The organic extract was dried and concentrated under reduced pressure to give a residue which was suspended in hexane (5 mL) and filtered. The filtrate was chromatographed (Biotage HPFC) on silica gel eluting with hexane to give 5-fluoro-1-(triisopropylsilyl)-1H-pyrrolo[2,3-b]pyridine (1.06 g, 50.2%) as a viscous oil.; Mass Spec.; MS 293 (M+1); $^1$H NMR(CDCl3, 500 MHz) 8.11(d,1H), 7.51(dd,1H), 7.34(d,1H), 6.50(d,1H), 1.84(q,3H), 1.10(d,18H).

4-(5-Fluoro-1H-pyrrolo[2,3-b]pyridin-3-yl)thiazol-2-amine

Tetrabutylamonium fluoride, 1M in THF (2 mL), was added to a stirred solution of 5-fluoro-1-(triisopropylsilyl)-1H-pyrrolo[2,3-b]pyridine (1 g, 3.94 mmol) in THF (10 mL) at room temperature and stirred for 15 min. The solvent was evaporated and the crude product was purified by Biotage HPFC system (40-75% EtOAc/Hexane) to afford 5-fluoro-1H-pyrrolo[2,3-b]pyridine as a white solid (0.45 g, 84); Mass Spec.; MS 137 (M+1); $^1$H NMR(DMSO-d6, 500 MHz) δ 11.75(s, 1H), 8.17(t,1H), 7.81(dd,1H), 7.55(t,1H), 6.44(dd, 1H).

4-(5-Fluoro-1H-pyrrolo[2,3-b]pyridin-3-yl)thiazol-2-amine

Aluminum chloride (0.48 g, 3.6 mmol) was added slowly to a stirred solution of 5-fluoro-1H-pyrrolo[2,3-b]pyridine (0.164 g, 1.2 mmol) in $CH_2Cl_2$ (5 mL)). Bromoacetyl bromide (0.1 mL, 1.5 mmol) was added and the resulting solution was heated at 50° C. for 1 h and cooled to room temperature. Water (25 mL) was added, the solution was basified with saturated $NaHCO_3$ and the mixture was extracted with EtOAc (3×25 mL). The organic extracts were dried and concentrated under reduced pressure to give 2-bromo-1-(5-fluoro-1H-pyrrolo[2,3-b]pyridin-3-yl)-ethanone as a pale brown solid. A mixture of 2-bromo-1-(5-fluoro-1H-pyrrolo[2,3-b]pyridin-3-yl)-ethanone (0.28 g) and thiourea (0.13 g) in ethanol (10 mL) were heated at 70° C. for 1 h. Water (50 mL) was added and the solution was basified with concentrated $NH_4OH$. The aqueous layer was extracted with EtOAc (3×25 mL). The organic extracts were dried and concentrated under reduced pressure to give 4-(5-fluoro-1H-pyrrolo[2,3-b]pyridin-3-yl) thiazol-2-amine (0.21 g, 75%, 2 steps) as pale brown solid. Mass Spec.; MS 235 (M+1); $^1$H NMR(DMSO-d6, 500 MHz) δ 11.86(s, 1H), 8.27(d, 1H), 8.22(s,1H), 7.83(d,1H), 6.95(brs, 2H), 6.81(s,1H).

Preparation of 4-(5-Chloro-1H-pyrrolo[2,3-b]pyridin-3-yl)-thiazol-2-ylamine

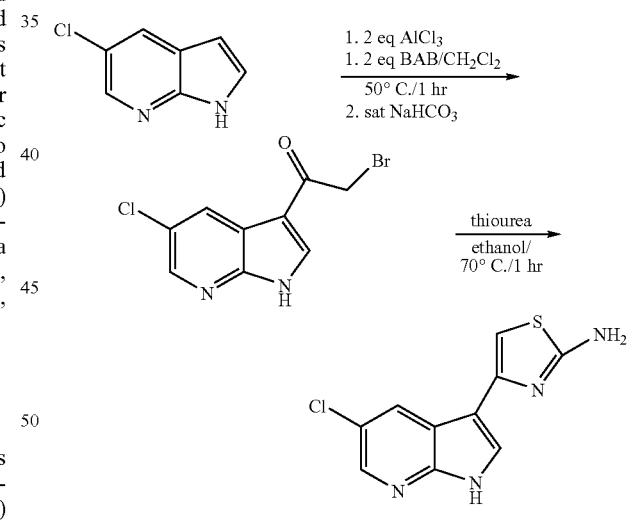

4-(5-Chloro-1H-pyrrolo[2,3-b]pyridin-3-yl)thiazol-2-amine

The title compound was synthesized in 2 steps in a manner similar to that described above using 5-chloro-7-azaindole (0.32 g, 1.17 mmol), $AlCl_3$ (0.47 g, 3.51 mmol), bromoacetyl-bromide (0.1 mL, 1.46 mmol) and thiourea (0.158 g, 2.08 mmol) (0.21 g, 67.5%, 2 steps) as pale brown solid. Mass Spec.; MS 251 (M+1); $^1$H NMR(DMSO-d6, 500 MHz) δ 11.97(s, 1H), 8.50(d, 1H), 8.22(d,1H), 7.84(d,1H),7.02(brs, 2H), 6.83(s,1H).

Preparation of 4-(5-Bromo-1H-pyrrolo[2,3-b]pyridin-3-yl)-thiazol-2-ylamine

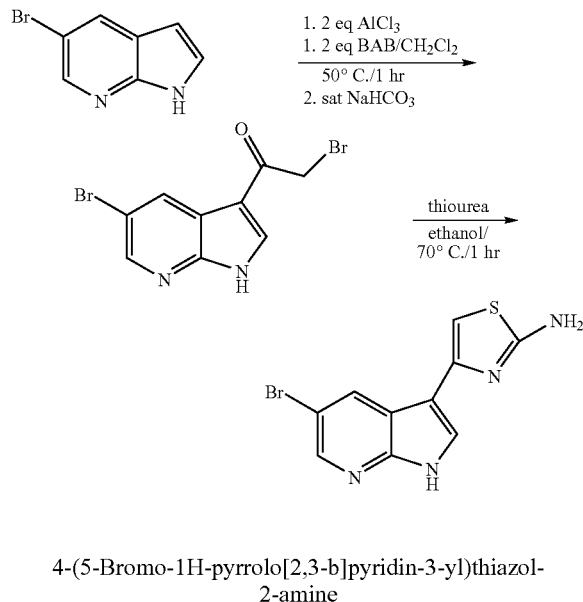

4-(5-Bromo-1H-pyrrolo[2,3-b]pyridin-3-yl)thiazol-2-amine

The title compound was synthesized in 2 steps in a manner similar to that described above using 5-bromo-7-azaindole (1.0 g, 5.07 mmol), AlCl$_3$ (1.35 g, 10.15 mmol), bromoacetyl-bromide (0.41 mL, 6.34 mmol) and thiourea (0.36 g, 4.72 mmol) (0.21 g, 48%, 2 steps) as a brown solid. Mass Spec.; MS 297 (M+1); $^1$H NMR(DMSO-d6, 500 MHz) δ 8.63(d, 1H), 8.28(d,1H), 7.82(s,1H), 6.98(s,2H), 6.82(s,1H).

Preparation of 4-(5-Hydroxy-1H-pyrrolo[2,3-b]pyridin-3-yl)thiazol-2-amine

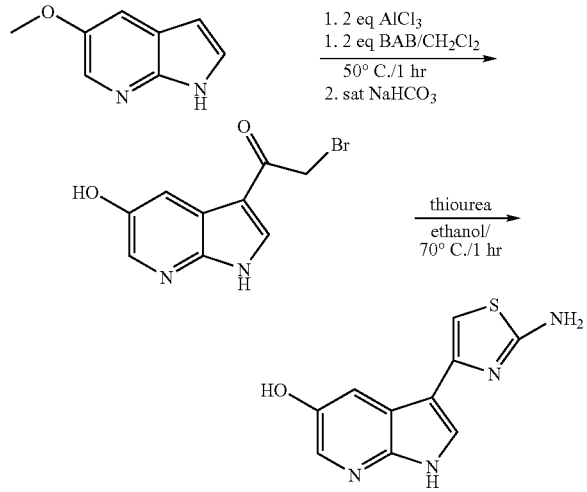

4-(5-Hydroxy-1H-pyrrolo[2,3-b]pyridin-3-yl)thiazol-2-amine

The title compound was synthesized in 2 steps in a manner similar to that described above using 5-methoxy-7-azaindole (0.37 g, 2.48 mmol), AlCl$_3$ (1 g, 7.54 mmol), bromoacetyl-bromide (0.2 mL, 3 mmol) and thiourea (0.14 g, 1.88 mmol) (0.21 g, 39%, 2 steps) as a brown solid. Mass Spec.; MS 233 (M+1); $^1$H NMR(DMSO-d6, 500 MHz) δ 11.37 (s,1H), 9.10 (s,1H), 7.86(d,1H), 7.70(d,1H), 7.61(d,1H), 6.88(s,2H), 6.67 (s,1H).

Preparation of 4-[1-(Toluene-4-sulfonyl)-1H-pyrrolo[2,3-b]pyridin-3-yl]-thiophen-2-ylamine

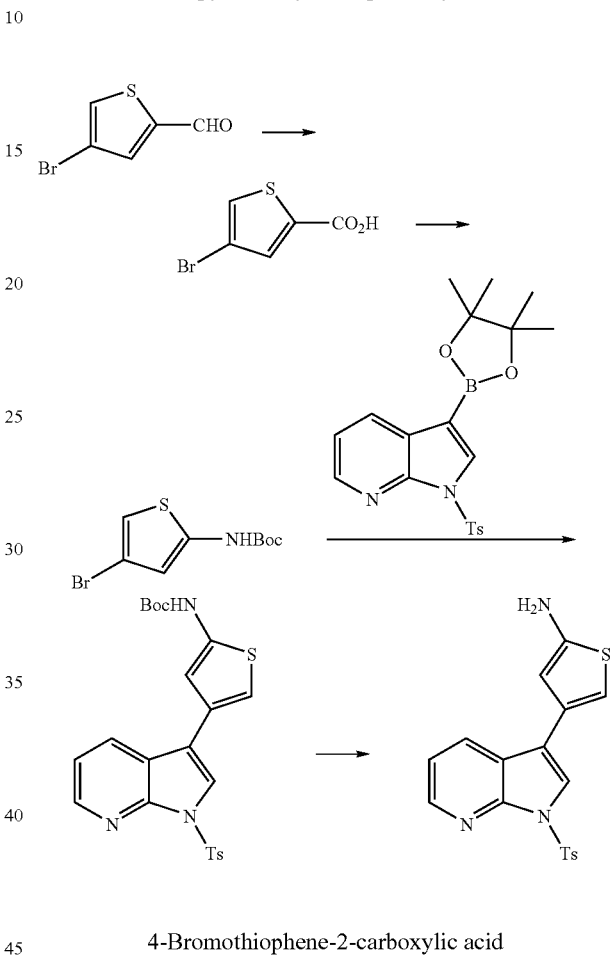

4-Bromothiophene-2-carboxylic acid

4-Bromothiophene-2-carbaldehyde (1.9 g, 10 mmol) was dissolved in 40 mL of t-BuOH and 4 mL of 2-methyl-2-butene. The reaction mixture was cooled to 0° C. and NaClO$_2$ (1.1 g, 12 mmol) dissolved in 12 mL of 1M NaH$_2$PO$_4$ was added. The reaction mixture was let warm to room temperature and stirred for 5 hours. The reaction mixture was concentrated to about half the volume, and poured into 20 mL 1N NaOH and 50 mL Et2O. The aqueous layer was made acidic with 6N HCl and extracted with EtOAc. This organic layer was dried over sodium sulfate and concentrated to obtain the product as a white solid, 1.75 g, 8.5 mmol, 85% yield. $^1$H NMR 500 MHz (DMSO-d6) 8.02 (1H, s), 7.78 (1H, s).

tert-Butyl 4-bromothiophen-2-ylcarbamate

4-Bromothiophene-2-carboxylic acid (1.75 g, 8.5 mmol) was dissolved in 40 mL of t-BuOH. To this solution diphenylphosphoryl azide (2.8 g, 10.2 mmol) and triethylamine (1.4 mL, 10.1 mmol) were added. The reaction mixture was heated to reflux for 5 hours, cooled room temperature, and diluted with EtOAc. The organic layer was washed with 10% citric acid, saturated sodium bicarbonate and brine, and concentrated to an oil, which was purified by column chromatography on silica (0 to 25% EtOAc/hexanes) to give the product, 1.3 g, 4.7 mmol, 55%. $^1$H NMR 500 MHz (CDCl3) 6.96 (1H, br s), 6.83 (1H, s), 6.43 (1H, s), 1.54 (9H, s).

tert-Butyl 4-(1-tosyl-1H-pyrrolo[2,3-b]pyridin-3-yl)thiophen-2-ylcarbamate 3-(4,4,5,5-tetramethyl-1,3,2-dioxaborolan-2-yl)-1-tosyl-1H-pyrrolo[2,3-b]pyridine (398 mg, 1 mmol), tert-butyl 4-bromothiophen-2-ylcarbamate (190 mg, 0.68 mmol), potassium carbonate (310 mg, 2.25 mmol), and tetrakis(triphenylphosphine) palladium (0) (20 mg) were combined in 4 mL DME, 1 mL water, and heated to 160° C. in the microwave for 10 minutes, followed by 170° C. for 10 minutes. The reaction mixture was diluted with EtOAc and washed with saturated sodium bicarbonate. The organic layer was filtered through celite and concentrated to an oil which was purified by column chromatography on silica (15 to 60% EtOAc/hexanes) to give the product as a brown foam, 0.12 g, 0.26 mmol, 38% yield. MH+ 470.1.

4-[1-(Toluene-4-sulfonyl)-1H-pyrrolo[2,3-b]pyridin-3-yl]-thiophen-2-ylamine tert-Butyl 4-(1-tosyl-1H-pyrrolo[2,3-b]pyridin-3-yl)thiophen-2-ylcarbamate (120 mg, 0.26 mmol) was dissolved in 2 mL CH$_2$Cl$_2$, 2 mL TFA. After 15 minutes the reaction mixture was concentrated to an oil, dissolved in EtOAc, and washed with 0.1 NaOH. The organic layer was dried to a brown oil which was used as obtained.

Preparation of N-(4-(1H-pyrrolo[2,3-b]pyridin-3-yl)thiophen-2-yl)-2-(3-methoxyphenyl)acetamide

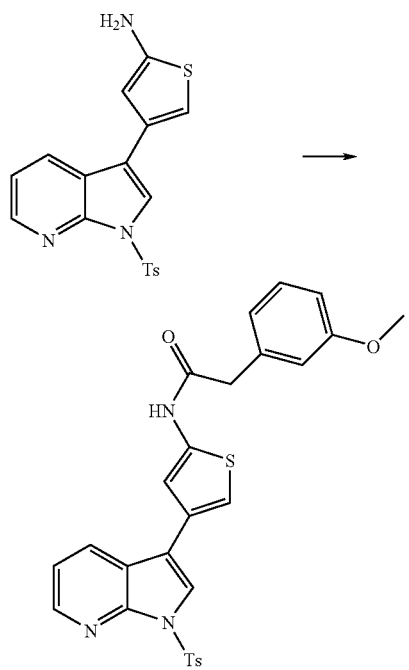

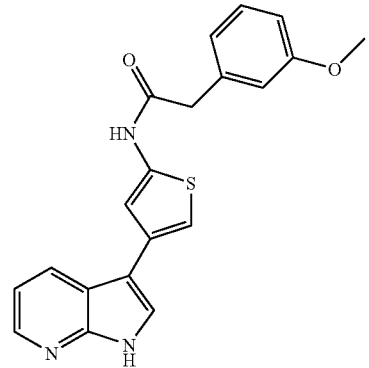

4-[1-(Toluene-4-sulfonyl)-1H-pyrrolo[2,3-b]pyridin-3-yl]-thiophen-2-ylamine was coupled to 3-methoxyphenylacetic acid according to General Method B and the product 2-(3-methoxyphenyl)-N-(4-(1-tosyl-1H-pyrrolo[2,3-b]pyridin-3-yl)thiophen-2-yl)acetamide (70 mg, 0.14 mmol) was dissolved in 6 mL THF and LiOH hydrate (63 mg, 1.5 mmol) was added in 1 mL of water. The reaction mixture was heated to 150° C. by microwave irradiation for 15 minutes and then diluted with EtOAc and water and the organic layer dried over sodium sulfate and concentrated to an oil, which was purified by column chromatography on silica (40 to 100% EtOAc/hexanes to give 20 mg of a light brown solid, 0.055 mmol, 39%. $^1$H NMR 500 MHz (DMSO-d6) 11.80 (1H, s), 11.37 (1H, s) 8.28 (2H, m), 7.78 (1H, s), 7.25 (1H, t), 7.16 (2H, m), 7.07 (1H, s) 6.88 (2H, m), 6.82 (1H, m), 3.78 (3H, s), 3.69 (2H, s). MH+ 364.20.

Preparation of 5-(1H-pyrrolo[2,3-b]pyridin-3-yl)thiophene-2-carboxylic acid

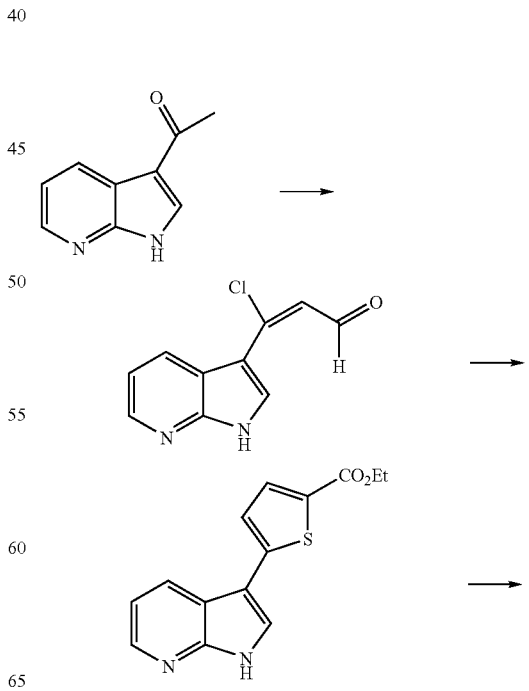

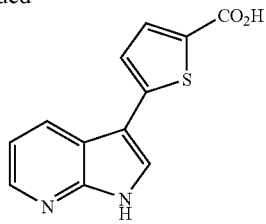

(E)-3-chloro-3-(1H-pyrrolo[2,3-b]pyridin-3-yl)acrylaldehyde

Phosphorous oxychloride (3.7 mL, 40 mmol) was added dropwise to DMF (6.2 mL, 80 mmol) at 0° C. The reaction mixture was let warm to room temperature and stirred for 15 minutes. 1-(1H-Pyrrolo[2,3-b]pyridin-3-yl)-ethanone was added in DMF (20 mL) and the reaction heated to 60° C. for 4 hours, cooled to 0° C. and 150 mL of saturated NaOAc solution added. The reaction mixture was heated briefly to 50° C. and then extracted with EtOAc. The organic layer was washed with brine, dried over sodium sulfate and concentrated to an oil which contains impure product. Upon standing a solid precipitated from the aqueous layer to give 0.9 g of a brown solid, 4.3 mmol, 22% yield.

Ethyl 5-(1H-pyrrolo[2,3-b]pyridin-3-yl)thiophene-2-carboxylate (E)-3-chloro-3-(1H-pyrrolo[2,3-b]pyridin-3-yl)acrylaldehyde (0.9 g, 4.3 mmol) was dissolved in EtOH (20 mL) and ethyl 2-mercaptoacetate (0.76 g, 6.3 mmol) and sodium ethoxide (1.0 g, 14.7 mmol) were added. The reaction mixture was heated to reflux for 90 minutes. The reaction mixture was diluted with EtOAc and the organic layer was washed with saturated sodium bicarbonate, dried over sodium sulfate, and concentrated to a solid, which was purified by column chromatography on silica (20 to 100% EtOAc/hexanes) to give the product, 890 mg, 3.3 mmol, 74% yield. $^1$H NMR 500 MHz (DMSO-d6) 12.19 (1H, br s), 8.32 (2H, m), 8.13 (1H, s), 7.78 (1H, d), 7.48 (1H, d), 7.23 (1H, dd), 4.31 (2H, q), 1.30 (3H, t).

5-(1H-pyrrolo[2,3-b]pyridin-3-yl)thiophene-2-carboxylic acid

Ethyl 5-(1H-pyrrolo[2,3-b]pyridin-3-yl)thiophene-2-carboxylate (0.89 g, 3.3 mmol) was partly dissolved in 1,4 dioxane and 10 mL 1N NaOH added. The reaction mixture was heated to 80° C. where it became homogenous. After 2 hours the reaction mixture was cooled to room temperature, diluted with ethyl acetate, and a 10% citric acid solution. A precipitate formed which was filtered off, washed with water and dried to 0.71 g, 2.9 mmol, 88% yield.

Preparation of tert-butyl 5-(1H-pyrrolo[2,3-b]pyridin-3-yl)thiophen-2-ylcarbamate

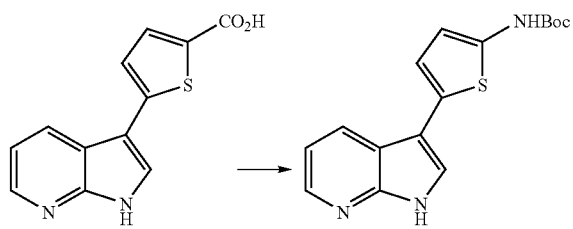

tert-butyl 5-(1H-pyrrolo[2,3-b]pyridin-3-yl)thiophen-2-ylcarbamate 5-(1H-pyrrolo[2,3-b]pyridin-3-yl)thiophene-2-carboxylic acid (0.60 g, 2.5 mmol) was dissolved in 20 mL t-BuOH. To this solution diphenylphosphoryl azide (0.81 g, 2.9 mmol) and triethylamine (0.4 mL, 2.9 mmol) were added. The reaction mixture was heated to reflux for 6 hours, then let stand overnight. The reaction mixture was concentrated to a green residue that was dissolved in EtOAc. The organic layer was washed with saturated sodium bicarbonate and concentrated to an solid, which was purified by column chromatography on silica (20 to 100% EtOAc/hexanes) to give the product as a yellow solid, 0.33 g, 1.05 mmol, 42% yield. MH+ 316.0. The Boc-amine was deprotected with 4N HCl in dioxane and coupled using the usual method.

Preparation of N-(3-methoxybenzyl)-5-(1H-pyrrolo[2,3-b]pyridin-3-yl)thiophene-3-carboxamide

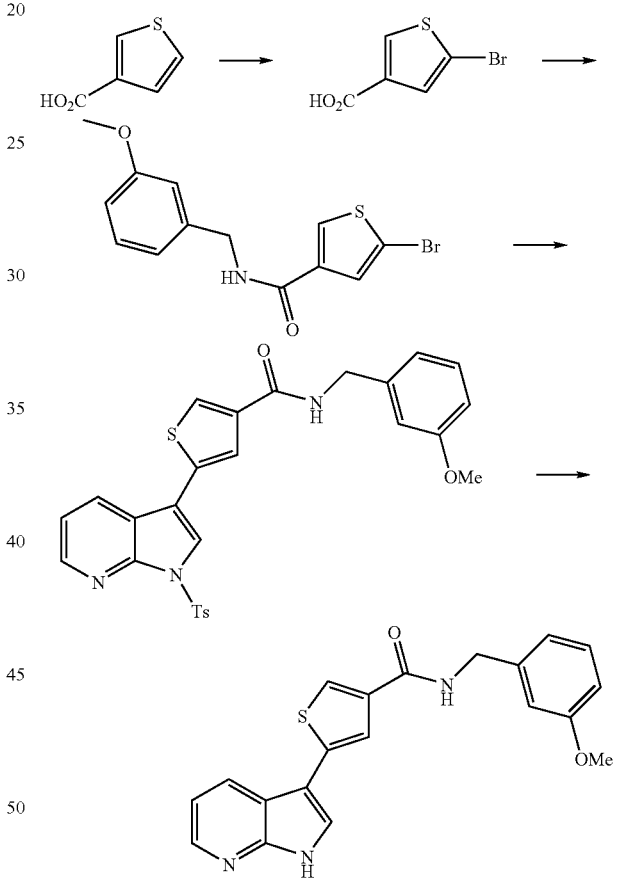

5-Bromothiophene-3-carboxylic acid

Thiophene-3-carboxylic acid (0.51 g, 4 mmol) was dissolved in HOAc (5 mL) and Br$_2$ (0.21 mL, 4 mmol) was added in 1 mL HOAc. The reaction mixture was stirred for 40 minutes, poured into water and a white precipitate formed, which was filtered and dried to 0.70 g grams of product that contains about 30% 2,5-dibromothiophane-3-carboxylic acid.

N-(3-Methoxybenzyl)-5-bromothiophene-3-carboxamide

5-Bromothiophene-3-carboxylic acid (70%) (200 mg, 0.6 mmol of monobromide) was dissolved in DMF with 3-methoxybenzyl amine (0.3 g, 2.2 mmol), EDCI (0.42 g, 2.2 mmol), and HOBt hydrate (0.06 g, 0.4 mmol). The reaction mixture was stirred at room temperature for 3 days, diluted with EtOAc and the organic layer washed with 10% citric acid, saturated sodium bicarbonate, and brine. The organic layer was then dried over sodium sulfate and concentrated to an oil, which was purified by column chromatography on silica (10 to 30 5 EtOAc/hexanes) to give the product as a colorless oil, 195 mg, 0.6 mmol, 100%. $^1$H NMR 500 MHz (CDCl$_3$) 7.81 (1H, s), 7.35 (1H, s), 7.28 (1H, m), 6.93 (1H, m), 6.87 (2H, m), 6.23 (1H, br s), 4.57 (2H, d), 3.84 (3H, s).

N-(3-Methoxybenzyl)-5-(1-tosyl-1H-pyrrolo[2,3-b]pyridin-3-yl)thiophene-3-carboxamide N-(3-Methoxybenzyl)-5-bromothiophene-3-carboxamide (100 mg, 0.3 mmol), 3-(4,4,5,5-tetramethyl-1,3,2-dioxaborolan-2-yl)-1-tosyl-1H-pyrrolo[2,3-b]pyridine (122 mg, 0.3 mmol), potassium carbonate (125 mg, 0.9 mmol), and tetrakis(triphenylphosphine) palladium (0) (20 mg) were combined in 4 mL DME, 1 mL water, and heated to 160° C. in the microwave for 10 minutes. The reaction mixture was diluted with EtOAc and water. The organic layer was filtered through celite and concentrated to an oil which was purified by column chromatography on silica (20 to 60% EtOAc/hexanes) to give the product as a brown oil, 0.07 g, 0.14 mmol, 45% yield. MH+ 518.0

N-(3-Methoxybenzyl)-5-(1H-pyrrolo[2,3-b]pyridin-3-yl)thiophene-3-carboxamide

N-(3-Methoxybenzyl)-5-(1-tosyl-1H-pyrrolo[2,3-b]pyridin-3-yl)thiophene-3-carboxamide (70 mg, 0.14 mmol) was dissolved in THF (4 mL) and LiOH hydrate (42 mg, 1 mmol) was added in water (1 mL). The reaction mixture was heated to 150° C. in the microwave for 10 minutes. The reaction mixture was diluted with EtOAc and the organic layer was washed with 10% citric acid, saturated sodium bicarbonate, and then dried over sodium sulfate and concentrated to an oil, which was purified by column chromatography on silica (50 to 100% EtOAc/hexanes) to give the product as a white solid 30 mg, 0.083 mmol, 59%. $^1$H NMR 500 MHz (DMSO-d6) 12.00 (1H, s), 8.88 (1H, t), 8.32 (2H, m), 8.01 (1H, s), 7.87 (1H, s), 7.83 (1H, s), 7.26 (2H, m), 6.92 (2H, m), 6.93 (2H, m), 6.82 (1H, d), 4.43 (2H, d), 3.70 (3H, s). MH+ 364.10

Preparation of N-(3-Methoxybenzyl)-4-(1H-pyrrolo[2,3-b]pyridin-3-yl)thiophene-2-carboxamide

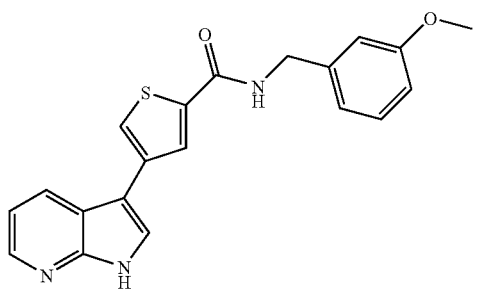

N-(3-Methoxybenzyl)-4-(1H-pyrrolo[2,3-b]pyridin-3-yl)thiophene-2-carboxamide

The above compound was made by the same procedure as N-(3-methoxybenzyl)-5-(1H-pyrrolo[2,3-b]pyridin-3-yl)thiophene-3-carboxamide starting with the regioisomer, 4-bromothiophene-2-carboxylic acid.

Preparation of 3-(3-Methoxy-phenyl)-1-[4-(1H-pyrrolo[2,3-b]pyridin-3-yl)-thiazol-2-yl]-piperidin-2-one

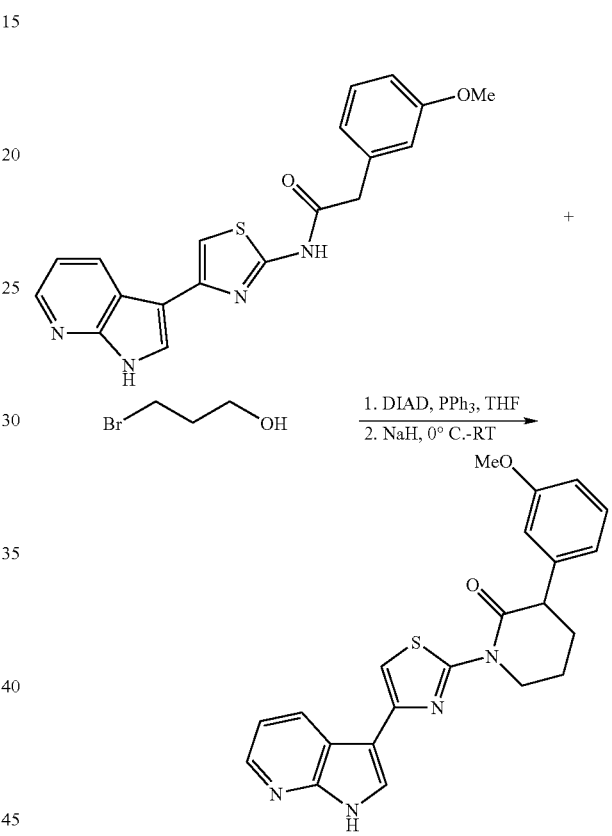

3-(3-Methoxy-phenyl)-1-[4-(1H-pyrrolo[2,3-b]pyridin-3-yl)-thiazol-2-yl]-piperidin-2-one To 2-(3-methoxy-phenyl)-N-[4-(1H-pyrrolo[2,3-b]pyridin-3-yl)-thiazol-2-yl]-acetamide (1 mmol) in THF was added 1.2 mmol of PPh$_3$, 1.2 mmol of 3-bromopropanol and 1.2 mmol of DIAD and the reaction mixture was stirred at room temperature for 16 h. The reaction mixture was cooled to 0° C. and 1.2 mmol of NaH was added and reaction mixture was stirred at 0° C. for 30 minutes. MeOH was added to quench reaction and the solvent evaporated. The residue was redissolved in EtOAc and the organic layer was washed with H2O and dried over Na2SO4. After removal of solvent, the final product was purified by preparative HPLC to afford 3-(3-methoxy-phenyl)-1-[4-(1H-pyrrolo[2,3-b]pyridin-3-yl)-thiazol-2-yl]-piperidin-2-one in 30% yield.

Preparation of 2-[3-(3-Piperidin-1-yl-propane-1-sulfonylamino)-phenyl]-N-[4-(1H-pyrrolo[2,3-b]pyridin-3-yl)-thiazol-2-yl]-acetamide

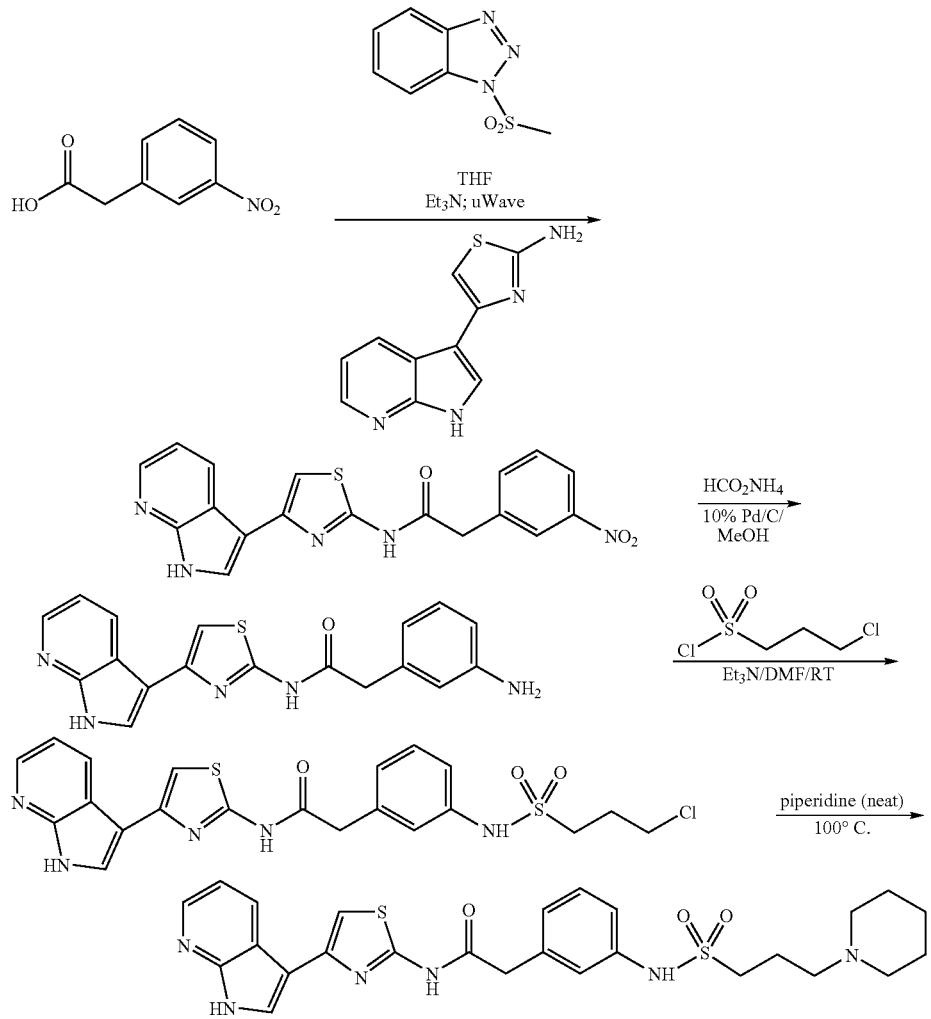

2-(3-Nitro-phenyl)-N-[4-(1H-pyrrolo[2,3-b]pyridin-3-yl)-thiazol-2-yl]-acetamide Prepared from 3-nitrophenyl acetic acid (1 g, 5.52 mmol), N-(1-methanesulfonyl)-benzotriazole (1.5 eq, 1.6 g), 4-(1H-pyrrolo[2,3-b]pyridin-3-yl)-thiazol-2-ylamine and triethylamine (3eq, 2.3 ml) in THF (20 mL) by microwave irradiation at 170° C. for 10 mins as described above. The reaction mixture was concentrated to dryness and CH3CN added. The desired final product was filtered and washed with ether to give clean 2-(3-nitrophenyl)-N-[4-(1H-pyrrolo[2,3-b]pyridin-3-yl)-thiazol-2-yl]-acetamide (1.4 g, 66% yield.)

2-(3-Amino-phenyl)-N-[4-(1H-pyrrolo[2,3-b]pyridin-3-yl)-thiazol-2-yl]-acetamide 2-(3-Nitro-phenyl)-N-[4-(1H-pyrrolo[2,3-b]pyridin-3-yl)-thiazol-2-yl]-acetamide (200 mg, 0.5 mmol) was taken in DMF-MeOH (5 mL) and added to sat. NH4OH (5 ml) and Fe powder (3eq, 83 mg). Then the suspension was heated overnight at 100° C. The brown colored reaction mixture was passed through a celite plug and washed with ethyl acetate. Then the reaction mixture was concentrated to dryness and taken up in ethyl acetate and extracted with water. The organic layer was dried and concentrated to give the desired product as a tan solid (50 mg, 30% yield).

2-[3-(3-Chloro-propane-1-sulfonylamino)-phenyl]-N-[4-(1H-pyrrolo[2,3-b]pyridin-3-yl)-thiazol-2-yl]-acetamide 2-(3-Amino-phenyl)-N-[4-(1H-pyrrolo[2,3-b]pyridin-3-yl)-thiazol-2-yl]-acetamide (100 mg, 0.28 mmol) was dissolved in DMF (5 mL) and 3-chloro-propane-1-sulfonyl chloride (1 eq, 35 □L) was added followed by triethylamine (2 eq, 80 □L). The reaction mixture was stirred at RT for 3 hours and then diluted with EtOAc and extracted with water. The organic layer was dried and concentrated to give brown oil, which was used without further purification.

2-[3-(3-Piperidin-1-yl-propane-1-sulfonylamino)-phenyl]-N-[4-(1H-pyrrolo[2,3-b]pyridin-3-yl)-thiazol-2-yl]-acetamide The crude 2-[3-(3-chloro-propane-1-sulfonylamino)-phenyl]-N-[4-(1H-pyrrolo [2,3-b]pyridin-3-yl)-thiazol-2-yl]-acetamide was treated with neat piperidine and heated to 100° C. overnight. The reaction mixture was diluted with DMF and purified by preparative HPLC to give the desired compound.

Preparation of 2-[3-(1,1-Dioxo-1I6-isothiazolidin-2-yl)-phenyl]-N-[4-(1H-pyrrolo[2,3-b]pyridin-3-yl)-thiazol-2-yl]-acetamide

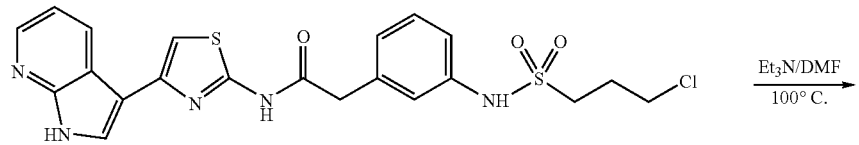

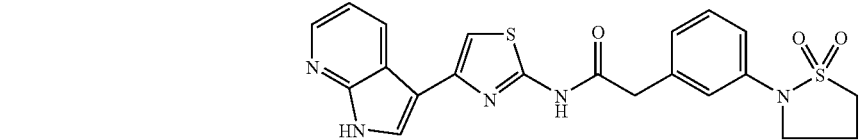

2-[3-(1,1-Dioxo-1I6-isothiazolidin-2-yl)-phenyl]-N-[4-(1H-pyrrolo[2,3-b]pyridin-3-yl)-thiazol-2-yl]-acetamide: 2-[3-(3-Chloro-propane-1-sulfonylamino)-phenyl]-N-[4-(1H-pyrrolo[2,3-b]pyridin-3-yl)-thiazol-2-yl]-acetamide was prepared as described above, then was dissolved in DMF in a refluxing tube and triethylamine added. Heated to 100° C. overnight. The reaction mixture was diluted with DMF and purified by prep HPLC to give the desired compound. (25.0 mg, 20% yield).

Preparation of 2-(3-(N-Dimethylsulfamoyl)-amino-phenyl)-N-[4-(1H-pyrrolo[2,3-b]pyridin-3-yl)-thiazol-2-yl]-acetamide

2-(3-Amino-phenyl)-N-[4-(1H-pyrrolo[2,3-b]pyridin-3-yl)-thiazol-2-yl]-acetamide 2-(3-Nitro-phenyl)-N-[4-(1H-pyrrolo[2,3-b]pyridin-3-yl)-thiazol-2-yl]-acetamide (1 g, 2.6 mmol) was dissolved in MeOH (100 ml) and added 10% Pd/C (100 mg) followed by ammonium formate (3eq, 500 mg). The reaction mixture was refluxed overnight. Then the reaction mixture was filtered and concentrated to give a white solid. The solid was taken up in EtOAc, filtered again, concentrated to give white solid. (500 mg, 55% yield).

2-(3-(N-Dimethylsulfamoyl)-amino-phenyl)-N-[4-(1H-pyrrolo[2,3-b]pyridin-3-yl)-thiazol-2-yl]-acetamide 2-(3-Amino-phenyl)-N-[4-(1H-pyrrolo[2,3-b]pyridin-3-yl)-thiazol-2-yl]-acetamide (100 mg, 0.28 mmol) was dissolved in THF (5 mL) and dimethyl sulfamoyl chloride (3eq, 90 □L) was added, followed by triethylamine (3eq, 120 □L). The reaction mixture was heated to 80° C. overnight, then was concentrated and taken up in DMF/H2O and purified by preparative HPLC to afford 2-(3-(N-dimethylsulfamoyl)-amino-phenyl)-N-[4-(1H-pyrrolo[2,3-b]pyridin-3-yl)-thiazol-2-yl]-acetamide (24.5 mg, 20% yield)

Preparation of 2-(1H-Pyrrolo[2,3-b]pyridin-3-yl)-thiazol-4-ylamine

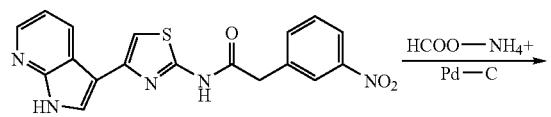

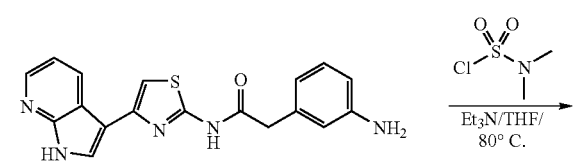

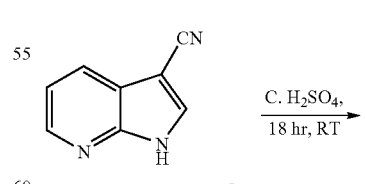

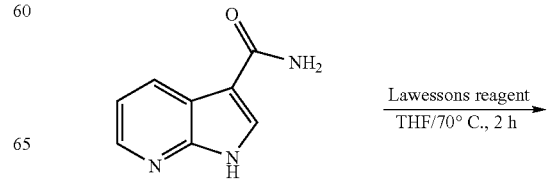

201

-continued

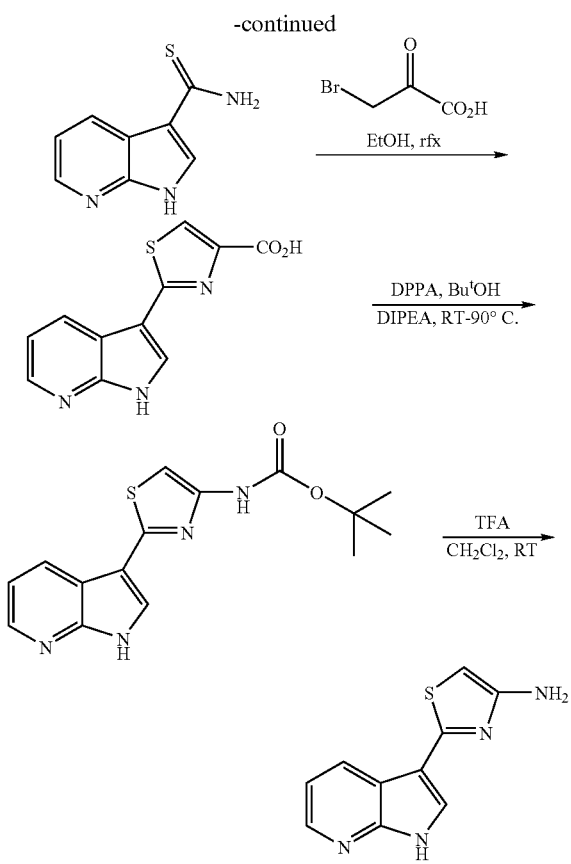

1H-Pyrrolo[2,3-b]pyridin-3-carboxylic acid amide

A solution of 3-cyano-7-azaindole (3 g, 20.98 mmol) in concentrated sulfuric acid (50 mL) was stirred at room temperature for 1 h. The solution was slowly poured into ice and basified with concentrated NH$_4$OH. The solution was concentrated under reduced pressure to produce brown residue which was extracted with acetone (4×100 mL). The organic extracts were dried and concentrated under reduced pressure to give title compound as a brown solid (3 g, 91%); Mass Spec.; MS 162 (M+1); $^1$H NMR (DMSO-d6; 500 MHz) 8.44(dd,1H),8.25(dd,1H), 8.14(s,1H), 7.45(brs,1H), 7.15(dd, 1H), 6.89(brs,1H).

1H-Pyrrolo[2,3-b]pyridin-3-carbothioc acid amide

A mixture of Lawesson's reagent (11 g, 27.93 mmol) and 1H-Pyrrolo[2,3-b]pyridin-3-caboxylic acid amide (3 g, 18.63 g) in THF (150 mL) was heated at 70° C. for 2 h. The solution was cooled to room temperature and the solvent was removed under reduced pressure to produce a yellow foam. Saturated K$_2$CO$_3$ (100 mL) and EtOAc (100 mL) were added and stirred for 30 min at room temperature. Organic layer was separated and the aqueous layer was extracted EtOAc (3×25 mL). The combined organic extracts were dried and concentrated to give yellow residue which was triturated with CH$_2$Cl$_2$ (50 mL) to produce a solid. The solid was filtered and dried to give title compound 3 (2.53 g, 77%); Mass Spec; MS 178 (M+1); $^1$H NMR(DMSO-d6,500 MHz) 12.26 (s,1H), 9.05(s,1H), 8.97(d,1H), 8.94(s,1H), 8.26(dd,1H), 8.20(d,1H), 7.19(dd, 1H),

202

2-(1H-Pyrrolo[2,3-b]pyridin-3-yl)-thiazole-4-carboxylic acid

A mixture of 1H-pyrrolo[2,3-b]pyridine-3-carbothioic acid amide (2.53 g, 14.37 mmol), bromopyruvic acid (2.4 g, 14.37 mmol) in ethanol (50 mL) was refluxed for 2 h. The solution was left at room temperature for 16 h and precipitated solid was filtered to give 2-(1H-pyrrolo[2,3-b]pyridin-3-yl)-thiazole-4-carboxylic acid (3.5 g, 100%) as a yellow solid MS 246 (M+1).

[2-(1H-Pyrrolo[2,3-b]pyridin-3-yl)-thiazol-4-yl]-carbamic acid tert-butyl ester

A mixture of 2-(1H-pyrrolo[2,3-b]pyridin-3-yl)-thiazole-4-carboxylic acid (3 g, 12.24 mmol), diphenylphosphoryl azide (4.4 g, 15.91 mmol) and Et$_3$N (4 mL) in tertiary butanol (100 mL) was refluxed for 2 h and cooled to room temperature and concentrated. The residue was dissolved in EtOAC (10 mL) and insoluble material was filtered. The filtrate was chromatographed on silica gel (Biotage) eluting with EtOAc/hexane to give [2-(1H-pyrrolo[2,3-b]pyridin-3-yl)-thiazol-4-yl]-carbamic acid tert-butyl ester as a off white solid (1.8 g, 46%); Mass Spec; MS 317 (M+1); $^1$H NMR(DMSO-d6,500 MHz) 12.19 (s,1H), 10.15(s,1H), 8.57(dd,1H),8.32(dd,1H), 8.12(d,1H), 7.23(dd,1H), 7.03(s,1H), 1.49(s,9H).

2-(1H-Pyrrolo[2,3-b]pyridin-3-yl)-thiazol-4-yl amine

Trifluoroacetic acid (1 mL) was added to a stirred solution of [2-(1H-pyrrolo[2,3-b]pyridin-3-yl)-thiazol-4-yl]-carbamic acid tert-butyl ester (0.1 g, 0.316 mmol) in CH$_2$Cl$_2$ (2 mL) and stirred at room temperature for 2 h. The solution was poured into ice/water and basified with saturated NaHCO$_3$ and extracted with EtOAc (3×25 mL). The combined organic extracts were dried and concentrated to afford title compound as a pale green solid (0.058 g, 85%); Mass Spec.; MS 217 (M+1)

Preparation of 5-Methyl-4-(1H-pyrrolo[2,3-b]pyridin-3-yl)thiazol-2-amine

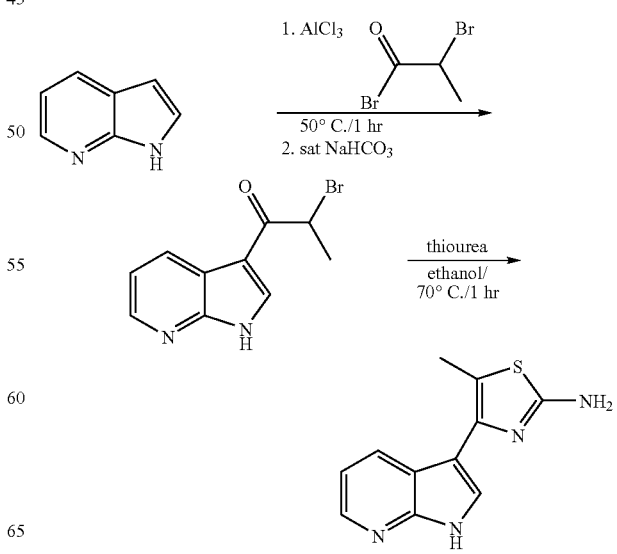

5-Methyl-4-(1H-pyrrolo[2,3-b]pyridin-3-yl)thiazol-2-amine

The title compound was synthesized in 2 steps in a manner similar to that described for 4-(1H-pyrrolo[2,3-b]pyridin-3-yl)-thiazol-2-ylamine, using 7-azaindole (1.0 g, 8.47 mmol), AlCl₃ (3.4 g, 25.41 mmol, 3 eq),2-bromopropionylbromide (1.1 mL, 10.58 mmol) and thiourea (0.57 g, 7.5 mmol) (0.93 g, 41%, 2 steps) as a brown solid. Mass Spec.; MS 231 (M+1); ¹H NMR(DMSO-d6, 500 MHz) δ 11.71 (s,1H), 8.36(dd, 1H), 8.21(dd,1H), 7.53(d,1H), 7.06(dd,1H), 6.67(brs,2H),2.31(s, 3H).

It will be appreciated that a variety of compounds can be prepared according to the general methods described above. Tables 3 and 4 includes exemplary data for certain compounds prepared according to the general methods described above. Compound numbers in Tables 1 and 2 correspond to the numbers assigned to compounds in Tables 1 and 2, respectively.

TABLE 3

| Cmpd # | LC/MS (M + 1) (obs) | RT (mins) | ¹H NMR |
|---|---|---|---|
| I-1 | 335.00 | 2.80 | H1NMR(500MHz, DMSO-d6, ppm)12.39(s, 1H), 11.83(s, 1H), 8.50(d, 1H, J=7.91Hz), 8.27(m, 1H), 7.84(d, 1H, J=2.48Hz), 7.36-7.15(m, 7H,), 3.81(s, 2H) |
| I-2 | 365.00 | 2.84 | H1NMR(500MHz, DMSO-d6, ppm)12.37(s, 1H), 11.83(s, 1H), 8.49(d, 1H, J=7.42), 8.27(dd, 1H, J=5.17, 1.4Hz), 7.84(d, 1H, J=2.48), 7.36(s, 1H,), 7.25(t, 1H, J=7.86Hz), 7.16(dd, 1HJ=7.92, 3.26Hz), 6.93(m, 2H), 6.84(dd, 1H, J=8.37, 2.3Hz), 3.77(s, 2H), 3.75(s, 3H) |
| I-3 | 353.00 | 2.86 | |
| I-4 | 353.00 | 2.93 | |
| I-5 | 427.90, 428.10, 428.10, 428.10, 428.10, 428.24, 428.20, 428.00, 428.10, 428.10, 428.10, 428.10 | 2.43, 2.46, 2.59, 2.59, 2.45, 2.43, 2.43, 2.42, 2.72, 2.80, 2.38, 2.38 | H1NMR(500MHz, DMSO-d6, ppm)12.41(s, 1H), 11.83(s, 1H), 9.74(s, 1H), 8.50(dd, 1H, J=7.95, 1.43Hz), 8.28(dd, 1H, J=4.64, 1.52Hz), 7.85(d, 1H, J=2.46), 7.37-7.10, (m, 6H), 3.80(s, 2H), 3.00(s, 3H), H1NMR(500MHz, DMSO-d6, ppm)12.61(s, 1H), 12.50(s, 1H), 9.78(s, 1H), 8.88(d, 1H, J=7.83Hz), 8.44(d, 1H, J=4.78Hz), 8.03(s, 1H), 7.51(s, 1H), 7.44(m, 1H), 7.30(t, 1H, J=7.83Hz), 7.23(s, 1H), 7.12(m, 2H), 3.82(s, 2H), 3.00(s, 3H), 2.35(s, 3H), H1NMR(500MHz, DMSO-d6, ppm)12.61(s, 1H), 12.50(s, 1H), 9.78(s, 1H), 8.88(d, 1H, J=7.83Hz), 8.44(d, 1H, J=4.78Hz), 8.03(s, 1H), 7.51(s, 1H), 7.44(m, 1H), 7.30(t, 1H, J=7.83Hz), 7.23(s, 1H), 7.12(m, 2H), 3.82(s, 2H), 3.00(s, 3H), H1NMR(500MHz, DMSO-d6, ppm)12.41(s, 1H), 11.83(s, 1H), 9.74(s, 1H), 8.50(dD, 1H, J=7.95, 1.43Hz), 8.28(dd, 1H, J=4.64, 1.52Hz), 7.85(d, 1H, J=2.46), 7.37-7.10, (m, 6H), 3.80(s, 2H), 3.00(s, 3H), H1NMR(500MHz, DMSO-d6, ppm)12.41(s, 1H), 8.48(dd, 1H, J=7.95, 1.43Hz), 8.25(dd, 1H, J=4.64, 1.52Hz), 7.85(d, 1H, J=2.46), 7.20-7.13, (m, 2H), 6.94-6.74, (m, 3H), 6.52, (d, 1H, J=7.48), 3.54(s, 2H), 2.58(s, 3H), H1NMR(500MHz, DMSO-d6, ppm)12.41(s, 1H), 11.83(s, 1H), 9.74(s, 1H), 8.50(dd, 1H, J=7.91, 1.20Hz), 8.27(dd, 1H, J=4.61, 1.46Hz), 7.84(d, 1H, J=2.58), 7.37-7.09, (m, 6H), 3.79(s, 2H), 3.00(s, 3H), H1NMR(500MHz, DMSO-d6, ppm)12.61(s, 1H), 12.50(s, 1H), 9.78(s, 1H), 8.88(d, 1H, J=7.83Hz), 8.44(d, 1H, J=4.78Hz), 8.03(s, 1H), 7.51(s, 1H), 7.44(m, 1H), 7.30(t, 1H, J=7.83Hz), 7.23(s, 1H), 7.12(m, 2H), 3.82(s, 2H), 3.00(s, 3H), H1NMR(500MHz, DMSO-d6, ppm) 12.61(s, 1H), 12.50(s, 1H), 9.78(s, 1H), 8.88(d, 1H, J=7.83Hz), 8.44(d, 1H, J=4.78Hz), 8.03(s, 1H), 7.51(s, 1H), 7.44(m, 1H), 7.30(t, 1H, J=7.83Hz), 7.23(s, 1H), 7.12(m, 2H), 3.82(s, 2H), 3.00(s, 3H), 2.35(s, 3H), H1NMR(500MHz, DMSO-d6, ppm)12.41(s, 1H), 9.75(s, 1H), 8.48(dd, 1H, J=7.95, 1.43Hz), 8.25(dd, 1H, J=4.64, 1.52Hz), 7.85(d, 1H, J=2.46), 7.20-7.13, (m, 2H), 6.94-6.74, (m, 3H), 6.52, (d, 1H, J=7.48), 3.80(s, 2H), 3.02(s, 3H), H1NMR(500MHz, DMSO-d6, ppm)12.61(s, 1H), 12.50(s, 1H), 9.78(s, 1H), 8.88 (d, 1H, J=7.83Hz), 8.44(d, 1H, J=4.78Hz), 8.03(s, 1H), 7.51(s, 1H), 7.44(m, 1H), 7.30(t, 1H, J=7.83Hz), 7.23(s, 1H), 7.12(m, 2H), 3.82(s, 2H), 3.00(s, 3H), H1NMR(500MHz, DMSO-d6, ppm)12.43(s, 1H), 12.10(s, 1H), 9.74(s, 1H), 8.66(m, 1H), 8.35(m, 1H), 7.90(m, 1H) |

TABLE 3-continued

| Cmpd # | LC/MS (M + 1) (obs) | RT (mins) | ¹H NMR |
|---|---|---|---|
| | | | 7.51(s, 1H), 7.44(m, 1H), 7.30(t, 1H, J=7.83Hz), 7.25(m, 1H), 7.23(s, 1H), 7.16-7.06(m, 4H), 3.82(s, 2H), 2.30(s, 3H) |
| I-6 | 371.00 | 2.98 | |
| I-7 | 349.00 | 3.05 | |
| I-8 | 379.00 | 2.77 | |
| I-9 | 576.00 | 4.39 | |
| I-10 | 428.90 | 2.73 | |
| I-11 | 476.20 | 2.17 | H1NMR(500MHz, DMSO-d6, ppm)9.04(s, 1H), 8.85(d, 1H, J=7.75Hz), 8.80(s, 1H), 8.44(, 1H, J=4.31Hz), 8.02(d, 1H, J=2.03Hz), 7.49(s, 1H,), 7.42(dd, 1H, J=7.92, 5.22Hz), 7.24(t, 1H, J=7.88Hz), 6.92(m, 2H), 6.84(m, 1H), 6.64(bs, 1H), 3.96(t, 2H, J=6.36), 3.78(s, 3H), 3.20(m, 2H), 2.79(m, 2H), 2.8(m, 4H), 2.50(m, 1H), 1.40(m, 4H) |
| I-12 | 351.00 | 2.31 | |
| I-13 | 412.90 | 2.99 | H1NMR(500MHz, DMSO-d6, ppm)12.59(s, 1H), 12.10(s, 1H), 8.75(d, 1H, J=6.87Hz), 8.27(dd, 1H, J=4.67, 1.44Hz), 8.08(d, 1H, J=2.47), 7.58(s, 1H,), 7.40(dd, 1H, J=7.94, 4.71Hz), 7.29(s, 1H), 7.26(s, 1H), 6.29(s, 2H), 4.10(s, 1H) |
| I-14 | 477.00 | 1.56 | H1NMR(500MHz, DMSO-d6, ppm)12.42(s, 1H), 12.08(s, 1H), 9.68(bs, 2H), 8.61(d, 1H, J=7.82Hz), 8.33(dd, 1H, J=4.83, 1.38Hz), 7.90(d, 1H, J=2.36Hz), 7.41(s, 1H), 7.25(m, 2H), 6.96(m, 2H), 6.87(m, 1H,), 6.90(bs, 1H), 4.07(t, 2H, J=6.0Hz), 3.80(s, 2H), 3.77(bs, 1H), 3.20-3.60(m, 8H), 2.21(m, 1H) |
| I-15 | 491.00 | 1.67 | H1NMR(500MHz, DMSO-d6, ppm)12.44(s, 1H), 12.28(s, 1H), 8.71(d, 1H, J=7.73Hz), 8.37(dd, 1H, J=4.79, 1.25Hz), 7.94(d, 1H, J=2.42), 7.44(s, 1H), 7.30(m, 2H), 6.94(m, 2H), 6.86(m, 1H), 4.08(t, 2H, J=5.91Hz), 3.79(s, 2H), 3.31-3.75(m, 10H), 2.83(s, 3H), 2.23(m, 2H) |
| I-16 | 463.00 | 1.51 | H1NMR(500MHz, DMSO-d6, ppm)12.45(s, 1H), 12.17(s, 1H), 9.73(bs, 2H), 8.66(d, 1H, J=7.87Hz), 8.34(dd, 1H, J=4.85, 1.45Hz), 7.92(d, 1H, J=2.18Hz), 7.42(s, 1H), 7.29(m, 2H), 7.01(m, 2H), 6.92(dd, 1H, J=8.14, 2.19Hz), 6.45(bs, 1H), 4.42(t, 2H, J=4.68Hz), 3.81(s, 2H), 3.36-3.83(m, 8H) |
| I-17 | 477.00, 477.00, 477.30, 477.00, 477.10 | 1.69, 1.87, 1.67, 1.70, 1.60 | H1NMR(500MHz, DMSO-d6, ppm)12.43(s, 1H), 12.09(s, 1H), 8.62(d, 1H, J=7.73Hz), 8.33(dd, 1H, J=4.79, 1.25Hz), 7.90(d, 1H, J=2.42), 7.41(s, 1H), 7.24-7.31(m, 2H), 7.00(m, 2H), 6.92(dd, 1H, J=8.27, 2.12Hz), 5.90(bs, 1H), 4.40(bs, 2H, J=4.68Hz), 3.80(s, 2H), 3.38-3.76(m, 9H), 2.82(s, 3H), DMSO-d6: 12.37(s, 1H), 11.87(s, 1H), 8.48(d, 1H), 8.27(dd, 1H), 7.84(d, 1H), 7.36(s, 1H), 7.25(t, 1H), 7.17(dd, 1H), 6.95(m, 2H), 6.84(dd, 1H), 4.09(t, 2H), 3.76(s, 2H), 3.02(brm, 4H), 2.81(t, 2H), 2.67& 2.57(dAB, J=15.3HZ, 8H), 2.63(s, 3H), 2.60-2.80(brm, 4H), H NMR(500MHz, DMSO-d6)ppm 12.35(s, 1H), 11.83(s, 1H), , 8.49(d, J=7.9Hz, 1H), 8.27(d, J=6.1Hz, 1H), 7.85(d, J=2.5Hz, 1H), 7.36(s, 1H), 7.24(t, J=7.9Hz, 1H), 7.18-7.15(m, 1H), 6.95-6.90(m, 2H), 6.84(dd, J=8.1, 2.2Hz, 1H), 4.06(m, 3H), 3.76(s, 2H), 3.29(s, 2H), 3.17(d, J=4.9Hz, 2H), 2H), 2.51-2.49(m, 10H), 2.31(s, 3H), H NMR(400MHz, acetic acid-d4)ppm 12.37(s, 1H), 11.84(s, 1H), 8.49(dd, J=7.9, 1.4Hz, 1H), 8.28(dd, J=4.6, 1.5Hz, 1H), 7.85(d, J=2.0Hz, 1H), 7.36(s, 1H), 7.27-7.24(m, 1H), 7.18-7.15(m, 1H), 6.95-6.84(m, 3H), 4.09(t, J=5.5Hz, 2H), 3.17(s, 2H), 2.93-2.49(m, 20H), H NMR(500MHz, DMSO-d6)ppm 12.39(s, 1H), 11.85(s, 1H), 10.36(m, 1H), 8.50-8.49(m, 1H), 8.28(dd, J=4.6, 1.4Hz, 1H), 7.85(d, J=2.5Hz, 1H), 7.37(s, 1H), 7.26(t, J=7.8Hz, 1H), 7.17(dd, J=7.9, 4.6Hz, 1H), 6.94(m, 2H), 6.87-6.85(m, 1H), 4.09(s, 2H), 3.78(s, 2H), 3.32(s, 4H), 3.04(s, 3H), 2.80(s, 2H), 2.72(s, 2H), 2.54(s, 1H) |

TABLE 3-continued

| Cmpd # | LC/MS (M + 1) (obs) | RT (mins) | ¹H NMR |
|---|---|---|---|
| I-18 | 399.00, 399.00 | 3.29, 3.46 | H1NMR(500MHz, DMSO-d6, ppm)12.39(s, 1H), 11.83(s, 1H), 8.50(d, 1H, J=7.89Hz), 8.28(dd, 1H, J=4.62, 1.42Hz), 6.91-7.85(m, 6H), 3.91(s, 2H), 3.78(s, 3H), MeOD8.52d(2H), 8.23d(1H), 7.83s(1H), 7.32d(1H), 7.20m(2H), 7.01s(1H), 6.90m(1H), 3.92s(2H), 3.80s(3H) |
| I-19 | 442.10 | 2.96 | H1NMR(500MHz, MeOH-d4, ppm)8.54(t, 1H, J=6.72), 8.88(dd, 1H, J=4.81Hz, 1.27Hz), 7.75-7.90. m, 4H), 7.51-7.66(m, 2H), 7.20-7.22(m, 1H), 3.95 s, 1H), 3.73(s, 1H), 2.9(m, 2H), 1.07(t, 3H, J=7.24) |
| I-20 | 375.20 | 3.39 | H1NMR(500MHz, DMSO-d6, ppm)11.92(s, 1H), 8.63(d, 1H, J=7.88Hz), 8.29(dd, 1H, J=4.71, 1.49Hz), 8.96(d, J=2.58, 1H), 7.44(s, 1H), 7.36-7.19(m, 6H), 4.27(s, 2H), 3.29(t, 1H, J=3.78), 1.33(m, 2H), 1.06(m, 2H) |
| I-21 | 366.00 | 2.93 | DMSO-d6: 12.71(s, 1H), 12.29(s, 1H), 8.52(d, 1H), 8.33(dd, 1H), 8.23(d, 1H), 7.24(m, 2H), 6.92(m, 2H), 6.84(dd, 1H), 3.81(s, 2H), 3.75(s, 3H). |
| I-22 | 372.00 | 2.95 | DMSO-d6: 12.77(s, 1H), 12.30(s, 1H), 8.52(d, 1H), 8.34(d, 1H), 8.23(d, 1H), 7.46(m, 1H), 7.24(m, 2H), 7.08(m, 1H), 3.92(s, 2H). |
| I-23 | 354.00 | 2.84 | DMSO-d6: 12.90(brs, 1H), 12.31(brs, 1H), 8.51(d, 1H), 8.34(d, 1H), 8.23(s, 1H), 7.42(m, 1H), 7.34(m, 1H), 7.17-7.26(m, 3H), 3.94(s, 2H). |

TABLE 4

| Cmpd # | LC/MS (M + 1) (obs) | RT (mins) | ¹H NMR |
|---|---|---|---|
| II-1 | 408.20 | 2.60 | |
| II-2 | 408.20 | 2.60 | |
| II-3 | 257.02, 257.10 | 1.62, 1.66 | A1919-180A: H1NMR(500MHz, DMSO-d6, ppm) 12.22(s, 1H), 9.20(bs, 1H), 8.42(d, 1H, J=7.82Hz), 8.36(dd, 1H, J=4.81, 1.22Hz), 8.00(s, 1H), 7.25(m, 1H), 6.12(s, 1H), 2.77(t, 1H, J=4.75), 0.86(m, 2H), 0.71(m, 2H) |
| II-4 | 456.30 | 3.12 | |
| II-5 | 456.20 | 3.12 | |
| II-6 | 454.20 | 3.05 | |
| II-7 | 354.00 | 2.94 | DMSO-d6: 12.72(s, 1H), 12.30(s, 1H), 8.52(d, 1H), 8.34(dd, 1H), 8.23(d, 1H), 7.37(m, 2H), 7.24(dd, 1H), 7.17(t, 2H), 3.84(s, 2H). |
| II-8 | 336.00 | 2.93 | DMSO-d6: 12.73(s, 1H), 12.29(s, 1H), 8.51(dd, 1H), 8.33(dd, 1H), 8.23(d, 1H), 7.34(m, 4H), 7.25(m, 2H), 3.84(s, 2H). |
| II-9 | 429.00 | 2.39 | DMSO-d6: 12.75(s, 1H), 12.29(s, 1H), 9.73(s, 1H), 8.52(dd, 1H), 8.33(dd, 1H), 8.24(d, 1H), 7.30(t, 1H), 7.24(m, 1H), 7.21(s, 1H), 7.10(m, 2H), 3.82(s, 2H), 2.99(s, 3H). |
| II-10 | 414.00 | 3.07 | DMSO-d6: 12.71(s, 1H), 12.30(s, 1H), 8.51(dd, 1H), 8.34(dd, 1H), 8.23(d, 1H), 7.09(s, 1H), 7.05(s, 1H), 6.07(s, 2H), 3.92(s, 2H). 2.99(s, 3H). |
| II-11 | 371.10 | 3.38 | H CD3OD: 3.92(s, 2H), 6.99(m, 1H), 7.1(dd, 1H), 7.15(dd, 1H), 7.25(s, 1H), 7.32(m, 1H), 7.37(dd, 1H), 7.87(s, 1H), 8.25(m, 1) |
| II-12 | 371.10 | 3.48 | H CD3OD &CDCl3: 3.8(s, 2H), 6.97(m, 1H), 7.06(dd, 1H), 7.25(s, 1H), 7.35(m, 1H), 7.85(s, 1H), 8.25(m, 1H) |
| II-13 | 388.90 | 3.23 | H CD3OD: 3.85(s, 2H), 6.95(m 2H), 7.02(m, 1H), 7.27(s, 1H), 7.39(m, 1H), 7.89(s, 1H), 8.25(m, 1H) |
| II-14 | 446.20 | 2.96 | H CD3OD: 2.97(s, 3H), 3.8(s, 2H), 7.0(m, 1H), 7.13(dd, 1H), 7.16(dd, 1H), 7.25(s, 1H), 7.32(dd, 1H), 7.87(s, 1H), 8.25(m, 1H) |
| II-15 | 367.00 | 3.60 | H CD3OD: 2.78(t, 2H), 3.02(t, 2H), 7.02(m, 1H), 7.15(m, 1H), 7.25(m, 5H), 7.84(s, 1H), 8.25(m, 1H) |
| II-16 | 353.10 | 3.34 | H DMSOd-6: 3.76(s, 2H), 7.0(m, 1H), 7.3(m, 6H), 7.78(s, 1H), 8.25(m, 1H) |

TABLE 4-continued

| Cmpd # | LC/MS (M + 1) (obs) | RT (mins) | ¹H NMR |
|---|---|---|---|
| II-17 | 494.40 | 2.35 | H CD3OD: 1.37(m, 2H), 1.49(m, 2H), 1.67(m, 1H), 1.83(m, 2H), 1.97(m, 2H), 2.95(t, 2H), 3.75(s, 2H), 4.04(t, 2H), 6.82(dd, 1H), 6.95(m, 3H), 6.23(dd, 1H0, 6.25(s, 1H), 7.85(s, 1H), 8.22(m, 1H) |
| II-18 | 397.10 | 3.32 | H DMSO d-6: 3.7(s, 2H), 6.0(s, 2H), 6.8(d, 1H), 6.85(d, 1H), 6.9(s, 1H), 7.0(m, 1H), 7.2(s, 1H), 7.77(s, 1H), 8.25(m, 1H) |
| II-19 | 383.00 | 3.38 | H CD3OD: 3.77(s, 2H), 3.81(s, 3H), 6.8(dd, 1H), 6.9(dd, 1H), 6.9(s, 1H), 6.97(m, 1H), 7.24(m, 2H), 7.87(s, 1H), 8.25(m, 1H) |
| II-20 | 431.10 | 3.47 | H CD3OD: 3.9(s, 2H), 6.0(s, 2H)6.9(m, 3H), 7.25(s, 1H), 7.84(s, 1H), 8.2(m, 1H) |
| II-21 | 365.00 | 3.17 | DMSO-d6: 12.31(s, 1H), 8.96(t, 1H), 8.84(dd, 1H), 8.34(dd, 1H), 8.30(d, 1H)8.13(s, 1H), 7.24(m, 2H), 6.92(m, 2H), 6.82(dd, 1H), 4.51(d, 2H), 3.73(s, 3H). |
| II-22 | 477.00 | 2.14 | DMSO-d6: 12.71(s, 1H), 12.31(s, 1H), 8.52(d, 1H), 8.34(dd, 1H), 8.23(d, 1H), 7.24(m, 2H), 6.90(m, 2H), 6.83(dd, 1H), 3.95(t, 2H), 3.79(s, 2H), 3.24(m, 2H), 2.82(m, 2H), 1.83(m, 2H), 1.79(m, 2H), 1.75(brm, 1H), 1.26-1.40(m, 4H). |
| II-23 | 364.20 | 3.20 | 1H NMR 500MHz(DMSO-d6)11.80ppm, 1H, s; 11.37ppm, 1H, s; 8.28ppm, 2H, m; 7.78ppm, 1H, s; 7.25PPM, 1H, t; 7.16ppm, 2H, m; 7.07ppm, 1H, s; 6.88ppm, 2H, m; 6.82ppm, 1H, m; 3.78ppm, 3H, s 3.69ppm, 2H, s. |
| II-24 | 470.30, 470.10 | 3.16, 3.21 | 1H NMR 500MHz(DMSO-d6)12.45ppm, 1H, s; 11.82ppm, 1H, s; 8.60ppm, 1H, m; 8.25ppm, 1H, m; 7.82ppm, 2H, m; 7.70ppm, 1H, m; 7.63ppm, 1H, m; 7.58ppm, 1H, m; 7.38ppm, 1H, s; 7.17ppm, 1H, m; 3.93ppm, 2H, s; 3.15ppm, 4H, m; 1.04ppm, 6H, m. |
| II-25 | 483.30, 483.10 | 1.83, 1.87 | |
| II-26 | 484.30, 484.10 | 2.97, 3.06 | 1H NMR 500MHz(DMSO-d6)12.44ppm, 1H, br s; 11.80ppm, 1H, s; 8.47ppm, 1H, d; 8.26ppm, 1H, d; 7.83ppm, 1H, s; 7.78ppm, 1H, s; 7.70ppm, 1H, m; 7.62ppm, 2H, m; 7.36ppm, 1H, s; 7.17ppm, 1H, m; 3.97ppm, 2H, s; 3.60ppm, 4H, m; 2.88ppm, 4H, m. |
| II-27 | 468.20 | 281.00 | H1NMR(500MHz, DMSO-d6, ppm)11.92(s, 1H), 9.70, (s, 1H), 8.63(d, 1H, J=7.91Hz), 8.28(dd, 1H, J=4.71, 1.49Hz), 7.96(d, 1H, J=2.46), 7.44, (s, 1H), 7.31-7.05(m, 5H), 4.25(s, 2H), 3.30, (m, 1H), 2.98(t, 1H, J=3.78), 1.31(m, 2H), 1.05(m, 2H) |
| II-28 | 370.00 | 2.86 | |
| II-29 | 333.96 | 2.73 | |
| II-30 | 364.04 | 2.73 | |
| II-31 | 347.97 | 2.84 | |
| II-32 | 366.03 | 2.86 | |
| II-33 | 427.00 | 2.76 | 1H NMR 500MHz(CDCl3/CD3OD)8.60ppm, 1H, d; 8.28ppm, 1H, m; 7.63ppm, 1H, s; 7.40ppm, 1H, m; 7.32ppm, 1H, m; 7.18ppm, 3H, m; 6.93ppm, 2H, m; 3.72ppm, 2H, s; 3.00ppm, 3H, s. |
| II-34 | 384.00 | 2.16 | CD3CN 12.92s(1H), 10.86s(1H), 9.08d(1H), 8.40d(1H), 8.07s(1H), 7.68s(2H), 7.59m(1H), 7.32s(1H), 7.20d(1H), 6.85s(1H), 6.71m(1H), 3.89s(2H) |
| II-35 | 476.00, 476.00 | 2.71, 2.77 | CD3CN12.80s(1H), 10.46s(1H), 9.02s(1H), 8.38d(1H), 8.04s(1H), 7.76s(1H), 7.54m(1H), 7.42d(1H), 7.36s(1H), 7.30s(1H), 7.22m(1H), 3.99q(1H), 3.15q(2H), 1.31t(3H), |
| II-36 | 495.10 | 1.92 | |
| II-37 | 509.10 | 2.02 | |

TABLE 4-continued

| Cmpd # | LC/MS (M + 1) (obs) | RT (mins) | ¹H NMR |
|---|---|---|---|
| II-38 | 477.10, 477.10 | 2.21, 2.44 | |
| II-39 | 472.00 | 2.51 | |
| II-40 | 360.10 | 2.72 | |
| II-41 | | 2.10 | |
| II-42 | 484.00 | 2.47 | |
| II-43 | 390.00 | 3.17 | 9.95(s, 1H), 8.46(d, 1H), 8.28(d, 1H), 7.87(d, 1H), 6.83(s, 1H), 4.1-4.8(s, 2H), 3.92(m, dH), 3.29(m, 2H), 2.12(s, 3H), 1.35(m, 6H) CD3CN |
| II-44 | 393.10 | 3.32 | H1NMR(500MHz, DMSO-d6, ppm)12.15(s, 1H), 8.74(d, 1H, J=7.87), 8.33(m, 1H), 8.02(d, 1H, J=2.41Hz), 7.49(s, 1H), 7.42-7.17, (m, 5H), 4.34(s, 2H), 3.38(m, 1H), 1.36(m, 2H), 1.10(m, 1H) |
| II-45 | 411.10 | 3.46 | H1NMR(500MHz, DMSO-d6, ppm)12.44(s, 1H), 8.89(d, 1H, J=7.87), 8.40(d, 1H), 8.08(d, 1H, J=1, 80Hz), 7.55(s, 1H), 7.47(m, 1H), 7.39(m, 1H), 7.25(m, 1H), 7.11(m, 1H), 4.34(s, 2H), 3.40(m, 1H), 1.36(m, 2H), 1.10(m, 1H). |
| II-46 | 428.00 | 2.69 | CD3OD: 8.65(d, 1H), 8.29(d, 1H), 8.00(s, 1H), 7.44(s, 1H), 7.16-7.32(m, 5H), 3.75(s, 2H), 2.97(s, 3H) |
| II-47 | 462.00 | 2.63 | CD3CN9.48s(1H), 8.35d(1H), 7.63s(1H), 7.52 m(1H), 7.42s(1H), 7.29m(1H), 7.07m(1H), 6.94 m(2H), 6.87m(1H). 3.81s(3H), 3.70s(2H), |
| II-48 | 490.00 | 2.90 | CD3CN12.81s(1H), 10.44s(1H), 9.05d(1H), 8.38d(1H), 8.04s(1H), 7.70s(1H), 7.54m(1H), 7.39m(2H), 7.30s(1H), 7.24m(1H), 3.34m(1H), 1.36d(6H), |
| II-49 | 456.10 | 2.95 | |
| II-50 | 442.00, 442.10, 442.08 | 2.75, 3.11, 2.98 | H1NMR(500MHz, DMSO-d6, ppm)12.90(s, 1H), 12.62(s, 1H), 11.67(bs, 1H), 9.01(d, 1H, J=7.91), 8.49(d, 1H, J=5.31Hz), 8.08(s, 1H), 7.80(s, 1H), 7.72-7.52(m, 6H), 4.02(s, 2H), 2.51(s, 3H), 2.50(s, 3H) |
| II-51 | 497.00, 497.10 | 1.86, 1.82 | |
| II-52 | 511.10 | 1.92 | |
| II-53 | 393.30 | 3.38 | |
| II-54 | 389.10 | 3.60 | H1NMR(500MHz, DMSO-d6, ppm)11.81(s, 1H), 8.58(d, 1H, J=7.92), 8.26(m, 1H), 7.92(d, 1H, J=2.58Hz), 7.41(s, 1H), 7.30-7.14(m, 6H), 3.25(m, 3H), 2.97(t, 2H, J=7.42Hz), 1.23(m, 2H), 0.95(m, 1H) |
| II-55 | 365.00 | 3.13 | CDCl3: 10.71(brs, 1H), 8.40(d, 1H), 8.33(m, 2H), 7.77(d, 1H), 7.51(s, 1H), 7.24(t, 1H), 7.17(m, 1H), 6.86(m, 1H), 6.80(m, 2H), 3.79(s, 3H), 3.69(s, 2H). |
| II-56 | 371.00 | 3.30 | CD3OD: 8.82(d, 1H), 8.34(d, 1H), 8.08(s, 1H), 7.45(s, 1H), 7.31-7.42(m, 2H), 6.95(m, 2H), 3.81(s, 2H), |
| II-57 | 484.00 | 3.02 | CD3OD: 8.95(d, 1H), 8.36(d, 1H), 8.10(s, 1H), 7.82(m, 1H), 7.55-7.75(m, 3H), 7.48(s, 1H), 7.35(m, 1H), 3.90(s, 2H), 3.66(m, 4H), 2.97(m, 4H) |
| II-58 | 485.00 | 2.72 | DMSO-d6: 12.80(s, 1H), 12.20(s, 1H), 8.52(dd, 1H), 8.33(dd, 1H), 8.24(d, 1H), 7.77(s, 1H), 7.70(m, 1H), 7.65(m, 12H), 7.25(dd, 1H), 4.02(s, 1H), 3.62(m, 4H), 2.87(m, 4H) |
| II-59 | 483.10 | 2.70 | 1H NMR 500MHz(DMSO-d6)8.25ppm, 2H, m; 7.71ppm, 3H, m; 7.63ppm, 2H, m; 7.14ppm, 2H, m; 7.05ppm, 1H, s; 3.88ppm, 2H, s; 3.60ppm, 4H, m; 2.88ppm, 4H, m. |
| II-60 | 353.00 | 3.16 | CD3OD: 8.93(d, 1H), 8.38(d, 1H), 8.12(d, 1H), 7.16-7.48(m, 6H). |
| II-61 | 353.00 | 3.22 | DMSO-d6: 12.27(s, 1H), 11.13(s, 1H), 8.57(d, 1H), 8.34(d, 1H), 8.15(d, 1H), 7.36-7.41(m, 3H), 7.26(dd, 1H), 7.14(t, 2H), 3.71(s, 2H) |
| II-62 | 335.00 | 3.13 | CD3OD: 8.45(d, 1H), 8.35(d, 1H), 8.08(s, 1H), 7.47(s, 1H), 7.24-7.40(m, 5H), 3.75(s, 1H) |
| II-63 | 470.00 | 3.38 | |
| II-64 | 471.00 | 3.07 | |

TABLE 4-continued

| Cmpd # | LC/MS (M + 1) (obs) | RT (mins) | $^1$H NMR |
|---|---|---|---|
| II-65 | 483.30 | 2.84 | 1H NMR 500MHz(DMSO-d6)9.07ppm, 1H, m; 8.30ppm, 2H, m; 7.99ppm, 1H, d; 7.79ppm, 1H, d; 7.70ppm, 2H, m; 7.63ppm, 2H, m; 7.42ppm, 1H, d; 7.20ppm, 1H, m; 4.57ppm, 2H, d; 3.61ppm, 4H, m; 2.84ppm, 4H, m. |
| II-66 | 502.00 | 3.16 | H NMR DMSO: 2.88(t, 4H), 3.64(t, 4H), 3.96(s, 2H), 7.03(m, 1H), 7.21(s, 1H), 7.62(m, 2H), 7.68(m 1H), 7.76(d, 1H), 7.81(d, 1H), 8.23(m, 1H) |
| II-67 | 488.20 | 3.56 | H NMD DMSO: 1.0(t, 6H), 3.16(q, 4H), 3.93(s, 2H), 7.02(m, 1H), 7.20(s, 1H), 7.55(m, 1H), 7.60(m, 1H), 7.65(dd, 1H), 7.77(d, 1H), 7.80(d, 1H), 8.24(m, 1H) |
| II-68 | 391.10 | 2.72 | H1NMR(500MHz, DMSO-d6, ppm)11.96(s, 1H), 8.66(d, 1H, J=7.80), 8.29(m, 1H), 7.97(d, 1H, J=2.72Hz), 7.45(s, 1H), 7.22(m, 1H), 7.12(m, 1H), 6.72-6.65(m, 4H), 4.17(s, 2H), 3.26(m, 1H), 1.33(m, 2H), 1.04(m, 2H) |
| II-69 | 419.10 | 3.20 | H1NMR(500MHz, DMSO-d6, ppm)11.91(s, 1H), 8.66(d, 1H, J=7.90), 8.29(m, 1H), 7.97(d, 1H, J=2.51Hz), 7.44(s, 1H), 7.20(m, 1H), 7.12(m, 1H), 6.88(m, 2H), 6.76(m, 1H), 5.99(s, 2H), 4.18(s, 2H), 3.28(m, 1H), 1.33(m, 2H), 1.04(m, 2H) |
| II-70 | 405.10 | 3.31 | |
| II-71 | 364.10 | 2.78 | 1H NMR 500MHz(DMSO-d6)11.82ppm, 1H, s; 9.04ppm, 1H, m; 8.35ppm, 1H, d; 8.25ppm, 2H, m; 7.93ppm, 1H, s; 7.79ppm, 1H, s; 7.23ppm, 1H, m; 7.14ppm, 1H, m; 6.88ppm, 2H, m; 6.83ppm, 1H, m; 4.46ppm, 2H, d; 3.73ppm, 3H, s. |
| II-72 | 498.00 | 2.64 | 1H-NMR(DMSO)12.45, s, 1H; 11.85, s, 1H; 8.50, d, 1H; 8.30, m, 1H; 7.85, d, 1H; 7.80, s, 1H; 7.70-7.75 m, 2H; 7.55-7.60, m, 2H; 7.38, s, 1H; 7.18-7.20, m, 1H; 4.00, s, 2H; 3.15, 2.80-2.83, m, 2H; 1.75-1.80, m, 3H; 1.70-1.75, m, 2H; 1.45-1.50, m, 2H |
| II-73 | 453.06 | 2.72 | H1NMR(500MHz, DMSO-d6, ppm)11.92(s, 1H), 8.64(d, 1H, J=7.18Hz), 8.29(m, 1H), 7.96(d, 1H, J=2.51Hz), 7.90(d, 2H, J=8.26Hz), 7.60(d, 2H, J=8.25Hz), 7.45(s, 1H), 7.20(m, 1H), 4.43(s, 2H), 3.20(m, 3H), 3.18(m, 1H), 1.34(m, 2H), 1.10(m, 2H) |
| II-74 | 413.05 | 2.32 | H1NMR(500MHz, DMSO-d6, ppm)12.48(s, 1H), 11.89(s, 1H), 8.52(d, 1H, J=7.28Hz), 8.29(m, 1H), 7.92-7.86(m, 3H), 7.62(d, 1H, J=8.22Hz), 7.38(s, 1H), 7.20(m, 1H), 3.96(s, 2H), 3.20(m, 3H) |
| II-75 | 439.10 | 3.60 | H1NMR(500MHz, DMSO-d6, ppm)11.87(s, 1H), 8.61(d, 1H, J=7.31Hz), 8.28(dd, 1H, J=4.62, 1.29Hz), 7.95(d, 1H, J=2.52Hz), 7.43(s, 1H), 7.35(d, 1H, J=8.51Hz), 7.19(m, 1H), 7.06(d, 1H, 2.57Hz), 6.92(m, 1H), 4.33(s, 2H), 3.36(m, 1H), 3.17(s, 3H), 1.36(m, 2H), 1.09(m, 2H) |
| II-76 | 515.10 | 2.44 | |
| II-77 | 444.90 | 3.80 | DMSO-d6: 12.35(brs, 1H), 12.09(s, 1H), 8.74(d, 1H), 8.32(d, 1H), 7.96(s, 1H), 7.43(s, 1H), 7.25(t, 1H), 7.91(m, 2H), 6.84(dd, 1H), 3.77(s, 2H), 3.75(s, 3H),. |
| II-78 | 507.90 | 3.32 | DMSO-d6: 12.40(s, 1H), 12.10(s, 1H), 9.73(s, 1H), 8.74(d, 1H), 8.32(d, 1H), 7.97(d, 1H), 7.43(s, 1H), 7.30(t, 1H), 7.21(s, 1H), 7.10(m, 1H), 3.79(s, 2H), 2.89(s, 3H), |
| II-79 | 414.90, 413.00 | 3.78, 9.60 | DMSO-d6: 12.39(s, 1H), 12.09(s, 1H), 8.74(d, 1H), 8.33(d, 1H), 7.97(d, 1H), 7.25-7.43(m, 6H), 3.77(s, 2H), 3.81(s, 2H)., 1H NMR(DMSO)3.81(2H, s), 7.20-7.49(6H, m), 7.99(1H, s), 8.35(1H, brs), 8.77(1H, brs), 12.15(1H, brs), 12.45(1H, brs). |

TABLE 4-continued

| Cmpd # | LC/MS (M + 1) (obs) | RT (mins) | $^1$H NMR |
|---|---|---|---|
| II-80 | 483.10 | 2.67 | 1H NMR 500MHz(DMSO-d6)11.85ppm, 1H, S; 9.20PPM, 1H, m; 8.36ppm, 1H, d; 8.24ppm, 2H, m; 7.93ppm, 1H, s; 7.82ppm, 1H, s; 7.67ppm, 4H, m; 7.15ppm, 1H, m; 4.62ppm, 2H, d; 3.60ppm, 4H, m; 2.82ppm, 4H, m. |
| II-81 | 321.00 | 2.43 | 12.29(s, 1H), 11.27(s, 1H), 8.68(d, 1H), 8.33(d, 1H), 8.20(s, 1H), 8.08(d, 2H), 7.65(s, 1H), 7.58(m, 1H), 7.51(m, 2H), 7.26(m, 1H) DMSO-d6 |
| II-82 | 446.00 | 2.49 | CD3OD 8.52d(1H), 8.23d(1H), 7.83s(1H), 7.21m(5H), 3.89s(2H), 2.96s(3H) |
| II-83 | 517.20 | 1.92 | H1NMR(500MHz, CDCl3 + MeOH-d4, ppm)9.09(d, 1H, J=7.85Hz), 8.28(d, 1H, J=5.59), 7.92(s, 1H), 7.45(m, 1H,), 7.25(m, 3H), 6.9(m, 1H), 6.8(m, 2H), 4.20(s, 2H), 4.05(m, 2H), 3.30(m, 2H), 3.20(m, 1H), 2.20(m, 2H), 1.38(m, 2H), 1.07(m, 2H) |
| II-84 | 531.20 | 1.96 | H1NMR(500MHz, CDCl3 + MeOH-d4, ppm) 9.12(d, 1H, J=7.56Hz), 8.28(m, 1H), 7.93(s, 1H), 7.47(m, 1H,), 7.25(m, 2H), 7.20(s, 1H), 6.95(m, 1H), 6.80(m, 2H), 4.25(s, 2H), 4.10(m, 2H), 3.35(m, 2H), 3.20(m, 1H), 2.93(s, 3H), 2.25(m, 2H), 1.41(m, 2H), 1.09(m, 2H) |
| II-85 | 503.20 | 1.96 | H1NMR(500MHz, CDCl3 + MeOH-d4, ppm) 9.11(d, 1H, J=7.88Hz), 8.28(m, 1H), 7.92(s, 1H), 7.47(m, 1H,), 7.25(m, 2H), 7.20(s, 1H), 6.95(m, 1H), 6.80(m, 2H), 4.30(m, 2H), 4.21(s, 2H), 3.60(m, 8H), 3.23(m, 1H), 2.25(m, 2H), 1.38(m, 2H), 1.07(m, 2H) |
| II-86 | 517.20 | 2.06 | H1NMR(500MHz, CDCl3 + MeOH-d4, ppm) 9.09(d, 1H, J=7.92Hz), 8.28(m, 1H), 7.92(s, 1H), 7.47(m, 1H,), 7.25(m, 2H), 7.18(s, 1H), 6.94(m, 1H), 6.87(s, 1H), 6.82(m, 1H), 4.28(m, 2H), 4.20(s, 2H), 3.50(m, 7H), 3.34(m, 2H), 3.22(m, 1H), 2.86(s, 3H), 2.25(m, 2H), 1.38(m, 2H), 1.07(m, 2H) |
| II-87 | 524.10 | 3.41 | H1NMR(500MHz, MeOH-d4, ppm)8.78(d, 1H, J=7.74Hz), 8.31(m, 1H), 7.95(s, 1H), 7.60(m, 6H,) 4.42(s, 2H), 3.70(m, 4H), 3.30(m, 1H), 2.95(m, 4H), 3.20(m, 1H), 2.20(m, 2H), 1.40(m, 2H), 1.10(m, 2H) |
| II-88 | 453.00 | 3.90 | H1NMR(500MHz, MeOH-d4, ppm)8.99(d, 1H, J=7.89Hz), 8.31(m, 1H), 7.98(s, 1H), 7.44(m, 2H,) 7.38(s, 1H), 6.80(m, 5H), 4.26(s, 2H), 3.30(m, 1H), 1.34(m, 2H), 1.05(m, 2H) |
| II-89 | | 1.91 | |
| II-90 | | 1.86 | |
| II-91 | 369.10 | 3.45 | H NMR CD3OD: 3.8(s, 2H), 7.2(s, 1H), 7.27(m, 1H), 7.35(m, 4H), 7.73(d, 1H), 8.20(d, 1H) |
| II-92 | 399.00 | 3.44 | H NMR CD3OD: 3.76(s, 2H), 3.80(s, 3H), 6.85(dd, 1H), 6.97(m 2H), 7.19(m, 2H), 7.26(dd, 1H), 7.7(s, 1H), 8.16(d, 1H) |
| II-93 | 504.00 | 3.66 | H NMR CD3OD: 1.15(t, 6H), 3.25(q, 4H), 3.95(s, 2H), 7.2(m, 2H), 7.6(dd, 1H), 7.65(dd, 1H), 7.69(s, 1H), 7.75(dd, 1H), 7.85(s, 1H), 8.13(d, 1H) |
| II-94 | 462.00 | 2.90 | H NMR DMSOd-6: 3.0(s, 3H), 3.78(s, 2H), 7.1(m, 2H), 7.24(m, 3H), 7.3(dd, 1H), 7.78(s, 1H), 8.25(d, 1H), 9.74(s, br, 1H) |
| II-95 | 510.10 | 2.24 | H NMR DMSO: 1.28(m, 2H), 1.38(m, 2H), 1.59(m, 1H), 1.75(m, 2H), 1.80(d, 2H), 2.83(m 2H), 3.25(d, 2H), 3.75(s, 2H), 3.97(t, 2H), 6.85(dd, 1H), 6.9(m, 2H), 7.20(m, 3H), 7.75(s, 1H), 8.20(d, 1H) |
| II-96 | 405.10 | 3.65 | CD3CN 13.11s(1H), 9.18d(1H), 8.39d(1H), 8.08s(1H), 7.57q(1H), 7.35s(1H), 7.29m(1H), 6.87m(3H), 4.57m(1H), 4.32m(1H), 3.94m(1H), 3.80s(3H), 2.24m(2H), 2.12m(2H) |

TABLE 4-continued

| Cmpd # | LC/MS (M + 1) (obs) | RT (mins) | ¹H NMR |
|---|---|---|---|
| II-97 | 485.10 | 1.71 | |
| II-98 | 349.00 | 3.11 | DMSO-d6: 12.21(brs, 1H), 11.99(s, 1H), 8.52(dd, 1H), 8.29(dd, 1H), 7.71(d, 1H), 7.26-7.36(m, 5H), 7.17(dd, 1H), 3.78(s, 2H), 2.41(s, 3H),.. |
| II-99 | 379.10 | 2.93 | DMSO-d6: 12.19(s, 1H), 12.04(s, 1H), 8.54(dd, 1H), 8.31(dd, 1H), 7.72(d, 1H), 7.19-7.26(m, 2H), 6.80-6.85(m, 3H), 7.10(m, 1H), 3.73(s, 3H), 3.69(s, 2H), 2.41(s, 3H). |
| II-100 | 442.00 | 2.88 | DMSO-d6: 12.22(s, 1H), 11.99(s, 1H), 9.73(s, 1H), 8.51(d, 1H), 8.29(dd, 1H), 7.71(d, 1H), 7.29(t, 1H), 7.08-7.21(m, 4H), 3.76(s, 2H), 2.99(s, 3H), 2.41(s, 3H). |
| II-101 | 498.00 | 2.70 | DMSO-d6: 12.26(s, 1H), 11.99(s, 1H), 8.51(d, 1H), 8.29(dd, 1H), 7.64-7.76(m, 5H), 7.17(dd, 1H), 3.96(s, 2H), 3.60(m, 4H), 2.87(m, 4H), 2.41(s, 3H). |
| II-102 | 369.00 | 3.74 | CDCl3: 11.85(brs, 1H), 9.59(brs, 1H), 8.15(d, 1H), 8.11(d, 1H), 7.76(s, 1H), 7.17-7.26(m, 5H), 6.84(s, 1H), 3.76(s, 2H),.. |
| II-103 | 399.00 | 3.75 | DMSO-d6: 12.36(s, 1H), 12.09(s, 1H), 8.61(d, 1H), 8.26(dd, 1H), 7.98(d, 1H), 7.43(s, 1H), 7.25(t, 1H), 6.83-6.96(m, 3H), 3.77(s, 2H), 3.75(s, 3H). |
| II-104 | 462.00 | 3.29 | CD3OD: 8.62(s, 1H), 8.20(s, 1H), 7.88(s, 1H), 7.32(t, 1H), 7.10-7.25(m, 3H), 3.82(s, 2H), 2.97(s, 3H) |
| II-105 | 518.00 | 3.54 | CD3OD: 8.63(d, 1H), 8.20(d, 1H), 7.89(s, 1H), 7.81(s, 1H), 7.71(m, 2H), 7.63(s, 1H), 7.22(d, 1H), 3.97(s, 2H), 3.68(m, 4H), 2.97(m, 4H) |
| II-106 | 427.10 | 2.79 | 1H NMR 500MHz(DMSO-d6)11.86ppm, 1H, s; 9.74ppm, 1H, s; 9.10ppm, 1H, t; 8.37ppm, 1H, d; 8.26ppm, 2H, m; 7.92ppm, 1H, s; 7.81ppm, 1H, s; 7.28ppm, 1H, m; 7.13ppm, 4H, m; 4.46ppm, 2H, d; 2.98ppm, 3H, s. |
| II-107 | 563.00 | 3.60 | DMSO-d6: 12.46(s, 1H), 12.10(s, 1H), 8.74(d, 1H), 8.32(d, 1H), 7.97(d, 1H), 7.77(s, 1H), 7.64-7.71(m, 3H), 7.44(s, 1H), 3.98(s, 2H), 3.61(m, 4H), 2.87(m, 4H) |
| II-108 | 497.10 | 1.54 | CD3CN13.6s(1H), 11.68s(1H), 10.85s(1H), 8.97d(1H), 8.35d(1H), 8.0s(1H), 7.50dd(1H), 7.34d(1H), 7.24s(1H), 7.07s(1H), 6.92m(1H), 4.36m(2H), 3.93s(2H), 3.65s(4H), 3.55m(6H), |
| II-109 | 511.10 | 1.70 | CD3CN13.18s(1H), 10.90s(1H), 9.03d(1H), 8.38d(1H), 8.04s(1H), 7.53dd(1H), 7.34d(1H), 7.28s(1H), 7.10s(1H), 6.92dd(1H), 4.36m(2H), 3.95s(2H), 3.55m(8H), 2.85s(3H) |
| II-110 | 511.10 | 1.45 | CD3CN13.18s(1H), 10.90s(2H), 9.05d(1H), 8.40d(1H), 8.06s(1H), 7.56dd(1H), 7.34d(1H), 7.30s(1H), 7.05s(1H), 6.92dd(1H), 4.11m(2H), 3.95s(2H), 3.59m(8H), 3.33m(2H), 2.22m(2H) |
| II-111 | 525.10 | 1.70 | CD3CN13.21s(1H), 11.19s(1H), 9.05d(1H), 8.40d(1H), 8.06s(1H), 7.53dd(1H), 7.34d(1H), 7.30s(1H), 7.05s(1H), 6.92dd(1H), 4.11m(2H), 3.95s(2H), 3.59m(8H), 3.33m(2H), 2.86s(3H), 2.22m(2H) |
| II-112 | 482.10 | 3.19 | |
| II-113 | 442.10 | 2.59 | H1NMR(500MHz, dmso-d6, ppm)8.55(d, 1H, J=7.85Hz), 8.25(d, 1H, J=5.59Hz), 7.40-7.10(m, 6H), 3.90(s, 2H), 3.30(s, 3H), 2.95(s, 3H) |
| II-114 | 364.10 | 2.87 | 1H NMR 500MHz(DMSO-d6)12.00ppm, 1H, s; 8.88ppm, 1H, t; 8.32ppm, 2H, m; 8.01ppm, 1H, s; 7.87ppm, 1H, s; 7.83ppm, 1H, s; 7.26ppm, 2H, m; 6.92ppm, 2H, m; 6.93ppm, 2H, m; 6.82ppm, 1H, d; 4.43ppm, 2H, d; 3.70ppm, 3H, s. |
| II-115 | 427.10 | 2.72 | 1H NMR 500MHz(DMSO-d6)12.10ppm, 1H, s; 9.72ppm, 1H, s; 8.98ppm, 1H, t; 8.32ppm, 2H, m; 7.99ppm, 1H, s; 7.81ppm, 1H, s; 7.42ppm, 1H, s; 7.28ppm, 1H, m; 7.20ppm, 2H, m; 7.11ppm, 2H, m; 4.43ppm, 2H, d; 2.95ppm, 3H, s. |

TABLE 4-continued

| Cmpd # | LC/MS (M + 1) (obs) | RT (mins) | ¹H NMR |
|---|---|---|---|
| II-116 | 284.00, 284.00 | 2.00, 1.92 | 1H NMR 500MHz(DMSO-d6)12.50ppm, 1H, s; 11.84ppm, 1H, s; 8.50ppm, 1H, d; 8.29ppm, 1H, d; 7.78ppm, 1H, d; 7.42ppm, 1H, s; 7.15ppm, 1H, m; 4.08ppm, 2H, s., 1H NMR 500MHz(DMSO-d6) 12.53ppm, 1H, s; 11.81ppm, 1H, s; 8.47ppm, 1H, d; 8.28ppm, 1H, d; 7.83ppm, 1H, s; 7.40ppm, 1H, s; 7.15ppm, 1H, m; 4.05ppm, 2H, s. |
| II-117 | 427.10 | 2.76 | 1H NMR 500MHz(DMSO-d6)9.78ppm, 1H, s; 8.88ppm, 1H, t; 8.27ppm, 2H, m; 8.00ppm, 1H, s; 7.88ppm, 1H, s; 7.77ppm, 1H, s; 7.25ppm, 1H, m; 7.15ppm, 2H, m, 7.08ppm, 2H, m; 4.43ppm, 2H, d; 2.97ppm, 3H, s. |
| II-118 | 353.00 | 3.46 | CD3OD: 8.33(dd, 1H), 8.15(dd, 1H), 7.90(s, 1H), 7.28-7.38(m, 4H), 7.28(m, 1H), 7.19(s, 1H), 3.81(s, 2H).. |
| II-119 | 383.00 | 3.49 | CD3OD: 8.33(dd, 1H), 8.15(s, 1H), 7.90(s, 1H), 7.25(m, 1H), 7.20(d, 1H), 6.94(m, 1H), 6.85(m, 1H), 3.80(s, 3H), 3.78(s, 2H). |
| II-120 | 446.00 | 3.03 | DMSO-d6: 12.38(s, 1H), 12.00(s, 1H), 9.73(s, 1H), 8.36(dd, 1H), 8.26(s, 1H), 7.97(d, 1H), 7.41(s, 1H), 7.30(t, 1H), 7.13(s, 1H), 7.10(m, 3H), 3.78(s, 2H), 2.99(s, 3H) |
| II-121 | 502.00 | 3.38 | CD3OD: 8.34((dd, 1H), 8.16(d, 1H), 7.91(s, 1H), 7.81(s, 1H), 7.70(m, 2H), 7.62(m, 1H), 7.21(s, 1H), 3.97(s, 2H), 3.67(m, 4H), 2.97(m, 4H) |
| II-122 | 389.00 | 3.72 | DMSO-d6: 12.42(s, 1H), 12.01(s, 1H), 8.36(dd, 1H), 8.26(s, 1H), 7.98(d, 1H), 7.46(m, 1H), 7.41(s, 1H), 7.23(m, 1H), 7.08(m, 1H), 3.88(s, 2H)3.78(s, 2H), 2.99(s, 3H) |
| II-123 | 540.00 | 1.54 | |
| II-124 | 484.10 | 2.40 | |
| II-125 | 554.20 | 2.60 | H1NMR(500MHz, MeOH-d4, ppm)8.88(d, 1H, J=8.04Hz), 8.34(d, 1H, J=5.34Hz), 7.96(s, 1H), 7.89(s, 1H,)7.79(d, 1H, J=7.17Hz), 7.64(d, 1HJ=8.00Hz), 7.58(m, 2H), 7.40(m, 1H), 7.32(s, 1H), 3.96(m, 2H), 2.97(m, 14H), 2.81(s, 3H) |
| II-126 | 541.00 | 1.89 | |
| II-127 | 364.10 | 2.75 | 1H NMR(DMSO-d6)8.25ppm, 1H, d; 8.18ppm, 1H, d; 7.76ppm, 1H, d; 7.25ppm, 1H, t; 7.16ppm, 1H, m; 7.08ppm, 1H, d; 6.91ppm, 2H, m; 6.87ppm, 1H, m; 6.67ppm, 1H, d; 3.78ppm, 3H, s; 3.63ppm, 2H, s. |
| II-128 | 427.10 | 2.69 | 1H NMR(DMSO-d6)11.80ppm, 1H, s; 11.33ppm, 1H, s; 9.70ppm, 1H, s; 8.27ppm, 1H, d; 8.18ppm, 1H, d; 7.71ppm, 1H, s; 7.25ppm, 1H, t; 7.15ppm, 5H, m; 6.66ppm, 1H, s; 3.67ppm, 2H, s; 2.98ppm, 3H, s. |
| II-129 | | | 1H NMR(DMSO-d6)8.24ppm, 1H, d; 8.18ppm, 1H, d; 7.74ppm, 1H, s; 7.70ppm, 2H, m; 7.64ppm, 3H, m; 7.18ppm, 1H, m; 7.11ppm, 1H, d; 6.69ppm, 1H, d; 3.87ppm, 2H, s; 3.60ppm, 4H, m; 2.85ppm, 4H, m. |
| II-130 | 483.10 | 2.73 | 1H NMR 500MHz(DMSO-d6)12.ooppm, 1H, s; 9.04ppm, 1H, t; 8.31ppm, 2H, m; 8.05ppm, 1H, s; 7.86ppm, 1H, d; 7.77ppm, 1H, s; 7.63ppm, 4H, m; 7.20ppm, 1H, m; 4.60ppm, 2H, d; 3.59ppm, 4H, m; 2.85ppm, 4H, m. |
| II-131 | 351.00 | 2.69 | CD3OD: 8.33(s, 1H), 7.95(s, 1H), 7.90(s, 1H), 7.27-7.38(m, 5H), 7.22(s, 1H), 3.82(s, 2H).. |
| II-132 | 444.00 | 2.50 | CD3OD: 8.49(s, 1H), 7.95(m, 2H), 7.26-7.32(m, 3H), 7.30(t, 1H), 7.17(m, 2H), 3.82(s, 2H), 2.96(s, 3H) |
| II-133 | 310.00 | 2.31 | 1HNMR(DMSO)12.30, s, 1H; 11.89, s, 1H; 8.49, s, 1H; 8.30, d, 1H; 7.91, s, 1H; 7.40, s, 1H; 7.18-7.20, m, 1H; 1.70-1.90, m, 4H |
| II-134 | 259.00 | 1.70 | 1HNMR(DMSO)12.12, s, 1H; 11.81, s, 1H; 8.49, d, 1H; 8.26, d, 1H; 7.83, s, 1H; 7.32, s, 1H; 7.15-7.17, m, 1H; 2.16, s, 3H |

TABLE 4-continued

| Cmpd # | LC/MS (M + 1) (obs) | RT (mins) | ¹H NMR |
|---|---|---|---|
| II-135 | 494.00 | 2.57 | CD3OD: 8.33(d, 1H), 8.15(t, 1H), 7.89(s, 1H), 7.22(t, 1H), 7.19(s, 1H), 6.92(m, 2H), 6.82(dd, 1H), 4.00(t, 2H), 3.78(s, 1H), 3.33(m, 1H), 2.91(m, 2H), 1.94(m, 2H), 1.80(m, 2H), 1.65(brs, 1H), 1.47(m, 2H), 1.37(m, 2H). |
| II-136 | 495.00 | 2.09 | CD3OD: 8.35(dd, 1H), 8.16(t, 1H), 7.91(s, 1H), 7.27(t, 1H), 7.19(s, 1H), 6.99(m, 2H), 6.90(dd, 1H), 4.29(brm, 2H), 3.32-3.50(m, 10H), 2.90(s, 3H) |
| II-137 | 509.00 | 2.05 | CD3OD: 8.32(dd, 1H), 8.15(t, 1H), 7.90(s, 1H), 7.26(t, 1H), 7.19(s, 1H), 6.99(m, 2H), 6.86(dd, 1H), 4.12(t, 2H), 3.79(s, 2H), 3.40-3.55(brm, 8H), 3.25(m, 2H), 2.91(s, 3H), 2.18(m, 2H). |
| II-138 | 442.10 | 2.83 | |
| II-139 | 456.10 | 2.78 | |
| II-140 | 456.10 | 2.73 | |
| II-141 | 470.10 | 3.37 | |
| II-142 | 289.20 | 1.90 | 1H NMR 500MHz(DMSO-d6)12.1ppm, 1H, s; 11.94ppm, 1H, s; 8.66ppm, 1H, d; 8.26ppm, 1H, d; 7.88ppm, 1H, s; 7.42ppm, 1H, s; 7.22ppm, 1H, d; 4.14ppm, 3H, s; 3.35ppm, 2H, s. |
| II-143 | 289.10 | 1.70 | |
| II-144 | 303.20 | 2.10 | |
| II-145 | 330.20 | 1.70 | |
| II-146 | 329.10 | 2.00 | 1H NMR 500MHz(DMSO-d6)12.60ppm, 1H, s; 11.91ppm, 1H, s; 8.58ppm, 1H, d; 8.32ppm, 1H, d; 7.91ppm, 1H, s; 7.40ppm, 1H, s; 7.25ppm, 1H, d; 5.20ppm, 1H, m; 2.52ppm, 2H, m; 2.49ppm, 2H, m. |
| II-147 | 329.10 | 1.45 | |
| II-148 | 328.10 | 1.69 | |
| II-149 | 316.10 | 1.41 | 1H NMR 500MHz(DMSO-d6)12.25ppm, 1H, s; 11.92ppm, 1H, s; 8.62ppm, 1H, d; 8.32ppm, 2H, m; 7.88ppm, 1H, s; 7.40ppm, 1H, s; 7.25ppm, 1H, m; 4.02ppm, 2H, s; 1.84ppm, 3H, s.. |
| II-150 | 417.00 | 3.78 | DMSO-d6: 12.38(s, 1H), 12.01(s, 1H), 8.38(dd, 1H), 8.26(d, 1H), 7.40(s, 1H), 7.36(d, 1H), 7.04(d, 1H), 6.91(dd, 1H), 3.91(s, 2H), 3.78(s, 3H) |
| II-151 | 464.00 | 3.13 | DMSO-d6: 12.43(s, 1H), 12.01(s, 1H), 9.67(s, 1H), 8.36(dd, 1H), 8.26(s, 1H), 7.98(d, 1H), 7.42(s, 1H), 7.24(d, 1H), 7.17(m, 2H), 6.91(dd, 1H), 3.88(s, 2H), 2.97(s, 3H) |
| II-152 | | | |
| II-153 | 328.00 | 1.72 | 1H NMR 500MHz(DMSO-d6)12.38ppm, 1H, s; 11.92ppm, 1H, s; 8.58ppm, 1H, d; 8.32ppm, 1H, s; 7.90ppm, 2H, m; 7.39ppm, 1H, s; 7.20ppm, 1H, d; 4.38ppm, 1H, m; 2.41ppm, 1H, m; 2.20ppm, 2H, m; 2.08ppm, 1H, m. |
| II-154 | 315.10 | 2.34 | 1H NMR 500MHz(DMSO-d6)12.02ppm, 1H, s; 11.98ppm, 1H, s; 8.62ppm, 1H, d; 8.40ppm, 1H, s; 7.40ppm, 1H, s; 7.24ppm, 1H, d; 4.60ppm, 1H, m; 4.03ppm, 1H, m; 3.86ppm, 1H, m; 2.24ppm, 1H, m; 1.96ppm, 3H, m. |
| II-155 | 329.00 | 1.88 | 1H NMR 500MHz(DMSO-d6)12.60ppm, 1H, s; 11.91ppm, 1H, s; 8.58ppm, 1H, d; 8.32ppm, 1H, d; 7.91ppm, 1H, s; 7.40ppm, 1H, s; 7.25ppm, 1H, d; 5.20ppm, 1H, m; 2.52ppm, 4H, m. |
| II-156 | 330.10 | 1.70 | 1H NMR 500MHz(DMSO-d6)12.25ppm, 1H, s; 11.92ppm, 1H, s; 8.60ppm, 1H, d; 8.32ppm, 2H, m; 7.88ppm, 1H, s; 7.43ppm, 1H, s; 7.25ppm, 1H, d; 4.53ppm, 1H, m; 1.88ppm, 3H, s; 1.30ppm, 3H, d. |
| II-157 | 275.10 | 1.60 | 1H NMR 500MHz(DMSO-d6)11.92ppm, 1H, s; 11.76ppm, 1H, s; 8.58ppm, 1H, d; 8.29ppm, 1H, d; 7.91ppm, 1H, s; 7.41ppm, 1H, s; 7.22ppm, 1H, d; 4.15ppm, 2H, s. |

TABLE 4-continued

| Cmpd # | LC/MS (M + 1) (obs) | RT (mins) | $^1$H NMR |
|---|---|---|---|
| II-158 | 301.16 | 1.89 | 1H NMR 500MHz(DMSO-d6)11.90ppm, 1H, s; 11.32ppm, 1H, s; 8.65ppm, 1H, d; 8.29ppm, 1H, d; 7.91ppm, 1H, s; 7.41ppm, 1H, s; 7.22ppm, 1H, d; 1.23ppm, 2H, m; 1.15ppm, 2H, m. |
| II-159 | 317.16 | 2.15 | 1H NMR 500MHz(DMSO-d6)11.95ppm, 1H, s; 11.60ppm, 1H, s; 8.61ppm, 1H, d; 8.32ppm, 1H, s; 7.92ppm, 2H, m; 7.42ppm, 1H, s; 7.22ppm, 1H, d; 4.00ppm, 1H, m; 2..05ppm, 1H, m; 1.04ppm, 6H, m. |
| II-160 | 329.21 | 2.89 | 1H NMR 500MHz(DMSO-d6)12.60ppm, 1H, s; 11.92ppm, 1H, s; 8.68ppm, 1H, d; 8.32ppm, 1H, d; 7.96ppm, 1H, s; 7.50ppm, 1H, s; 7.22ppm, 1H, d; 2.84ppm, 2H, d; 2.04ppm, 1H, m; 0.99ppm, 6H, d. |
| II-161 | 337.00, 336.90 | 2.36, 1.70 | 1H NMR 500MHz(DMSO-d6)12.60ppm, 1H, s; 11.95ppm, 1H, s; 8.58ppm, 1H, d; 8.32ppm, 1H, d; 7.93ppm, 1H, s; 7.51ppm, 1H, s; 7.22ppm, 1H, d; 4.50ppm, 2H, s; 3.20ppm, 3H, s., H NMR(500MHz, DMSO-d6)12.62(s, 1H), 11.86(s, 1H), 8.49(d, J=8.0Hz, 1H), 8.28(dd, J=4.6, 1.5Hz, 1H), 7.88(d, J=2.6Hz, 1H), 7.47(s, 1H), 7.18(dd, J=7.9, 4.6Hz, 1H), 4.47(s, 2H), 3.21(s, 3H). |
| II-162 | 287.10, 287.00 | 2.78, 8.04 | 1H NMR 500MHz(DMSO-d6)12.08ppm, 1H, s; 11.96ppm, 1H, s; 8.66ppm, 1H, d; 8.32ppm, 1H, d; 7.88ppm, 1H, s; 7.33ppm, 1H, s; 7.22ppm, 1H, d; 2.78ppm, 1H, m; 1.16ppm, 6H, d., 1H NMR(DMSO) 1.13(6H, d, J=6.8Hz), 2.71-2.86(1H, m), 7.11-7.21(1H, m), 7.38(1H, s), 7.85(1H, brs), 8.22-8.30(1H, m), 8.46-8.52(1H, m), 11.85(1H, brs), 12.12(1H, brs). |
| II-163 | 273.10 | 2.19 | 1H NMR 500MHz(DMSO-d6)12.08ppm, 1H, s; 11.95ppm, 1H, s; 8.58ppm, 1H, d; 8.32ppm, 1H, d; 7.88ppm, 1H, s; 7.38ppm, 1H, s; 7.22ppm, 1H, d; 2.50ppm, 2H, q; 1.16ppm, 3H, t. |
| II-164 | 330.20 | 1.65 | 1H NMR 500MHz(DMSO-d6)12.18ppm, 1H, s; 11.95ppm, 1H, s; 8.58ppm, 1H, d; 8.32ppm, 1H, d; 8.04ppm, 1H, s; 7.88ppm, 1H, s; 7.30ppm, 1H, s; 7.22ppm, 1H, d; 3.35ppm, 2H, m; 2.60ppm, 2H, m; 1.90ppm, 3H, s. |
| II-165 | 274.10 | 0.55 | !H NMR 500MHz(DMSO-d6)12.60ppm, 1H, s; 11.92ppm, 1H, s; 8.54ppm, 1H, d; 8.32ppm, 1H, d; 8.28ppm, 3H, s; 7.87ppm, 1H, s; 7.46ppm, 1H, s; 7.22ppm, 1H, d; 3.93ppm, 2H, s. |
| II-166 | 330.10 | 1.58 | 1H NMR 500MHz(DMSO-d6)12.95ppm, 1H, s; 11.93ppm, 1H, s; 8.48ppm, 1H, d; 8.36ppm, 3H, s; 8.32ppm, 1H, s; 7.90ppm, 1H, s; 7.51ppm, 1H, s; 7.18ppm, 1H, m; 4.13ppm, 1H, m; 1.70ppm, 3H, m; 0.96ppm, 6H, d. |
| II-167 | 554.20 | 1.83 | |
| II-168 | 539.20, 539.10 | 2.00, 1.92 | |
| II-169 | 541.20, 541.10 | 1.90, 1.80 | |
| II-170 | 339.00 | 1.27 | |
| II-171 | 314.10 | 0.90 | 1H NMR 500MHz(DMSO-d6)12.90(1H, s); 11.96(1H, s); 9.50(1H, s); 8.86(1H, s); 8.52(1H, d); 8.32(1H, d); 7.88(1H, s); 7.50(1H, s); 7.22(1H, m); 4.48(1H, m); 3.32(1H, m); 2.45(1H, m); 2.05(1H, m); 2.00(2H, m). |
| II-172 | 315.10 | 2.17 | 1H NMR 500MHz(DMSO-d6)12.25(1H, s); 11.89(1H, s); 8.58(1H, d); 8.30(1H, d); 7.86(1H, s); 7.40(1H, s); 7.18(1H, m); 3.95(1H, t); 3.63-3.75(3H, m); 3.34(1H, m); 2.14(2H, m). |

TABLE 4-continued

| Cmpd # | LC/MS (M + 1) (obs) | RT (mins) | $^1$H NMR |
|---|---|---|---|
| II-173 | 328.10 | 0.94 | 1H NMR 500MHz(DMSO-d6)12.41(1H, s); 11.97(1H, s); 8.62(2H, br s); 8.53(1H, d); 8.30(1H, d); 7.85(1H, d); 7.40(1H, s); 7.17(1H, m); 3.40(1H, m); 3.11-3.28(2H, m); 2.88-3.05(2H, m); 2.11(1H, m); 1.80(1H, m); 1.66(2H, m). |
| II-174 | 328.10 | 0.74 | 1H NMR 500MHz(DMSO-d6)12.28(1H, s); 11.92(1H, s); 8.61(1H, br s); 8.51(1H, d); 8.33(1H, br s); 8.28(1H, d); 7.85(1H, d); 7.36(1H, s); 7.17(1H, m); 3.38(2H, m); 2.96(2H, m); 2.83(1H, m); 2.04(2H, m); 1.84(2H, m). |
| II-175 | 329.10 | 2.51 | 1H NMR 500MHz(DSMO-d6)12.16(1H, s); 11.92(1H, s); 8.58(1H, d); 8.32(1H, d); 7.87(1H, d); 7.36(1H, s); 7.23(1H, m); 3.95(2H, m); 3.34(2H, m); 2.80(1H, m); 1.70(4H, m). |
| II-176 | 364.20 | 1.73 | H NMR(500MHz, DMSO-d6)12.73(s, 1H), 11.91(s, 1H), 8.48(d, J=7.9Hz, 1H), 8.43(s, 2H), 8.30(d, J=4.6Hz, 1H), 7.86(s, 1H), 7.48(s, 1H), 7.36(m, 2H), 7.29(m, 2H), 7.19(dd, J=7.9, 4.7Hz, 1H), 4.34(s, 1H), 3.26(m, 1H), 3.11(m, 1H). |
| II-177 | 364.20 | 1.73 | H NMR(500MHz, DMSO-d6)12.73(s, 1H), 11.91(s, 1H), 8.48(d, J=7.9Hz, 1H), 8.43(s, 2H), 8.30(d, J=4.6Hz, 1H), 7.86(s, 1H), 7.48(s, 1H), 7.36(m, 2H), 7.29(m, 2H), 7.19(dd, J=7.9, 4.7Hz, 1H), 4.34(s, 1H), 3.26(m, 1H), 3.11(m, 1H) |
| II-178 | 378.20 | 1.70 | H NMR(500MHz, DMSO-d6)12.81(s, 1H), 11.92(s, 1H), 9.23(d, J=24.1Hz, 2H), 8.47(d, J=7.8Hz, 1H), 8.29(d, J=4.5Hz, 1H), 7.86(s, 1H), 7.49(s, 1H), 7.33(m, 2H), 7.27(m, 2H), 7.19(dd, J=7.9, 4.7Hz, 1H), 3.97(m, 1H), 3.27(m, 2H), 2.59(s, 3H). |
| II-179 | 288.10 | 0.50 | H NMR(500MHz, DMSO-d6)12.73(s, 1H), 11.93(s, 1H), 8.95(s, 2H), 8.51(d, J=7.4Hz, 1H), 8.30(d, J=3.4Hz, 1H), 7.89(s, 1H), 7.48(s, 1H), 7.20(dd, J=7.9, 4.7Hz, 1H), 4.09(s, 2H), 2.68(s, 3H). |
| II-180 | 288.10 | 0.56 | H NMR(500MHz, DMSO-d6)12.35(s, 1H), 11.89(s, 1H), 8.51(d, J=7.0Hz, 1H), 8.29(d, J=6.0Hz, 1H), 7.86(s, 1H), 7.86(s, 2H), 7.40(s, 1H), 7.19(dd, J=7.9, 4.7Hz, 1H), 3.15(m, 2H), 2.85(m, 2H). |
| II-181 | 314.10 | 0.67 | H NMR(500MHz, DMSO-d6)12.05(s, 1H), 8.99(s, 1H), 8.44(d, J=7.9Hz, 1H), 8.32(d, J=4.4Hz, 1H), 8.20(s, 1H), 8.12(d, J=2.4Hz, 1H), 7.21(dd, J=7.9, 4.7Hz, 1H), 4.70(s, 2H), 3.91(s, 2H), 3.36(s, 2H), 3.29(s, 2H). |
| II-182 | 303.00 | 1.68 | H NMR(500MHz, DMSO-d6)12.03(s, 1H, 8.63(d, J=7.9Hz, 1H), 8.31(m, 2H), 8.14(m, 2H), 7.22(m, 1H), 4.05(m, 1H), 3.51(m, 2H), 2.50(d, J=1.6 Hz, 3H). |
| II-183 | 331.00 | 1.92 | H NMR(500MHz, DMSO-d6)12.07(s, 1H), 8.62(d, J=7.1Hz, 1H), 8.32(d, J=5.9Hz, 1H), 8.15(m, 2H), 7.23(dd, J=7.9, 4.7Hz, 1H), 3.79(m, 1H), 3.62(m, 2H), 1.99(m, 1H, 0.95(dd, J=14.8, 6.7Hz, 6H) |
| II-184 | 365.10 | 2.06 | H NMR(500MHz, DMSO-d6)12.10(s, 1H, 8.91(d, J=8.4Hz, 1H), 8.66(d, J=7.5Hz, 1H), 8.32(s, 1H), 8.18(m, 2H), 7.45(m, 2H), 7.35(m, 2H), 7.25(m, 2H), 5.11(m, 1H), 3.87(m, 1H), 3.79(m, 1H). |
| II-185 | 365.10 | 2.05 | H NMR(500MHz, DMSO-d6)12.10(s, 1H), 8.91(d, J=8.4Hz, 1H), 8.66(d, J=7.5Hz, 1H), 8.32(s, 1H), 8.18(m, 2H), 7.45(m, 2H), 7.35(m, 2H), 7.25(m, 2H), 5.11(m, 1H), 3.87(m, 1H), 3.79(m, 1H). |
| II-186 | 404.00 | 1.78 | H NMR(500MHz, DMSO-d6)12.04(s, 1H), 10.13(s, 1H), 9.11(d, J=6.9Hz, 1H), 9.00(m, 1H), 8.63(m, 1H), 8.31(m, 1H), 8.18(s, 1H), 8.12(d, J=9.6Hz, 1H), 7.55(m, 2H), 7.50(m, 2H), 1H), 4.60(m, 2H), 3.22-3.80(m, 4H), 2.2-2.3(m, 2H). |

TABLE 4-continued

| Cmpd # | LC/MS (M + 1) (obs) | RT (mins) | ¹H NMR |
|---|---|---|---|
| II-187 | 328.10 | 1.48 | |
| II-188 | 364.20 | 1.75 | H NMR(500MHz, DMSO-d6)12.68(s, 1H), 11.91(s, 1H), 9.50(s, 1H), 8.49(d, J=7.3Hz, 1H), 8.29(d, J=4.6Hz, 1H), 7.88(d, J=2.4Hz, 1H), 7.53(m, 2H), 7.47(m, 4H), 7.19(dd, J=7.9, 4.7Hz, 1H), 4.28(s, 2H), 4.08(s, 2H) |
| II-189 | 378.20 | 2.67 | MeOD-H9.07d(1H), 8.38d(1H), 8.03s(1H), 7.41 m(7H), 3.96m(1H), 2.98m(1H), 2.87m(1H), 2.49m(1H), 2.23m(1H) |
| II-190 | 394.10 | 2.98 | MeOD-H9.07d(1H), 8.38d(1H), 8.03s(1H), 7.50 m(3H), 7.38s(1H), 7.15 t(2H), 3.96 t(1H), 2.98m(1H), 2.87m(1H), 2.49m(1H), 2.23m(1H) |
| II-191 | 414.10 | 3.04 | MeOD-H9.07d(1H), 8.38d(1H), 8.03s(1H), 7.50 m(2H), 7.38s(1H), 7.05 t(2H), 4.30 t(1H), 3.04m (1H), 2.98m(1H), 2.52m(1H), 2.21m(1H) |
| II-192 | 412.10 | 3.01 | MeOD-H8.99d(1H), 8.33d(1H), 7.98s(1H), 7.48 m(3H), 7.34m(3H), 4.52 t(1H), 3.06m(2H), 2.53 m(1H), 2.23m(1H), |
| II-193 | 457.10 | 2.83 | 2.5(CH3), 2.7(CH3), 3.8(CH2), 7.05(H), 7.1(H), 7.2(2H), 7.25(H), 7.4(H), 7.89(H), |
| II-194 | 398.10 | 1.91 | CD3CN(H)13.02s(1H), 8.97d(1H), 8.37d(1H), 8.0s(1H), 7.90d(1H), 7.55d(1H), 7.42m(3H), 7.30s(1H)4.95s(2H), 4.90m(1H), 3.70q(1H), 4.43q(1H) |
| II-195 | 432.00 | 2.12 | CD3CN(H)12.84s(1H), 8.93d(1H), 8.37d(1H), 7.95s(1H), 7.62d(1H), 7.42m(3H), 7.28s(1H)4.98q(1H), 4.42s(2H), 3.70q(1H), 3.43q(1H) |
| II-196 | 416.10 | 2.00 | CD3CN(H)13.02s(1H), 8.93d(1H), 8.35d(1H), 7.95s(1H), 7.46d(2H), 7.36m(1H), 7.24s(1H)7.15m(1H), 5.45s(2H), 4.90q(1H), 3.70q(1H), 3.37q(1H) |
| II-197 | 344.00 | 1.30 | H NMR(500MHz, MeOD)ppm 8.63(dd, J=8.0, 1.3Hz, 1H), 8.41(dd, J=5.3, 1.3Hz, 1H), 8.07(s, 1H), 7.45(dd, J=8.0, 5.3Hz, 1H), 4.02(s, 2H), 3.82(s, 2H), 3.58(t, J=6.7Hz, 2H), 3.52(m, 2H), 3.35-3.26(m, 6H), 2.24(m, 2H) |
| II-198 | 357.20 | 1.26 | H NMR(500MHz, MeOD)ppm, 8.61(d, J=8.0Hz, 1H), 8.42(d, J=6.5Hz, 1H), 8.06(s, 1H),, 7.45(dd, J=8.0, 5.2Hz, 1H), 3.56-3.25(m, 13H), 3.15(m, 2H), 2.95(s, 3H)2.15(m, 2H) |
| II-199 | 297.00 | 1.82 | |
| II-200 | 301.10 | 1.61 | |
| II-201 | 475.10 | 1.91 | |
| II-202 | 505.20 | 1.90 | |
| II-203 | 568.10 | 1.76 | |
| II-204 | 399.10 | 1.56 | |
| II-205 | 336.00 | 1.30 | DMSO-d6: 12.5(brs, 1H), 11.81(s, 1H), 8.54(d, 1H), 8.47-8.49(m, 2H), 8.26(dd, 1H), 7.84(s, 1H), 7.75(d, 1H), 7.36(dd, 1H), 7.33(s, 1H), 7.15(dd, 1H), 3.84(s, 2H) |
| II-206 | 354.00 | 1.60 | CD3OD: 8.98(s, 1H), 8.78(d, 1H), 8.58(d, 1H), 8.33(dd, 1H), 8.16(t, 1H), 8.04(dd, 1H), 7.91(s, 1H), 7.22(s, 1H), 4.17(s, 2H) |
| II-207 | 351.10 | 3.10 | MeOD(H)8.56d(1H), 8.24d(1H), 7.85s(1H), 7.53d(2H), 7.37m(3H), 7.22m(2H), 5.33s(1H) |
| II-208 | 381.10 | 3.19 | MeOD(H)8.92d(1H), 8.34d(1H), 7.98s(1H), 7.42m(1H), 7.33s(1H), 7.28 t(1H), 7.12m(2H), 6.88d(1H), 5.31s(1H)3.80s(3H) |
| II-209 | 387.10 | 3.23 | MeOD(H)8.55d(1H), 8.24d(1H), 7.87s(1H), 7.57m(1H), 7.27s(1H), 7.21m(1H), 7.0m(2H), 5.58s(1H) |
| II-210 | 351.10 | 2.74 | MeOD(H) 8.56d(1H), 8.24d(1H), 7.85s(1H), 7.53d(2H), 7.37m(3H), 7.22m(2H), 5.33s(1H) |
| II-211 | 444.10 | 3.30 | DMSO(H)12.08s(1H), 11.97s(1H), 9.80s(1H), 8.62d(1H), 8.31d(1H), 7.92s(1H), 7.43s(2H), 7.35m(1H), 7.30m(1H), 7.22m(1H), 7.16 m(1H), 5.32s(1H) |
| II-212 | 366.10 | 2.00 | DMSO(H)12.17s(1H), 12.0s(1H), 8.62d(1H), 8.32d(1H), 7.92s(1H), 7.47m(4H), 7.23m(2H), 5.41s(1H) |

TABLE 4-continued

| Cmpd # | LC/MS (M + 1) (obs) | RT (mins) | ¹H NMR |
|---|---|---|---|
| II-213 | 368.10 | 1.76 | DMSO(H)-HCl salt<br>13.01s(1H), 12.24s(1H), 9.10s(3H), 8.67d(1H), 8.38d(1H), 7.95s(1H), 7.70m(2H), 7.55s(1H), 7.38m(2H), 7.30m(1H), 5.34s(1H) |
| II-214 | 350.00 | 1.67 | DMSO(H)-HCl salt<br>13.06s(1H), 12.40s(1H), 9.16s(3H), 8.70d(1H), 8.39d(1H), 8.0s(1H), 7.70m(2H), 7.59s(1H), 7.50m(3H), 7.33m(1H), 5.36s(1H) |
| II-215 | 336.00 | 0.26 | H1NMR(500MHz, DMSO-d6, ppm)8.63-8.59(m, 2H), 8.28(d, 1H, J=4.4Hz), 7.93(m, 1H), 7.86(s, 1H), 7.65(s, 1H), 7.57(d, 1H, J=2.8Hz), 7.55(d, 1H, J=2.8Hz), 7.44(m, 1H), 7.17(s, 1H), 3.33(s, 2H) |
| II-216 | 444.10 | 2.40 | H NMR(500MHz, DMSO-d6)ppm, 12.74(s, 1H), 12.43(s, 1H), 9.71(s, 1H),, 8.25-8.23(m, 2H), 7.85(s, 1H), 7.46(s, 1H), 7.31-7.28(m, 1H), 7.23-7.20(m, 2H), 7.13-7.09(m, 2H), 3.80(s, 2H), 3.00(s, 3H) |
| II-217 | 352.00 | 1.77 | H NMR(500MHz, DMSO-d6)12.23(s, 1H), 11.92(s, 1H), 8.54(s, 1H), 8.30(d, J=4.5Hz, 1H), 7.88(s, 1H), 7.56(s, 1H), 7.42(s, 1H), 7.21(dd, J=10.3, 2.4Hz, 1H), 4.02(d, J=5.4Hz, 2H), 3.00(s, 3H) |
| II-218 | 366.00 | 2.24 | H NMR(500MHz, DMSO-d6)12.22(s, 1H), 11.95(s, 1H), 8.56(d, J=9.1Hz, 1H), 8.30(s, 1H), 7.89(s, 1H), 7.56(t, J=5.9Hz, 1H), 7.42(s, 1H), 7.21(dd, J=7.9, 4.7Hz, 1H), 4.00(d, J=5.9Hz, 2H), 3.08(q, J=7.3Hz, 2H), 1.26(t, J=7.3Hz, 3H). |
| II-219 | 443.10 | 1.40 | MeOD<br>9.28d(1H), 8.48d(1H), 8.12s(1H), 7.66m(1H), 7.58s(1H), 7.53m(2H), 7.40m(2H), 5.36s(1H), 3.04s(3H) |
| II-220 | 380.10 | 2.14 | H NMR(500MHz, DMSO-d6)12.19(s, 1H), 11.95(s, 1H), 8.52(d, J=6.8Hz, 1H), 8.29(dd, J=4.7, 1.4Hz, 1H), 7.87(d, J=2.6Hz, 1H), 7.51(t, J=6.0Hz, 1H), 7.41(s, 1H), 7.19(dd, J=7.9, 4.7Hz, 1H), 4.01 (d, J=6.1Hz, 2H), 3.22(m, 1H), 1.27(d, J=6.8Hz, 3H). |
| II-221 | 365.00 | 2.26 | H NMR(500MHz, DMSO-d6)12.63(s, 1H), 11.93(s, 1H), 8.54(d, J=7.9Hz, 1H), 8.30(dd, J=4.7, 1.4Hz, 1H), 7.90(d, J=2.5Hz, 1H), 7.48(s, 1H), 7.20(dd, J=7.9, 4.7Hz, 1H), 4.39(q, J=7.1Hz, 1H), 3.25(m, 2H), 1.60(d, J=7.0Hz, 3H), 1.26(t, J=7.4Hz, 3H). |
| II-222 | 366.00 | 2.24 | H NMR(500MHz, DMSO-d6)12.23(s, 1H), 11.95(s, 1H), 8.57(d, J=7.9Hz, 1H), 8.31(dd, J=4.7, 1.4Hz, 1H), 7.90(d, J=2.5Hz, 1H), 7.67(d, J=7.8Hz, 1H)1H), 7.22(dd, J=7.9, 4.7Hz, 1H), 4.30(m, 1H), 2.93(s, 3H), 1.38(d, J=7.0Hz, 3H). |
| II-223 | 394.00 | 2.30 | H NMR(500MHz, DMSO-d6)12.31(s, 1H), 11.89(s, 1H), 8.53(d, J=6.8Hz, 1H), 8.29(dd, J=4.7, 1.5Hz, 1H), 7.88(d, J=2.6Hz, 1H), 7.60(d, J=9.2Hz, 1H), 7.42(s, 1H), 7.19(dd, J=7.9, 4.7Hz, 1H), 4.00(q, J=5.4Hz, 1H), 2.87(s, 3H), 2.05(m, 1H), 0.94(d, J=6.7Hz, 6H). |
| II-224 | 379.00 | 2.65 | H NMR(500MHz, DMSO-d6)12.74(s, 1H), 11.93(s, 1H), 8.53(dd, J=7.9, 1.1Hz, 1H), 8.30(dd, J=4.7, 1.5Hz, 1H), 7.90(d, J=2.6Hz, 1H), 7.49(s, 1H), 7.20(dd, J=7.9, 4.7Hz, 1H), 4.25(dd, J=11.3, 3.3Hz, 1H), 3.08(s, 3H), 2.13(m, 1H), 1.96(m, 1H), 1.34(m, 2H), 0.94(t, J=7.3Hz, 3H). |
| II-225 | 393.00 | 2.74 | H NMR(500 MHZ, DMSO-d6)12.72(s, 1H), 11.91(s, 1H), 8.52(d, J=6.8Hz, 1H), 8.29(dd, J=4.7, 1.5Hz, 1H), 7.89(d, J=2.6Hz, 1H), 7.48(s, 1H), 7.20(dd, J=7.9, 4.7Hz, 1H), 4.32(dd, J=11.4, 3.3Hz, 1H), 3.24(m, 2H, 2.14(m, 1H), 1.93(m, 1H), 1.33(m, 1H), 1.26(t, J=7.4Hz, 3H, 1.11(t, J=7.5Hz) |
| II-226 | 351.00 | 2.06 | H NMR(500MHz, DMSO-d6)12.65(s, 1H), 11.95(s, 1H), 8.55(d, J=9.2Hz, 1H), 8.30(dd, J=4.7, 1.5Hz, 1H), 7.91(d, J=2.6Hz, 1H), 7.49(s, 1H), 7.21(dd, J=7.9, 4.7Hz, 1H), 4.32(q, J=7.0Hz, 1H), 3.09(s, 3H), 1.61(d, J=7.1Hz, 3H). |

TABLE 4-continued

| Cmpd # | LC/MS (M + 1) (obs) | RT (mins) | ¹H NMR |
|---|---|---|---|
| II-227 | 394.00 | 2.41 | H NMR(500MHz, DMSO-d6)12.31(s, 1H), 11.93(s, 1H), 8.55(d, J=7.9Hz, 1H), 8.30(dd, J=4.7, 1.5Hz, 1H), 7.89(d, J=2.5Hz, 1H), 7.60(d, J=9.1Hz, 1H), 7.43(s, 1H), 7.21(dd, J=7.9, 4.7Hz, 1H), 4.00(m, 1H), 2.87(s, 3H), 2.06(m, 1H), 0.94(d, J=6.7Hz, 3H). |
| II-228 | 366.00 | 1.92 | H NMR(500MHz, DMSO-d6)12.23(s, 1H), 11.92(s, 1H), 8.55(d, J=6.6Hz, 1H), 8.30(dd, J=4.7, 1.5Hz, 1H), 7.89(d, J=2.5Hz, 1H), 7.67(d, J=7.8Hz, 1H), 7.43(s, 1H), 7.20(dd, J=7.9, 4.7Hz, 1H), 4.29(m, 1H), 2.93(s, 3H), 1.38(d, J=7.1Hz, 3H). |
| II-229 | 392.00 | 2.18 | H NMR(500MHz, DMSO-d6)12.13(s, 1H), 11.91(s, 1H), 8.54(dd, J=7.9, 1.2Hz, 1H), 8.30(dd, J=4.7, 1.5Hz, 1H), 7.89(d, J=2.6Hz, 1H), 7.42(s, 1H), 7.20(dd, J=7.9, 4.7Hz, 1H), 4.50(m, 1H), 3.72(m, 1H), 3.51(m, 1H), 3.42(m, 1H), 3.00(s, 3H), 2.29(m, 1H, 2H), 1.92(m, 1H). |
| II-230 | 392.00 | 2.18 | |
| II-231 | 366.00 | 2.13 | H NMR(500MHz, DMSO-d6)12.31(s, 1H), 11.90(s, 1H), 8.53(dd, J=7.9, 1.2Hz, 1H), 8.29(dd, J=4.7, 1.2Hz, 1H), 7.87(d, J=2.6Hz, 1H), 7.43(s, 1H), 7.19(dd, J=7.9, 4.7Hz, 1H), 4.21(s, 2H), 3.03(s, 3H), 2.93(s, 3H). |
| II-232 | 472.20 | 2.89 | H NMR(500MHz, DMSO-d6)12.35(s, 1H), 11.84(s, 1H), 8.50(dd, J=7.9, 1.2Hz, 1H), 8.28(dd, J=4.6, 1.4Hz, 1H), 7.87(d, J=2.4Hz, 1H), 7.80(d, J=8.4Hz, 1H), 7.43(s, 1H), 7.30(m, 4H), 7.26(m, 1H), 7.17(dd, J=7.9, 4.6Hz, 1H), 4.55(d, J=2.9Hz, 2H), 4.51(m, 1H), 3.73(dd, J=6.2, 1.5Hz, 2H), 2.94(s, 3H). |
| II-233 | 472.00 | 2.87 | H NMR(500MHz, DMSO-d6)12.35(s, 1H), 11.84(s, 1H), 8.50(dd, J=7.9, 1.2Hz, 1H), 8.28(dd, J=4.6, 1.4Hz, 1H), 7.87(d, J=2.4Hz, 1H), 7.80(d, J=8.4Hz, 1H), 7.43(s, 1H), 7.30(m, 4H), 7.26(m, 1H), 7.17(dd, J=7.9, 4.6Hz, 1H), 4.55(d, J=2.9Hz, 2H), 4.51(m, 1H), 3.73(dd, J=6.2, 1.5Hz, 2H), 2.94(s, 3H). |
| II-234 | 288.10 | 1.90 | H NMR(500MHz, DMSO-d6)ppm 14.12(s, 1H), 12.40(s, 1H), 9.53(t, J=5.5Hz, 1H), 8.60(dd, J=7.9, 1.3Hz, 1H), 8.46(dd, J=4.8, 1.3Hz, 1H), 8.30(s, 1H), 7.43(m, 2H), 7.12(s, 1H), 3.47(m, 2H), 1.24(t, J=7.2Hz, 3H) |
| II-235 | 304.10 | 1.60 | H NMR(500MHz, DMSO-d6)ppm 12.48(s, 1H), 9.68(t, J=5.5Hz, 1H), 8.60(dd, J=8.0, 1.3Hz, 1H), 8.46(dd, J=4.8, 1.2Hz, 1H), 8.31(s, 1H), 7.43(m, 2H), 7.13(s, 1H), 3.61(t, J=5.5Hz, 2H), 3.51(q, J=5.5Hz, 2H), 2.54(s, 1H) |
| II-236 | 329.70 | 1.60 | H NMR(500MHz, dmso-d6)ppm 11.54(s, 1H), 8.49(d, J=7.9Hz, 1H), 8.40(m, 1H), 7.96(s, 1H), 7.35-7.32(m, 2H), 7.04(s, 1H), 3.72(t, J=4.6Hz, 4H), 3.52(s, 4H), 2.54(s, 1H), 2.07(s, 1H) |
| II-237 | 343.10 | 1.30 | H NMR(500MHz, dmso-d6)ppm 14.53(s, 1H), 9.91-9.87(m, 1H), 8.54(dd, J=7.9, 1.3Hz, 1H), 8.42(dd, J=4.7, 1.3Hz, 1H), 7.95(s, 1H), 7.52-7.10(m, 2H), 7.06(s, 1H), 4.13(m, 2H), 3.51-3.41(m, 4H), 3.27(s, 2H), 2.90(s, 3H) |
| II-238 | 327.80 | 1.90 | H NMR(500MHz, dmso-d6)ppm 8.47(d, J=8.0Hz, 1H), 8.39(d, J=4.7Hz, 1H), 7.97(s, 1H), 7.33(q, J=4.2Hz, 1H), 7.06(s, 1H), 3.46(s, 4H), 2.07(s, 6H) |
| II-239 | 386.00 | 1.60 | H NMR(500MHz, DMSO-d6)ppm 12.35(s, 1H), 11.90(s, 1H), 9.53(d, J=7.6Hz, 1H), 8.61(dd, J=7.9, 1.3Hz, 1H), 8.46(dd, J=4.8, 1.2Hz, 1H), 8.29(s, 1H), 7.45-7.42(m, 2H), 7.13(s, 1H), 3.74(m, 1H), 2.28(m, 1H), 2.10-1.94(m, 5H), 1.79(m, 1H), 1.47(m, 4H) |
| II-240 | 287.80 | 1.50 | H NMR(500MHz, DMSO-d6)ppm 14.62(s, 1H), 13.49(s, 1H), 8.48(m, 1H), 8.40(dd, J=4.6, 1.2Hz, 1H), 7.95(s, 1H), 7.62(s, 1H), 7.33(dd, J=7.9, 4.6Hz, 1H), 7.05(s, 1H), 3.04(s, 6H) |
| II-241 | 314.10 | 1.70 | H NMR(500MHz, DMSO-d6)ppm 13.06(s, 1H), 8.47(dd, J=8.0, 1.3Hz, 1H), 8.40(dd, J=4.7, 1.3Hz, 1H), 8.01(s, , 7.66(m, 1H), 7.33(q, J=4.2Hz, 1H), 7.06(s, 1H), 3.53(s, 4H), 2.07(s, 4H) |

TABLE 4-continued

| Cmpd # | LC/MS (M + 1) (obs) | RT (mins) | ¹H NMR |
|---|---|---|---|
| II-242 | 345.80 | 1.40 | H NMR(500MHz, DMSO-d6)ppm 13.83(s, 1H), 11.58(s, 1H), 9.61(d, J=8.7Hz, 1H), 9.15(s, 1H), 8.65(d, J=7.9Hz, 1H), 8.47(d, J=4.8Hz, 1H), 8.27(s, , 7.45(dd, J=7.9, 4.8Hz, 1H), 7.27(m, 1H), 7.13(s, 1H)4.53(d, J=8.1Hz, 1H), 3.52(t, J=11.0Hz, 1H), 3.27(m, 1H), 2.93(d, J=4.5Hz, 3H), 2.83(d, J=4.5Hz, 3H), 1.35(d, J=6.7Hz, 3H) |
| II-243 | 329.10 | 1.20 | H NMR(400MHz, acetic acid-d4)ppm 15.76(s, 1H), 13.54(s, 1H), 8.83(s, 2H), 8.54(d, J=8.2Hz, 1H), 8.40(d, J=4.4Hz, , 8.12(m, 1H), 7.94(s, , 7.36(q, J=4.2Hz, 1H), 7.04(s, , 3.73(s, 4H), 3.29(s, 4H) |
| II-244 | 301.80 | 2.10 | H NMR(400MHz, acetic acid-d4)□ 13.87(s, 1H), 12.48(s, 1H), 11.07(m, 1H), 9.48(d, J=7.4Hz, 1H), 8.60(dd, J=8.0, 1.2Hz, 1H), 8.47(dd, J=4.8, 1.2Hz, 1H), 8.30(s, 1H), 8.12(m, 1H), 7.50(m, 2H), 7.13(s, 1H), 6.93(m, 1H), 4.09(m, , 2.07(s, 6H) |
| II-245 | 418.50 | 4.09 | 1H NMR(DMSO): 1.40(2H, t), 1.80-1.95(3H, m), 2.88(2H, t), 3.22-3.31(4H, m), 7.39(1H, t), 7.51(2H, t), 7.85(2H, d), 8.15(1H, s), 8.29(2H, br s), 8.60(1H, s), 8.78(1H, s), 8.99(1H, t), 12.17(1H, s). |
| II-246 | 439.00 | 10.13 | 1H NMR(DMSO)3.11-3.30(4H, m), 3.50-3.65(1H, m), 7.10-7.29(4H, m), 7.45(1H, s), 8.00(1H, s), 8.35(1H, brs), 8.79(1H, brs), 12.15(1H, brs), 12.35(1H, brs). |
| II-247 | 363.00 | 9.01 | 1H NMR(DMSO)0.89-0.96(4H, m), 1.95-2.05 91H, m), 7.41(1H, s), 7.98(1H, s), 8.35(1H, s), 8.75(1H, s), 12.11(1H, brs), 12.44(1H, s). |
| II-248 | 405.00 | 9.24 | 1H NMR(DMSO)1.11-1.28(2H, m), 1.46-1.83(6H, m), 2.20-2.30(1H, m), 2.40-2.50(2H, m), 7.42(1H, s), 7.98 91(1H, brs), 8.35(1H, brs), 8.76(1H, brs), 12.13(2H, brs). |
| II-249 | 427.00 | 9.88 | 1H NMR(DMSO)2.70-2.85(2H, m), 2.90-3.00(2H, m), 7.11-7.34(5H, m), 7.45(1H, s), 8.00(1H, brs), 8.35 91H, brs), 8.75(1H, brs), 12.10-12.24 92H, m). |
| II-250 | 491.00 | 10.16 | 1H NMR(DMSO)3.80 92H, s), 7.29-7.36(2H, m), 7.45 91H, s), 7.50-7.60(2H, m), 8.00 91H, brs), 8.33 91H, brs), 8.75 91H, brs), 12.15 91H, brs), 12.49(1H, brs). |
| II-251 | 433.00 | 10.78 | 1H NMR(DMSO)0.79-0.98(2H, m), 1.05-1.30(5H, m), 1.47-1.78(6H, m), 2.41-2.50(2H, m), 7.40(1H, s), 7.98(1H, brs), 8.32(1H, brs), 8.76(1H, brs), 12.10(2H, brs). |
| II-252 | 393.00 | 8.58 | 1H NMR(DMSO)2.06-2.19(2H, m), 3.103.35(1H, m), 3.69-4.00(4H, m), 7.45(1H, s), 8.00(1H, s), 8.35(1H, brs), 8.76(1H, brs), 12.15(1H, brs), 12.30(1H, brs). |
| II-253 | 491.00 | 8.97 | 1H NMR(DMSO)2.85(2H, t, J=7.3Hz), 3.69(2H, t, J=7.3Hz), 7.45(1H, s), 7.64-7.80(3H, m), 7.90-8.02(3H, m), 8.34(1H, brs), 8.75(1H, brs), 12.10-12.33(2H, m). |
| II-254 | 443.00 | 9.79 | 1H NMR(DMSO)2.97(2H, t, J=6.0Hz), 4.31(2H, t, J=6.0Hz), 6.90-7.00(3H, m), 7.25-7.34(2H, m), 7.47(1H, s), 8.00(1H, brs), 8.35(1H, brs), 8.78(1H, brs), 12.13(1H, brs), 12.35(1H, brs). |
| II-255 | 500.00 | 9.43 | 1H NMR(DMSO)2.62-2.71(2H, m), 3.30-3.38(2H, m), 5.03(2H, s), 7.25-7.49(7H, m), 7.99(1H, brs), 8.35(1H, brs), 8.76(1H, brs), 12.10-12.25(2H, m). |
| II-256 | 433.00 | 5.37 | CDCl3 1.08-1.30(3H, m), 1.42-1.53(1H, m), 1.55-1.74(4H.m), 1.94-2.03(2H, m), 2.39-2.55(2H, m), 2.68(2H, d), 4.36-4.43(2H, m), 7.05(1H, s), 7.80(1H, s), 8.40(1H, s), 8.65(1H, s), 9.50(1H, br s) |

Biological Testing

Example 1

Rock Inhibition Assay

Compounds were screened for their ability to inhibit ROCK I (AA 6-553) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 2 mM DTT and 1.5% DMSO. Final substrate concentrations in the assay were 45 μM ATP (Sigma Chemicals, St Louis, Mo.) and 200 μM peptide (American Peptide, Sunnyvale, Calif.). Reactions were carried out at 30° C. and 45 nM ROCK I. Final concentrations of the components of the coupled enzyme system were 2.5 mM phosphoenolpyruvate, 350 µM NADH, 30 µg/ml pyruvate kinase and 10 µg/ml lactate dehydrogenase.

Example 2

ERK Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 µM NADH, 150 µg/mL pyruvate kinase, 50 µg/mL lactate dehydrogenase, and 200 µM erktide peptide. The reaction was initiated by the addition of 65 µM ATP. The rate of decrease of absorbance at 340 nM was monitored. The $K_i$ was determined from the rate data as a function of inhibitor concentration.

Example 3

GSK Inhibition Assay

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µ/g/ml lactate dehydrogenase.

An assay stock buffer solution was prepared containing all of the reagents listed above with the exception of ATP and the test compound of interest. The assay stock buffer solution (175 µl) was incubated in a 96 well plate with 5 µl of the test compound of interest at final concentrations spanning 0.002 µM to 30 µM at 30° C. for 10 min. Typically, a 12 point titration was conducted by preparing serial dilutions (from 10 mM compound stocks) with DMSO of the test compounds in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The $K_i$ values were determined from the rate data as a function of inhibitor concentration.

Example 4

PKA Inhibition Assay

Compounds were screened for their ability to inhibit PKA using a standard coupled enzyme assay (Fox et al., *Protein Sci*, 1998, 7, 2249). Assays were carried out in a mixture of 100 mM HEPES (pH 7.5), 10 mM $MgCl_2$, 25 mM NaCl, 1 mM DTT and 3% DMSO. Final substrate concentrations in the assay were 50 µM ATP (Sigma Chemicals) and 80 µM peptide (Kemptide, American Peptide, Sunnyvale, Calif.). Assays were carried out at 30° C. and 18 nM PKA. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of ATP, and the test compound of the present invention. 55 µl of the stock solution was placed in a 96 well plate followed by addition of 2 µl of DMSO stock containing serial dilutions of the test compound of the present invention (typically starting from a final concentration of 5 µM). The plate was preincubated for 10 minutes at 30° C. and the reaction initiated by addition of 5 µl of ATP (final concentration 50 µM). Initial reaction rates were determined with a Molecular Devices SpectraMax Plus plate reader over a 15 minute time course. $IC_{50}$ and $K_i$ data were calculated from non-linear regression analysis using the Prism software package (GraphPad Prism version 3.0a for Macintosh, GraphPad Software, San Diego Calif., USA).

Example 5

Itk Inhibition Assay

Compounds were screened for their ability to inhibit Itk using a standard coupled enzyme assay (Fox et al., Protein Sci., (1998) 7, 2249). Assays were carried out in a mixture of 20 mM MOPS (pH 7.0), 10 mM MgCl2, 0.1% BSA, 1 mM DTT, 2.5 mM phosphoenolpyruvate, 300 µM NADH, 30 µg/ml pyruvate kinase and 10 µg/ml lactate dehydrogenase. Final substrate concentrations in the assay were 100 µM ATP (Sigma Chemicals) and 3 µM peptide (Biotinylated SAM68 D332-443). Assays were carried out at 25° C. and in the presence of 100 nM Itk.

An assay stock buffer solution was prepared containing all of the reagents listed above, with the exception of ATP and the test compound of interest. 60 µl of the stock solution was placed in a 96 well plate followed by addition of 2 µl of DMSO stock containing serial dilutions of the test compound (typically starting from a final concentration of 15 µM). The plate was preincubated for 10 minutes at 25° C. and the reaction initiated by addition of 5 µl of ATP. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Tables 5 and 6 depict enzyme inhibition data ($K_i$) for certain exemplary compounds. Compound numbers in Tables 5 and 6 correspond to those compounds depicted in Tables 1 and 2, respectively.

In Tables 5 and 6, "A" represents a $K_i$ of less than 0.5 µM, "B" represents a $K_i$ of between 0.5 and 5.0 µM, and "C" represents a $K_i$ greater than 5.0 µM for the indicated enzyme. If more than one value of $K_i$ has been determined, the average $K_i$ is indicated. If no value is indicated, then the $K_i$ was not determined. For ROCK, the term "Enzyme" indicates that an enzyme-linked assay was used; the term "$^{33}P$" indicates that a radioactive assay was used.

TABLE 5

| Cmpd # | Itk | PKA | $^{33}P$ | ROCK Enzyme |
|---|---|---|---|---|
| I-1 | B | A | A | A |
| I-2 | | A | | A |
| I-3 | | A | | A |
| I-4 | | A | | A |
| I-5 | | A | A | A |
| I-6 | | A | | A |

TABLE 5-continued

| Cmpd # | Itk | PKA | ROCK $^{33}$P | ROCK Enzyme |
|---|---|---|---|---|
| I-7 |  | A |  | A |
| I-8 |  | A |  | A |
| I-9 |  | B |  | A |
| I-10 |  | A |  | A |
| I-11 |  | A |  | A |
| I-12 |  | A |  | A |
| I-13 |  | A |  | A |
| I-14 |  | A | A |  |
| I-15 |  | B | A | A |
| I-16 |  | A | A | A |
| I-17 |  | A | A | A |
| I-18 |  | A |  | A |
| I-19 |  | A |  | A |
| I-20 | B | A |  | A |
| I-21 |  | A |  | A |
| I-22 |  | A |  | A |
| I-23 |  | A |  | A |

TABLE 6

| Cmpd # | Itk | PKA | ROCK $^{33}$P | ROCK Enzyme |
|---|---|---|---|---|
| II-1 |  |  |  |  |
| II-2 |  |  |  |  |
| II-3 |  | B |  | B |
| II-4 |  | A |  | A |
| II-5 |  | A |  | A |
| II-6 |  | A |  | A |
| II-7 |  | A |  | A |
| II-8 |  | A |  | A |
| II-9 |  | A |  | A |
| II-10 |  | B |  | A |
| II-11 |  | A |  | A |
| II-12 |  | A |  | A |
| II-13 |  | A |  | A |
| II-14 |  | B |  | A |
| II-15 |  | A |  | A |
| II-16 |  | A |  | A |
| II-17 |  | B |  | A |
| II-18 |  | A |  | A |
| II-19 |  | A |  | A |
| II-20 |  | A |  | A |
| II-21 |  |  |  | A |
| II-22 |  |  |  | A |
| II-23 |  | A |  | A |
| II-24 |  | B |  | A |
| II-25 |  | A |  | A |
| II-26 |  | B |  | A |
| II-27 |  | A |  | A |
| II-28 |  | A |  | A |
| II-29 |  | A |  | A |
| II-30 |  | A |  | A |
| II-31 |  | A |  | A |
| II-32 |  | A |  | A |
| II-33 |  | A |  | A |
| II-34 |  | A |  | A |
| II-35 |  | B |  | A |
| II-36 |  | B |  | A |
| II-37 |  | B |  | A |
| II-38 |  | B |  | A |
| II-39 |  | A |  | A |
| II-40 |  | A |  | A |
| II-41 |  | A |  | A |
| II-42 |  | A |  | A |
| II-43 |  | B |  | B |
| II-44 |  | A |  | A |
| II-45 |  | A |  | A |
| II-46 |  | A |  | A |
| II-47 |  | A |  | A |
| II-48 |  | A |  | A |

TABLE 6-continued

| Cmpd # | Itk | PKA | ROCK $^{33}$P | ROCK Enzyme |
|---|---|---|---|---|
| II-49 |  |  |  |  |
| II-50 |  | A | A | A |
| II-51 |  | A | A | A |
| II-52 |  | A |  | A |
| II-53 | B | A |  | A |
| II-54 | B | A |  | A |
| II-55 |  | A |  | A |
| II-56 |  | A |  | A |
| II-57 |  | B |  | A |
| II-58 |  | B |  | B |
| II-59 |  | A |  | A |
| II-60 |  | A |  | A |
| II-61 |  | A |  | A |
| II-62 |  | A |  | A |
| II-63 |  | B |  | A |
| II-64 |  | B |  | B |
| II-65 |  | A |  | A |
| II-66 |  | B |  | A |
| II-67 |  | B |  | A |
| II-68 |  | A |  | A |
| II-69 |  | A |  | A |
| II-70 |  | A |  | A |
| II-71 |  | A |  | A |
| II-72 |  | A |  | A |
| II-73 |  | B |  | A |
| II-74 |  | B |  | A |
| II-75 |  | A |  | A |
| II-76 |  | B |  | A |
| II-77 |  | B |  | A |
| II-78 |  | B |  | A |
| II-79 | B | A | A | A |
| II-80 |  | B |  | A |
| II-81 |  | B |  | A |
| II-82 |  | A |  | A |
| II-83 |  | B |  | A |
| II-84 |  | B |  | A |
| II-85 |  | A |  | A |
| II-86 |  | B |  | A |
| II-87 |  | A |  | A |
| II-88 |  | A |  | A |
| II-89 |  | B |  | A |
| II-90 |  | A |  | A |
| II-91 |  | A |  | A |
| II-92 |  | A |  | A |
| II-93 |  | B |  | B |
| II-94 |  | A |  | A |
| II-95 |  | A |  | A |
| II-96 |  | A |  | A |
| II-97 |  | A |  | A |
| II-98 |  | B |  | A |
| II-99 |  | B |  | A |
| II-100 |  | B |  | A |
| II-101 |  | B |  | B |
| II-102 |  | A |  | A |
| II-103 |  | A |  | A |
| II-104 |  | B |  | A |
| II-105 |  | B |  | A |
| II-106 |  | A |  | A |
| II-107 |  | B |  | A |
| II-108 |  | B | A | A |
| II-109 |  | B | A | A |
| II-110 |  | B | A | A |
| II-111 |  | B | A | A |
| II-112 |  | B |  | A |
| II-113 |  | A |  | A |
| II-114 |  | A | A | A |
| II-115 |  | A | A | A |
| II-116 |  | A | A | A |
| II-117 |  | A | A | A |
| II-118 |  | A | A | A |
| II-119 |  | A | A | A |
| II-120 |  | A | A | A |
| II-121 |  | B | A | A |
| II-122 |  | A | A | A |
| II-123 |  | A | A | A |

TABLE 6-continued

| Cmpd # | Itk | PKA | ROCK $^{33}$P | Enzyme |
|---|---|---|---|---|
| II-124 |  | A | A | A |
| II-125 |  | A | A | A |
| II-126 |  | A | A | A |
| II-127 |  | A | A | A |
| II-128 |  | A | A | A |
| II-129 |  | B | A | A |
| II-130 |  | B | A |  |
| II-131 |  | A | A |  |
| II-132 |  | B | A |  |
| II-133 |  | A | A |  |
| II-134 |  | B | A |  |
| II-135 |  | A | A |  |
| II-136 |  | B | A |  |
| II-137 |  | B | A |  |
| II-138 |  | A | A |  |
| II-139 |  | A | A |  |
| II-140 |  | A | A |  |
| II-141 |  | A | A |  |
| II-142 |  | B | A |  |
| II-143 |  | B | A |  |
| II-144 |  | B | A |  |
| II-145 |  | B | A |  |
| II-146 |  | B | A |  |
| II-147 |  | A | A |  |
| II-148 |  | A | A |  |
| II-149 |  | B | A |  |
| II-150 |  | A | A |  |
| II-151 |  | A | A |  |
| II-152 |  | A | A |  |
| II-153 |  | B | A |  |
| II-154 |  | A | A |  |
| II-155 |  | A | A |  |
| II-156 |  | B | A |  |
| II-157 |  | B | A |  |
| II-158 |  | A | A |  |
| II-159 |  | A | A |  |
| II-160 |  | A | A |  |
| II-161 |  | A | A |  |
| II-162 | B | B | A |  |
| II-163 |  | B | A |  |
| II-164 |  | B | A |  |
| II-165 |  | A | A |  |
| II-166 |  | A | A |  |
| II-167 |  | A | A |  |
| II-168 |  | A | A |  |
| II-169 |  | A | A |  |
| II-170 |  | A | A |  |
| II-171 |  | A | A |  |
| II-172 |  | A | A |  |
| II-173 |  | A | A |  |
| II-174 |  | B | A |  |
| II-175 |  | A | A |  |
| II-176 |  | A | A |  |
| II-177 |  | A | A |  |
| II-178 |  | A | A |  |
| II-179 |  | A | A |  |
| II-180 |  | A | A |  |
| II-181 |  | A | A |  |
| II-182 |  | B | A |  |
| II-183 |  | B | A |  |
| II-184 |  | A | A |  |
| II-185 |  | B | A |  |
| II-186 |  | B | A |  |
| II-187 |  | A | A |  |
| II-188 |  | A | A |  |
| II-189 |  | A | A |  |
| II-190 |  | A | A |  |
| II-191 |  | A | A |  |
| II-192 |  | A | A |  |
| II-193 |  | A | A |  |
| II-194 |  | A | A |  |
| II-195 |  | A | A |  |
| II-196 |  | A | A |  |
| II-197 |  | B | B |  |
| II-198 |  | B | B |  |
| II-199 |  | B | A |  |
| II-200 |  | B | B |  |
| II-201 |  | A | A |  |
| II-202 |  | A | A |  |
| II-203 |  | A | A |  |
| II-204 |  | B | A |  |
| II-205 |  | A | A |  |
| II-206 |  | A | A |  |
| II-207 |  | A | A |  |
| II-208 |  | A | A |  |
| II-209 |  | A | A |  |
| II-210 |  | A | A |  |
| II-211 |  | A | A |  |
| II-212 |  | A | A |  |
| II-213 |  | A | A |  |
| II-214 |  | A | A |  |
| II-215 |  | A | A |  |
| II-216 |  | B | A |  |
| II-217 |  | A | A |  |
| II-218 |  | A | A |  |
| II-219 |  | A | A |  |
| II-220 |  | A | A |  |
| II-221 |  | A | A |  |
| II-222 |  | A | A |  |
| II-223 |  | A | A |  |
| II-224 |  | B | A |  |
| II-225 |  | B | A |  |
| II-226 |  | A | A |  |
| II-227 |  | A | A |  |
| II-228 |  | A | A |  |
| II-229 |  | A | A |  |
| II-230 |  | A | A |  |
| II-231 |  | A | A |  |
| II-232 |  | A | A |  |
| II-233 |  | A | A |  |
| II-234 |  | B | B |  |
| II-235 |  | B | B |  |
| II-236 |  | B | B |  |
| II-237 |  | B | B |  |
| II-238 |  | B | B |  |
| II-239 |  | B | A |  |
| II-240 |  | B | B |  |
| II-241 |  | B | B |  |
| II-242 |  | B | B |  |
| II-243 |  | B | B |  |
| II-244 |  | B | A |  |
| II-245 | B | B | A |  |
| II-246 | B | B | A |  |
| II-247 | B | B | A |  |
| II-248 | B | A | B |  |
| II-249 | B | B | A |  |
| II-250 | B | A |  |  |
| II-251 | B | A | B |  |
| II-252 | B | B | A |  |
| II-253 | B | A | B |  |
| II-254 | B | B | A |  |
| II-255 | B | B |  |  |
| II-256 | B |  |  |  |

The invention claimed is:
1. A compound of formula I:

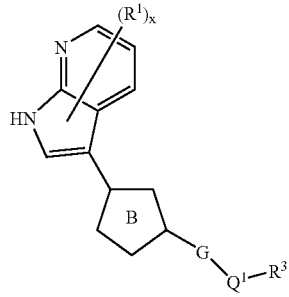

or a pharmaceutically acceptable salt thereof, wherein:
wherein

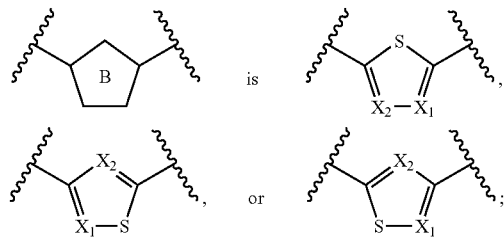 is x is 0, 1, 2, or 3;
$R^1$ is halogen, —CN, —$NO_2$, or —$V_mR'$;
G is —$NR^2$— or C=O;
$R^2$ is —$U_nR'$;
$X^1$ and $X^2$ are each independently $CR^4$ or N;
each occurrence of $R^4$ is independently halogen, CN, $NO_2$, or $V_mR$;
each occurrence of U or V is independently an optionally substituted $C_{1-6}$ alkylidene chain, wherein up to two methylene units of the chain are optionally and independently replaced by —NR—, —S—, —O—, —CS—, —$CO_2$—, —OCO—, —CO—, —COCO—, —CONR—, —NRCO—, —$NRCO_2$—, —$SO_2NR$—, —$NRSO_2$—, —CONRNR—, —NRCONR—, —OCONR—, —NRNR—, —$NRSO_2NR$—, —SO—, —$SO_2$—, —PO—, —$PO_2$—, or —POR—;
m and n are each independently 0 or 1;
each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;
$Q^1$ is —CO—, —$SO_2$—, —$NR^2$—, —$NR^2CO$—, —$CONR^2$—, or —$SO_2NR^2$—;
$R^3$ is $Q^2$-$Ar^1$, or when G is —$NR^2$—, $R^2$ and $Q^1$-$R^3$, taken together with the nitrogen atom, form the cyclic group:

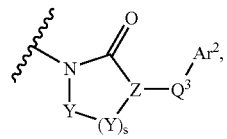

where s is 1 or 2, Z is CH or N; each occurrence of Y is independently, as valency and stability permit, —CO—, —CS—, —$SO_2$—, —O—, —S—, —$NR^5$—, or —$C(R^5)_2$—, and $R^5$ is $U_nR'$;
$Q^2$ and $Q^3$ are each independently a bond or a $C_{1-6}$ alkylidene chain, wherein up to two methylene units of the chain are each optionally and independently replaced by —NR'—, —S—, —O—, —CS—, —$CO_2$—, —OCO—, —CO—, —COCO—, —CONR'—, —NR'CO—, —$NR'CO_2$—, —$SO_2NR'$—, —$NR'SO_2$—, —CONR'NR'—, —NR'CONR'—, —OCONR'—, —NR'NR'—, —$NR'SO_2NR'$—, —SO—, —$SO_2$—, —PO—, —$PO_2$—, or —POR'—; and wherein any carbon atom in the one or more methylene units is optionally substituted with one or two occurrences of $R^6$, wherein each occurrence of $R^6$ is independently halogen, —CN, —$NO_2$, or —$U_nR'$, or two occurrences of $R^6$, or R' and $R^6$, taken together with the atoms to which they are bound, form an optionally substituted 3-6-membered cycloalkyl, heterocyclyl, aryl or heteroaryl ring; and
$Ar^1$ and $Ar^2$ are each independently a $C_{1-6}$ aliphatic, a 3-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ and $Ar^2$ are each optionally substituted with 0-5 independent occurrences of $TR^7$; wherein T is a bond or is a $C_1$-$C_6$ alkylidene chain wherein up to two methylene units of T are optionally and independently replaced by —NR—, —S—, —O—, —CS—, —$CO_2$—, —OCO—, —CO—, —COCO—, —CONR—, —NRCO—, —$NRCO_2$—, —$SO_2NR$—, —$NRSO_2$—, —CONRNR—, —NRCONR—, —OCONR—, —NRNR—, —$NRSO_2NR$—, —SO—, —$SO_2$—, —PO—, —$PO_2$—, or —POR—; and each occurrence of $R^7$ is independently —R', halogen, —$NO_2$, —CN or =O.

2. The compound according to claim 1, wherein:
$Ar^1$ and $Ar^2$ are each independently a 5-8 membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ and $Ar^2$ are each optionally substituted with 0-5 independent occurrences of $TR^7$; wherein T is a bond or is a $C_1$-$C_6$ alkylidene chain wherein up to two methylene units of T are optionally and independently replaced by —NR—, —S—, —O—, —CS—, —$CO_2$—, —OCO—, —CO—, —COCO—, —CONR—, —NRCO—, —$NRCO_2$—, —$SO_2NR$—, —$NRSO_2$—, —CONRNR—, —NRCONR—, —OCONR—, —NRNR—, —NRSO$_2$NR—, —SO—, —SO$_2$—, —PO—, —PO$_2$—, or —POR—; and each occurrence of R$^7$ is independently —R', halogen, —NO$_2$ or —CN.

3. The compound according to claim 2, wherein

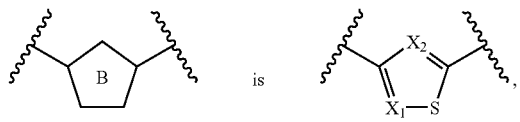

to provide a compound of formula I-B:

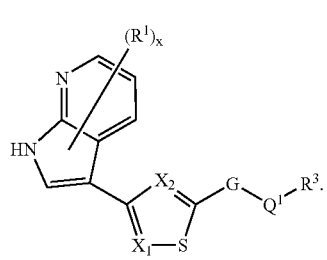

I-B

4. The compound according to claim 3, wherein X$_1$ is CR$^4$, X$_2$ is N and G is —NR$^2$—, to provide a compound of formula VII-A:

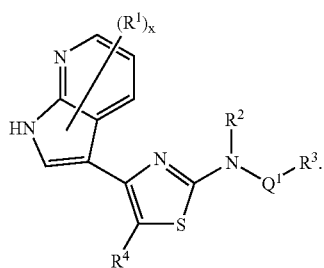

VII-A

5. The compound according to claim 4, wherein Q$^1$ is —CO—.

6. The compound according to claim 5, wherein R$^2$ is H, —C$_{1-4}$ aliphatic, —cyclopropyl or

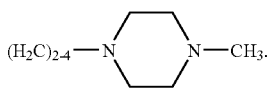

7. The compound according to claim 4, wherein R$^4$ is H or —C$_{1-4}$ aliphatic.

8. The compound according to claim 4, wherein x is 1 and said compound has a formula selected from formulae VII-B-i or VII-B-ii:

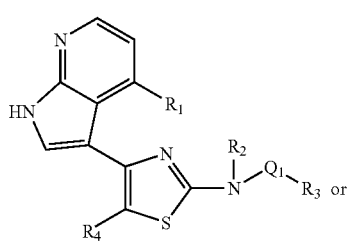

VII-B-i

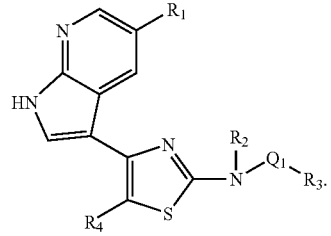

VII-B-ii

9. The compound according to claim 8, wherein R$^1$ is H or F, R$^2$ is H and R$^4$ is H, and the compound has a structure of formula V-B-iii:

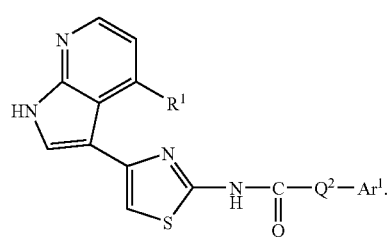

VII-B-iii

10. The compound according to claim 9, wherein Q$^2$ is —(CHR$^6$)$_q$—, —(CHR$^6$)$_q$O—, —(CHR$^6$)$_q$S—, —(CHR$^6$)$_q$S(O)$_2$—, —(CHR$^6$)$_q$S(O)—, —(CHR$^6$)$_q$NR—, or —(CHR$^6$)$_q$C(O)—, wherein q is 0, 1, 2, or 3, and each R$^6$ is R', —N(R)(R'), —(CH$_2$)$_{1-4}$N(R)(R'), —(CH$_2$)$_{1-4}$C(CH$_3$)$_2$N(R)(R'), —(CH$_2$)$_{1-4}$CH(CH$_3$)N(R)(R'), —OR', —(CH$_2$)$_{1-4}$OR', —NR(CH$_2$)$_{1-4}$N(R)(R'), —NR(CH$_2$)$_{1-4}$SO$_2$R', —NR(CH$_2$)$_{1-4}$COR', or —NR(CH$_2$)$_{1-4}$COR', or two occurrences of R$^6$, taken together with the atoms to which they are bound, form an optionally substituted 3-6-membered saturated, partially unsaturated, or fully unsaturated ring.

11. The compound according to claim 9, wherein Ar$^1$ is

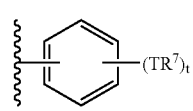

a

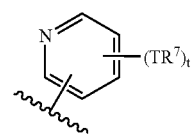

b

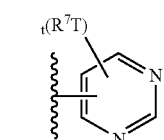

c

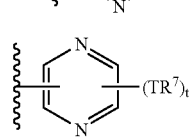

d

245
-continued
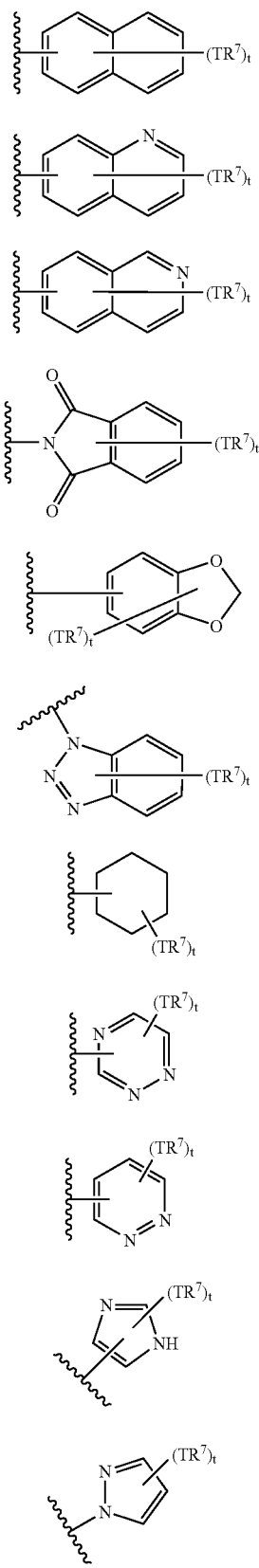
e
5
f
10
g
15
h
20
i 25
j 30
k
35
l
40
m
45
n
50
o 60
65
246
-continued
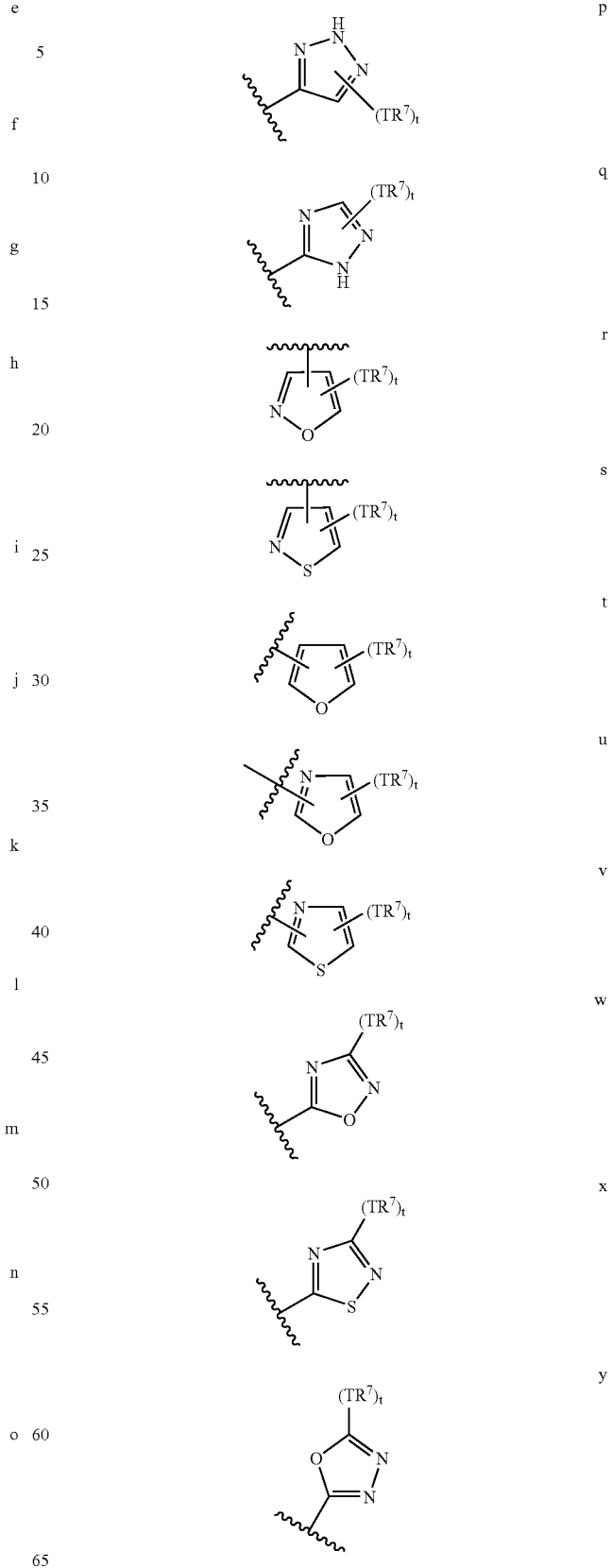
p
q
r
s
t
u
v
w
x
y

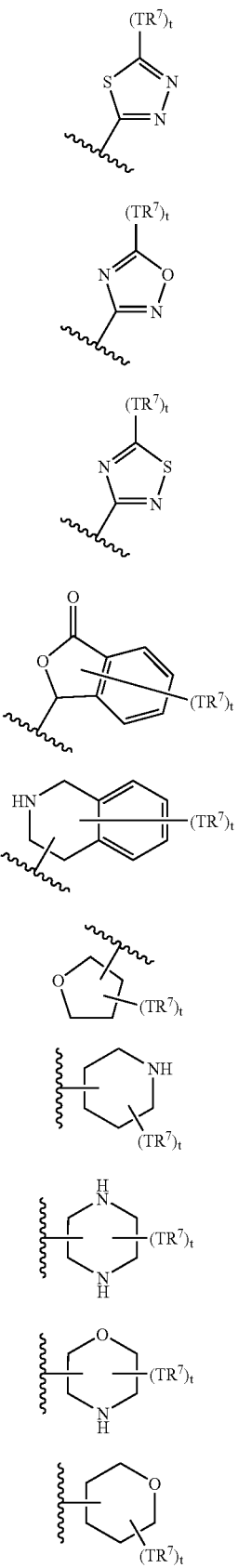
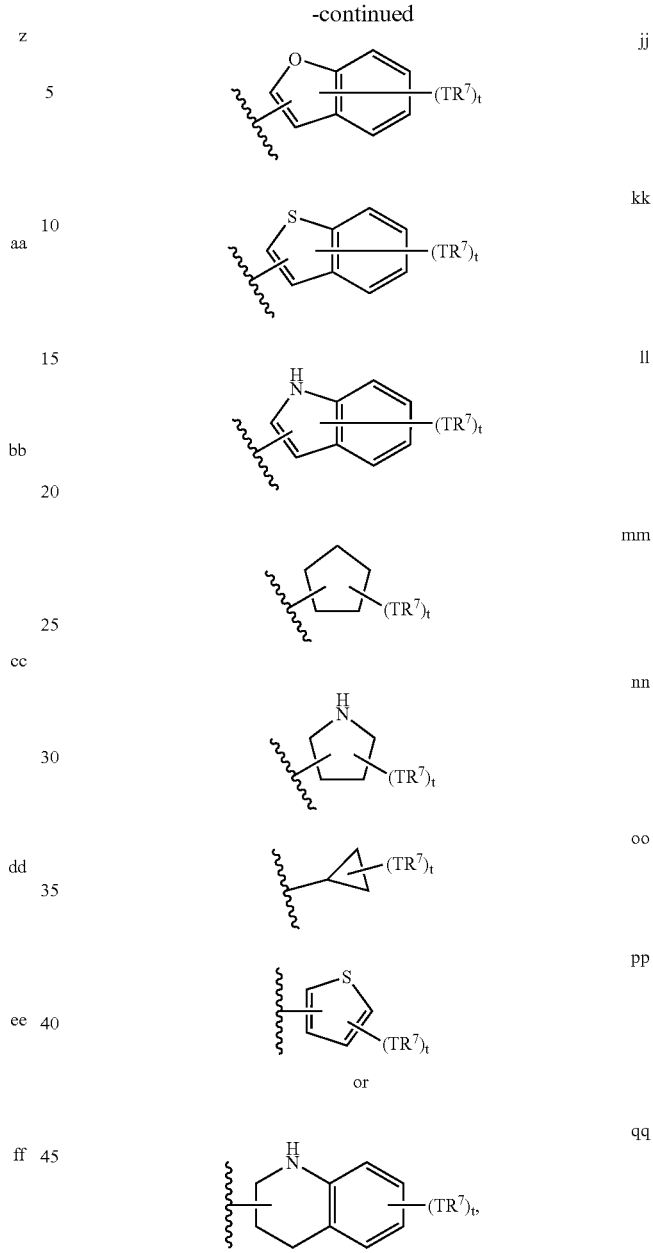

wherein t is 0, 1, 2, 3, 4, or 5, and wherein any $Ar^1$ is bonded to $Q^2$ through any substitutable nitrogen or carbon atom, and wherein one or more hydrogen atoms on any substitutable nitrogen or carbon atom is substituted with one or more independent occurrences of $TR^7$.

12. The compound according to claim 11, wherein t is 0, 1 or 2, and each $TR^7$ is independently selected from halogen, —CN, —R', —O(CH$_2$)$_{0-5}$R', —NRR', —OSO$_2$(CH$_2$)$_{0-4}$R', —NRSO$_2$(CH$_2$)$_{0-5}$R', —NRSO$_2$NR(CH$_2$)$_{0-5}$R', —SO$_2$NR(CH$_2$)$_{0-5}$R', —CONRR', —COR', —COOR', —NRCOR' or —SO$_2$(CH$_2$)$_{0-5}$R'.

13. The compound according to claim 9, wherein $Ar^1$ is a $C_{1-6}$ optionally substituted aliphatic.

14. The compound according to claim 1, wherein said compound is selected from:

| Compound | Cmpd # |
|---|---|
| 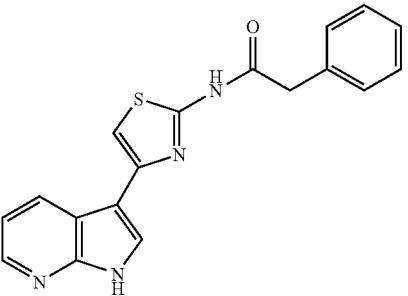 | I-1 |
| 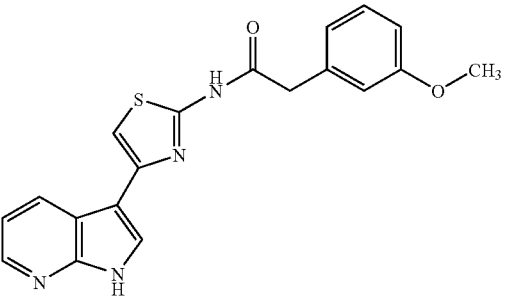 | I-2 |
| 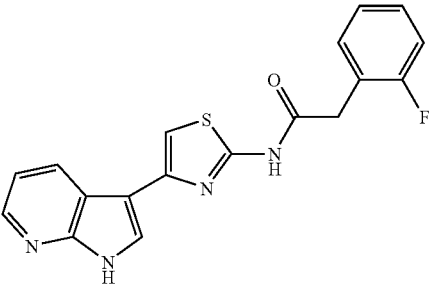 | I-3 |
| 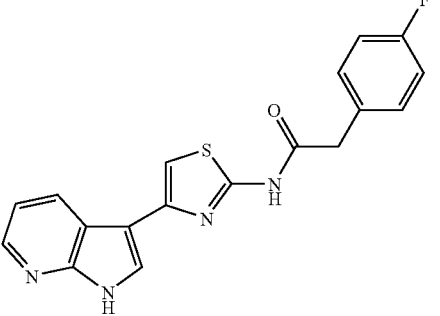 | I-4 |

-continued
| Compound | Cmpd # |
|---|---|
| 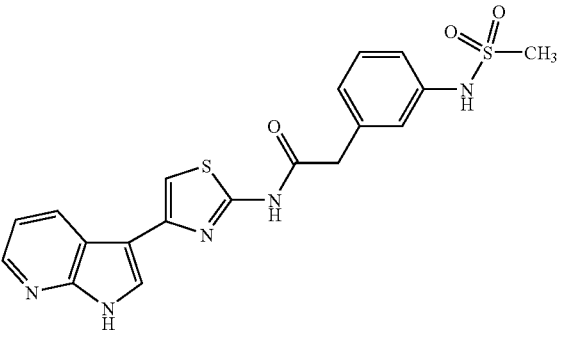 | I-5 |
| 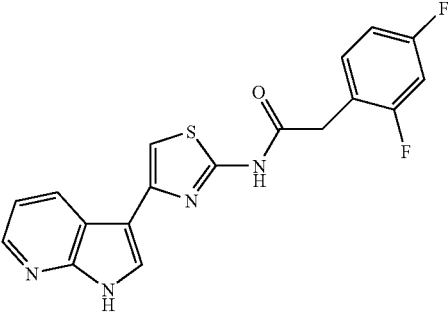 | I-6 |
| 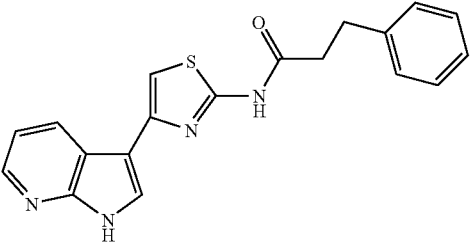 | I-7 |
| 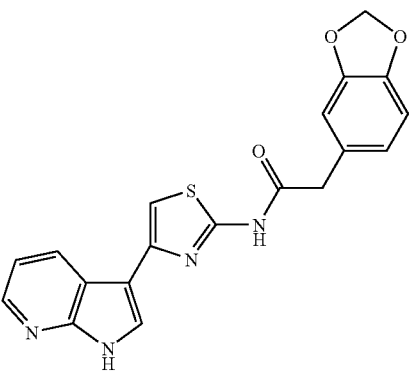 | I-8 |

| Compound | Cmpd # |
|---|---|
| (structure) | I-9 |
| (structure) | I-10 |
| (structure) | I-11 |
| (structure) | I-12 |

-continued
| Compound | Cmpd # |
|---|---|
| 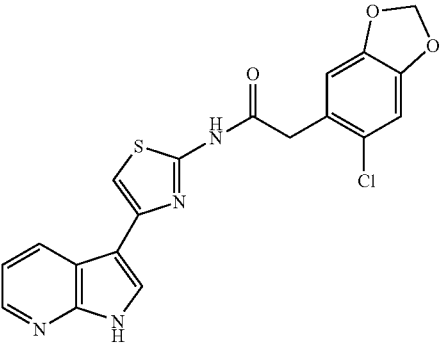 | I-13 |
| 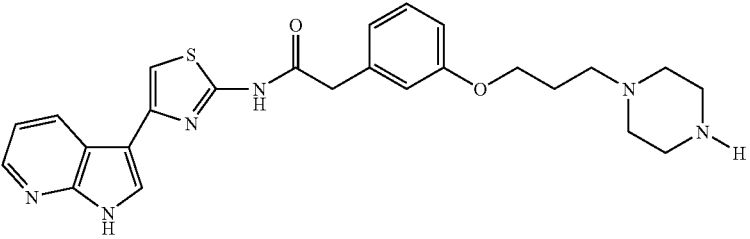 | I-14 |
| 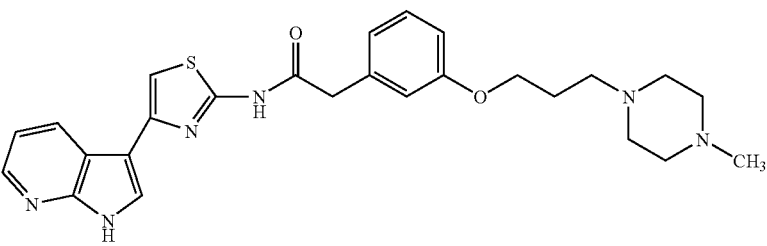 | I-15 |
| 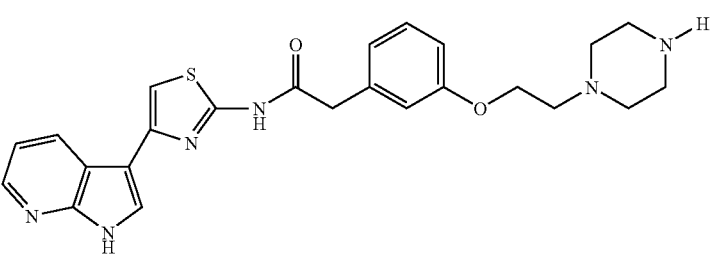 | I-16 |
| 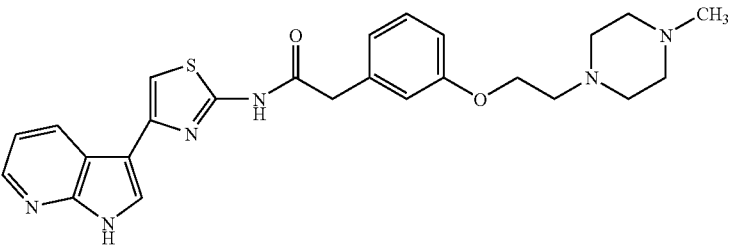 | I-17 |

-continued
| Compound | Cmpd # |
|---|---|
| 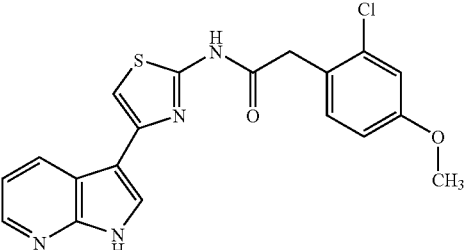 | I-18 |
| 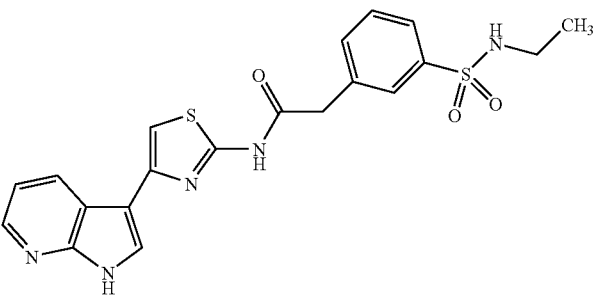 | I-19 |
| 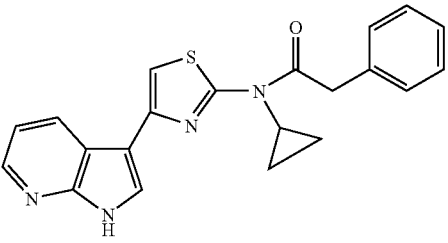 | I-20 |
| 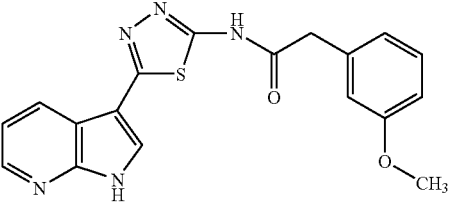 | I-21 |
| 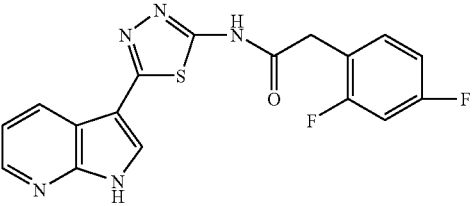 | I-22 |
| 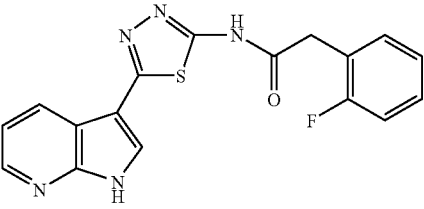 | I-23 |

-continued

| Compound | Cmpd # |
|---|---|
| | II-1 |
| | II-2 |
| | II-3 |
| | II-4 |
| | II-5 |
| | II-6 |

| Compound | Cmpd # |
|---|---|
| | II-7 |
| | II-8 |
| | II-9 |
| | II-10 |
| | II-11 |
| | II-12 |

| Compound | Cmpd # |
|---|---|
| | II-13 |
| | II-14 |
| | II-15 |
| | II-16 |
| | II-17 |

-continued

| Compound | Cmpd # |
|---|---|
| | II-18 |
| | II-19 |
| | II-20 |
| | II-21 |
| | II-22 |
| | II-23 |

| Compound | Cmpd # |
|---|---|
| | II-24 |
| | II-25 |
| | II-26 |
| | II-27 |
| | II-28 |
| | II-29 |
| | II-30 |

| Compound | Cmpd # |
|---|---|
| (structure) | II-31 |
| (structure) | II-32 |
| (structure) | II-33 |
| (structure) | II-34 |
| (structure) | II-35 |

-continued

| Compound | Cmpd # |
|---|---|
| | II-36 |
| | II-37 |
| | II-38 |
| | II-39 |
| | II-40 |
| | II-41 |
| | II-42 |
| | II-43 |

-continued
| Compound | Cmpd # |
|---|---|
| 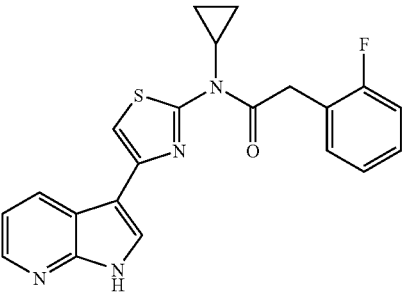 | II-44 |
| 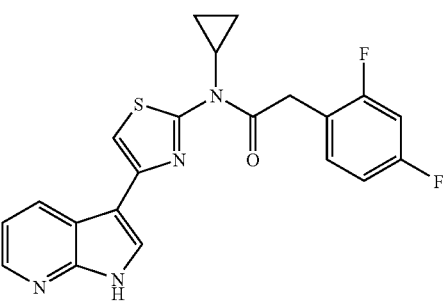 | II-45 |
| 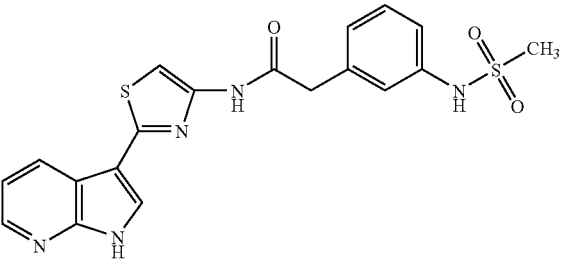 | II-46 |
| 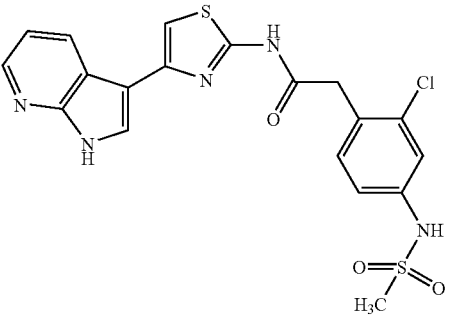 | II-47 |
| 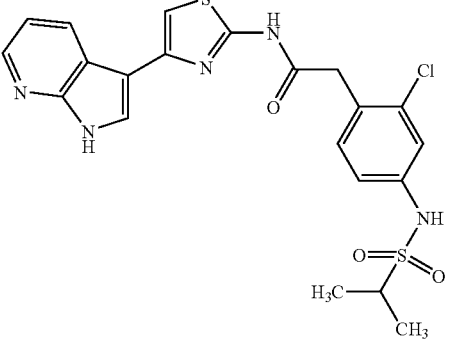 | II-48 |

-continued

| Compound | Cmpd # |
|---|---|
| | II-49 |
| | II-50 |
| | II-51 |
| | II-52 |
| | II-53 |
| | II-54 |
| | II-55 |

| Compound | Cmpd # |
|---|---|
| 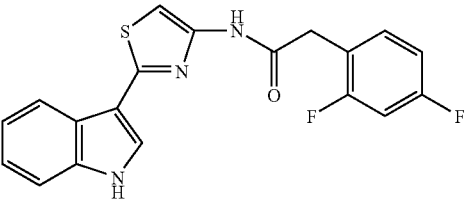 | II-56 |
| 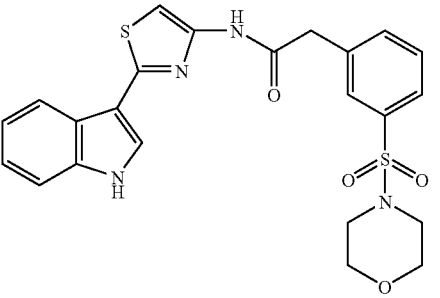 | II-57 |
| 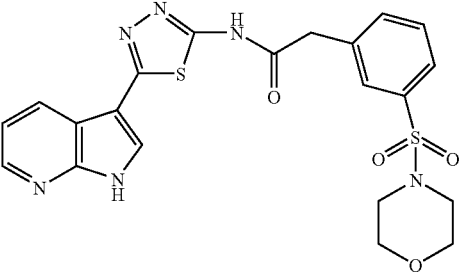 | II-58 |
| 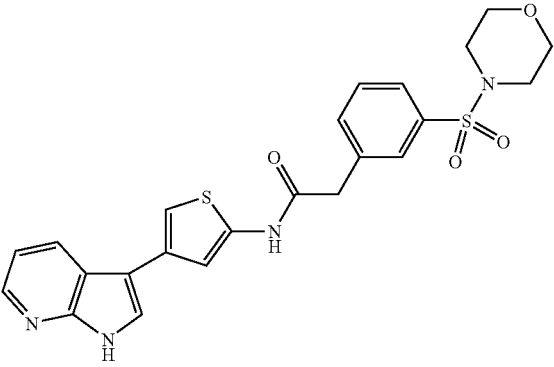 | II-59 |
| 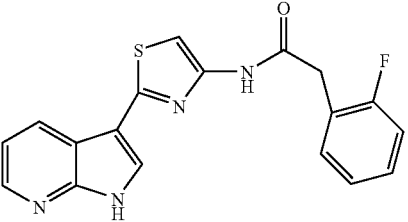 | II-60 |

| Compound | Cmpd # |
|---|---|
| 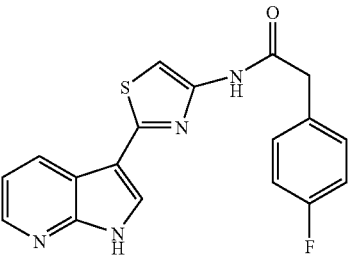 | II-61 |
| 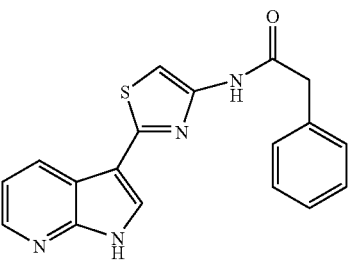 | II-62 |
| 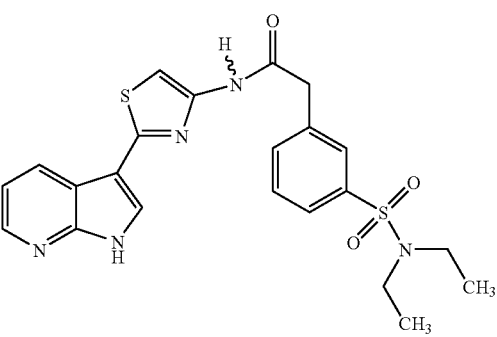 | II-63 |
| 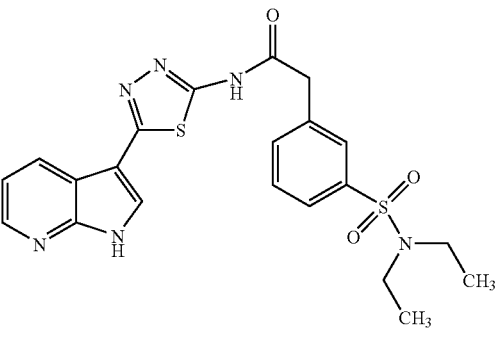 | II-64 |

-continued

| Compound | Cmpd # |
|----------|--------|
| | II-65 |
| | II-66 |
| | II-67 |
| | II-68 |
| | II-69 |

-continued

| Compound | Cmpd # |
|---|---|
| | II-70 |
| | II-71 |
| | II-72 |
| | II-73 |
| | II-74 |

| Compound | Cmpd # |
|---|---|
| | II-75 |
| | II-76 |
| | II-77 |
| | II-78 |
| | II-79 |

-continued
| Compound | Cmpd # |
|---|---|
| 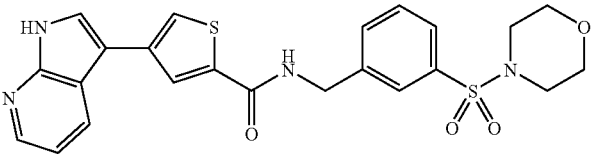 | II-80 |
|  | II-81 |
| 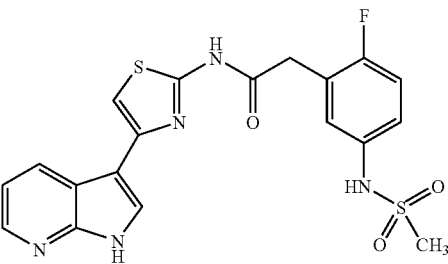 | II-82 |
| 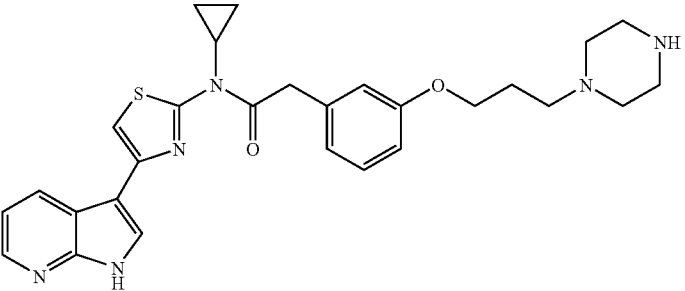 | II-83 |
| 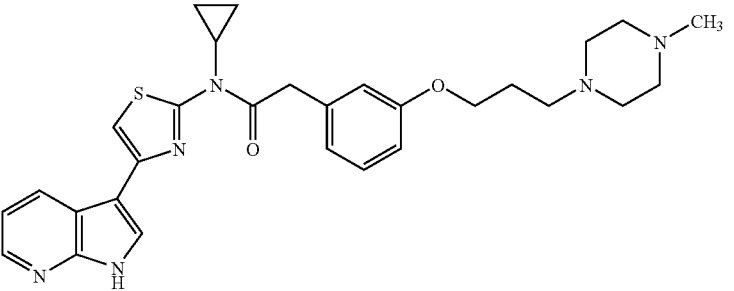 | II-84 |
| 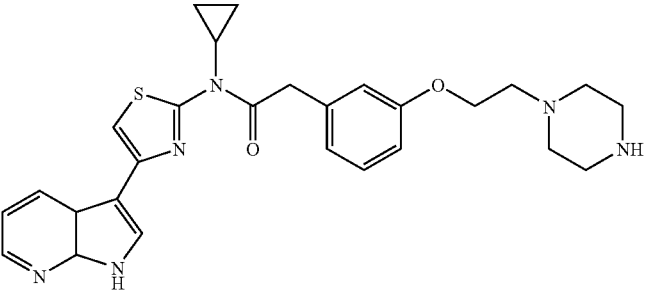 | II-85 |

| Compound | Cmpd # |
|---|---|
| 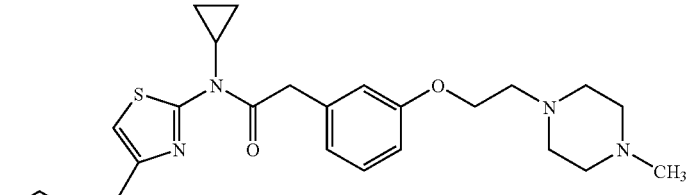 | II-86 |
| 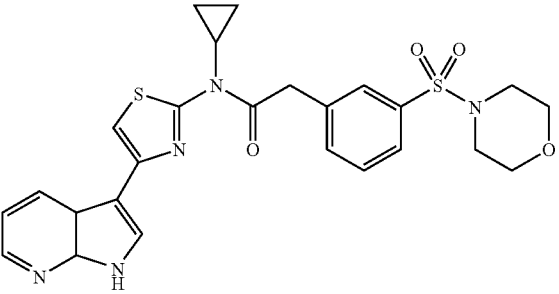 | II-87 |
| 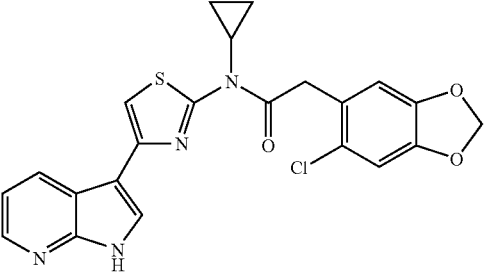 | II-88 |
| 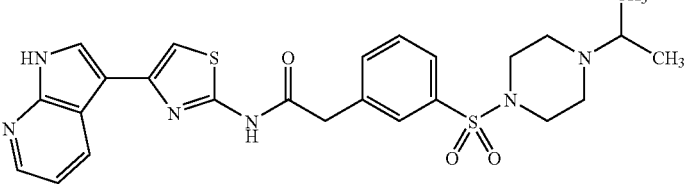 | II-89 |
| 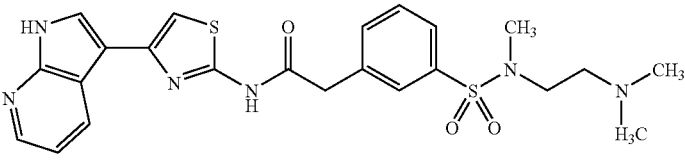 | II-90 |
| 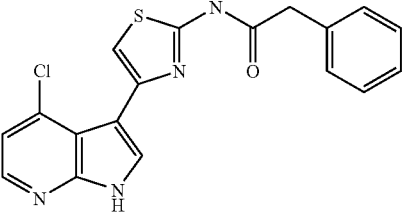 | II-91 |

| Compound | Cmpd # |
|---|---|
| | II-92 |
| | II-93 |
| | II-94 |
| | II-95 |
| | II-96 |
| | II-97 |

-continued

| Compound | Cmpd # |
|---|---|
| | II-98 |
| | II-99 |
| | II-100 |
| | II-101 |
| | II-102 |

-continued

| Compound | Cmpd # |
|---|---|
| (structure) | II-103 |
| (structure) | II-104 |
| (structure) | II-105 |
| (structure) | II-106 |
| (structure) | II-107 |

-continued
| Compound | Cmpd # |
|---|---|
| 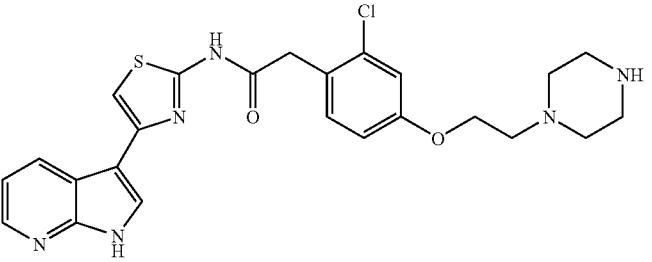 | II-108 |
| 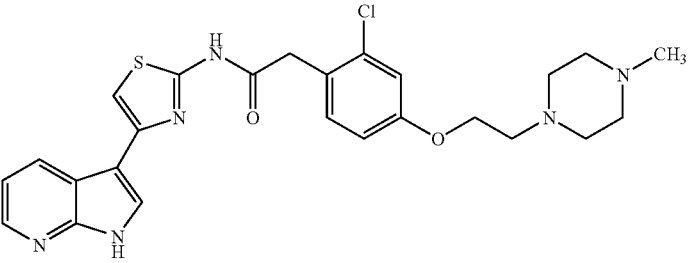 | II-109 |
| 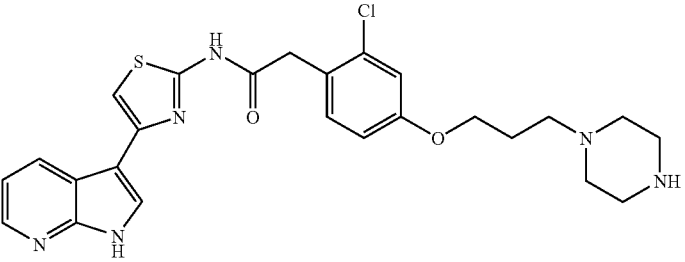 | II-110 |
| 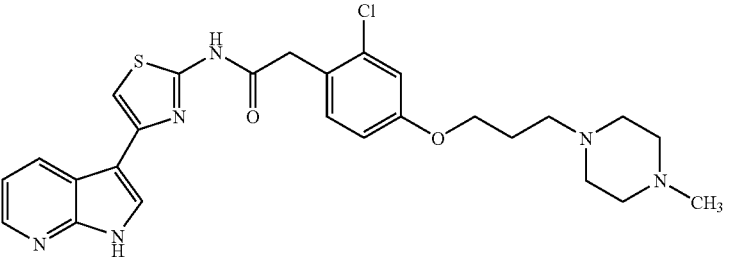 | II-111 |
|  | II-112 |
| 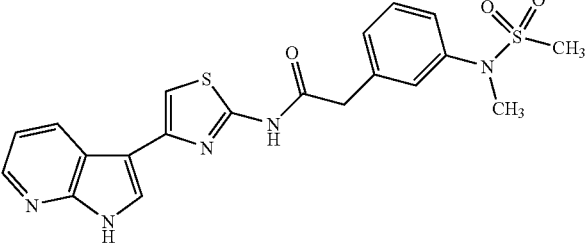 | II-113 |

| Compound | Cmpd # |
|---|---|
| 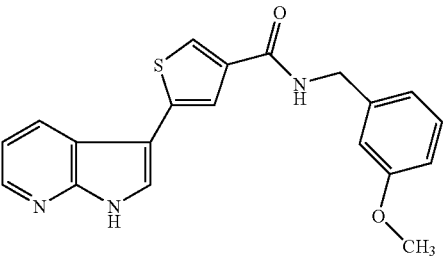 | II-114 |
| 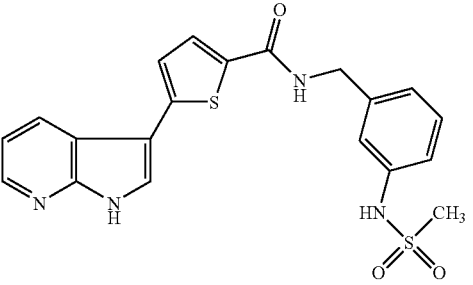 | II-115 |
| 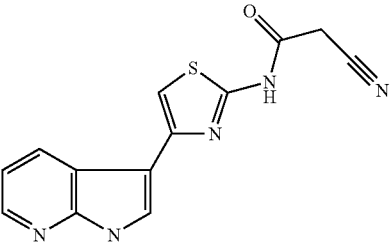 | II-116 |
| 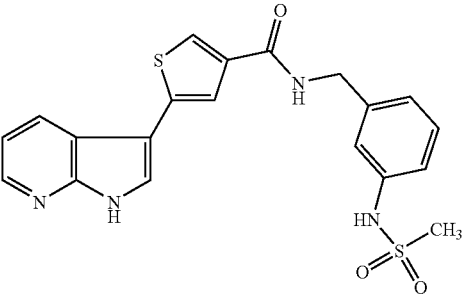 | II-117 |
| 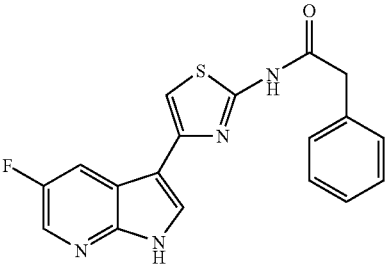 | II-118 |

| Compound | Cmpd # |
|---|---|
| | II-119 |
| | II-120 |
| | II-121 |
| | II-122 |
| | II-123 |

-continued
| Compound | Cmpd # |
|---|---|
| 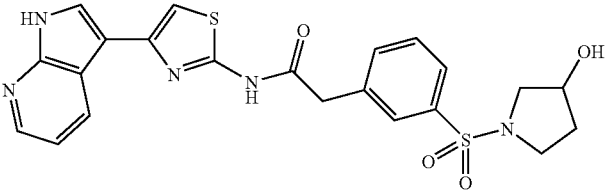 | II-124 |
| 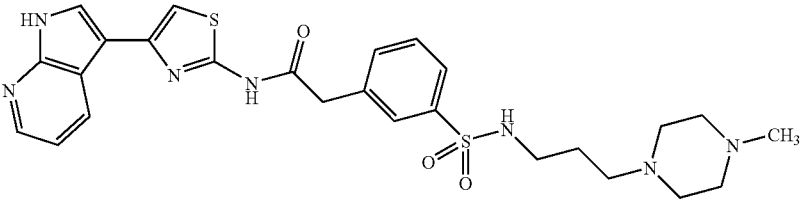 | II-125 |
| 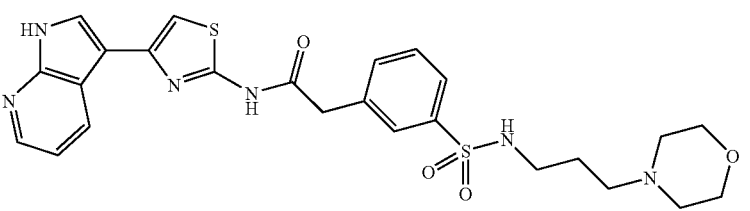 | II-126 |
| 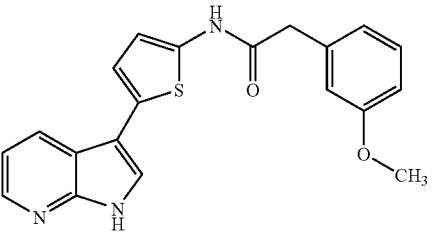 | II-127 |
| 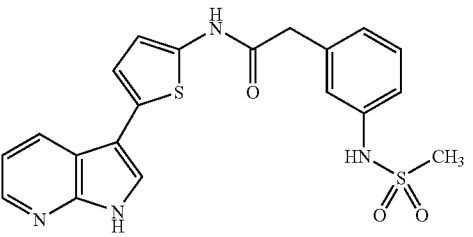 | II-128 |
| 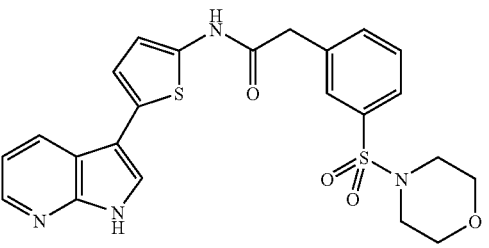 | II-129 |

| Compound | Cmpd # |
|---|---|
| 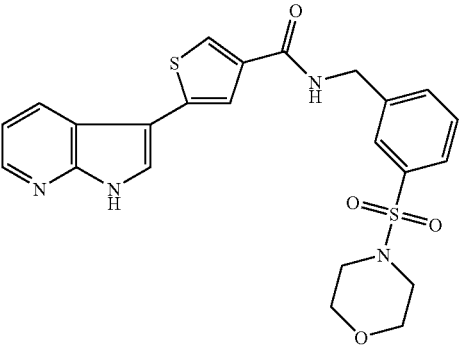 | II-130 |
| 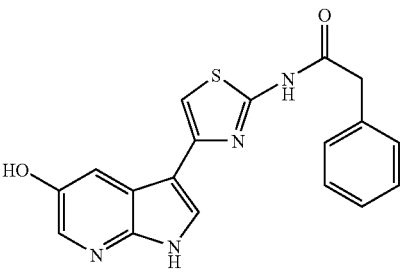 | II-131 |
| 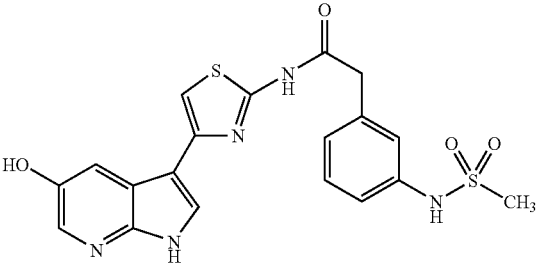 | II-132 |
| 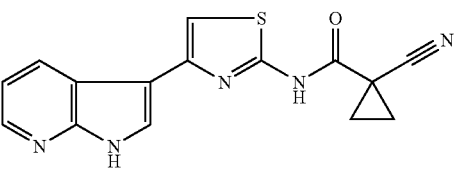 | II-133 |
| 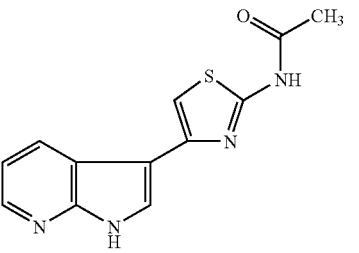 | II-134 |

| Compound | Cmpd # |
|---|---|
| | II-135 |
| | II-136 |
| | II-137 |
| | II-138 |
| | II-139 |
| | II-140 |

| Compound | Cmpd # |
|---|---|
| 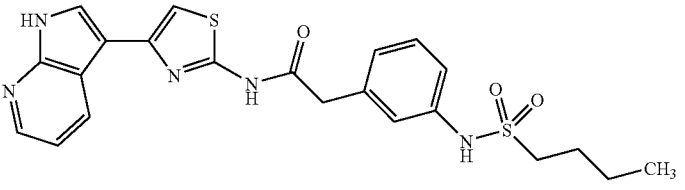 | II-141 |
| 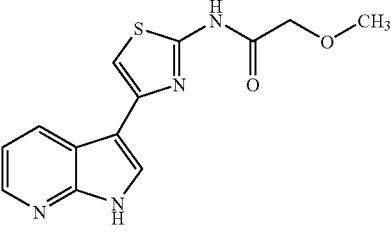 | II-142 |
| 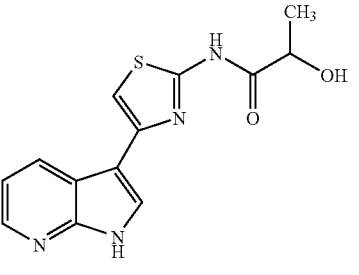 | II-143 |
| 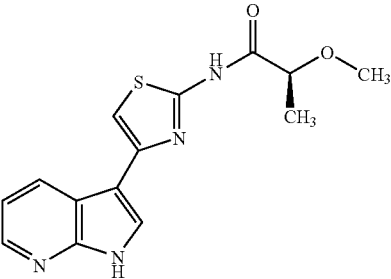 | II-144 |
| 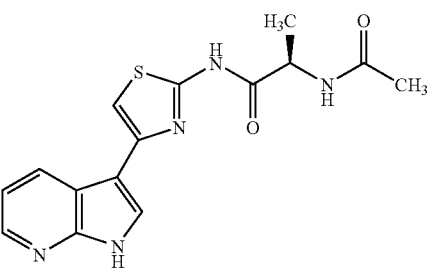 | II-145 |

-continued
| Compound | Cmpd # |
|---|---|
| 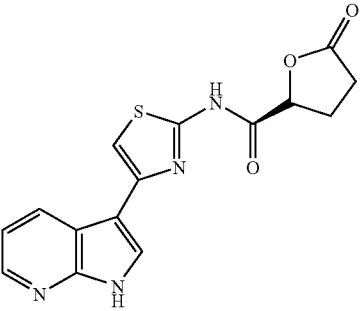 | II-146 |
| 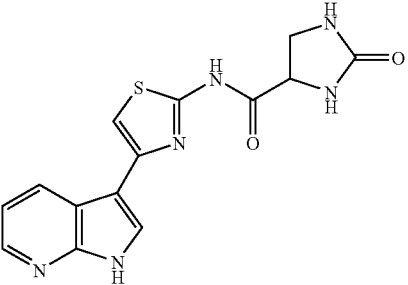 | II-147 |
| 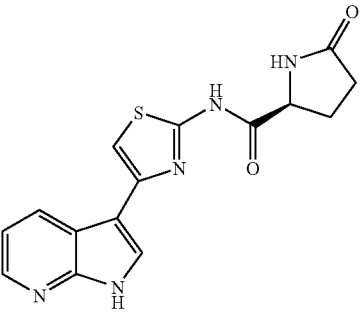 | II-148 |
| 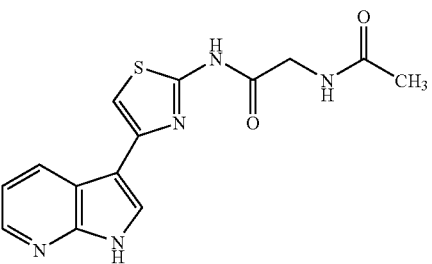 | II-149 |
| 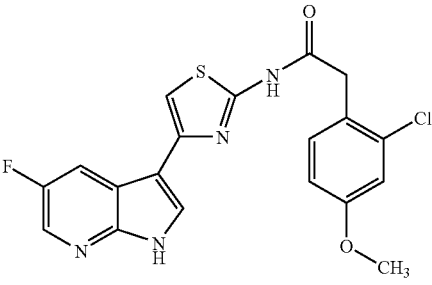 | II-150 |

-continued
| Compound | Cmpd # |
|---|---|
| 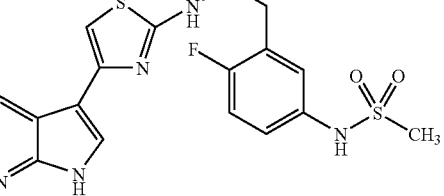 | II-151 |
| 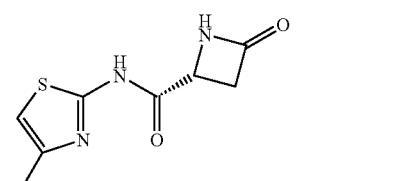 | II-152 |
| 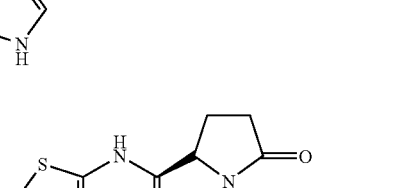 | II-153 |
| 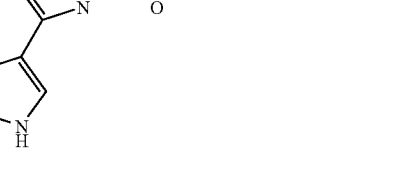 | II-154 |
| 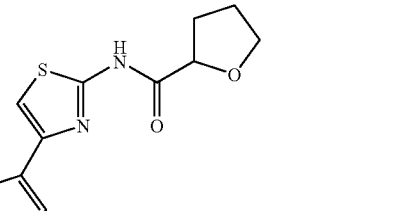 | II-155 |

| Compound | Cmpd # |
|---|---|
| (structure) | II-156 |
| (structure) | II-157 |
| (structure) | II-158 |
| (structure) | II-159 |
| (structure) | II-160 |
| (structure) | II-161 |

-continued

| Compound | Cmpd # |
|---|---|
| | II-162 |
| | II-163 |
| | II-164 |
| | II-165 |
| | II-166 |
| | II-167 |

-continued
| Compound | Cmpd # |
|---|---|
| 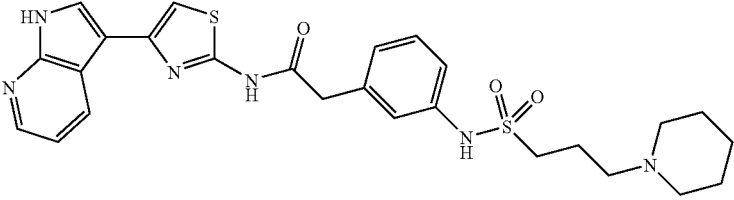 | II-168 |
| 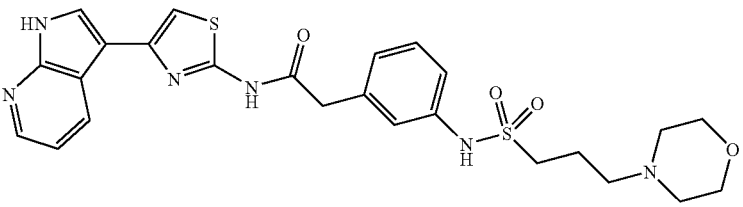 | II-169 |
| 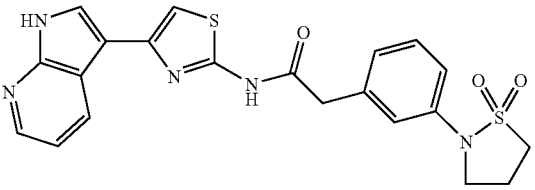 | II-170 |
| 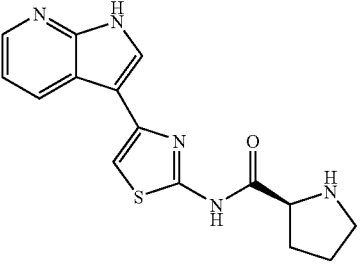 | II-171 |
| 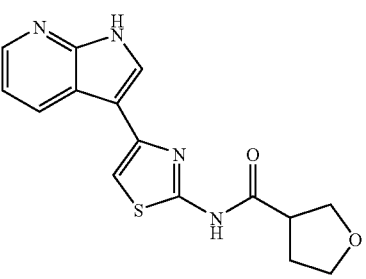 | II-172 |
| 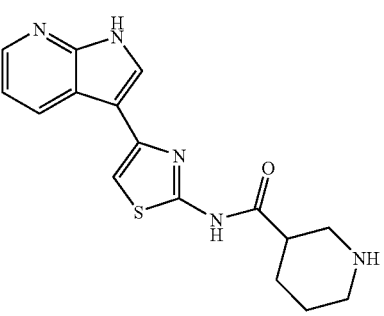 | II-173 |

| Compound | Cmpd # |
|---|---|
| | II-174 |
| | II-175 |
| | II-176 |
| | II-177 |

-continued
| Compound | Cmpd # |
|---|---|
| 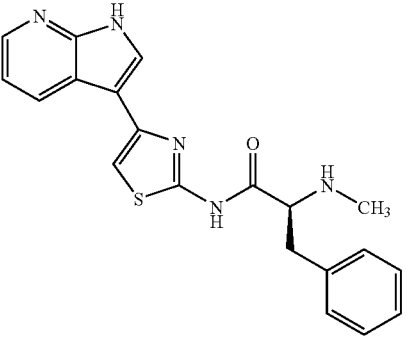 | II-178 |
| 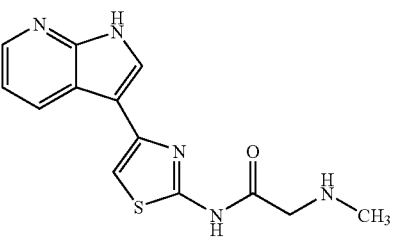 | II-179 |
| 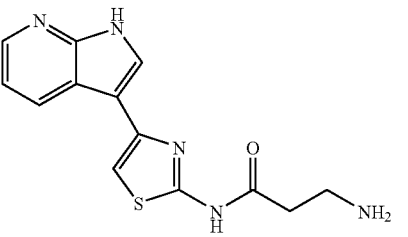 | II-180 |
| 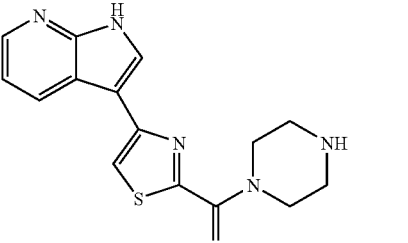 | II-181 |
| 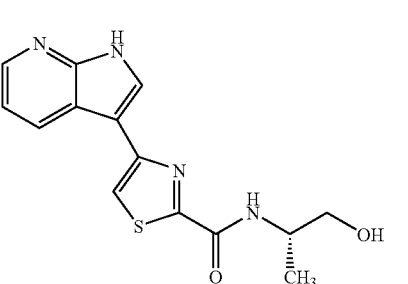 | II-182 |

| Compound | Cmpd # |
|---|---|
| (structure) | II-183 |
| (structure) | II-184 |
| (structure) | II-185 |
| (structure) | II-186 |

-continued
| Compound | Cmpd # |
|---|---|
| 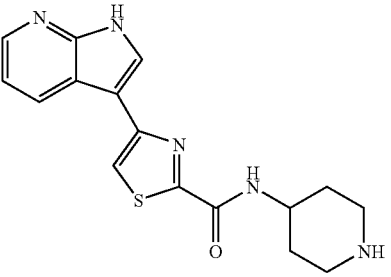 | II-187 |
| 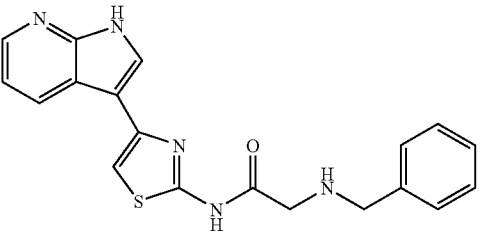 | II-188 |
| 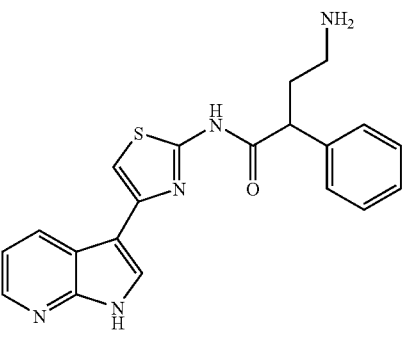 | II-189 |
| 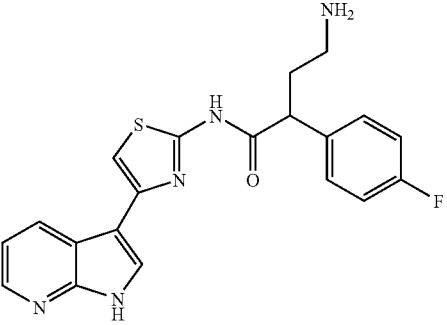 | II-190 |
| 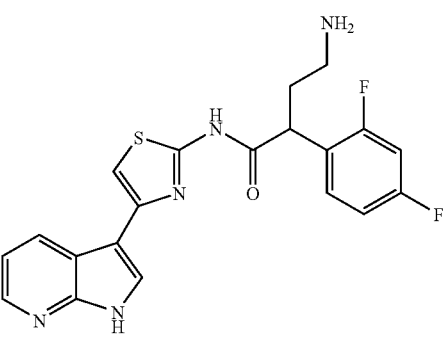 | II-191 |

-continued
| Compound | Cmpd # |
|---|---|
| 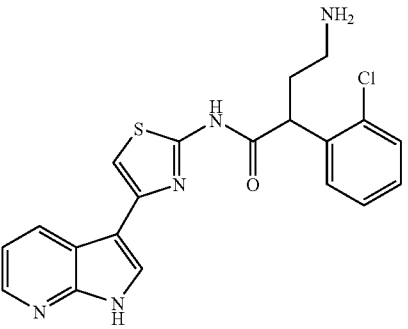 | II-192 |
| 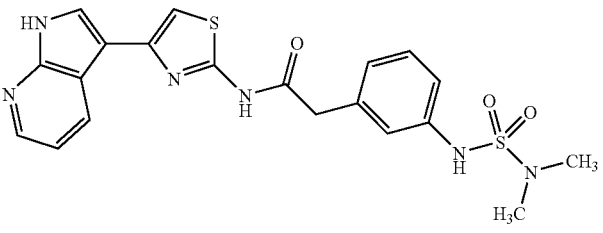 | II-193 |
| 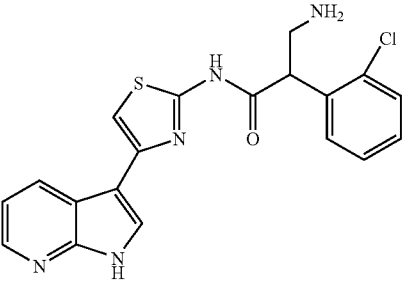 | II-194 |
| 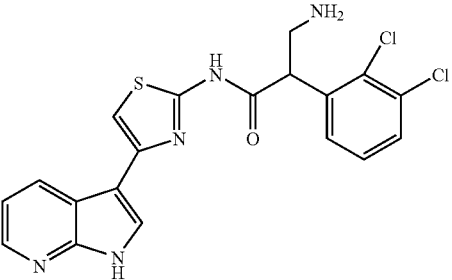 | II-195 |
| 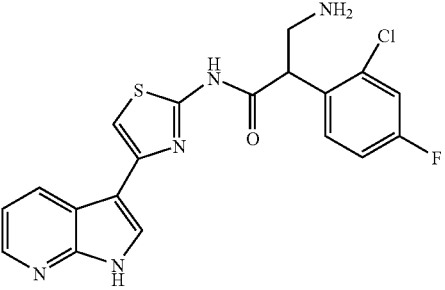 | II-196 |

-continued

| Compound | Cmpd # |
|---|---|
| | II-201 |
| | II-202 |
| | II-203 |
| | II-204 |
| | II-205 |

| Compound | Cmpd # |
|---|---|
| | II-206 |
| | II-207 |
| | II-208 |
| | II-209 |
| | II-210 |
| | II-211 |

-continued
| Compound | Cmpd # |
|---|---|
| 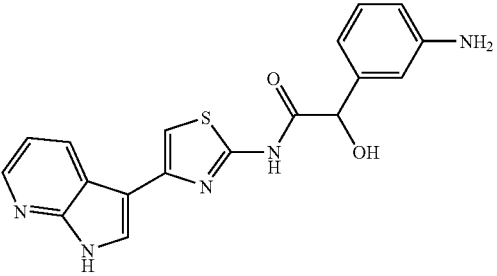 | II-212 |
| 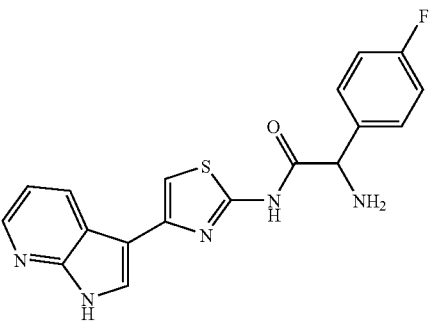 | II-213 |
| 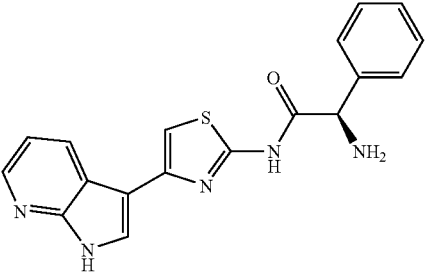 | II-214 |
| 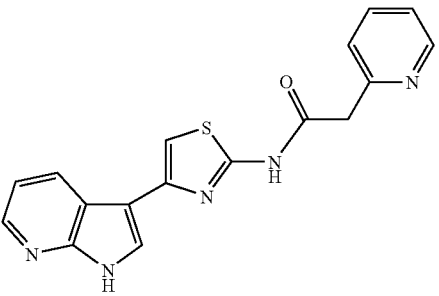 | II-215 |
| 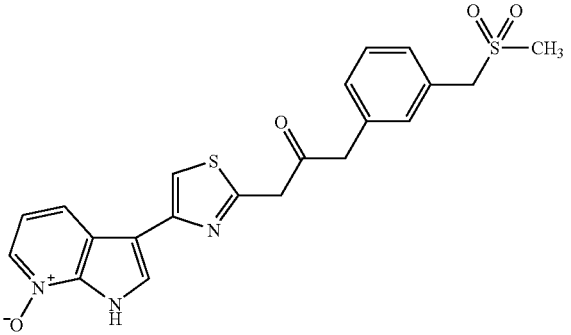 | II-216 |

| Compound | Cmpd # |
|---|---|
| | II-217 |
| | II-218 |
| | II-219 |
| | II-220 |
| | II-221 |

| Compound | Cmpd # |
|---|---|
| (structure) | II-222 |
| (structure) | II-223 |
| (structure) | II-224 |
| (structure) | II-225 |

| Compound | Cmpd # |
|---|---|
| 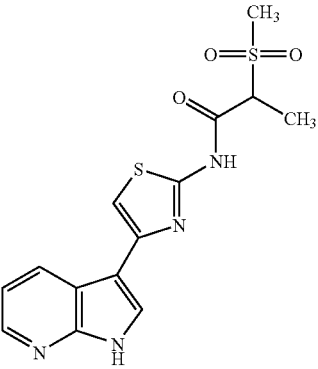 | II-226 |
| 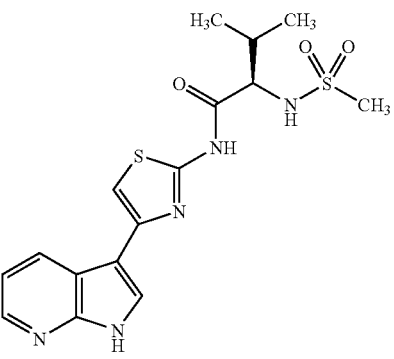 | II-227 |
| 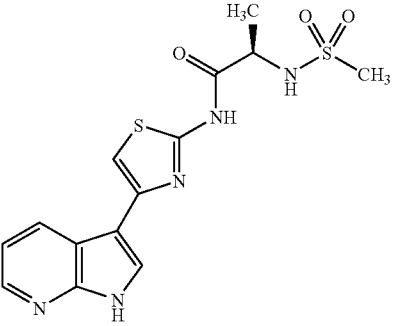 | II-228 |
| 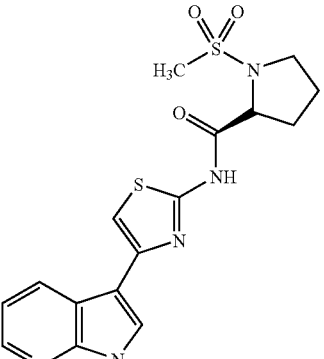 | II-229 |

-continued

| Compound | Cmpd # |
|---|---|
| | II-230 |
| | II-231 |
| | II-232 |
| | II-233 |
| | II-234 |

-continued
| Compound | Cmpd # |
|---|---|
| 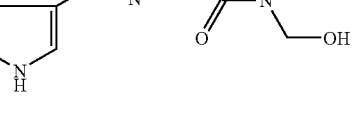 | II-235 |
| 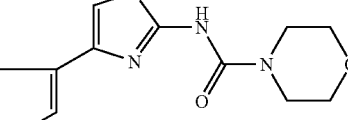 | II-236 |
| 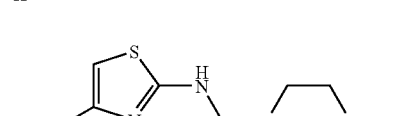 | II-237 |
| 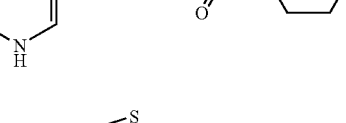 | II-238 |
| 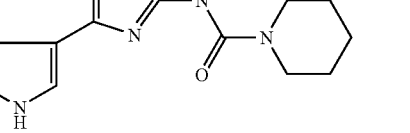 | II-239 |
| 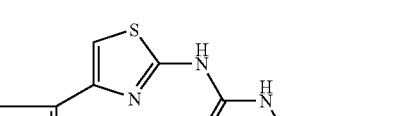 | II-240 |
|  | II-241 |

| Compound | Cmpd # |
|---|---|
| | II-242 |
| | II-243 |
| | II-244 |
| | II-245 |
| | II-246 |
| | II-247 |

-continued
| Compound | Cmpd # |
|---|---|
| 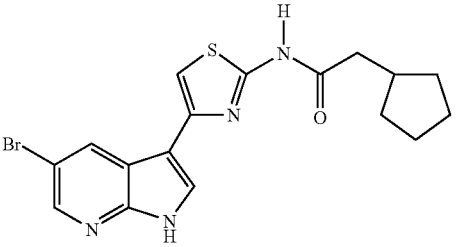 | II-248 |
| 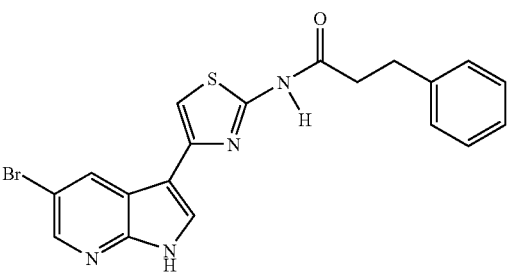 | II-249 |
| 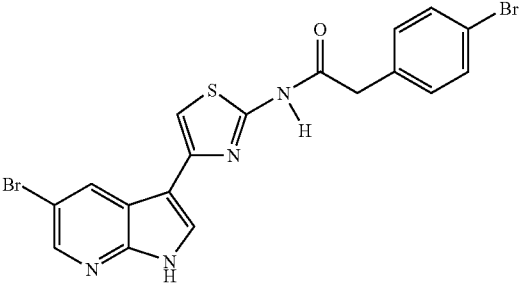 | II-250 |
| 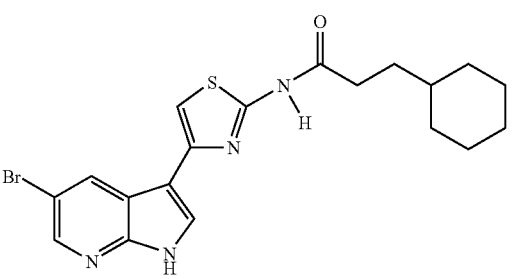 | II-251 |
| 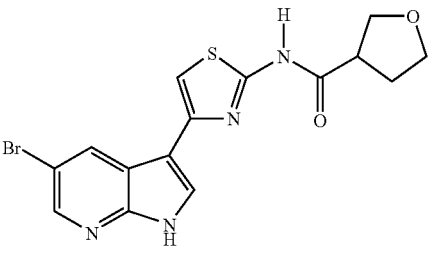 | II-252 |

-continued

| Compound | Cmpd # |
|---|---|
| | II-253 |
| | II-254 |
| | II-255 |
| | II-256. |

15. A composition comprising an effective amount of compound according to claim 1, and a pharmaceutically acceptable carrier, adjuvant, or vehicle.

16. A method of inhibiting ROCK, kinase activity in vitro in a biological sample selected from cell culture, saliva, urine, feces, semen, tears, or extracts thereof; which method contacting said biological sample with a compound of claim 1 or a composition comprising said compound.

17. A method of treating or lessening the severity of glaucoma in a patient, said method comprising the step of administering to said patient a compound of claim 1 or a composition comprising said compound.

* * * * *